US008835020B2

(12) United States Patent
Lee et al.

(10) Patent No.: US 8,835,020 B2
(45) Date of Patent: Sep. 16, 2014

(54) BLUE FLUORESCENT COMPOSITION AND ORGANIC ELECTROLUMINESCENT DEVICE USING THE SAME

(75) Inventors: Seung-Jae Lee, Seoul (KR); In-Bum Song, Uijeongbu-si (KR); Jung-Keun Kim, Gimpo-si (KR); Do-Han Kim, Goyang-si (KR); Chun-Gun Park, Seoul (KR); Hyoung-Yun Oh, Goyang-si (KR); Jong-Kwan Bin, Gyeonggi-do (KR); Kyung-Hoon Lee, Goyang-si (KR); Hyun-Cheol Jeong, Gyeongsangnam-do (KR); Dong-Hee Yoo, Seoul (KR); Nam-Sung Cho, Goyang-si (KR); Jong-Hyun Park, Seoul (KR); In-Sun Yoo, Paju-si (KR); Tae-Han Park, Seoul (KR); Soon-Wook Cha, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 404 days.

(21) Appl. No.: 12/591,796

(22) Filed: Dec. 1, 2009

(65) Prior Publication Data

US 2010/0141124 A1 Jun. 10, 2010

(30) Foreign Application Priority Data

Dec. 5, 2008 (KR) ........................ 10-2008-0123423

(51) Int. Cl.

| | |
|---|---|
| ***H01L 51/54*** | (2006.01) |
| ***C09K 11/06*** | (2006.01) |
| ***H01L 51/00*** | (2006.01) |
| ***H05B 33/14*** | (2006.01) |
| ***C07C 211/61*** | (2006.01) |
| ***C07C 255/58*** | (2006.01) |
| *H01L 51/50* | (2006.01) |

(52) U.S. Cl.

CPC ............ *C09K 11/06* (2013.01); *H01L 51/0054* (2013.01); *H05B 33/14* (2013.01); *C07C 211/61* (2013.01); *C09K 2211/1011* (2013.01); *H01L 51/5012* (2013.01); *C07C 255/58* (2013.01); *H01L 51/006* (2013.01); *H01L 51/0058* (2013.01); *C07C 2103/50* (2013.01); *C09K 2211/1014* (2013.01); *Y10S 428/917* (2013.01)

USPC ........... 428/690; 428/917; 313/504; 313/506; 252/301.16; 257/40; 257/102; 257/E51.049; 257/E51.05; 564/434

(58) Field of Classification Search

CPC C07C 211/61; C07C 255/58; C07C 2103/50; H01L 51/0054; H01L 51/006; H01L 51/5012; C09K 11/06; C09K 2211/1011

See application file for complete search history.

(56) References Cited

U.S. PATENT DOCUMENTS

| | | | | |
|---|---|---|---|---|
| 2003/0227001 | A1* | 12/2003 | Li et al. | 252/301.35 |
| 2004/0137270 | A1* | 7/2004 | Seo et al. | 428/690 |
| 2007/0009758 | A1 | 1/2007 | Funahashi | |
| 2010/0052526 | A1* | 3/2010 | Je et al. | 313/504 |

FOREIGN PATENT DOCUMENTS

| | | | |
|---|---|---|---|
| CN | 1535089 | | 10/2004 |
| KR | 1020040057862 | A | 7/2004 |
| KR | 1020070115588 | A | 12/2007 |

* cited by examiner

*Primary Examiner* — Michael H Wilson

(74) *Attorney, Agent, or Firm* — McKenna Long & Aldridge LLP

(57) ABSTRACT

A blue fluorescent compound includes a host material being capable of transporting an electron or a hole; and a dopant material represented by following Formula 1:

[Formula 1]

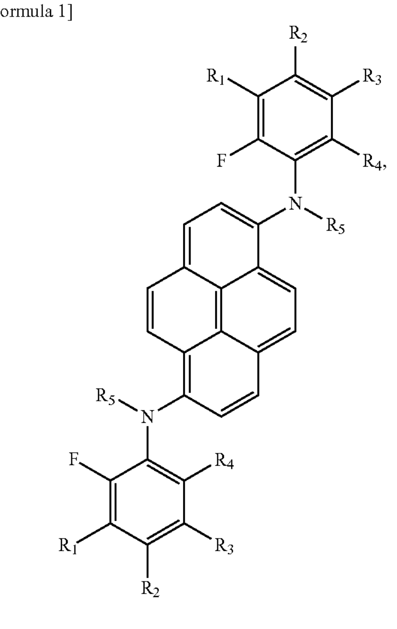

wherein at least two of the R1, the R2, the R3, and the R4 are selected from substituted or non-substituted aromatic group or substituted or non-substituted heterocyclic group, and the R5 is selected from substituted or non-substituted aromatic group or substituted or non-substituted heterocyclic group.

20 Claims, 2 Drawing Sheets

BLUE FLUORESCENT COMPOSITION AND ORGANIC ELECTROLUMINESCENT DEVICE USING THE SAME

The present application claims the benefit of Korean Patent Application No. 10-2008-0123423 filed in Korea on Dec. 5, 2008, which is hereby incorporated by reference.

BACKGROUND OF THE INVENTION

1. Field of the Invention

The present invention relates to a blue fluorescent compound and an organic electroluminescent device (OELD) and more particularly to a blue fluorescent compound having high color purity and high luminescent efficiency and an OELD using the red phosphorescent compound.

2. Discussion of the Related Art

Recently, a requirement for a flat panel display device having a relatively large display area and a relatively small occupancy has been increased. Among the flat panel display devices, an OELD has various advantages as compared to an inorganic electroluminescent device, a liquid crystal display device, a plasma display panel, and so on. The OELD device has excellent characteristics of a view angel, a contrast ratio and so on. Also, since the OELD device does not require a backlight assembly, the OELD device has low weight and low power consumption. Moreover, the OELD device has advantages of a high response rate, a low production cost and so on.

In general, the OELD emits light by injecting electrons from a cathode and holes from an anode into an emission compound layer, combining the electrons with the holes, generating an exciton, and transforming the exciton from an excited state to a ground state. A flexible substrate, for example, a plastic substrate, can be used as a base substrate where elements are formed. The OELD has excellent characteristics of a view angel, a contrast ratio and so on. Also, since the OELD does not require a backlight assembly, the OELD has low weight and low power consumption. Moreover, the OELD has advantages of a high response rate, a low production cost, a high color purity and so on. The OELD can be operated at a voltage (e.g., 10V or below) lower than a voltage required to operate other display devices. In addition, the OELD is adequate to produce full-color images.

A general method for fabricating OELDs will be briefly explained below. First, an anode is formed on a substrate by depositing a transparent conductive compound, for example, indium-tin-oxide (ITO). Next, a hole injection layer (HIL) is formed on the anode. For example, the HIL may be formed of copper phthalocyanine (CuPC), which is represented by following Formula 1-1, and have a thickness of about 10 nm to about 30 nm. Next, a hole transporting layer (HTL) is formed on the HIL. For example, the HTL may be formed of 4,4'-bis [N-(1-naphtyl)-N-phenylamino]-biphenyl (NPB) and have a thickness of about 30 nm to about 60 nm. Next, an emitting compound layer (EML) is formed on the HTL. A dopant may be doped onto the EML. For example, DPVBi, which is represented by following Formula 1-2, is used for the host, and BD-a, which is represented by following Formula 1-3, is used for the dopant. The EML includes the host and the dopant by about 1 to 10 weight % and has a thickness of about 20 nm to about 40 nm.

[Formula 1-1]

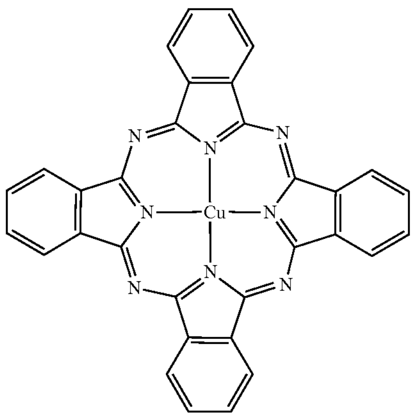

[Formula 1-2]

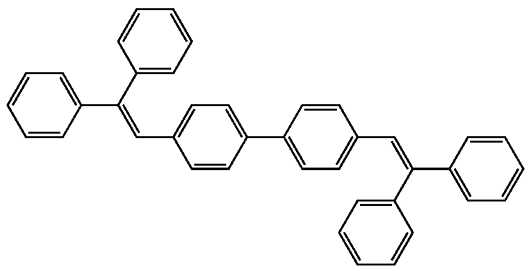

[Formula 1-3]

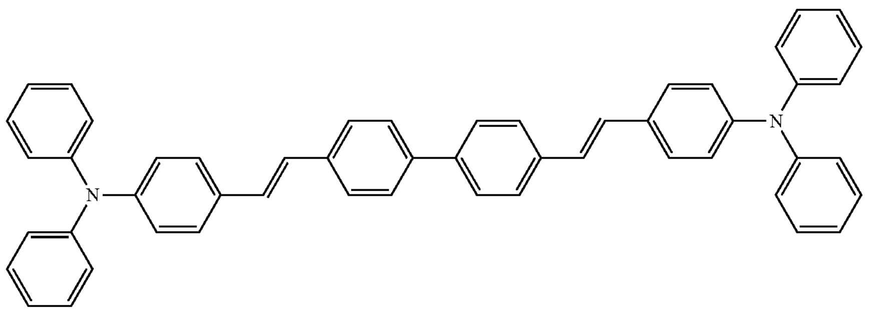

Next, an electron transporting layer (ETL) and an electron injection layer (EIL) are stacked on the EML. For example, the ETL may be formed of tris(8-hydroxy-quinolate)aluminum (Alq3). A cathode is formed on the EIL, and a passivation layer is formed on the cathode.

Various compounds for the EML have been introduced. However, there are limitations in the related art EML compound. As shown in FIG. 1, since the blue color has pure color purity, it is very difficult to produce a dark blue color. Accordingly, there is a problem to display a full color image. In addition, the blue color has lower luminescent efficiency.

SUMMARY OF THE INVENTION

Accordingly, the present invention is directed to a blue fluorescent compound and an organic electroluminescent device (OELD) using the same that substantially obviates one or more of the problems due to limitations and disadvantages of the related art.

An object of the present invention is to provide a blue fluorescent compound having high color purity, high luminescence efficiency, and long lifetime.

Another object of the present invention is to provide an OELD device using the blue fluorescent compound.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, a blue fluorescent compound includes a host material being capable of transporting an electron or a hole; and a dopant material represented by following Formula:

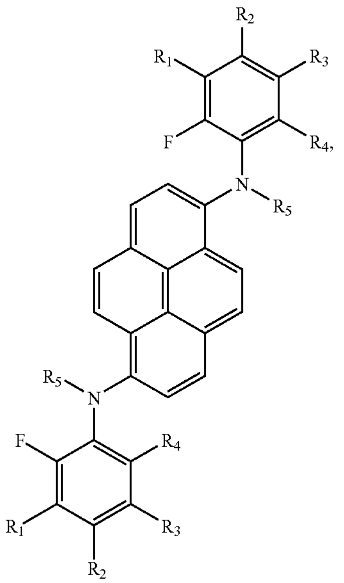

wherein at least two of the R1, the R2, the R3, and the R4 are selected from substituted or non-substituted aromatic group or substituted or non-substituted heterocyclic group, and the R5 is selected from substituted or non-substituted aromatic group or substituted or non-substituted heterocyclic group.

In another aspect of the present invention, a blue fluorescent compound includes a host material being capable of transporting an electron or a hole; and a dopant material represented by following Formula:

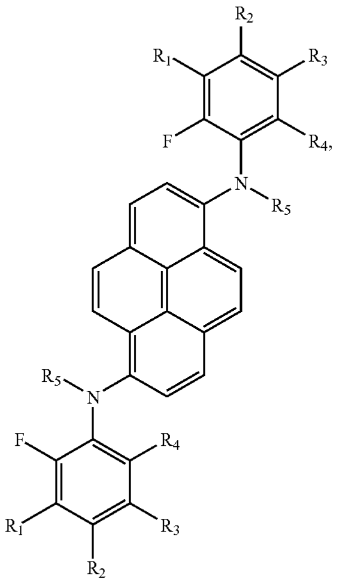

wherein at least one of the R1, the R2, the R3, the R4 and R5 is selected from a deuterium (D)-substituted aromatic group, and at least two of the R1, the R2, the R3, and the R4 are selected from hydrogen (H), substituted or non-substituted aromatic group, or substituted or non-substituted heterocyclic group, and wherein the R5 is selected from substituted or non-substituted aromatic group, or substituted or non-substituted heterocyclic group.

In another aspect, a blue fluorescent compound includes a host material being capable of transporting an electron or a hole; and a dopant material represented by following Formula:

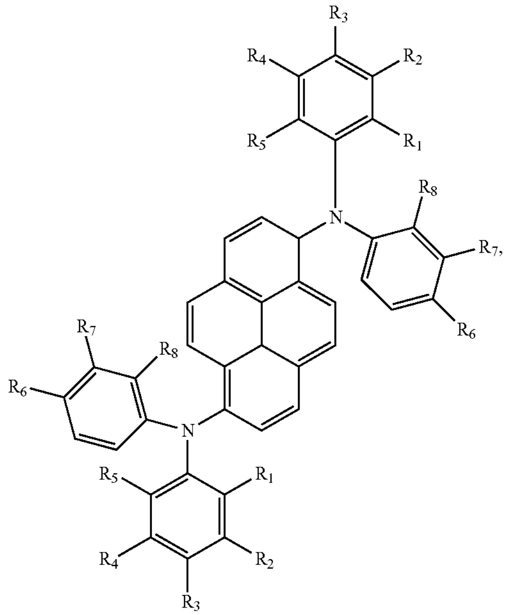

wherein each of the R1, the R2, the R3, the R4, and the R5 is hydrogen (H), C1 to C6 alkyl, or substituted or non-substituted aryl having at least six carbons (C), and at least two of the R1, the R2, the R3, the R4, and the R5 are selected from the substituted or non-substituted aryl having at least six carbons, and wherein each of the R6, the R7, and the R8 is selected from hydrogen (H), C1 to C6 alkyl, substituted or non-substituted aryl having at least six carbons, fluorine, cyanide, or tri-fluoromethyl, and at least one of the R6, the R7, and the R8 is selected from fluorine, cyanide, or tri-fluoromethyl.

In another aspect, an organic electroluminescent device includes a first electrode; a second electrode facing the first electrode: and an organic electroluminescent diode positioned between the first and second electrodes and includes an emitting material layer, the emitting material layer includes: a host material being capable of transporting an electron or a hole; and a dopant material represented by following Formula:

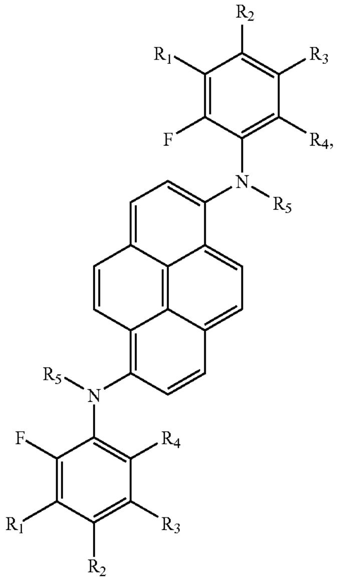

wherein at least two of the R1, the R2, the R3, and the R4 are selected from substituted or non-substituted aromatic group or substituted or non-substituted heterocyclic group, and the R5 is selected from substituted or non-substituted aromatic group or substituted or non-substituted heterocyclic group.

In another aspect, an organic electroluminescent device includes a first electrode; a second electrode facing the first electrode: and an organic electroluminescent diode positioned between the first and second electrodes and includes an emitting material layer, the emitting material layer includes: a host material being capable of transporting an electron or a hole; and a dopant material represented by following Formula:

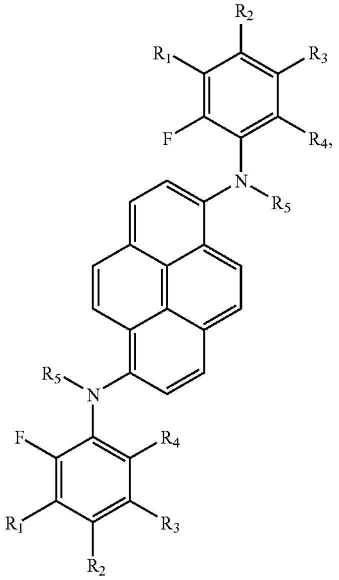

wherein at least one of the R1, the R2, the R3, the R4 and R5 is selected from a deuterium (D)-substituted aromatic group, and at least two of the R1, the R2, the R3, and the R4 are selected from hydrogen (H), substituted or non-substituted aromatic group, or substituted or non-substituted heterocyclic group, and wherein the R5 is selected from substituted or non-substituted aromatic group, or substituted or non-substituted heterocyclic group.

In another aspect, an organic electroluminescent device includes a first electrode; a second electrode facing the first electrode: and an organic electroluminescent diode positioned between the first and second electrodes and includes an emitting material layer, the emitting material layer includes: a host material being capable of transporting an electron or a hole; and a dopant material represented by following Formula:

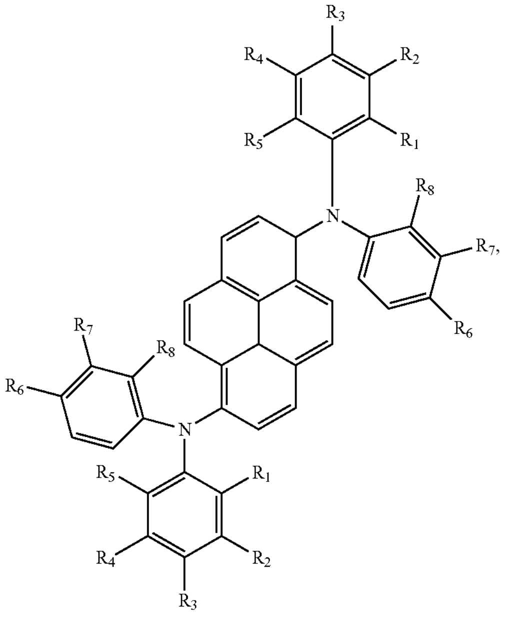

wherein each of the R1, the R2, the R3, the R4, and the R5 is hydrogen (H), C1 to C6 alkyl, or substituted or non-substituted aryl having at least six carbons (C), and at least two of the R1, the R2, the R3, the R4, and the R5 are selected from the substituted or non-substituted aryl having at least six carbons, and wherein each of the R6, the R7, and the R8 is selected from hydrogen (H), C1 to C6 alkyl, substituted or non-substituted aryl having at least six carbons, fluorine, cyanide, or tri-fluoromethyl, and at least one of the R6, the R7, and the R8 is selected from fluorine, cyanide, or tri-fluoromethyl.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
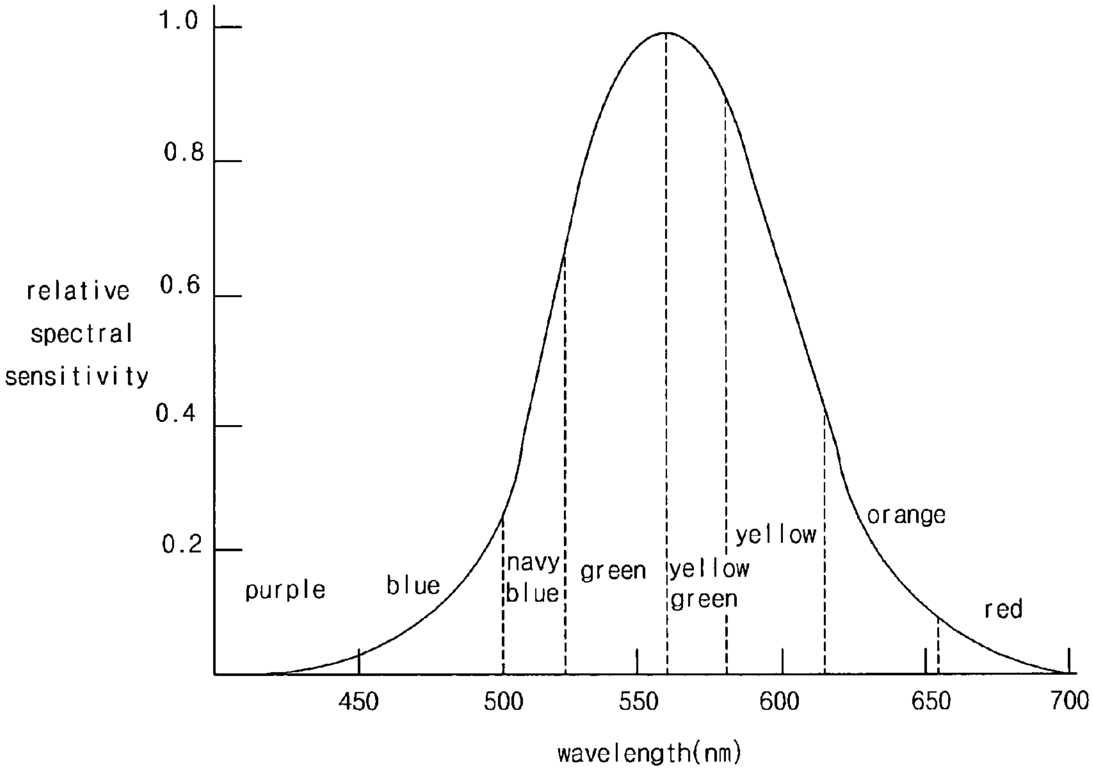
FIG. 1 is a graph showing a relation of a color purity and a visible degree.

Reference will now be made in detail to the preferred embodiments, examples of which are illustrated in the accompanying drawings.

-First Embodiment-

A blue fluorescent compound according to the first embodiment of the present invention includes 1,6-pyrene and 6-fluorophenylamine derivative. Namely, each of 1 and 6 positions of pyrene are substituted by 6-fluorophenylamine derivative. In addition, at least two of 2 to 5 positions of 6-fluorophenylamine derivative and one position of nitrogen (N) of 6-fluorophenylamine derivative are substituted by substituted or non-substituted aromatic group or substituted or non-substituted heterocyclic group. Accordingly, the blue fluorescent compound has improved color purity and luminescent efficiency.

The blue fluorescent compound according to the first embodiment of the present invention is represented by following Formula 2.

[Formula 2]

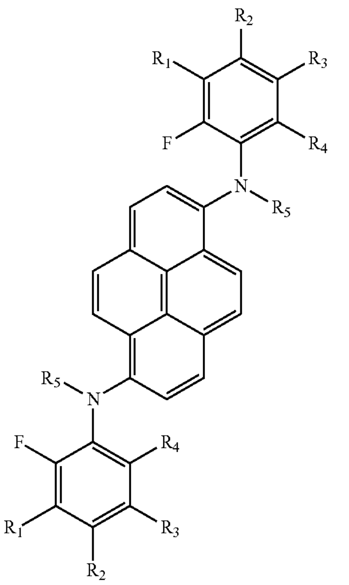

In the above Formula 2, at least two of R1, R2, R3, and R4 are selected from substituted or non-substituted aromatic group or substituted or non-substituted heterocyclic group. In addition, R5 is selected from substituted or non-substituted aromatic group or substituted or non-substituted heterocyclic group.

For example, each of R1 to R5 is one of aromatic group including phenyl, byphenyl, naphthyl, phenanthrene, terphenyl and fluorenyl and their substitution products. In addition, each of R1 to R5 is one of heterocyclic group including furan, thiophene, pyrrole, pyridine and pyrimidine and their substitution products.

A substituent for aromatic group or heterocyclic group is selected from C1 to C6 alkyl group including methyl, ethyl, propyl, i-propyl, and t-butyl. Alternatively, the substituent may be cyano group, silyl group or fluorine.

Namely, in the first embodiment, two 6-fluorophenylamine derivatives, where at least three substituents, such as substituted or non-substituted aromatic and substituted or non-substituted heterocyclic, are introduced, are symmetrically introduced at 1 and 6 position of pyrene such that the blue fluorescent compound has improved color purity and luminescent efficiency.

For example, the blue fluorescent compound represented by Formula 2 is one of compounds in following Formula 3. For convenience, A-1 to A-282 are respectively marked to compounds.

[Formula 3]

A-1

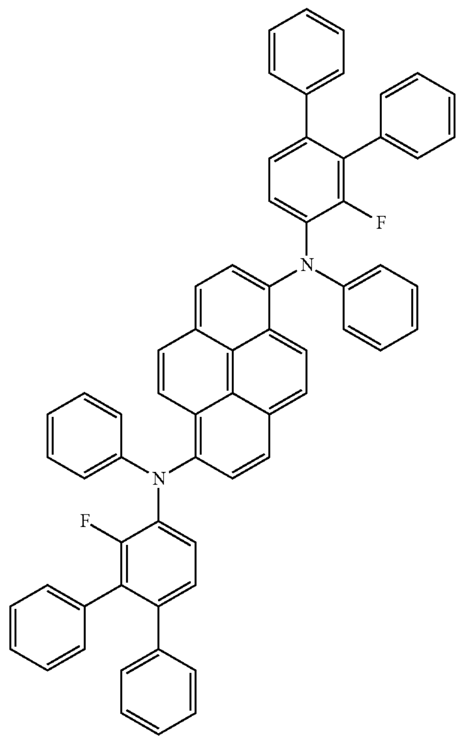

-continued
A-2
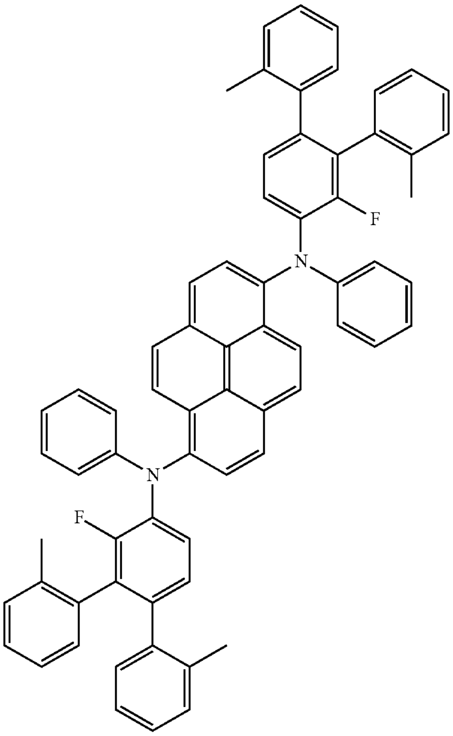
A-3
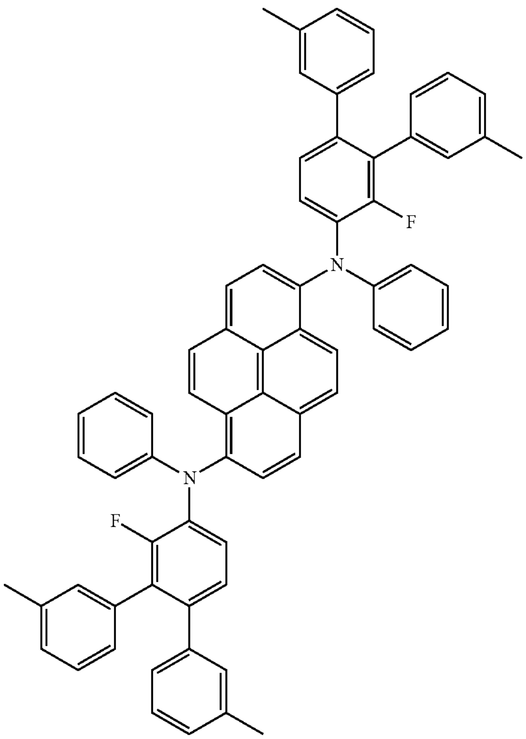
-continued
A-4
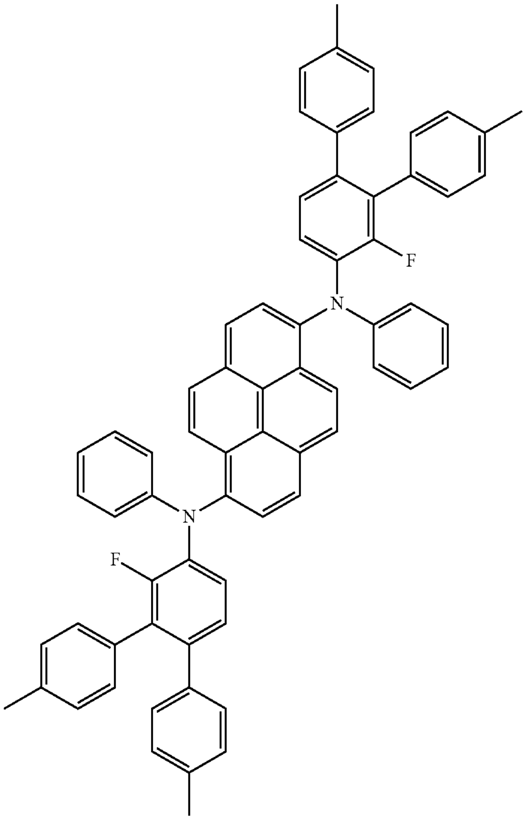
A-5
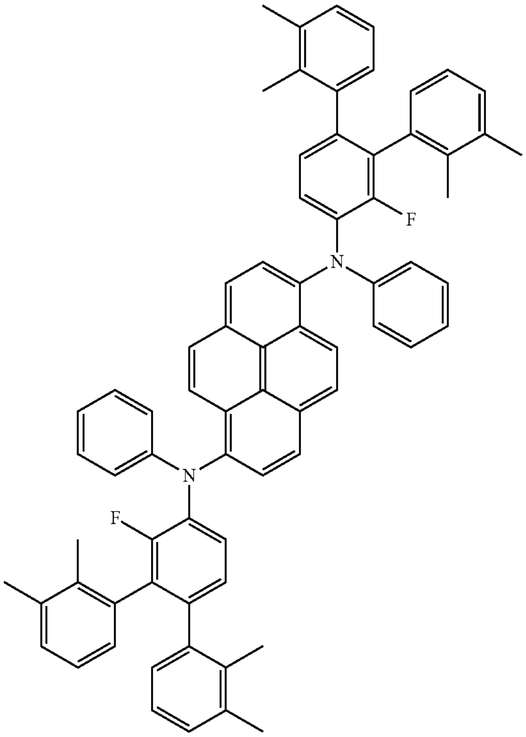

-continued
A-6
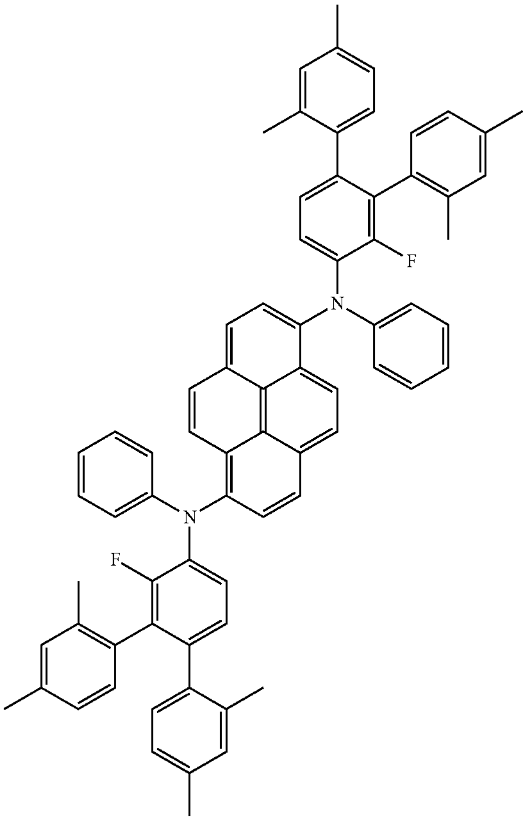
A-7
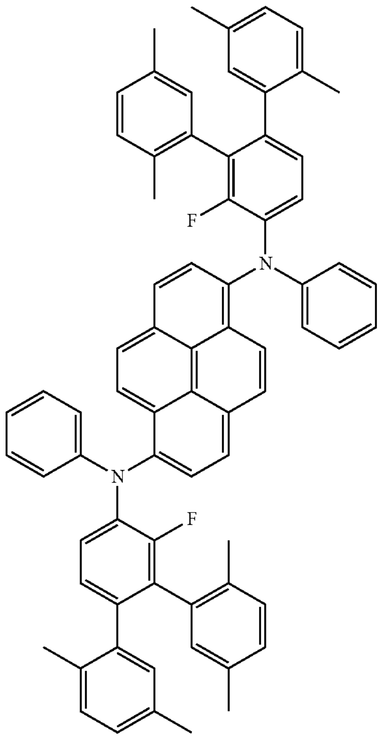
-continued
A-8
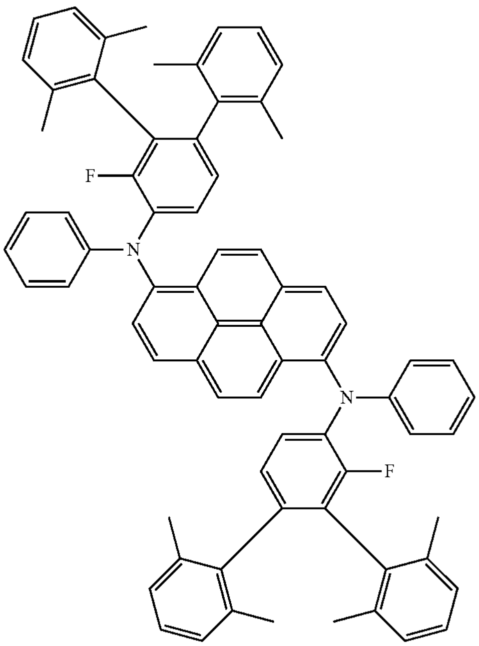
A-9
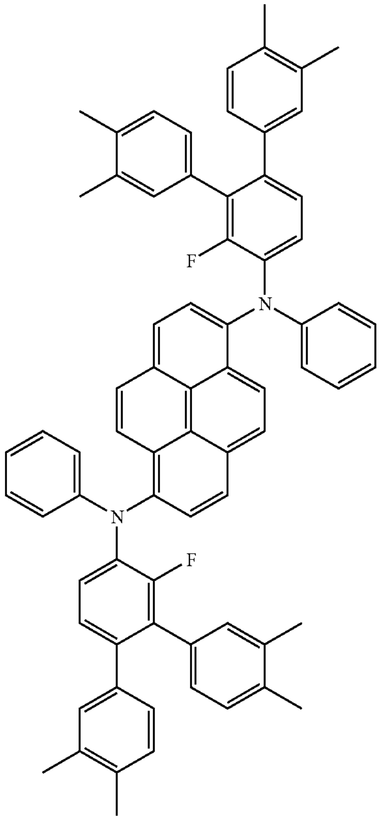

-continued
A-10
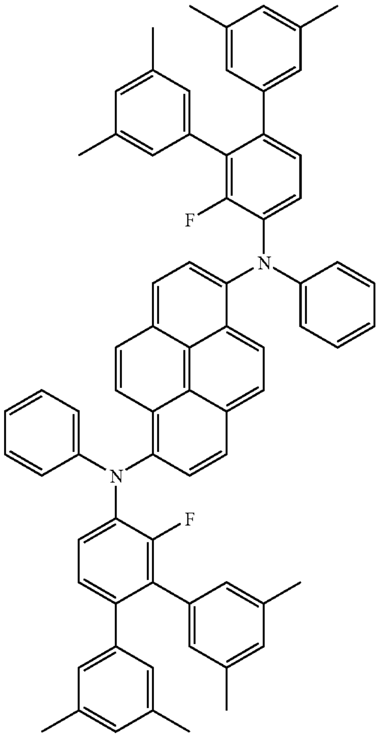
A-11
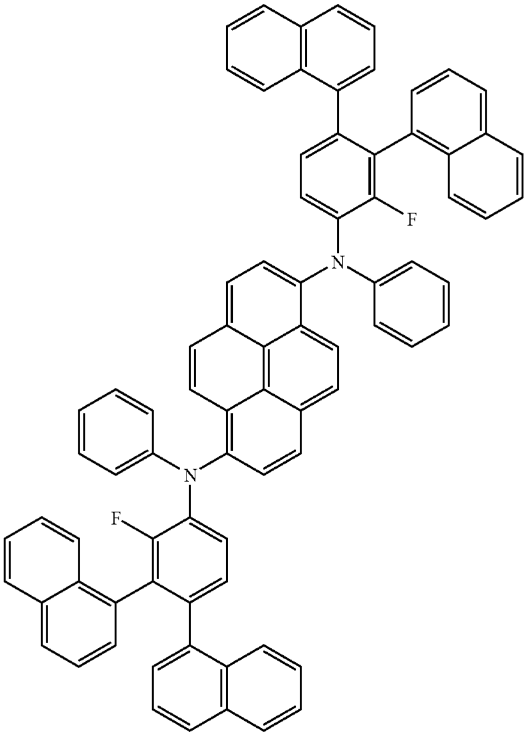
-continued
A-12
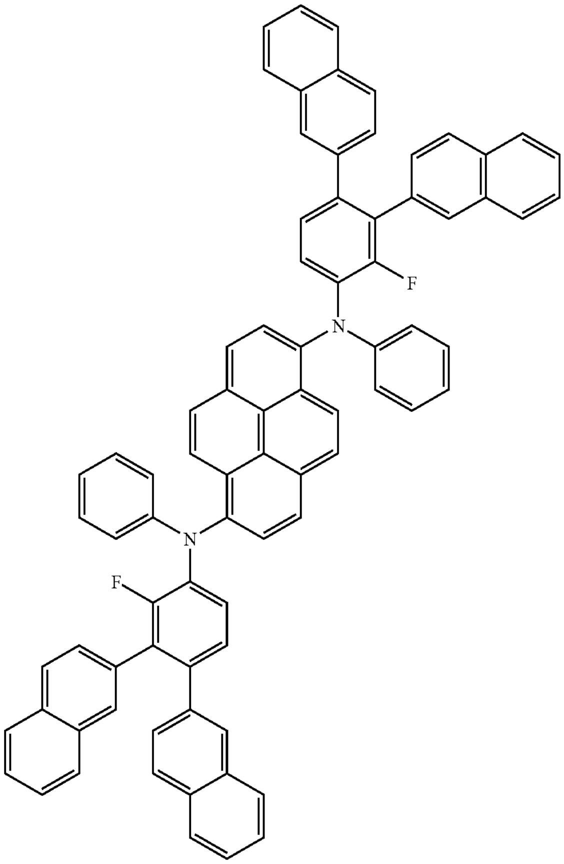
A-13
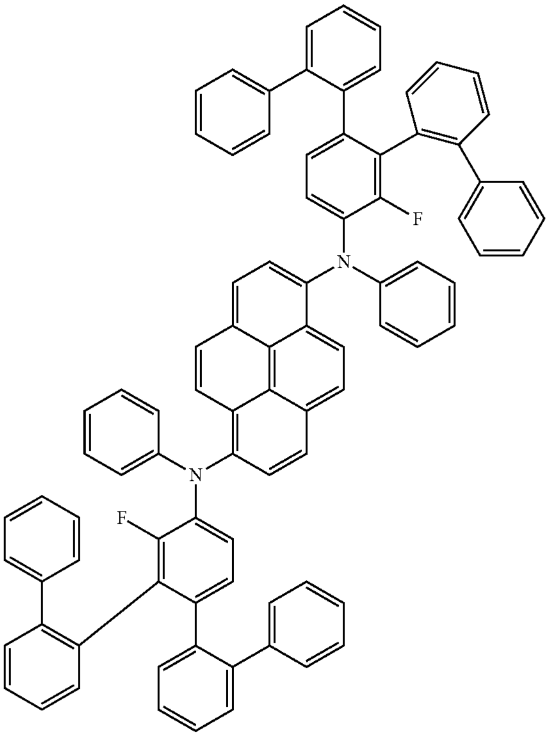

-continued
A-14
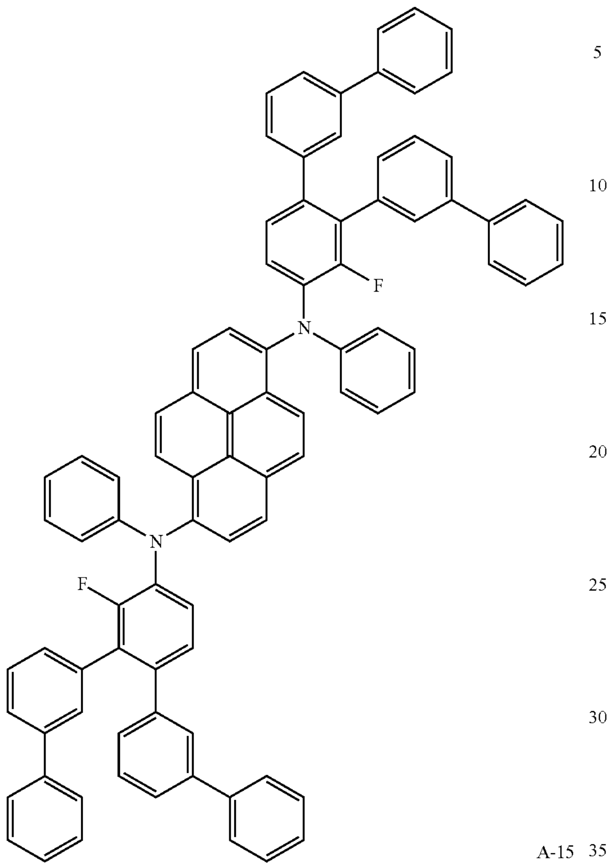
A-15
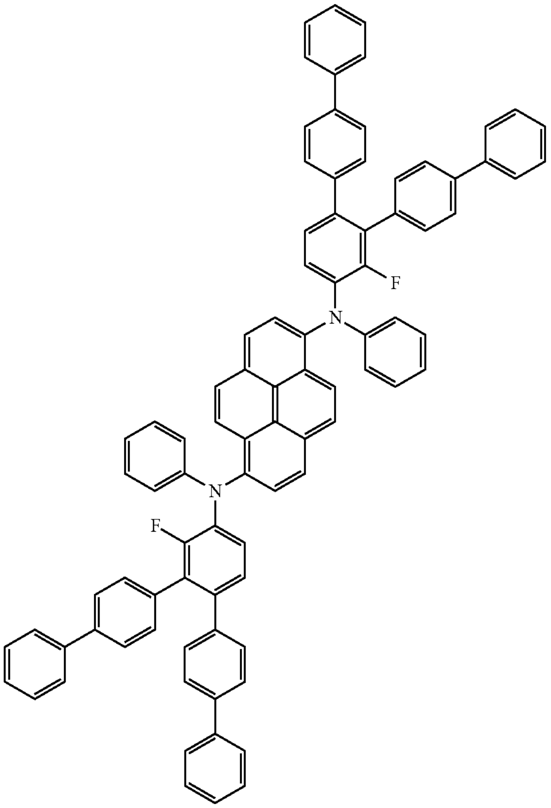
-continued
A-16
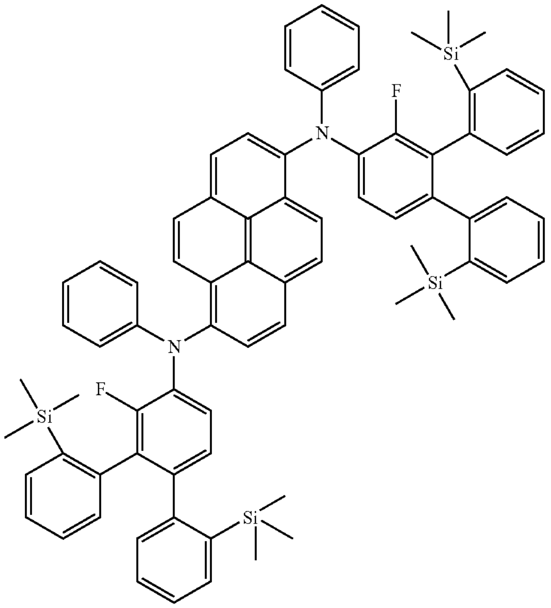
A-17
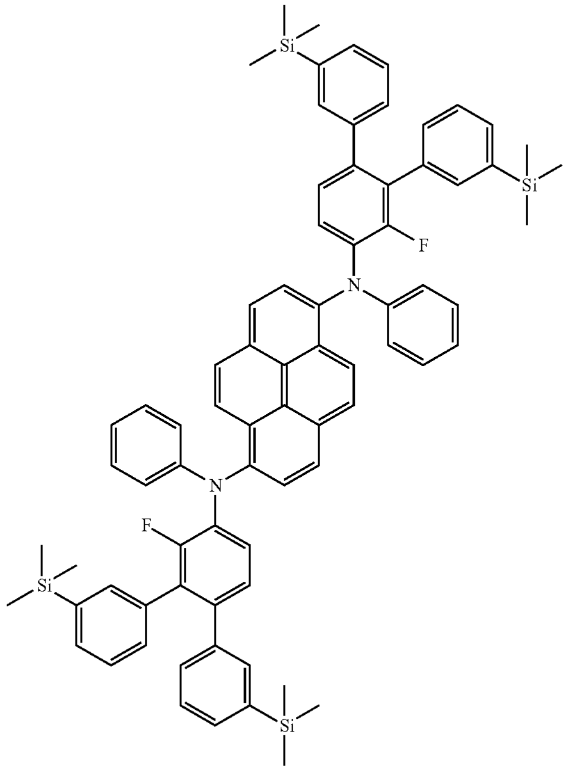

-continued
A-18
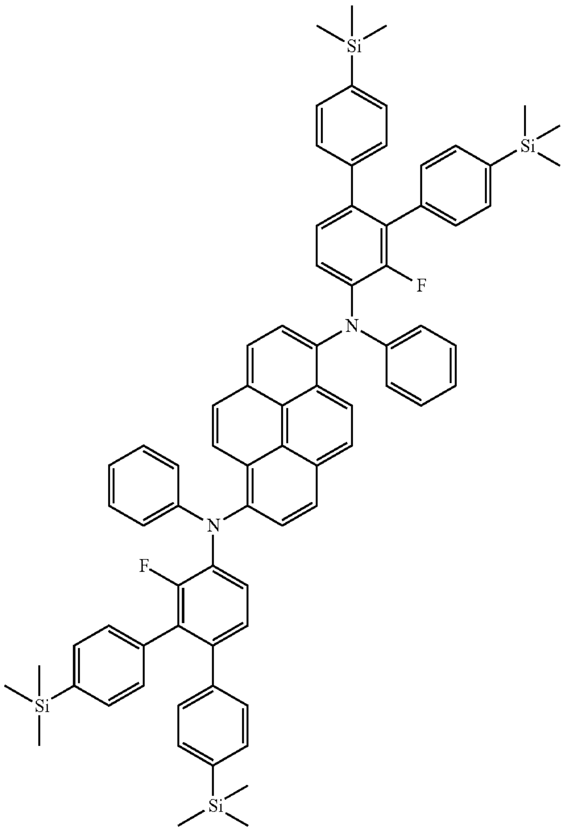
A-19
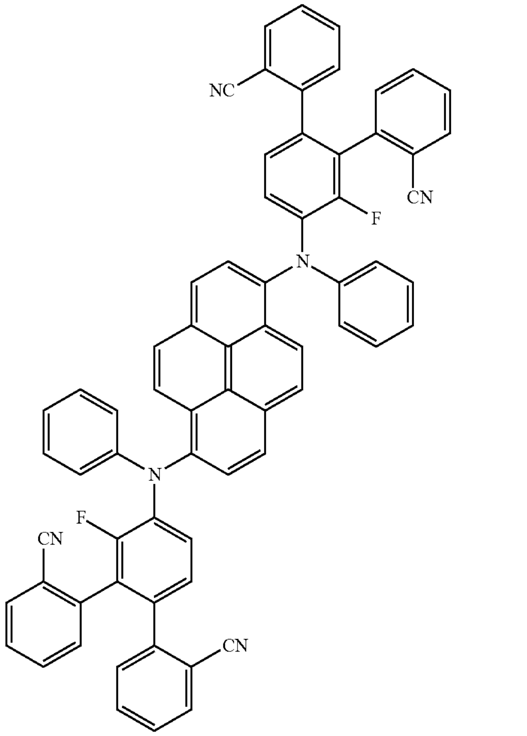
-continued
A-20
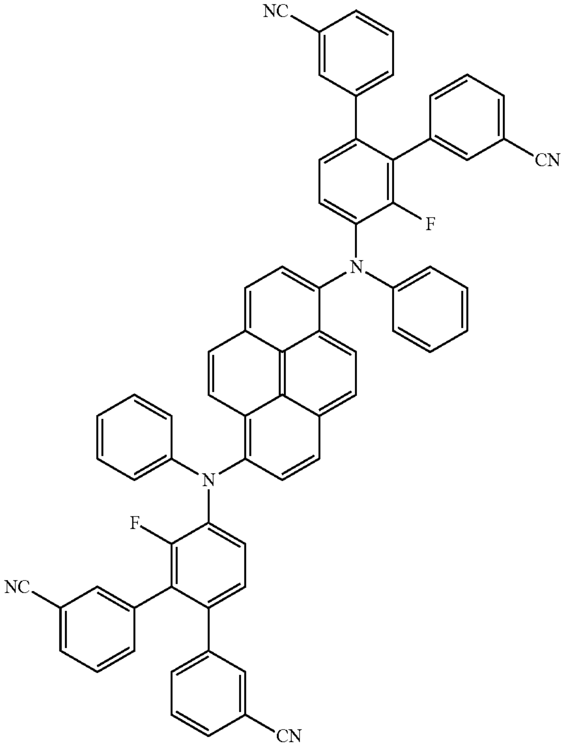
A-21
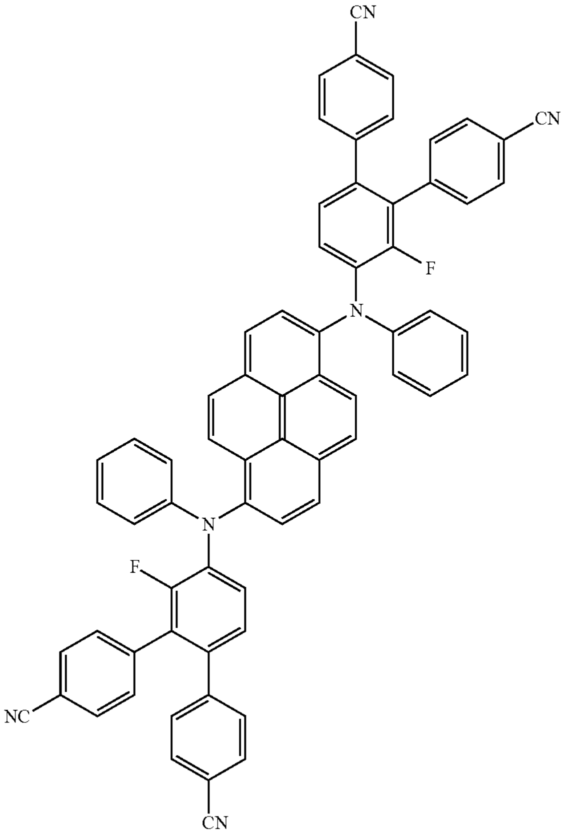

-continued
A-22
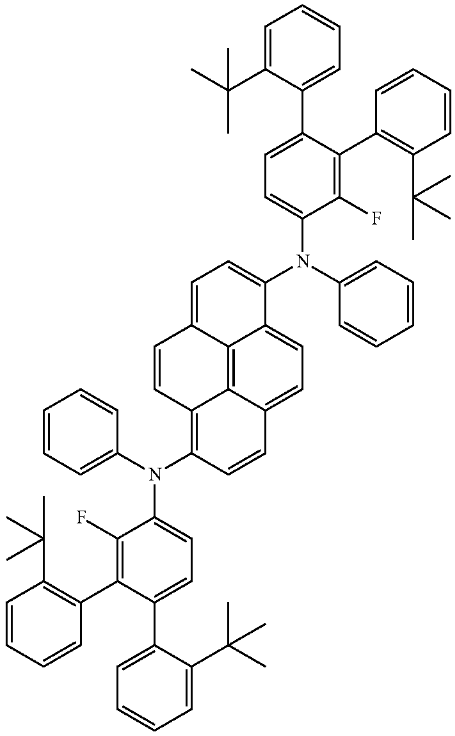
A-23
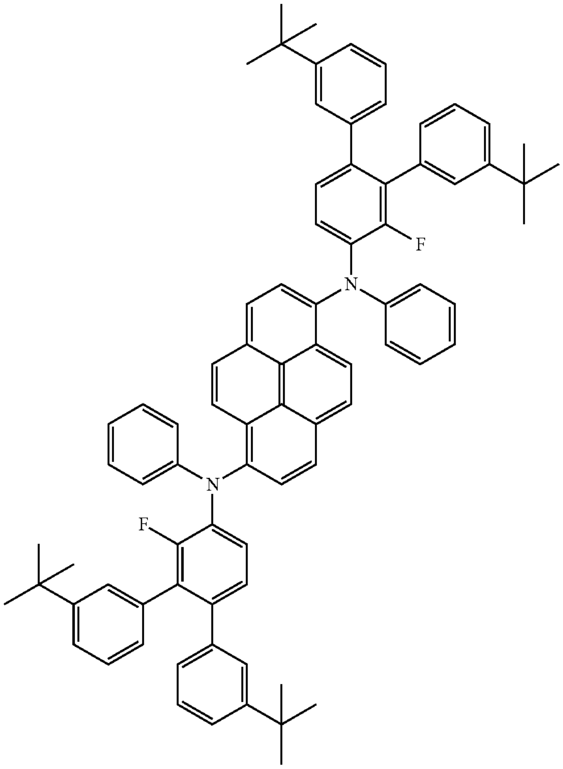
-continued
A-24
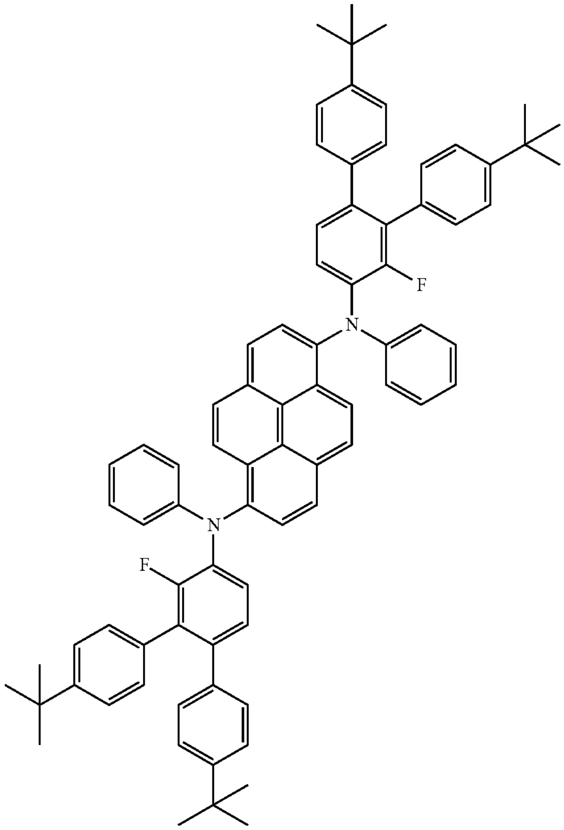
A-25
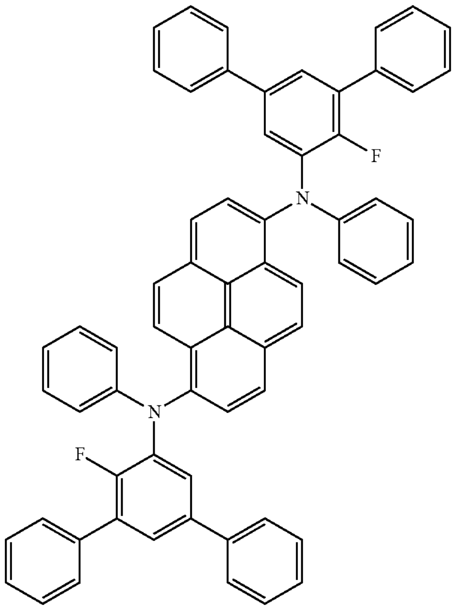

-continued
A-26
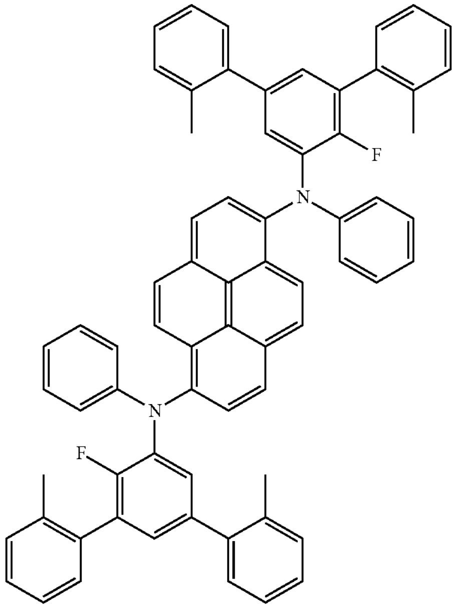
A-27
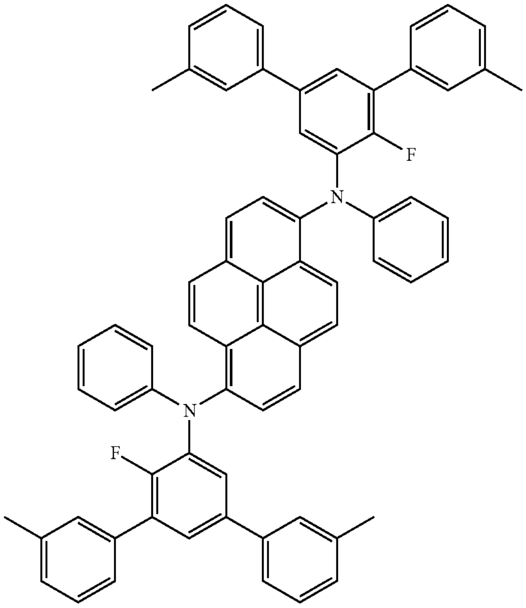
-continued
A-28
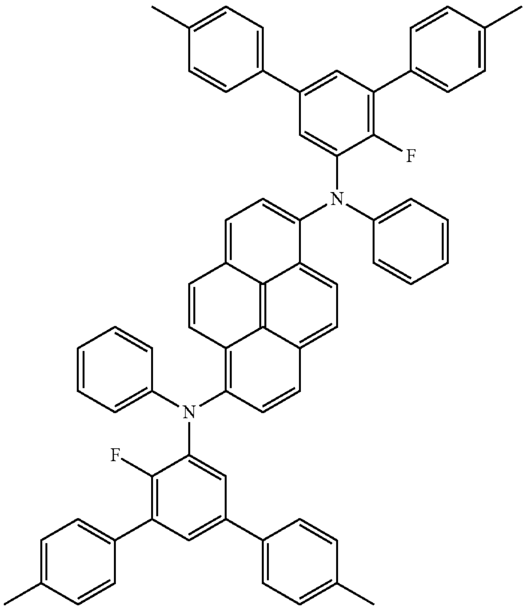
A-29
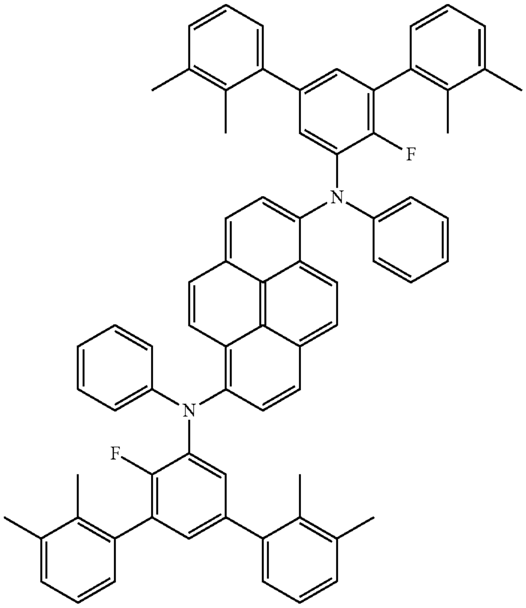

A-30
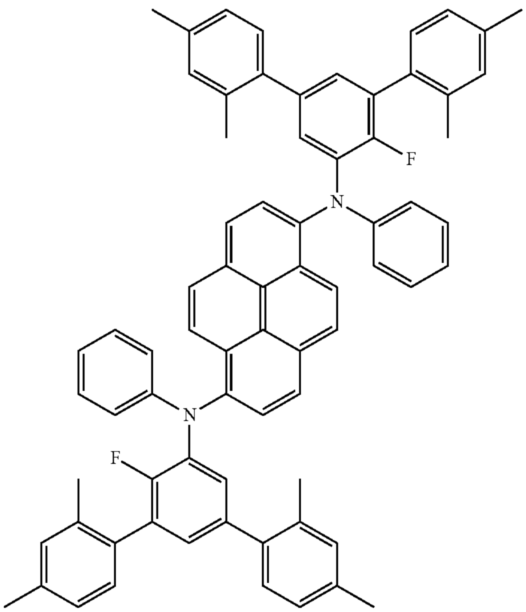
A-31
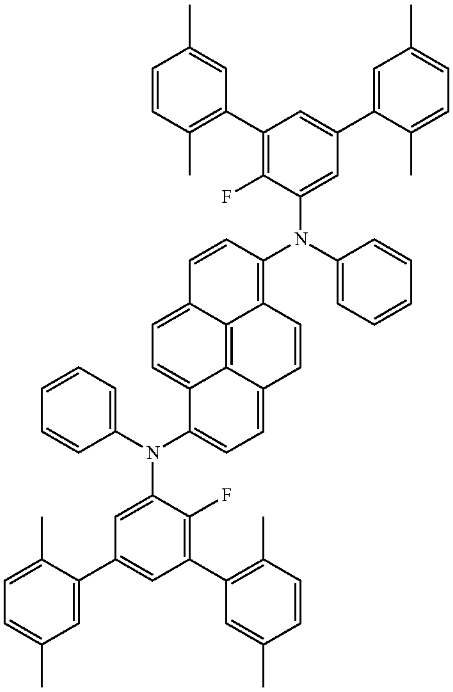
A-32
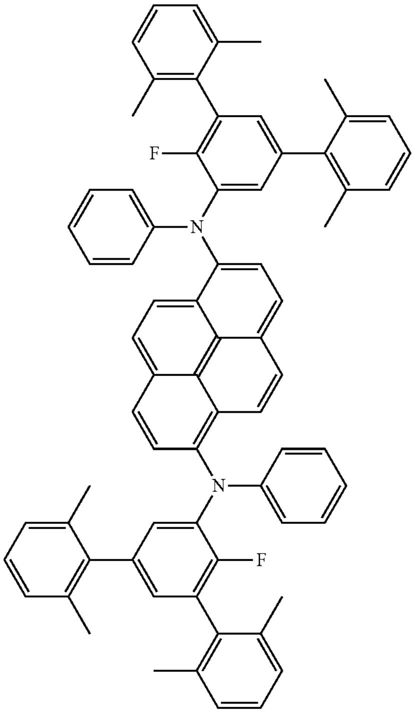
A-33
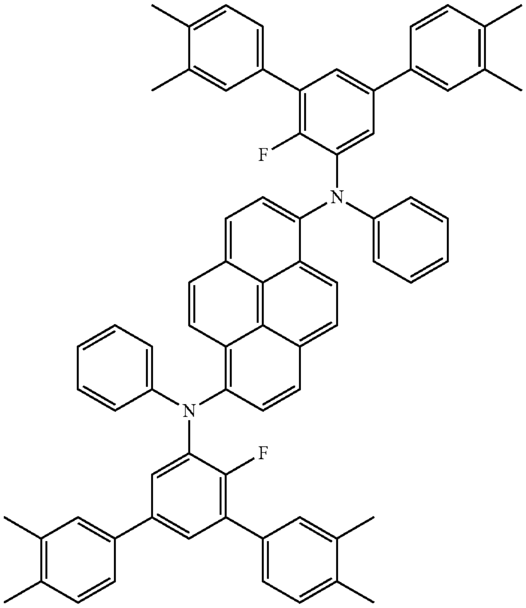

-continued
A-34
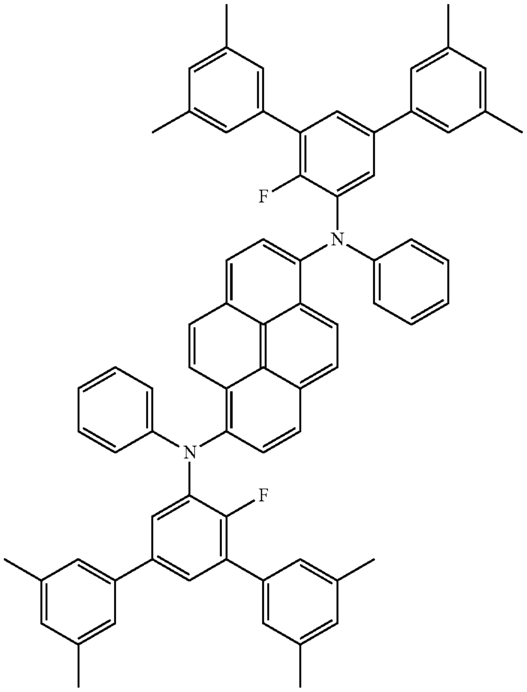
A-35
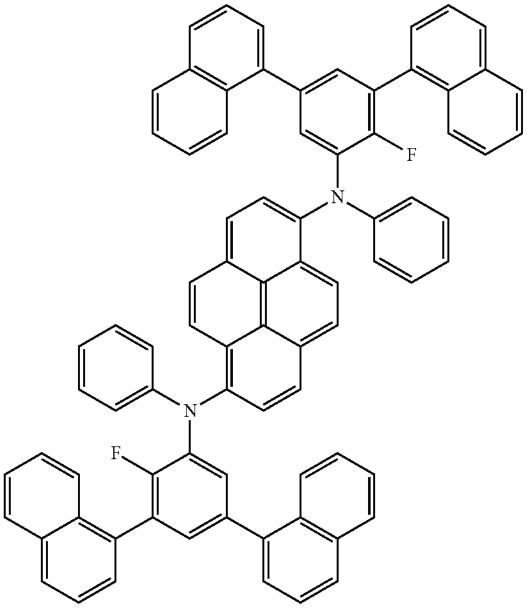
-continued
A-36
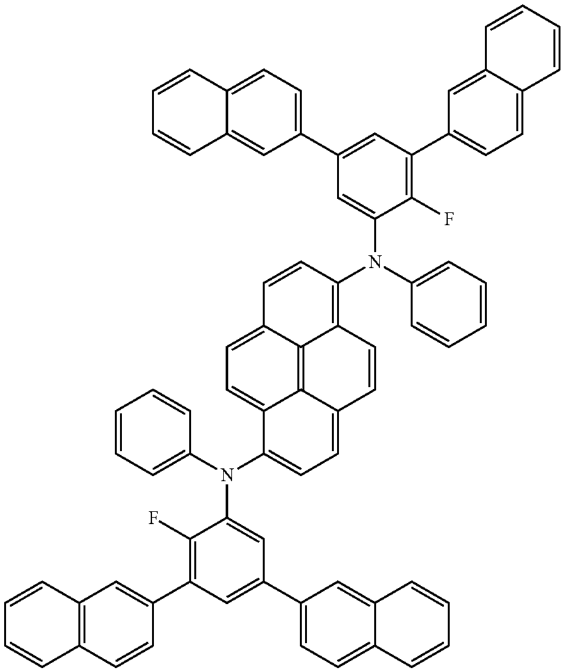
A-37
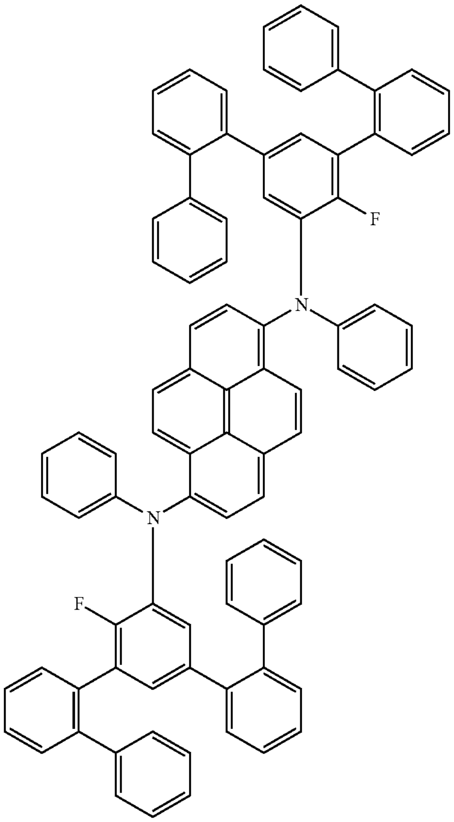

-continued
A-38
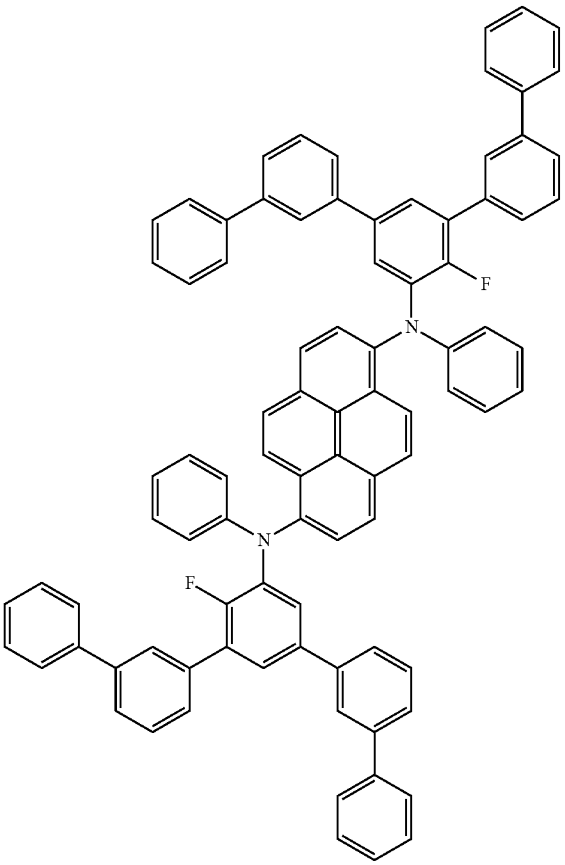
A-39
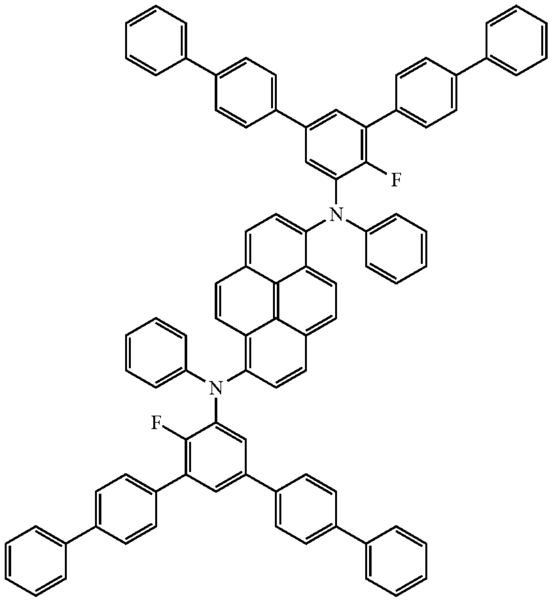
-continued
A-40
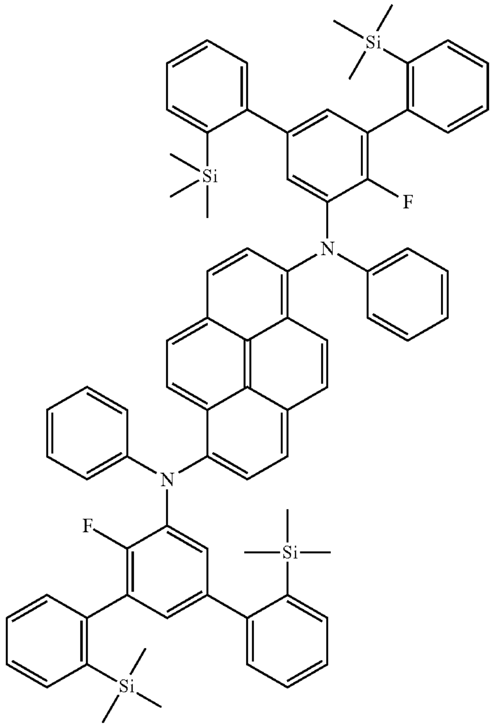
A-41
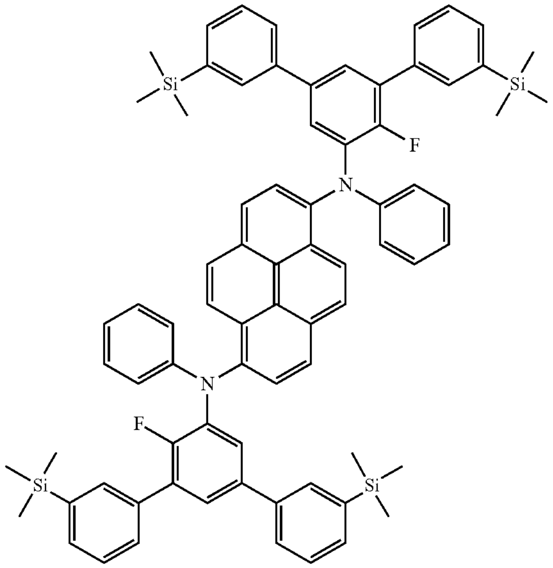

-continued
A-42
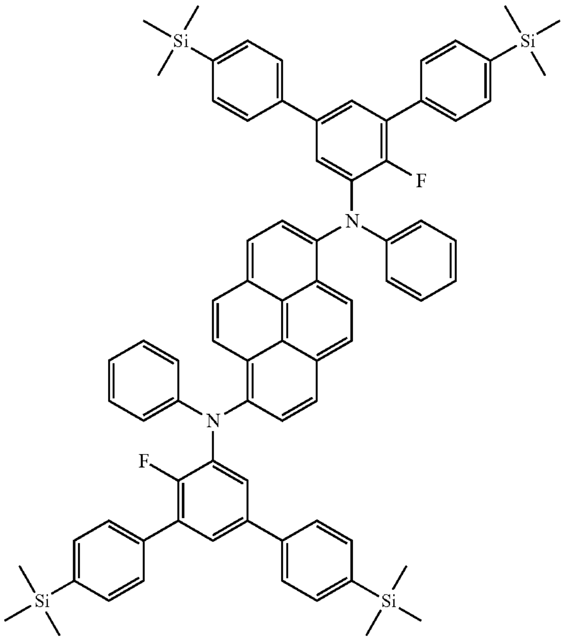
A-43
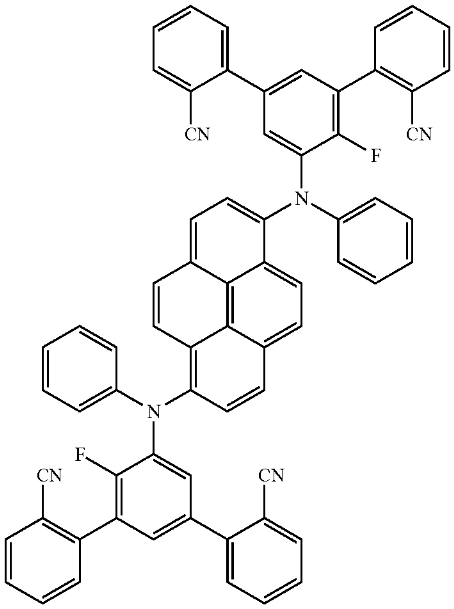
-continued
A-44
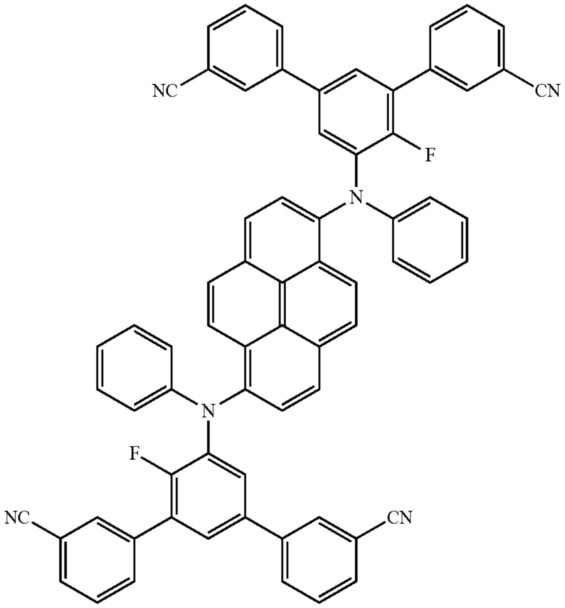
A-45
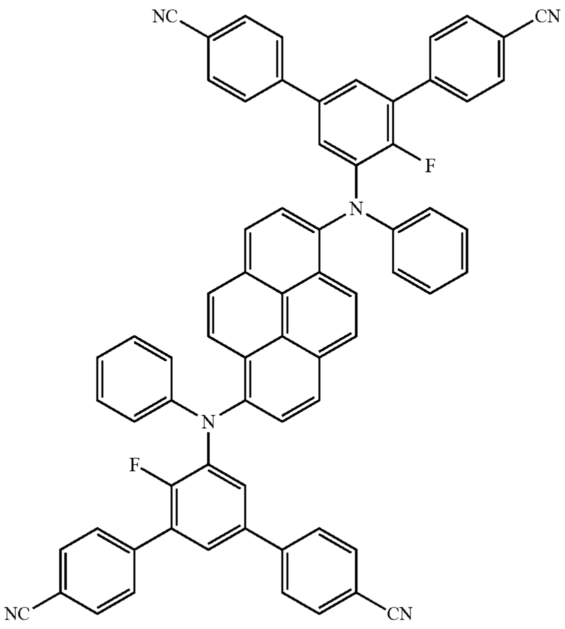

-continued
A-46
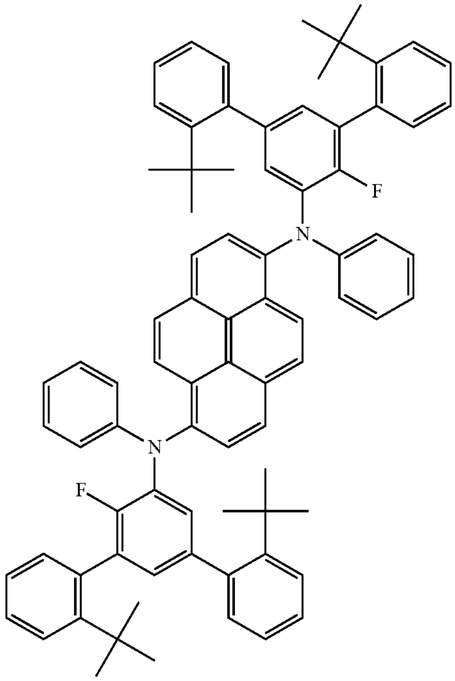
A-47
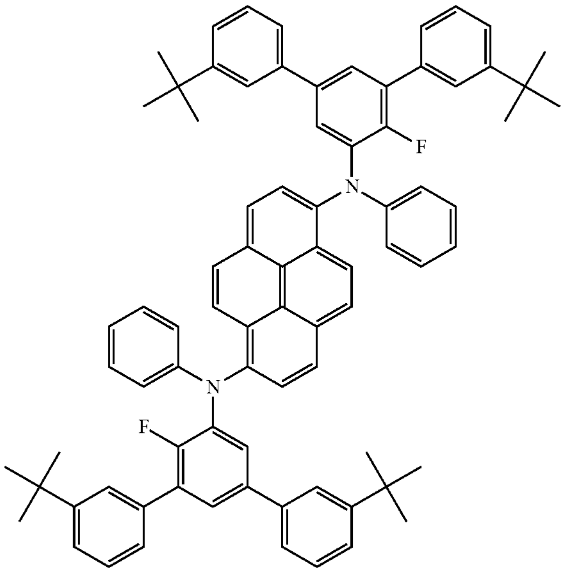
-continued
A-48
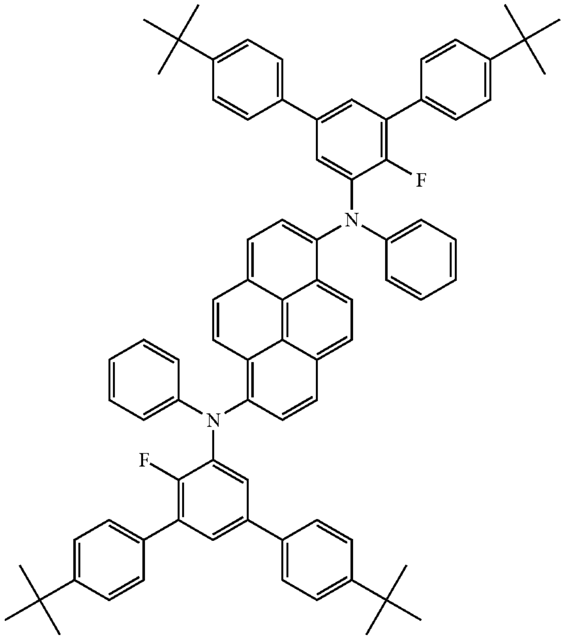
A-49
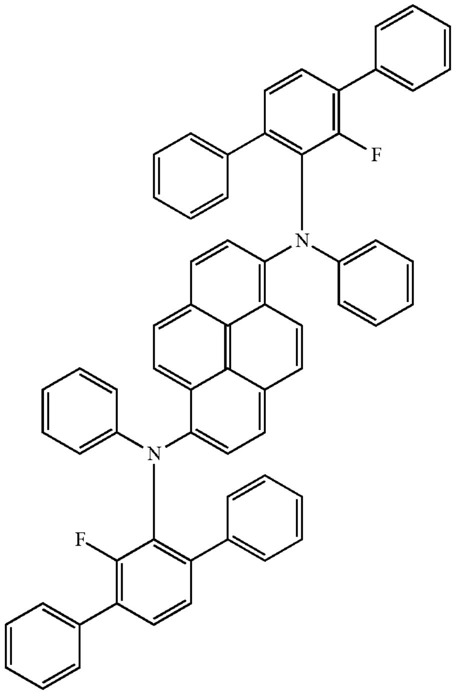

-continued
A-50
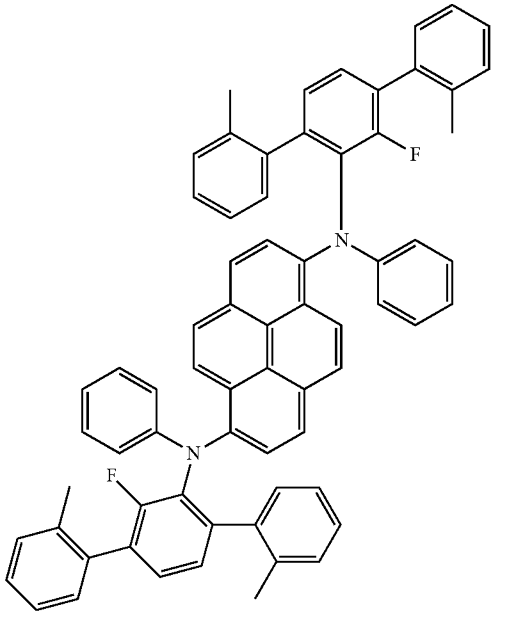
A-51
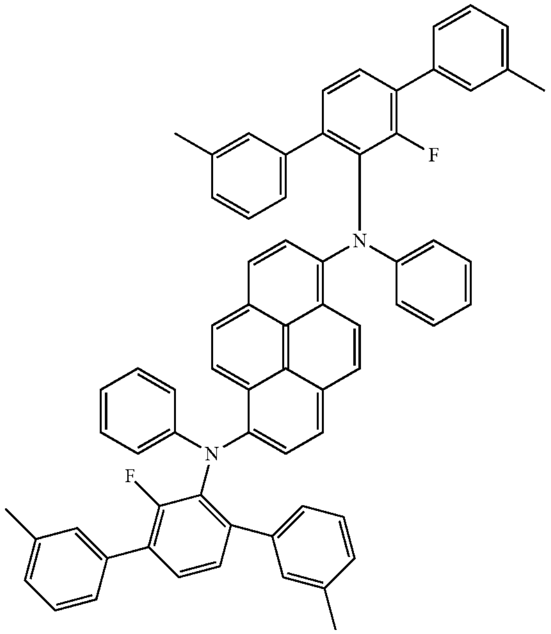
-continued
A-52
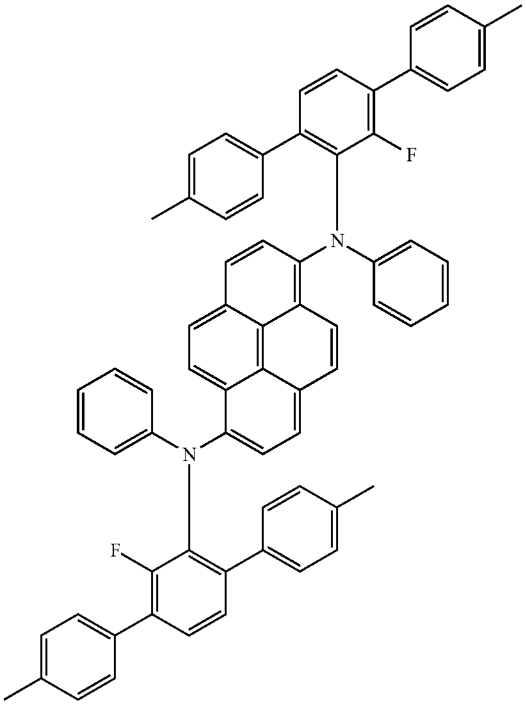
A-53
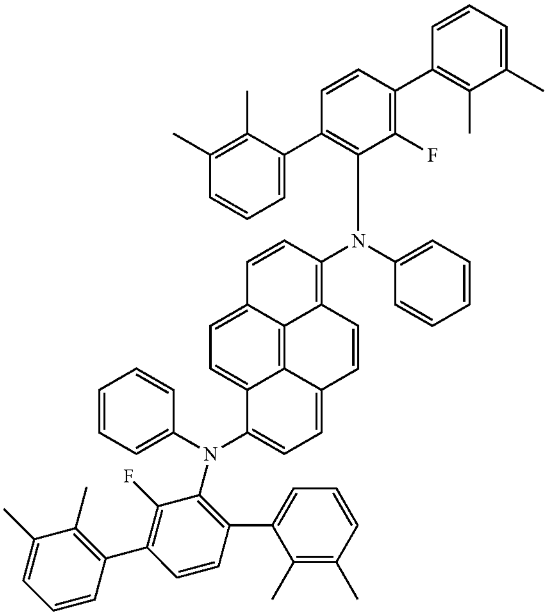

-continued
A-54
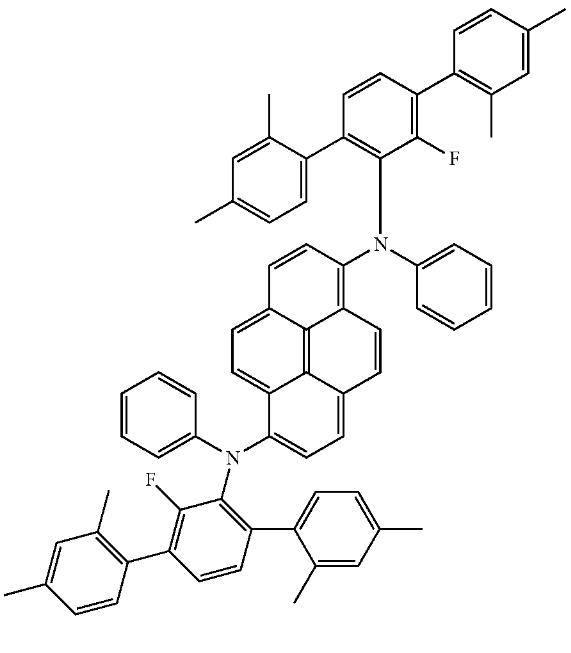
A-55
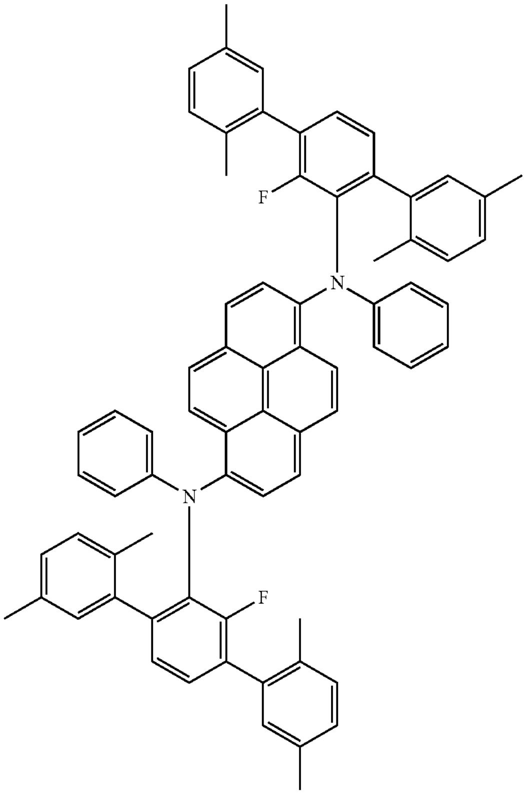
-continued
A-56
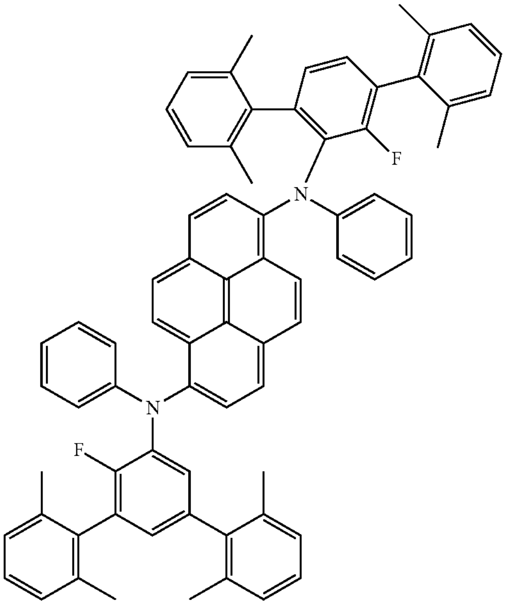
A-57
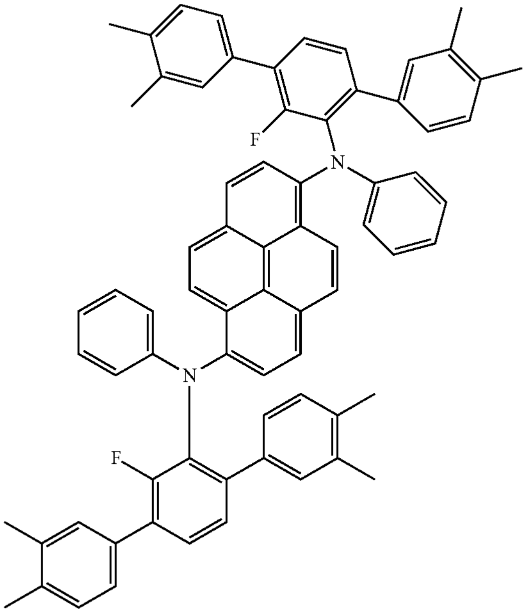

-continued
A-58
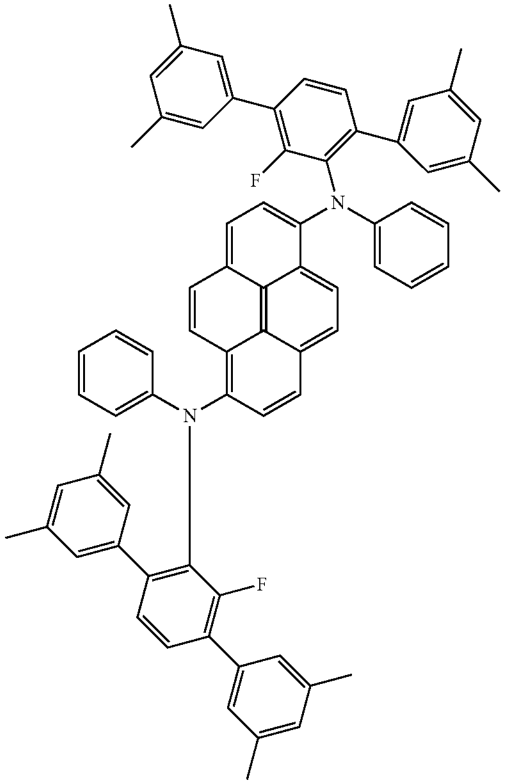
A-59
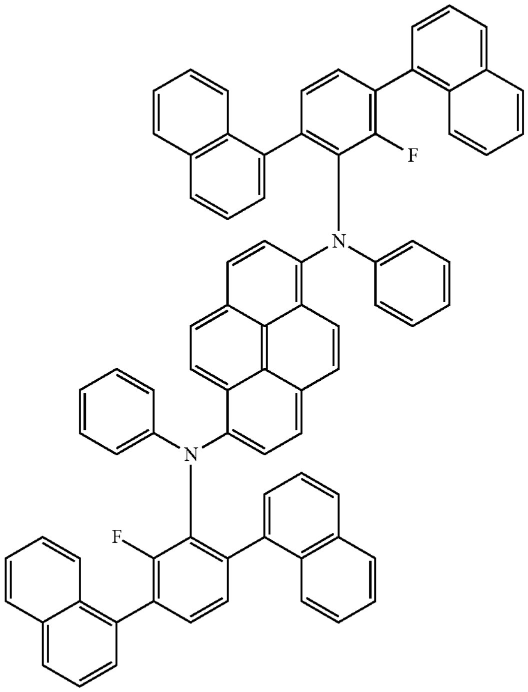
-continued
A-60
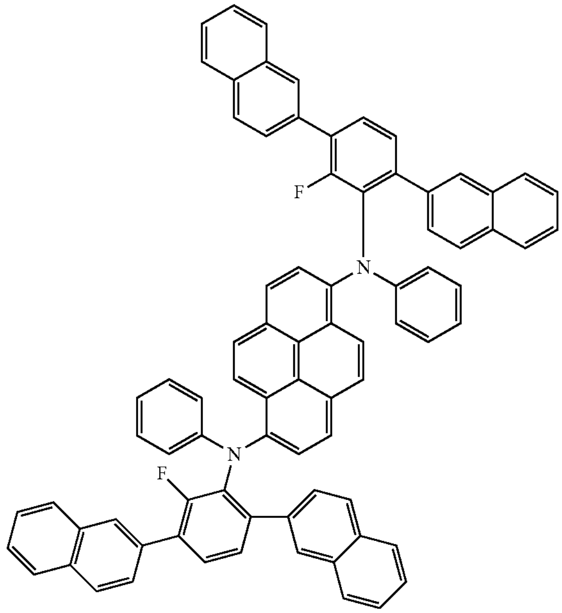
A-61
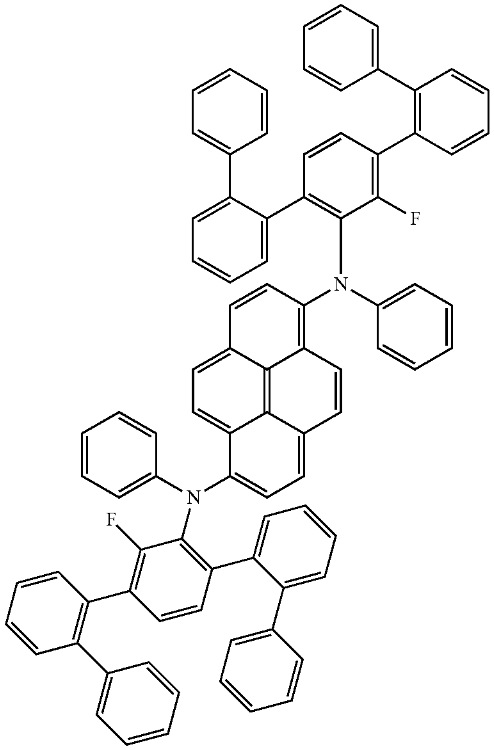

-continued
A-62
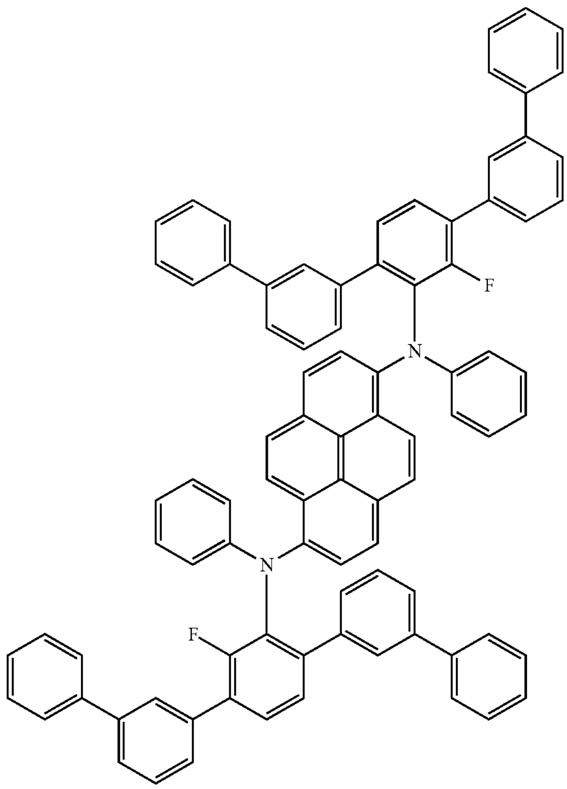
A-63
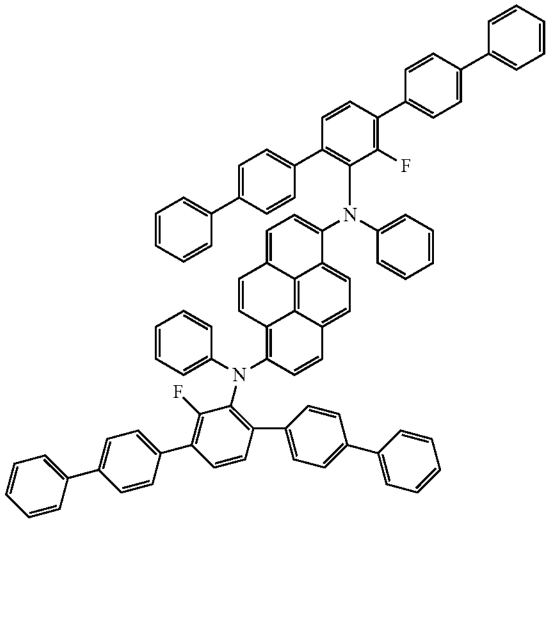
-continued
A-64
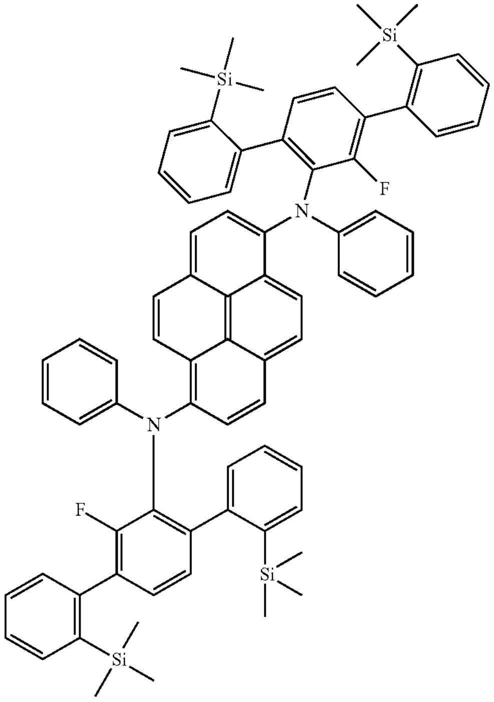
A-65
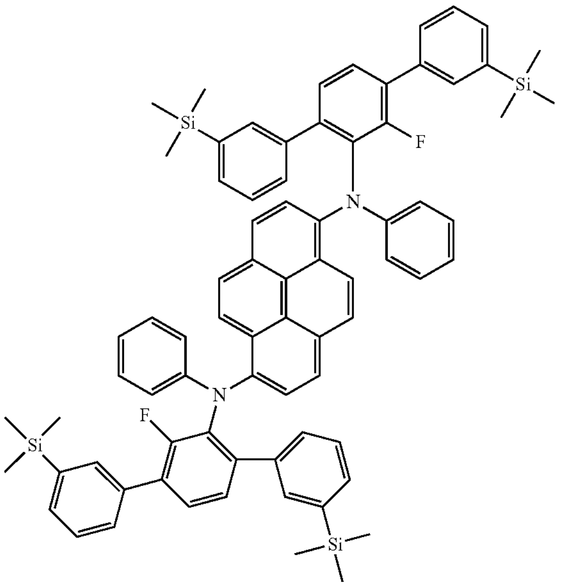

-continued
A-66
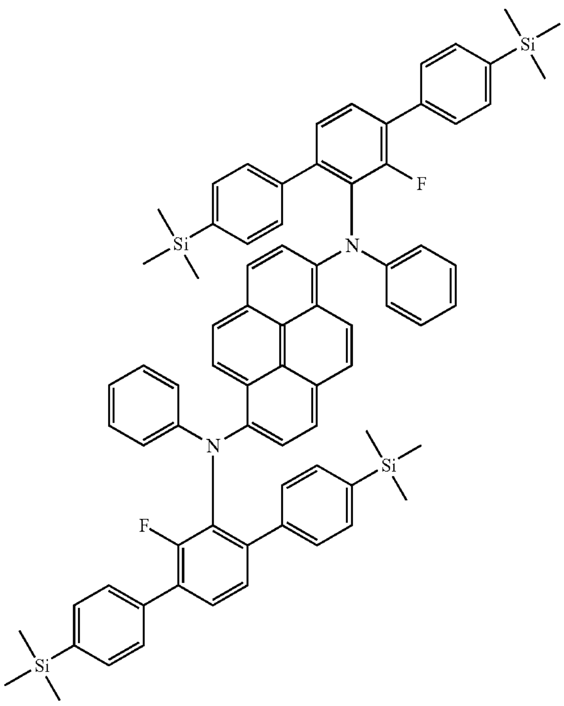
A-67
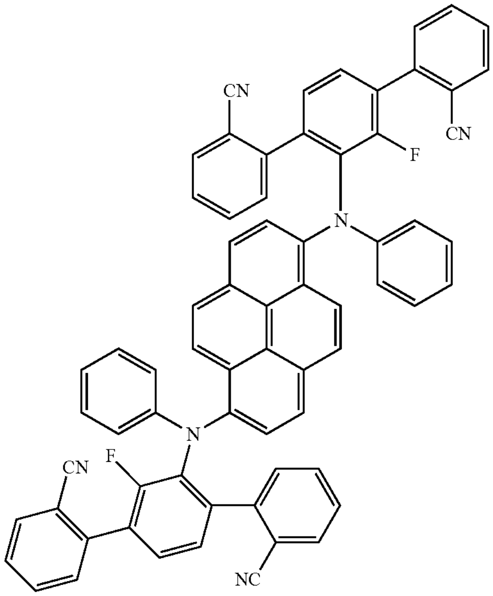
-continued
A-68
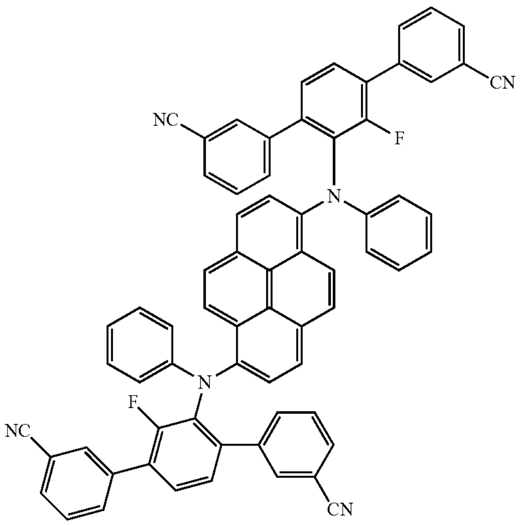
A-69
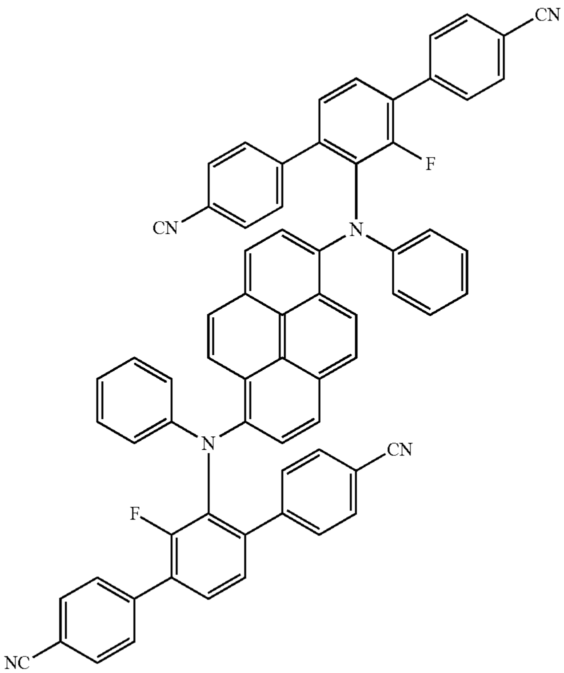

-continued
A-70
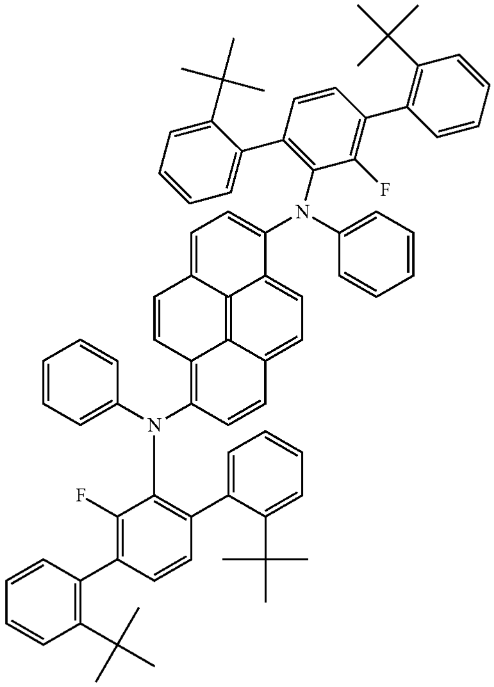
A-71
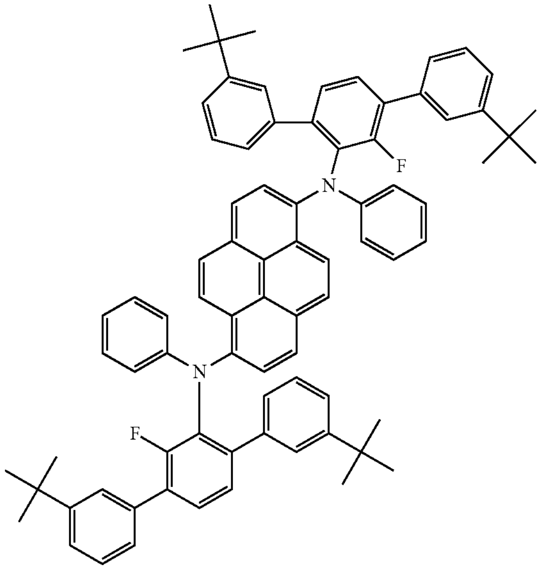
-continued
A-72
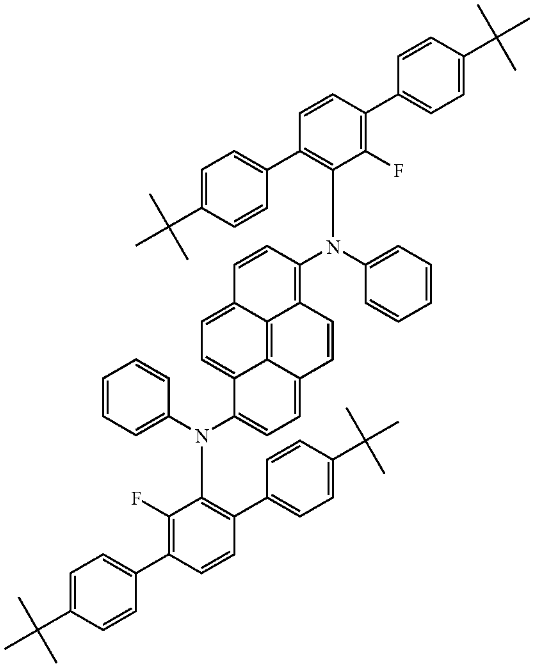
A-73
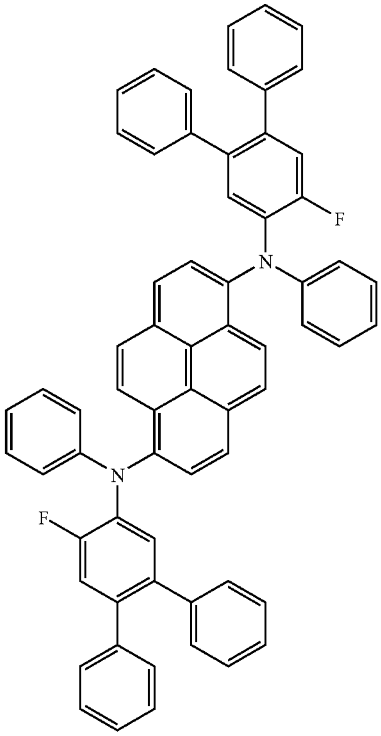

-continued
A-74
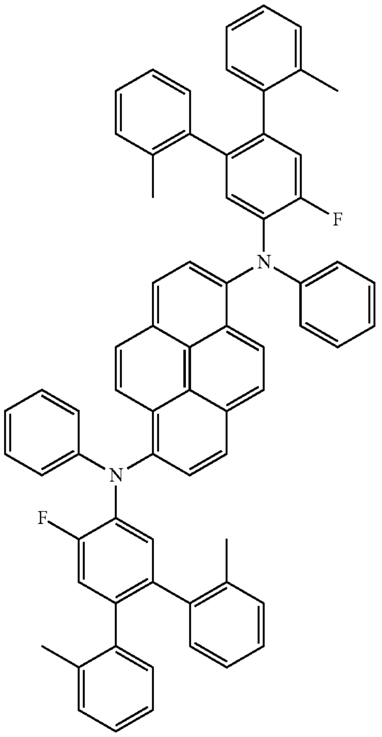
A-75
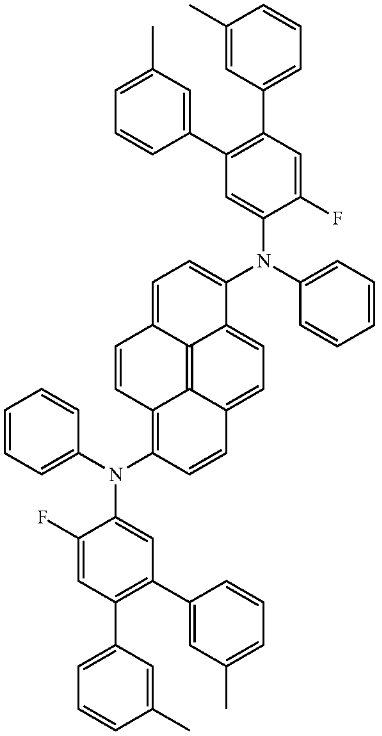
-continued
A-76
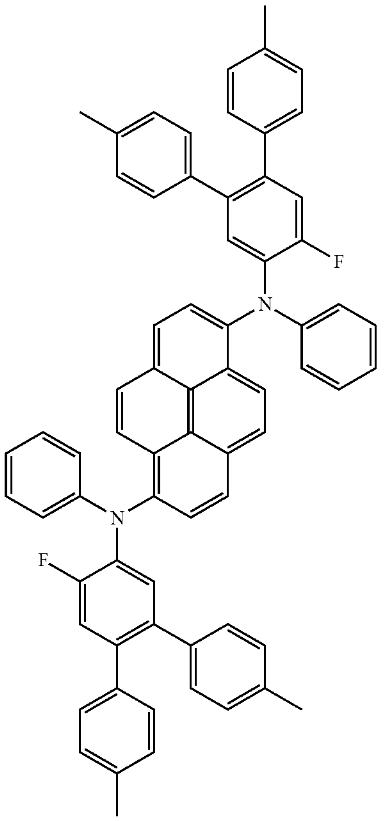
A-77
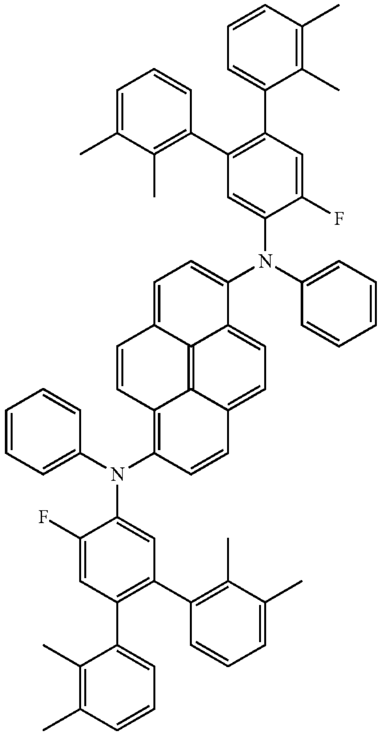

-continued
A-78
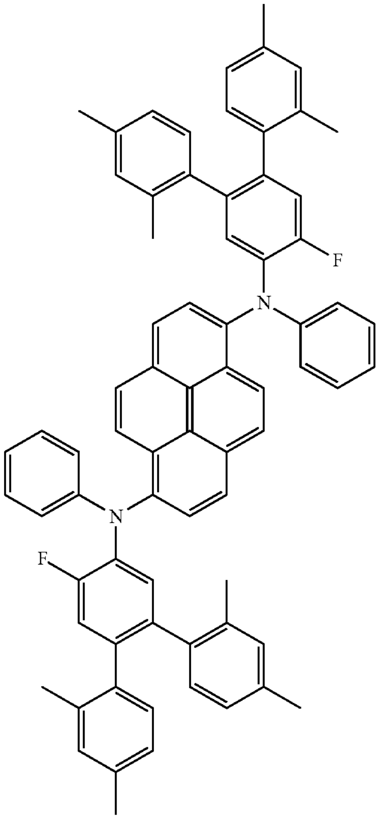
A-79
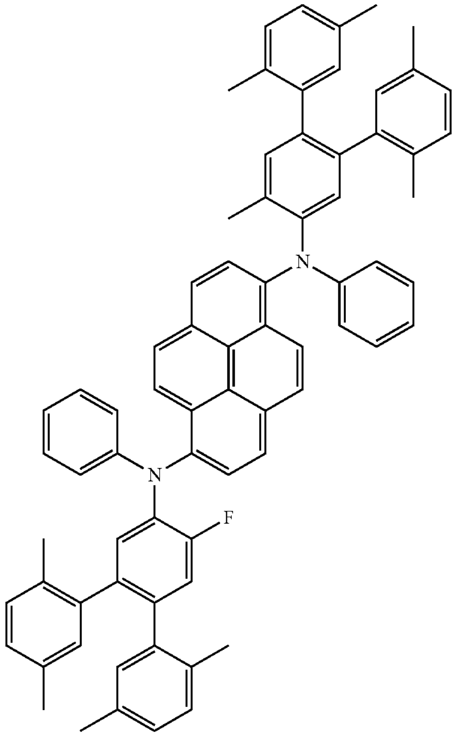
-continued
A-80
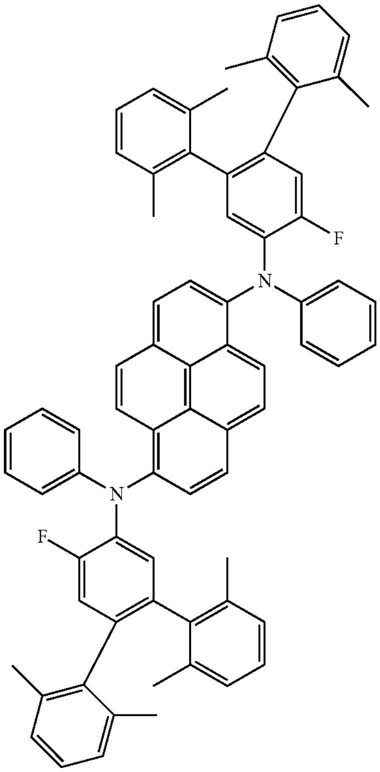
A-81
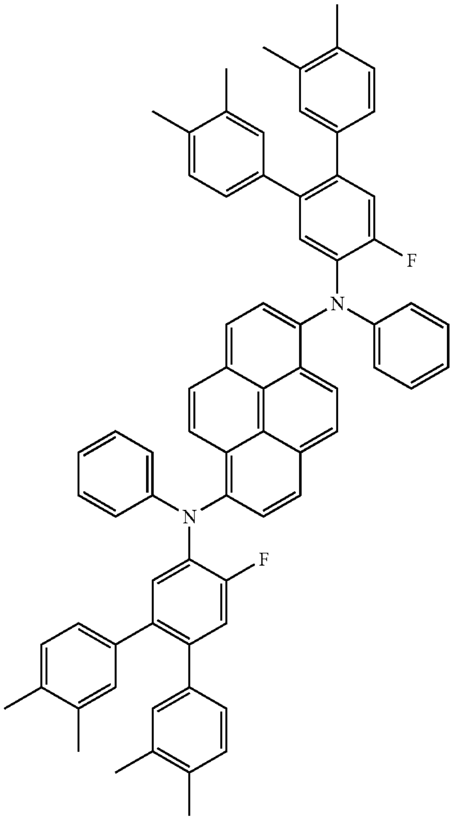

-continued
A-82
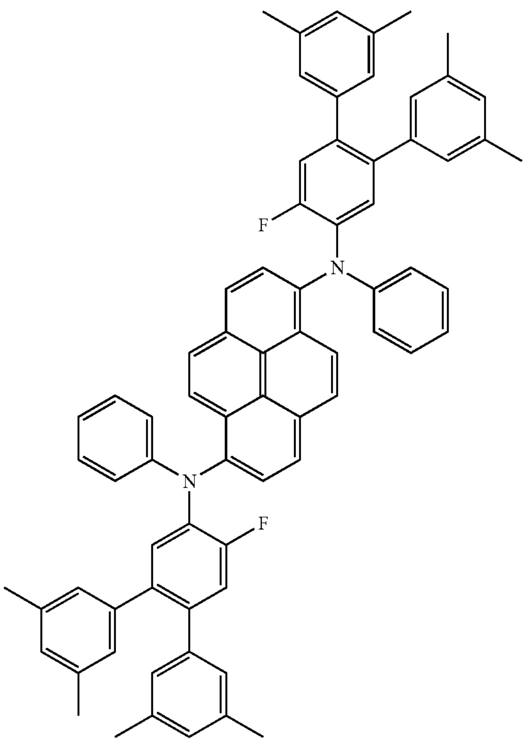
A-83
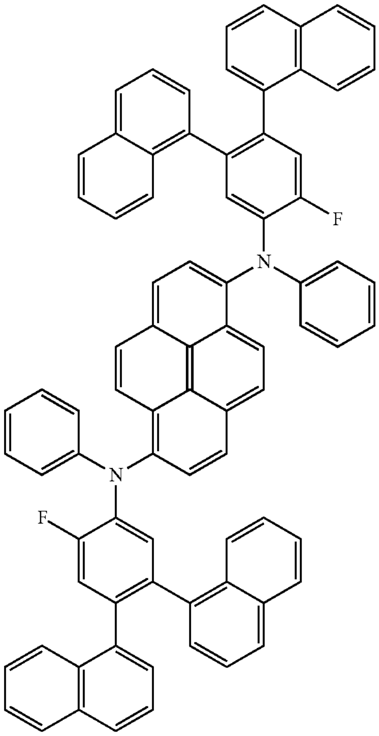
-continued
A-84
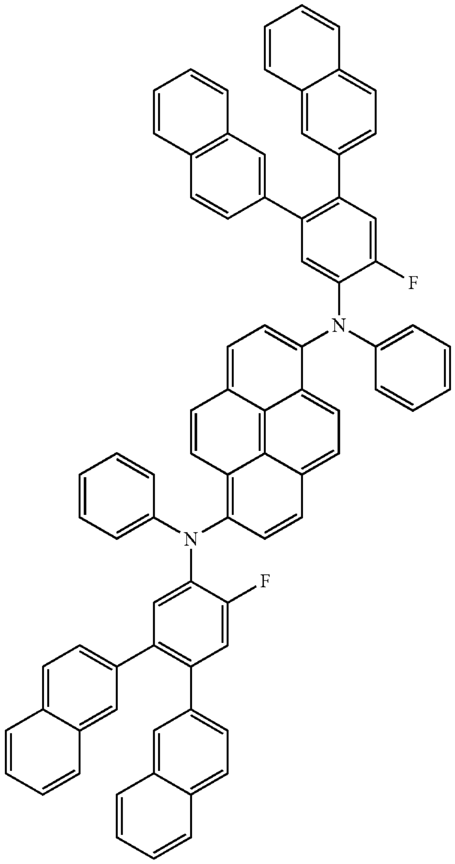
A-85
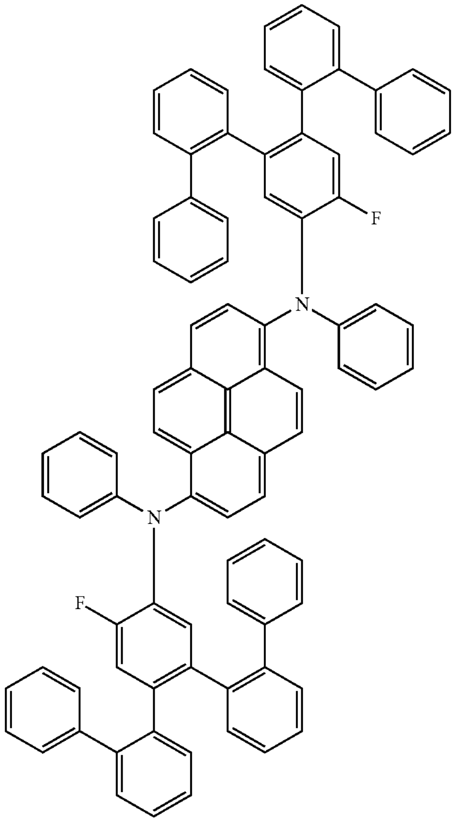

-continued
A-86
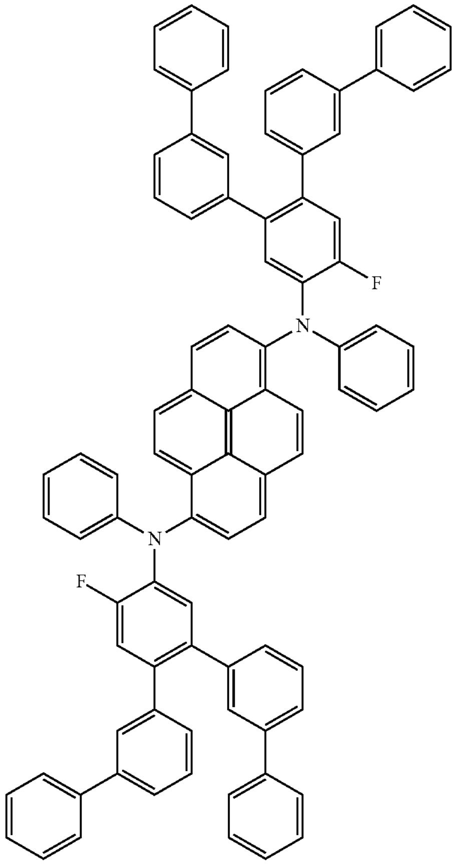
-continued
A-87
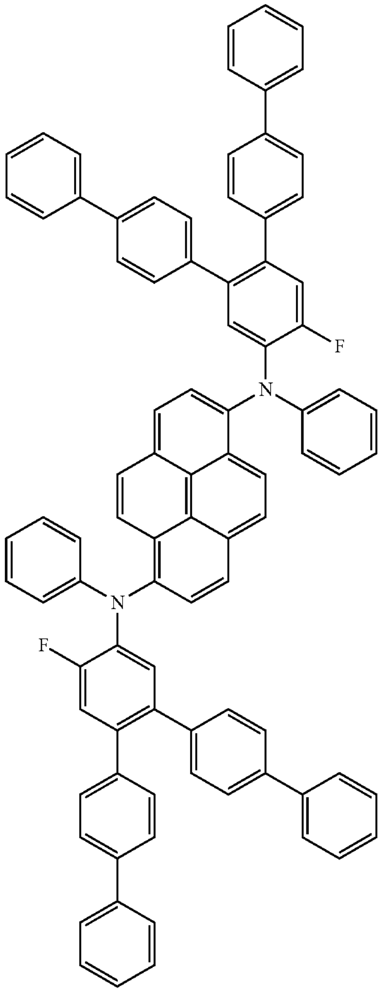

-continued
A-88
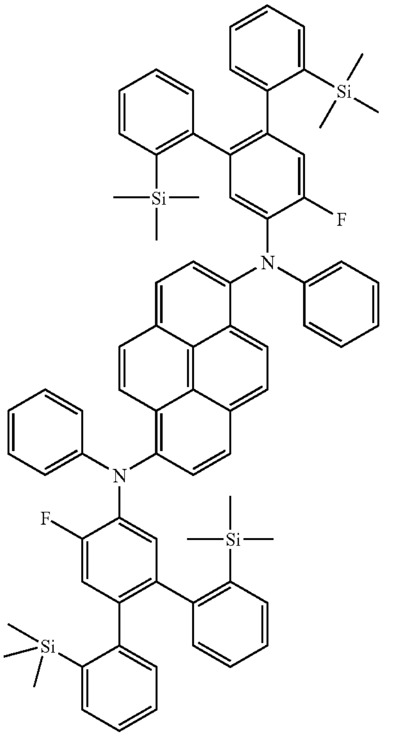
A-89
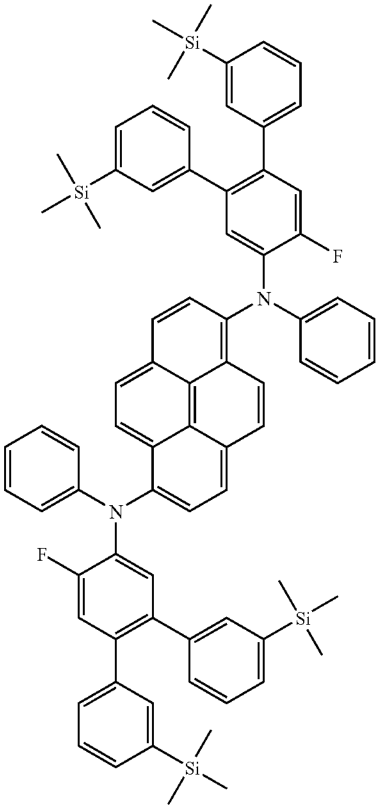
-continued
A-90
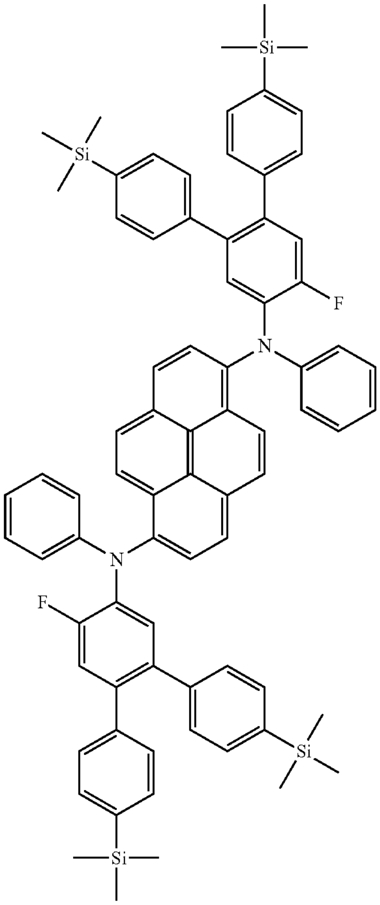
A-91
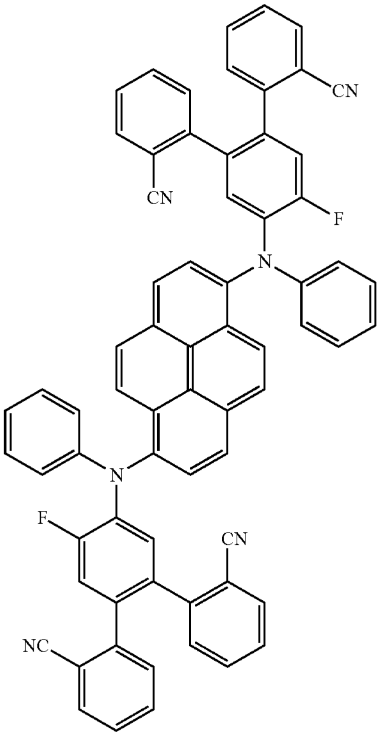

A-92
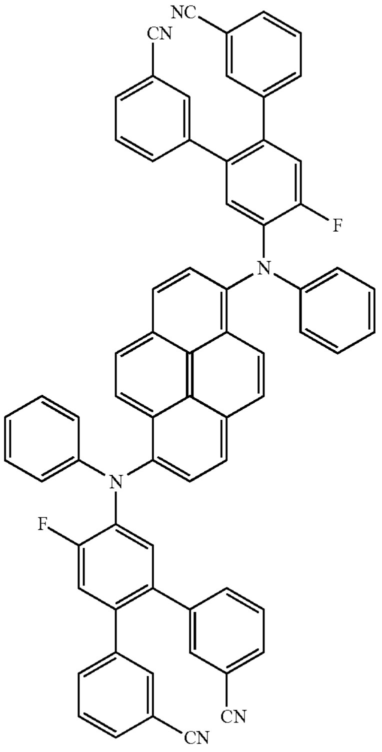
A-93
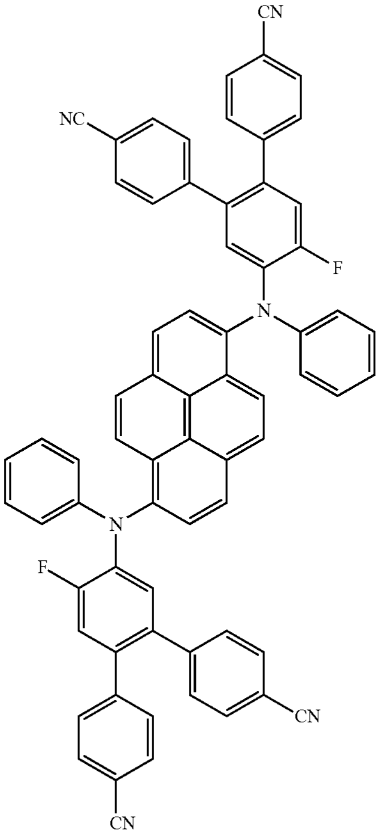
A-94
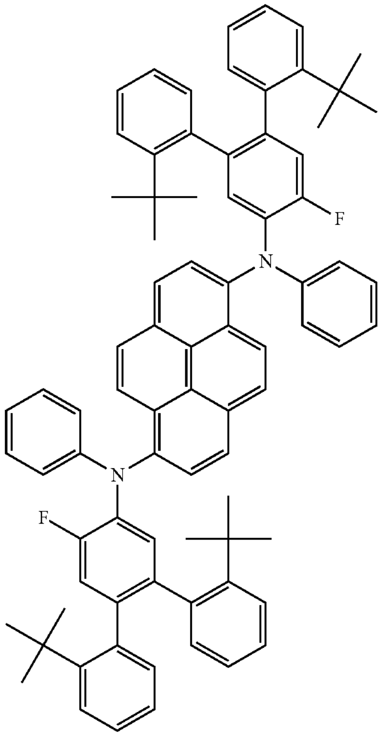
A-95
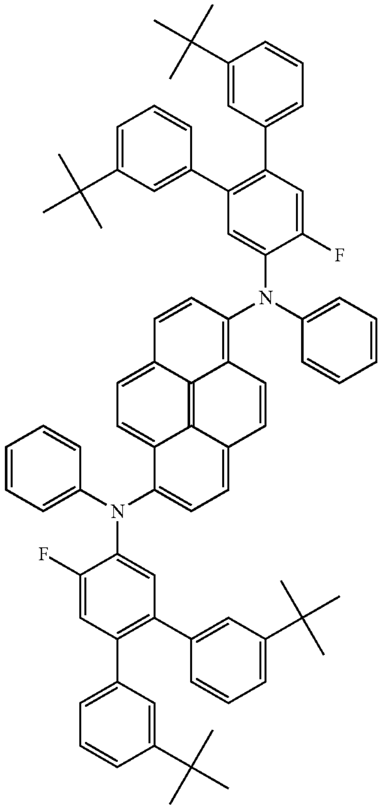

-continued
A-96
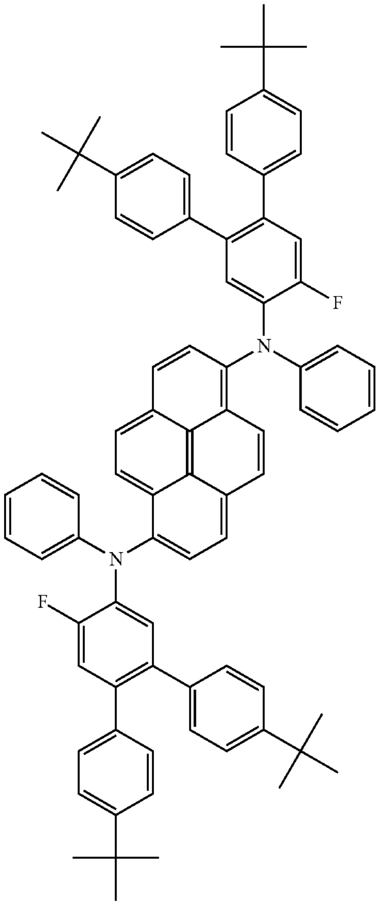
A-97
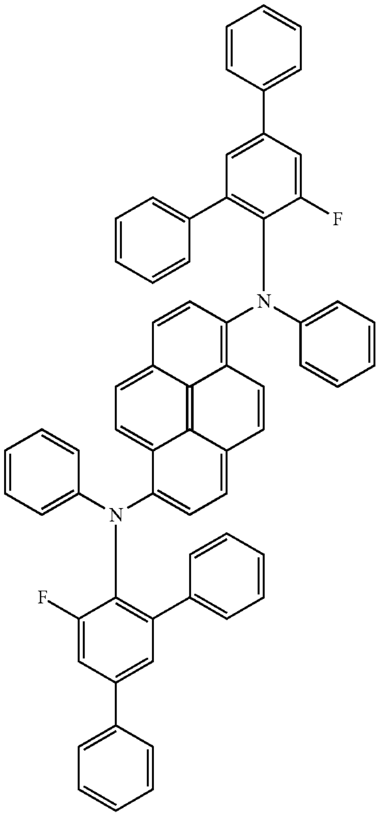
-continued
A-98
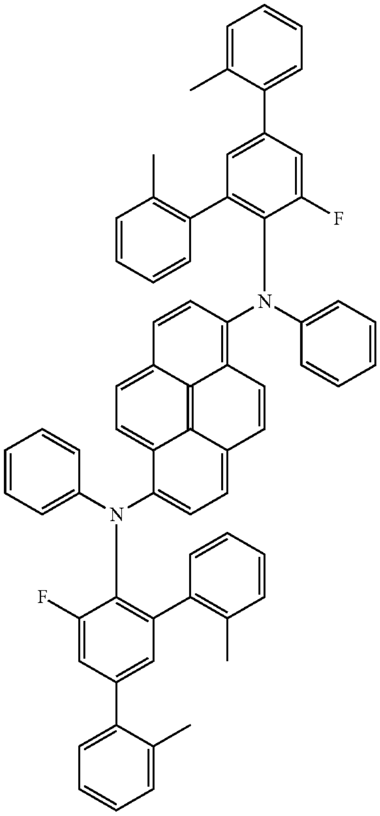
A-99
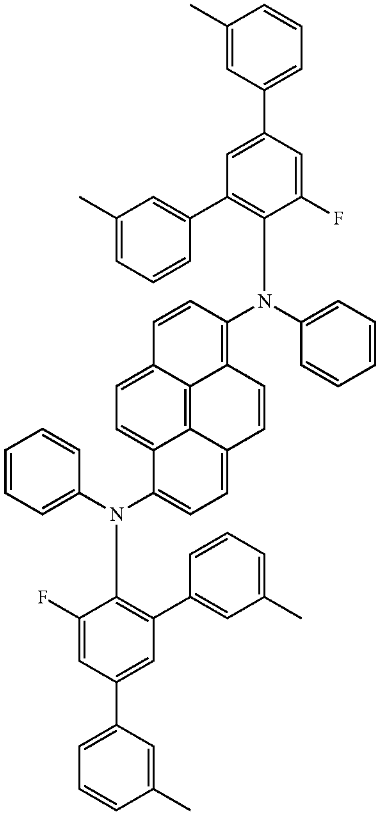

-continued
A-100
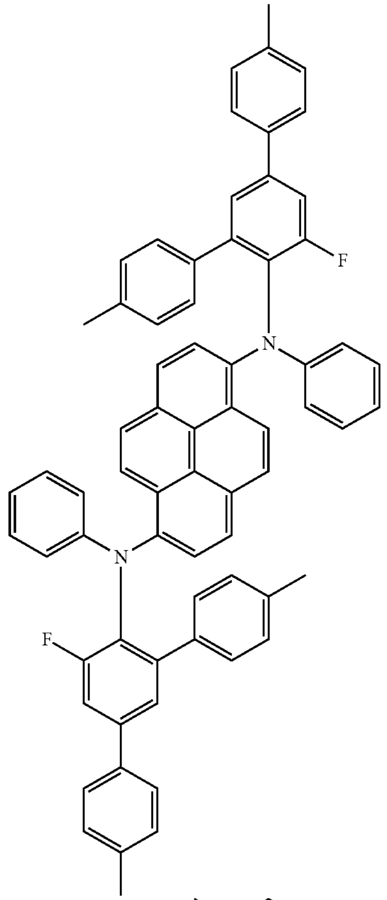
A-101
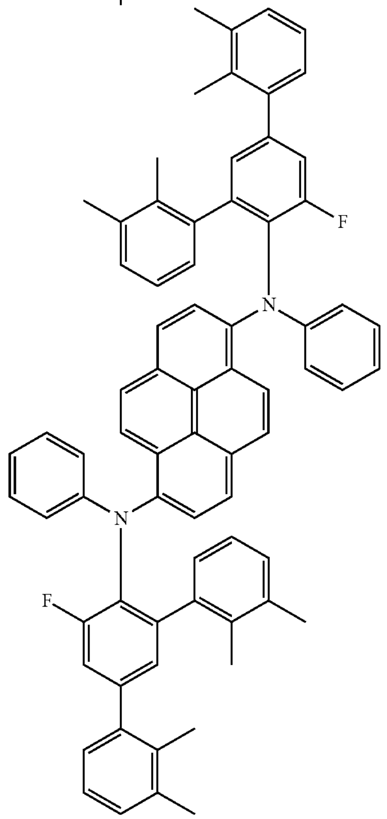
-continued
A-102
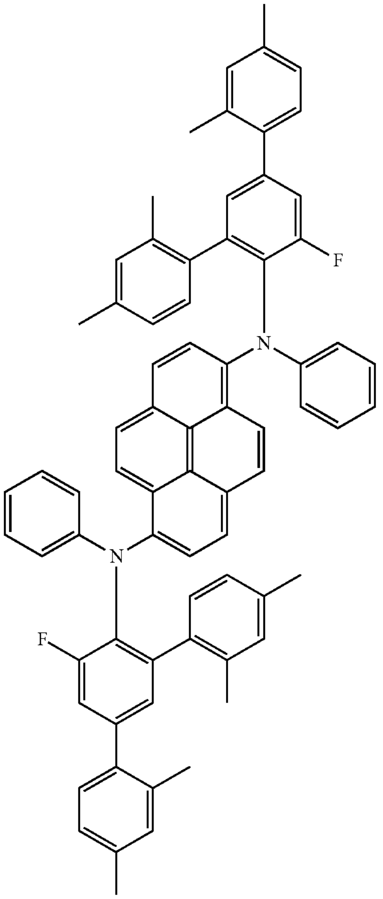
A-103
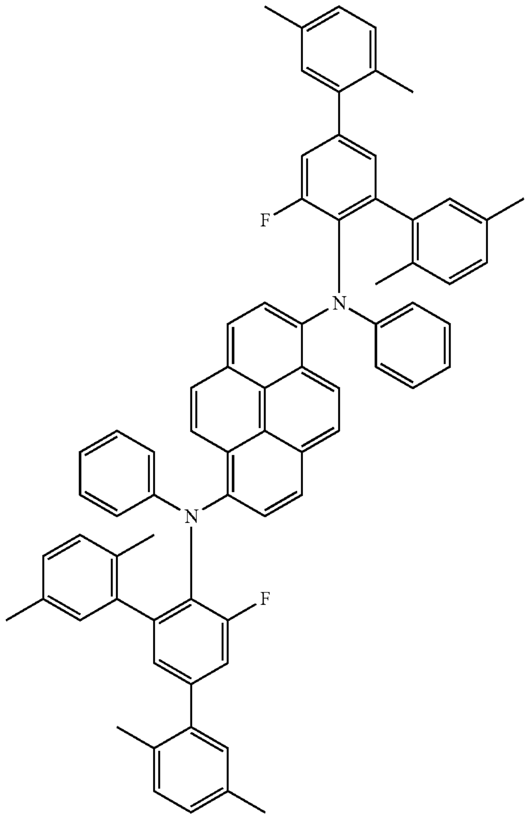

-continued
A-104
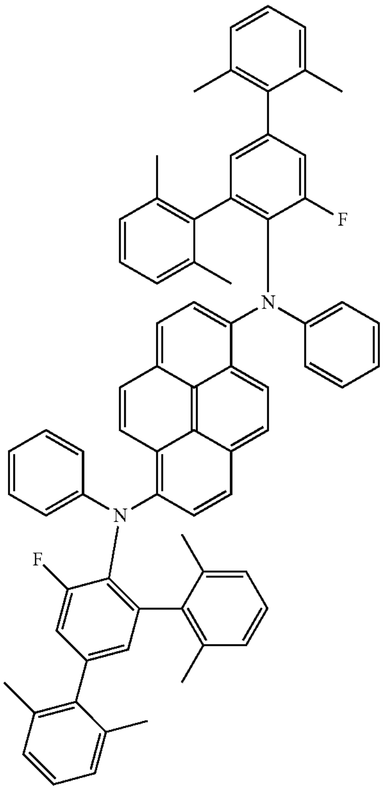
A-105
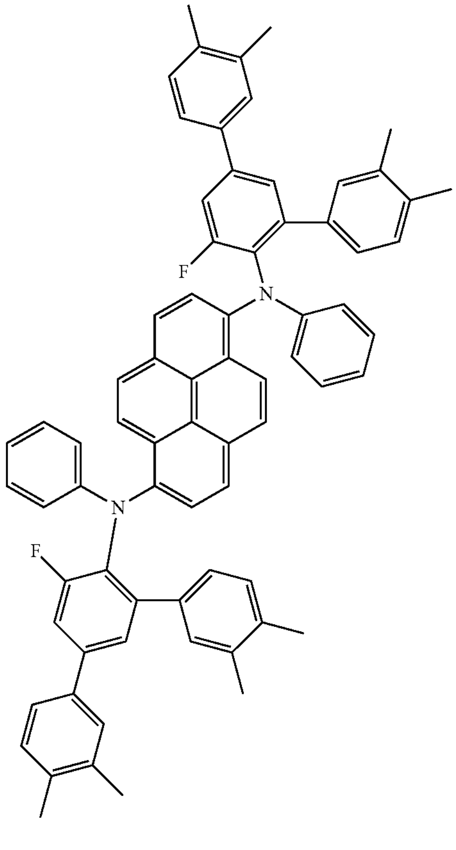
-continued
A-106
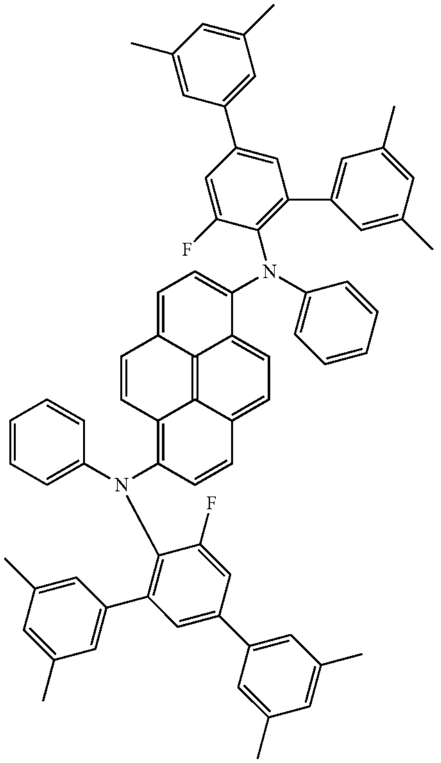
A-107
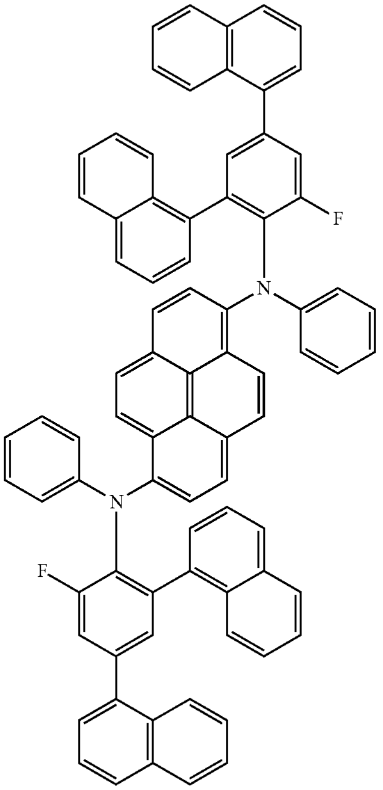

-continued
A-108
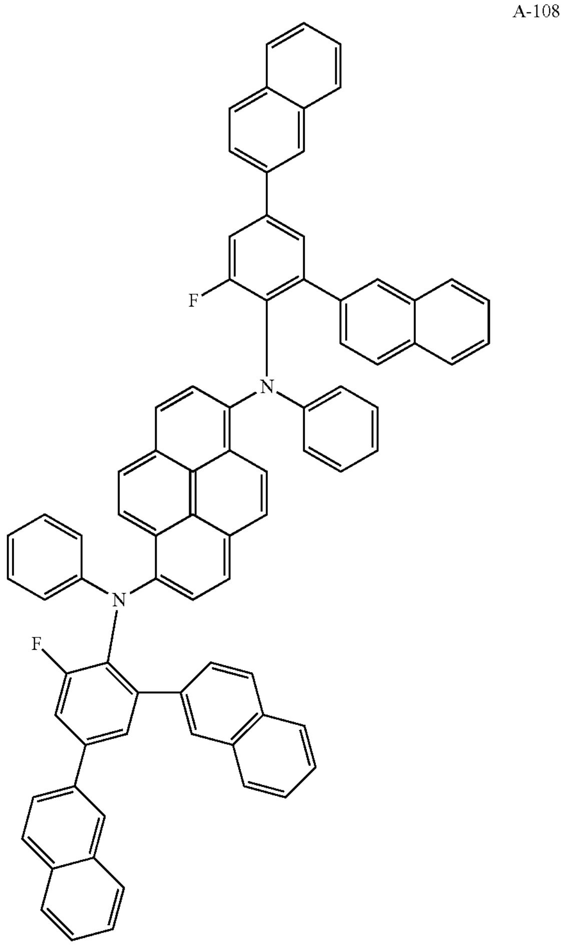
A-109
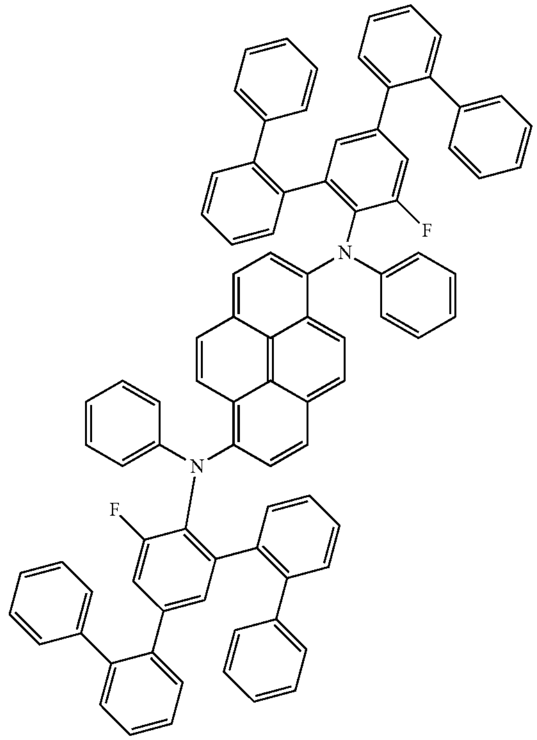
-continued
A-110
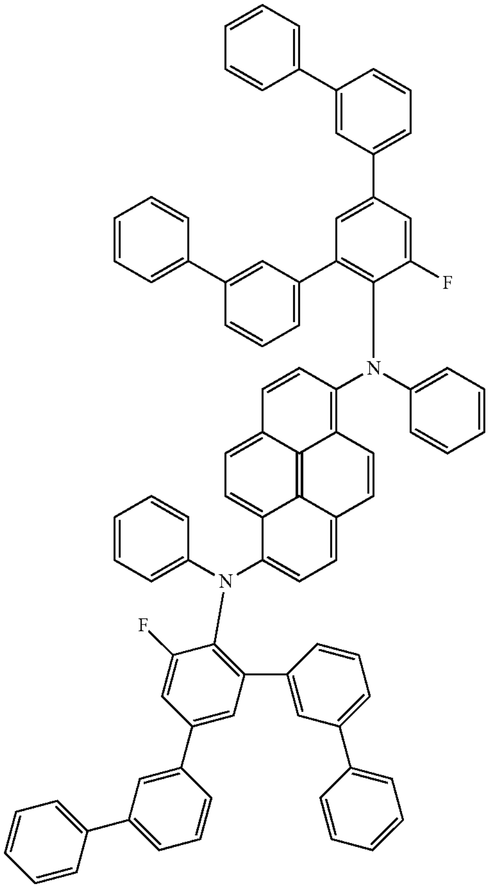

-continued
A-111
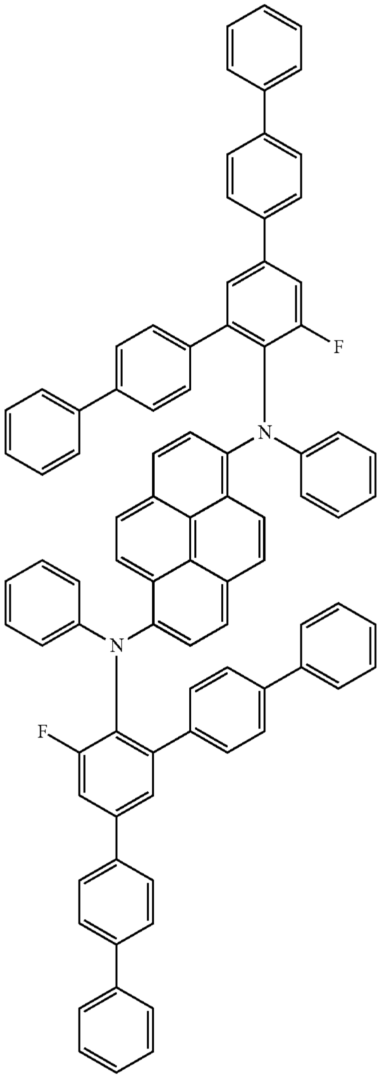
-continued
A-112
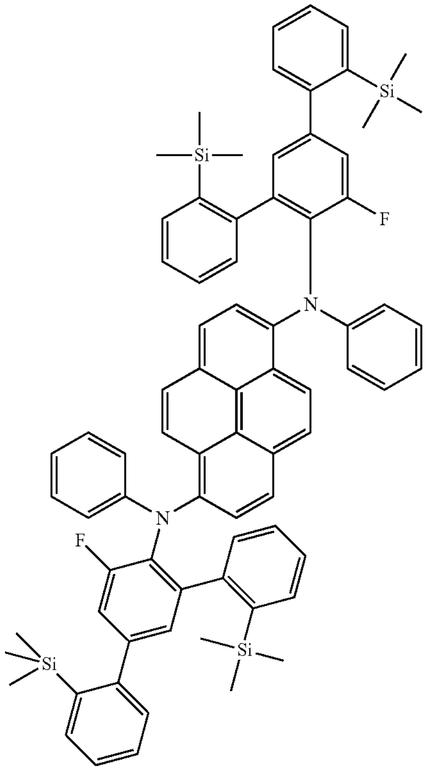
A-113
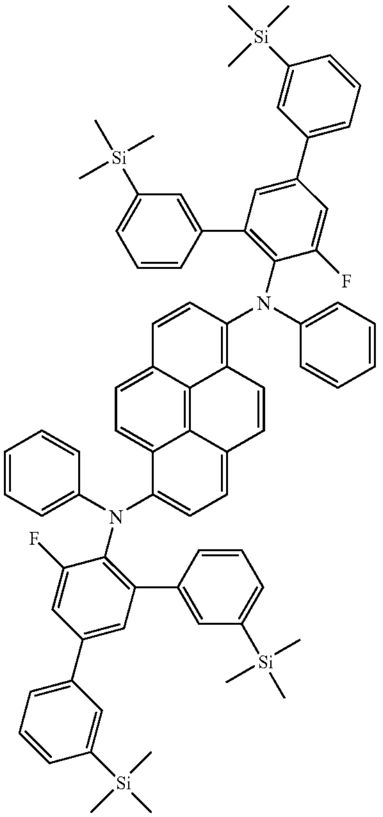

-continued
A-114
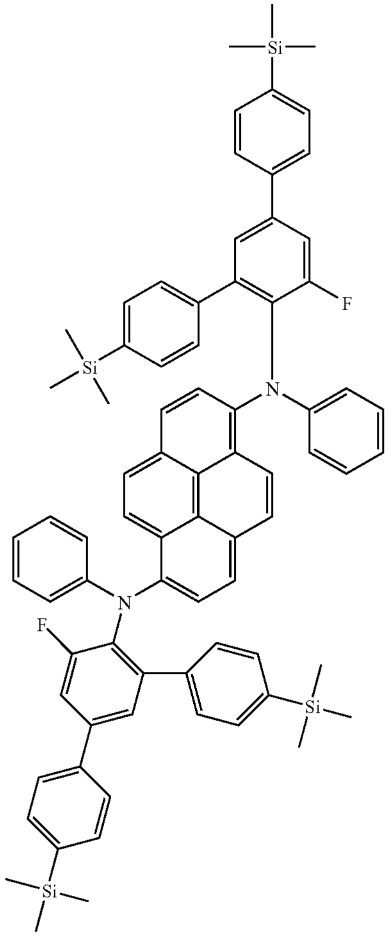
A-115
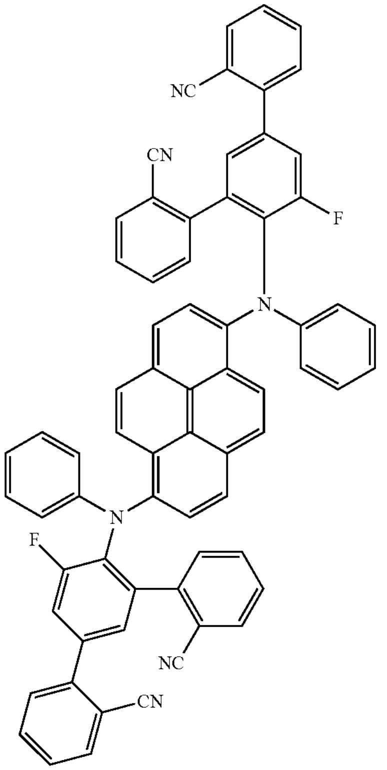
-continued
A-116
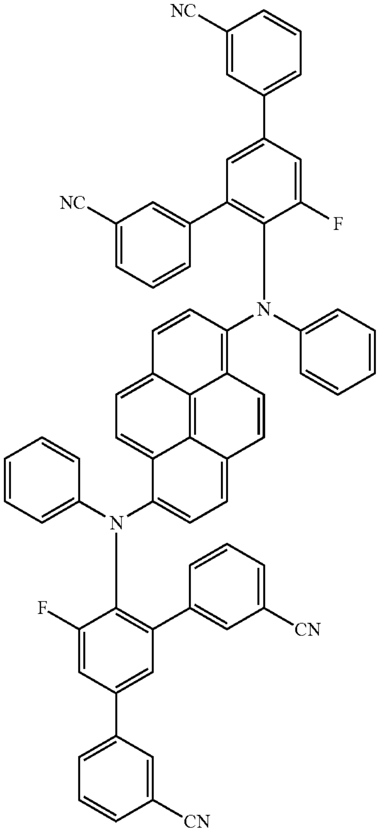

-continued
A-117
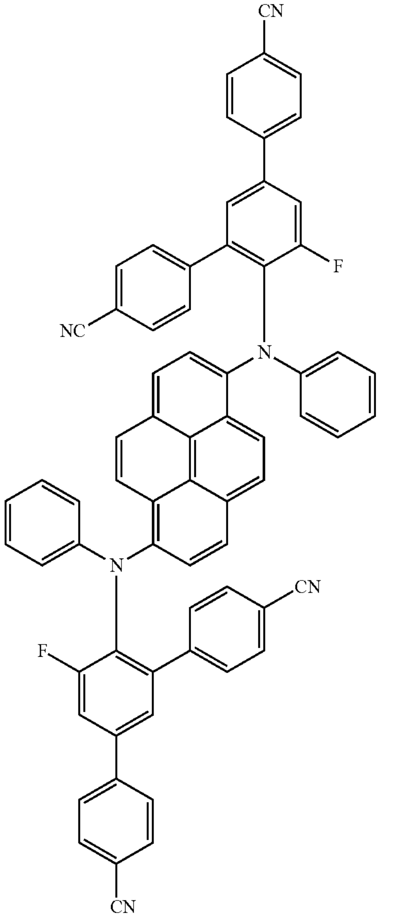
A-118
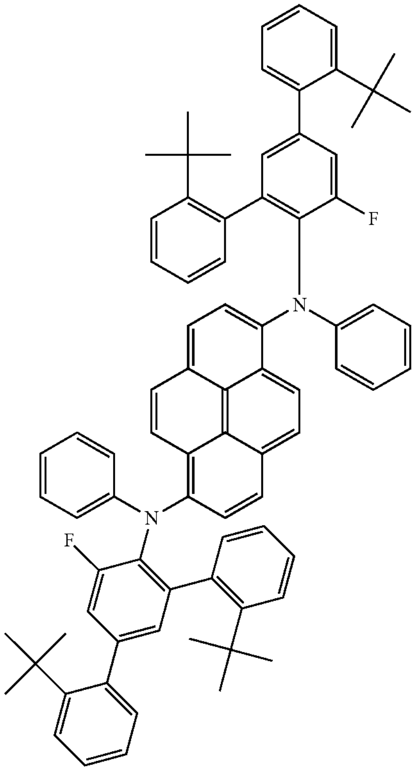
-continued
A-119
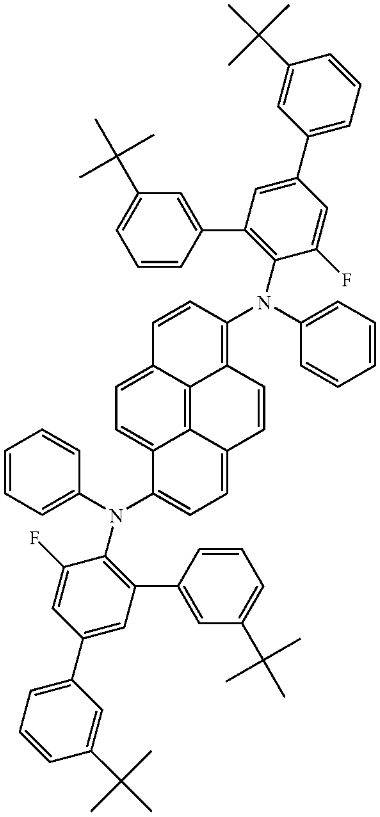

-continued
A-120
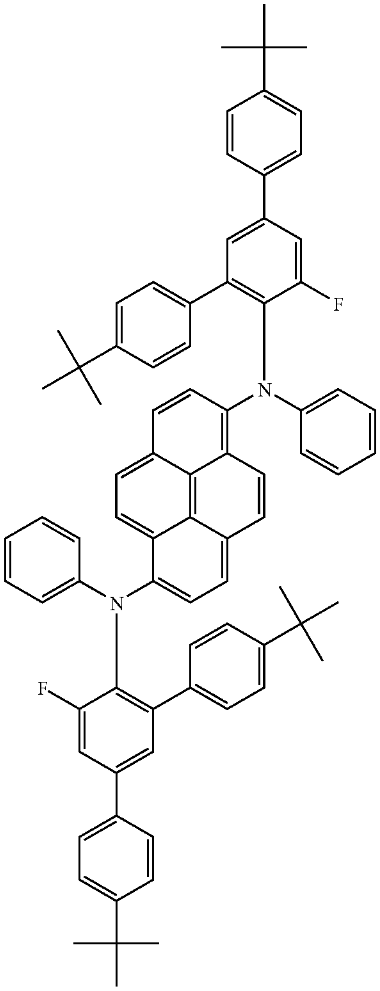
A-121
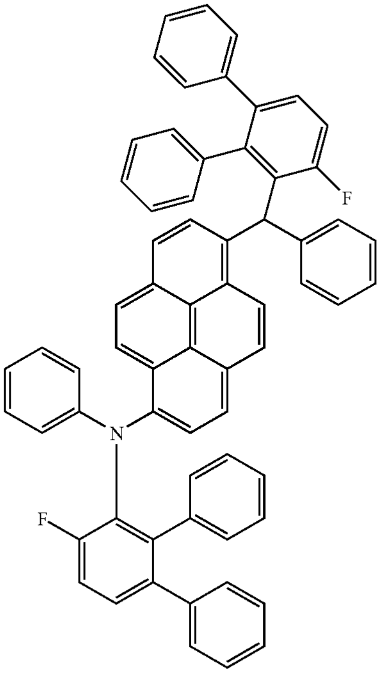
-continued
A-122
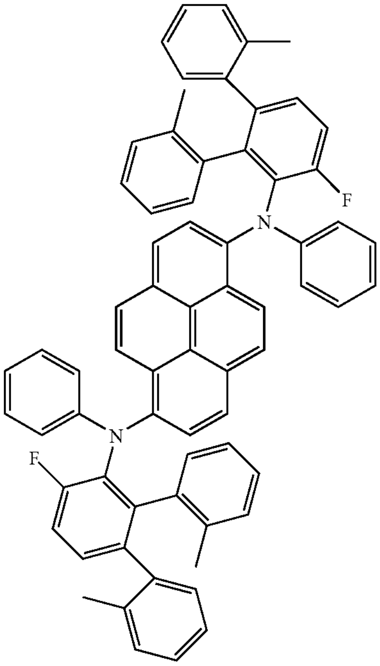
A-123
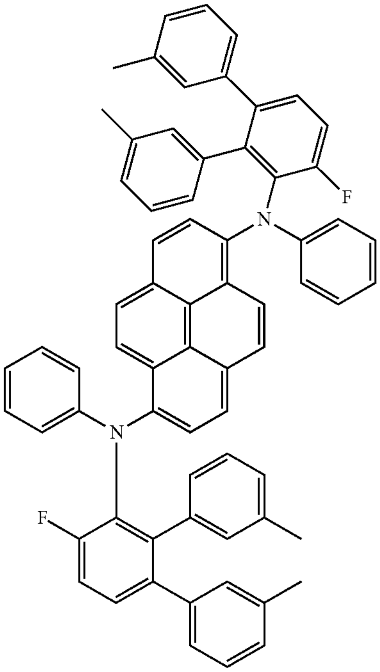

-continued
A-124
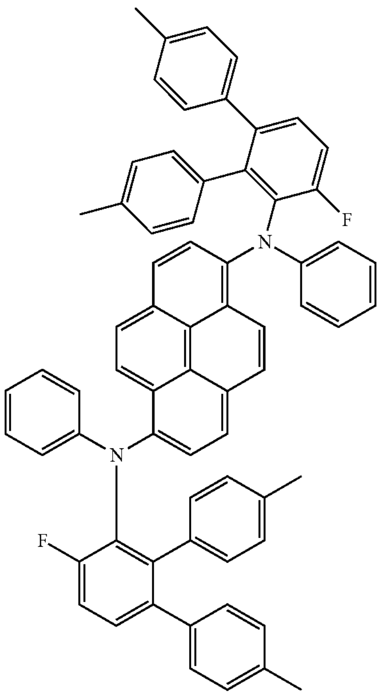
A-125
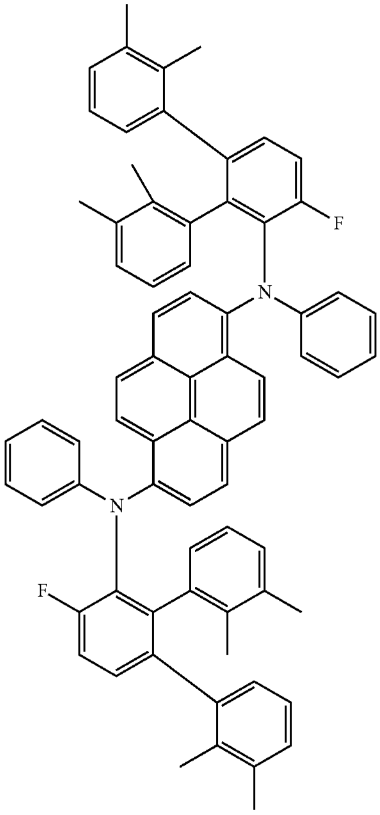
-continued
A-126
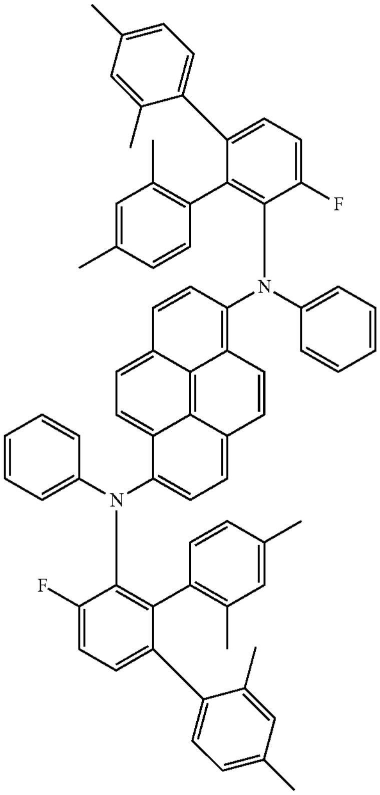
A-127
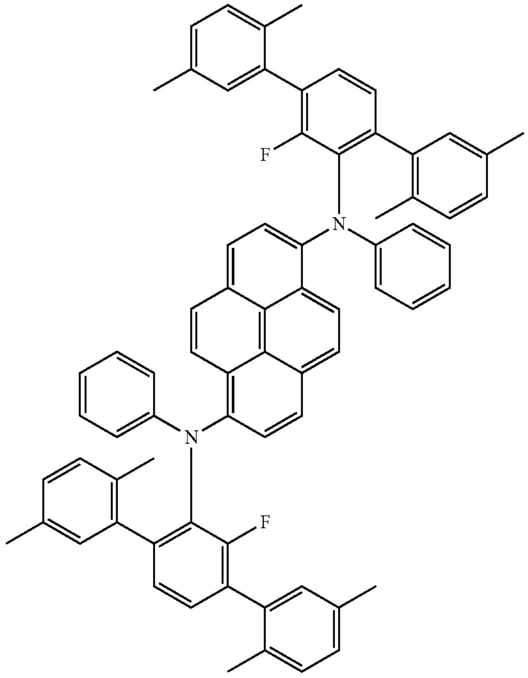

A-128
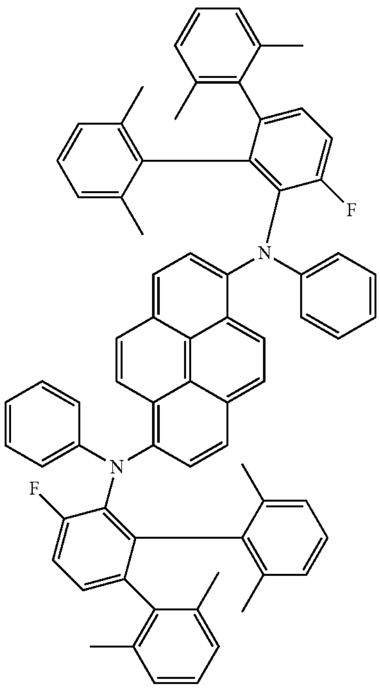
A-129
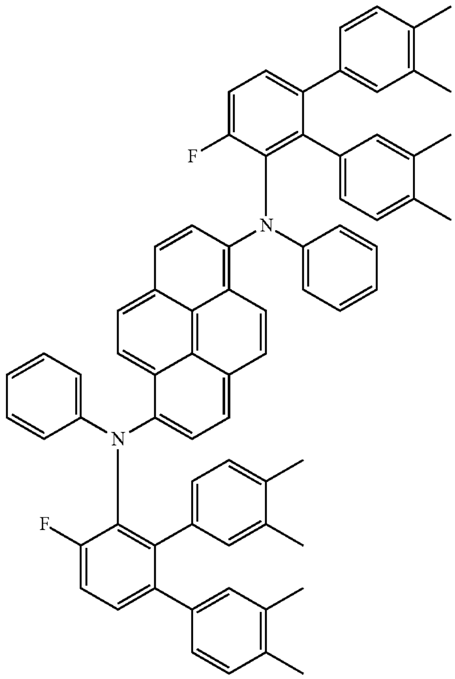
A-130
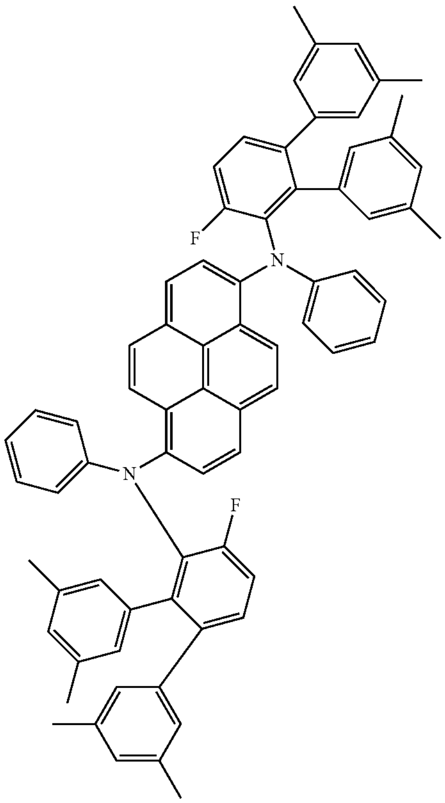
A-131
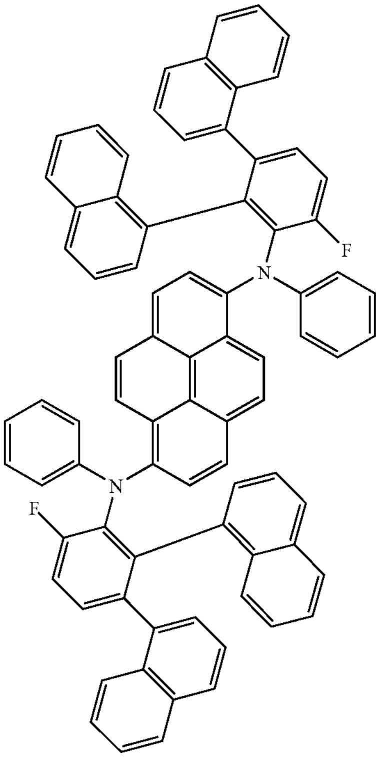

-continued
A-132
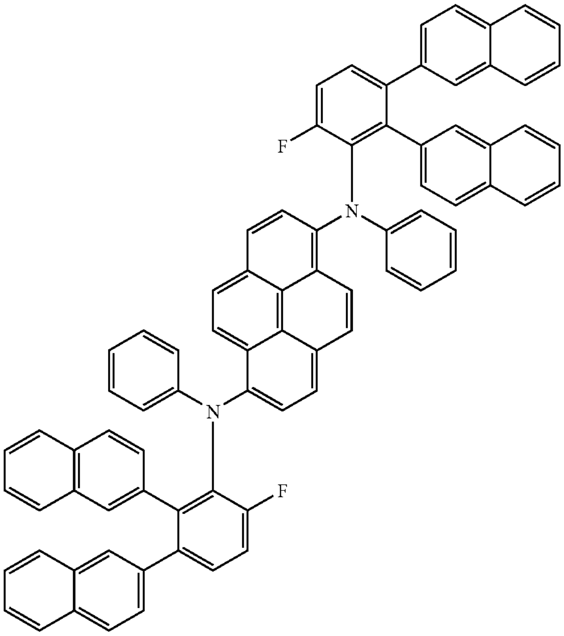
A-133
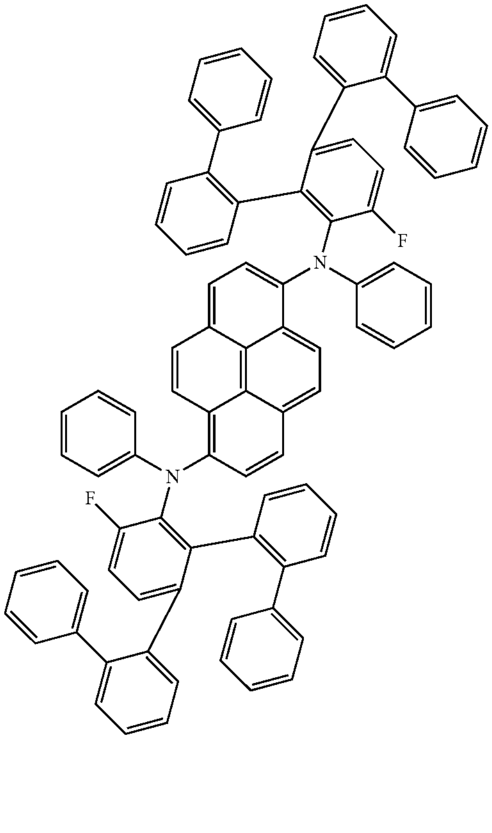
-continued
A-134
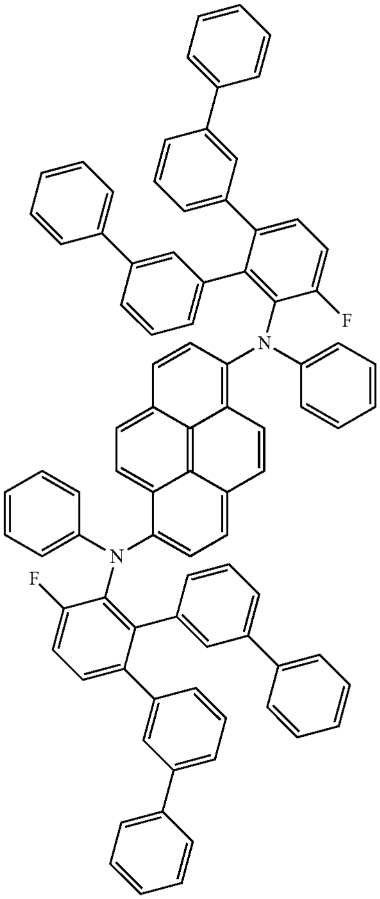
A-135
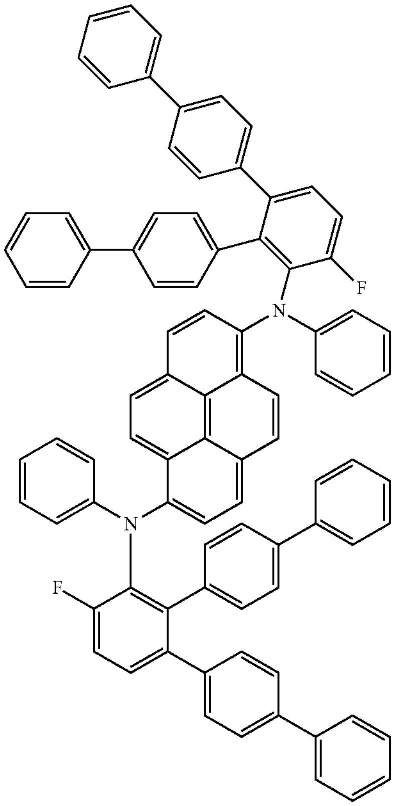

-continued
A-136
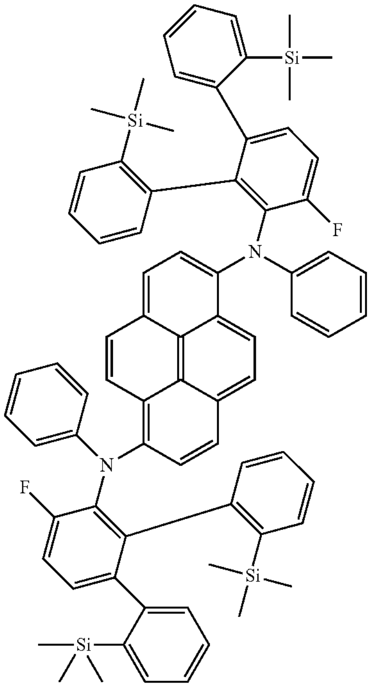
A-137
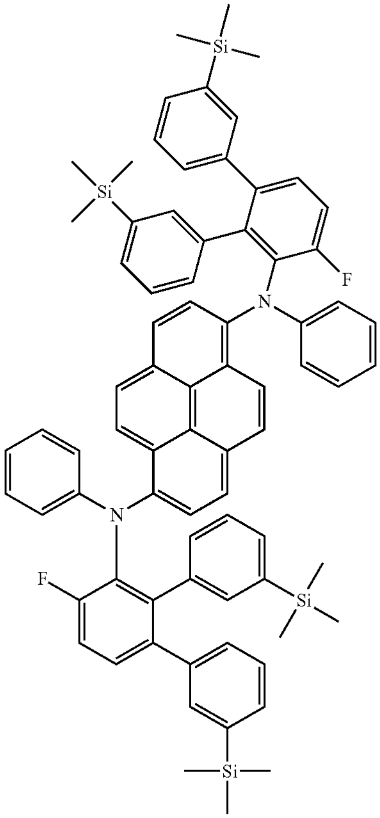
-continued
A-138
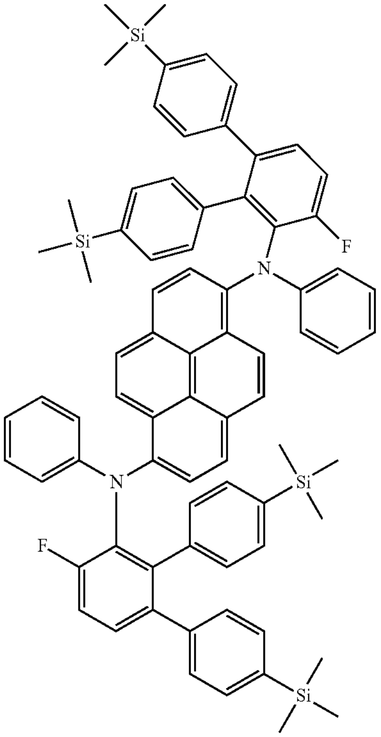
A-139
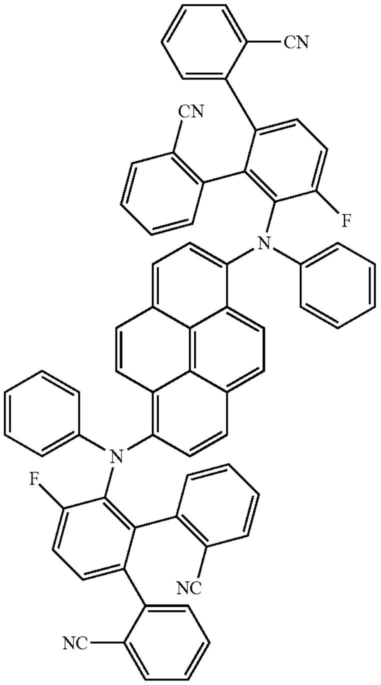

-continued
A-140
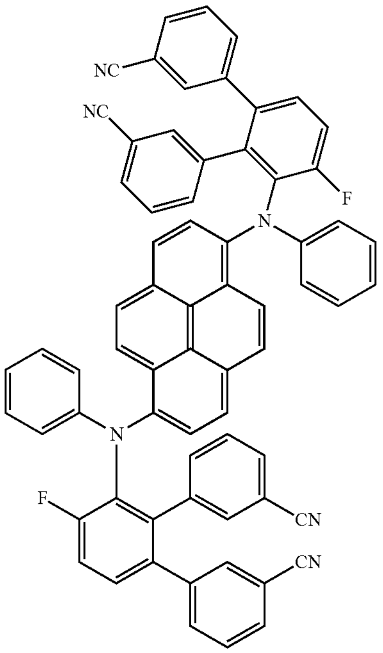
A-141
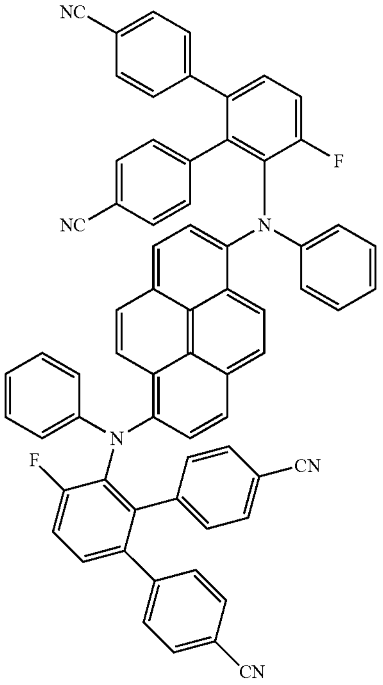
-continued
A-142
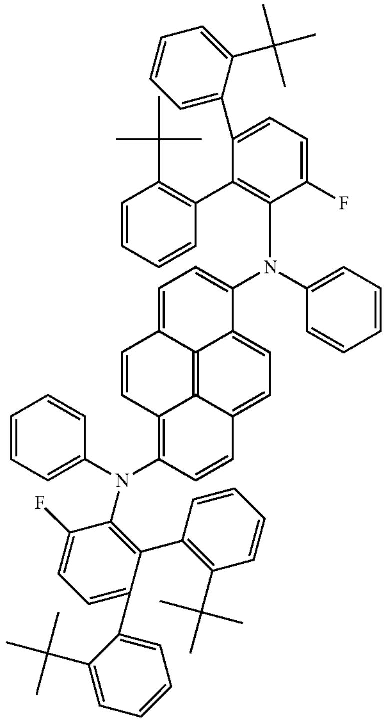
A-143
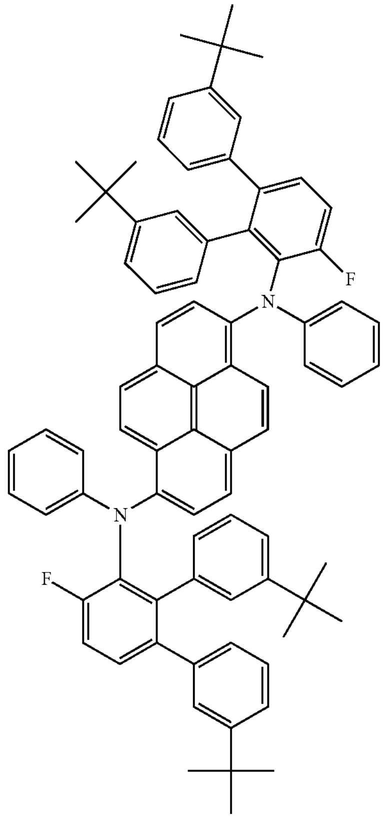

-continued
A-144
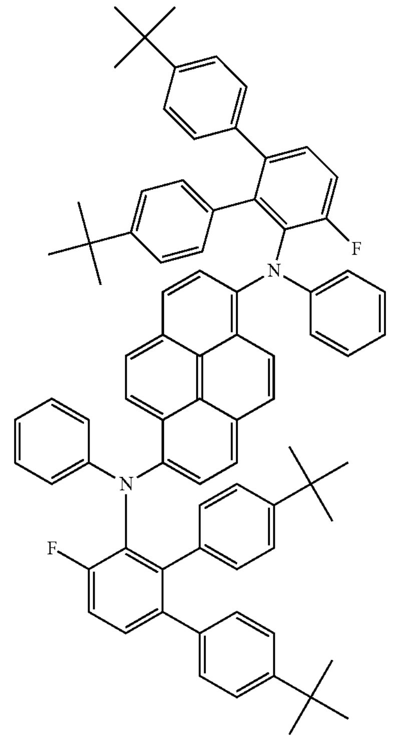
A-145
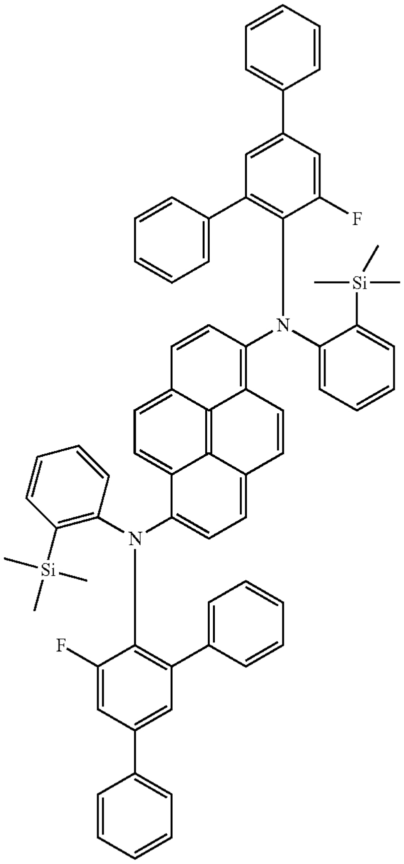
-continued
A-146
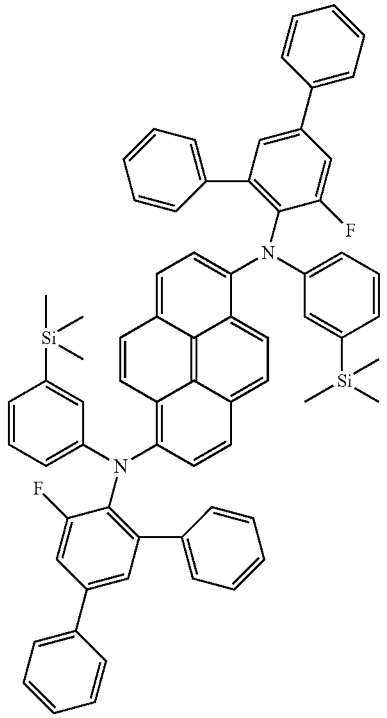
A-147
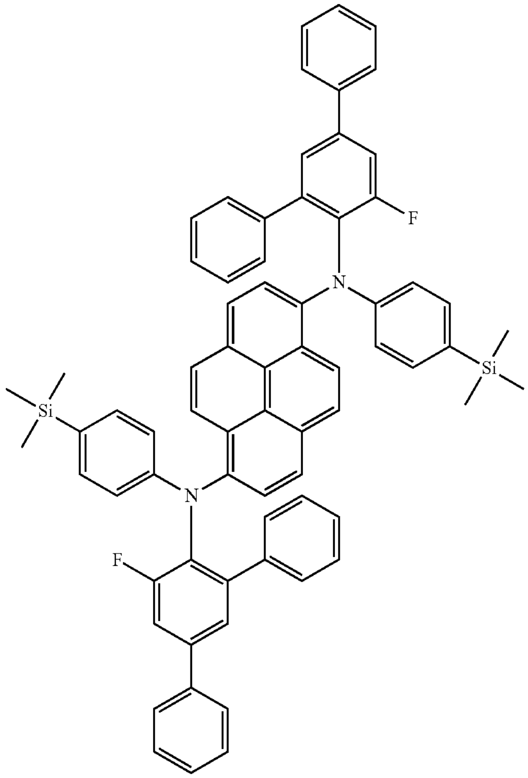

-continued
A-148
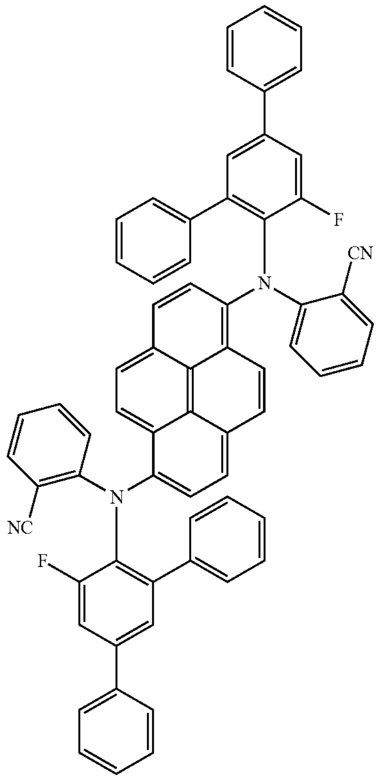
A-149
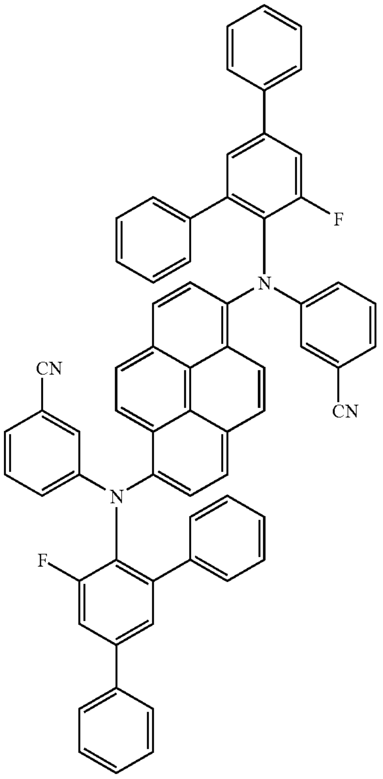
-continued
A-150
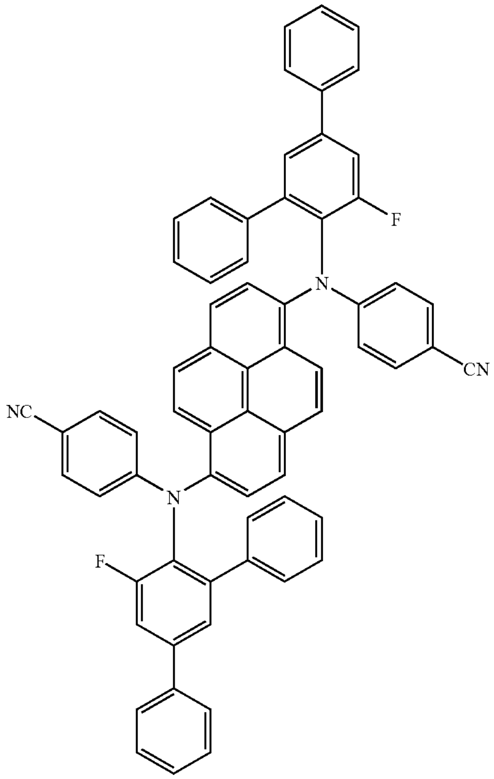
A-151
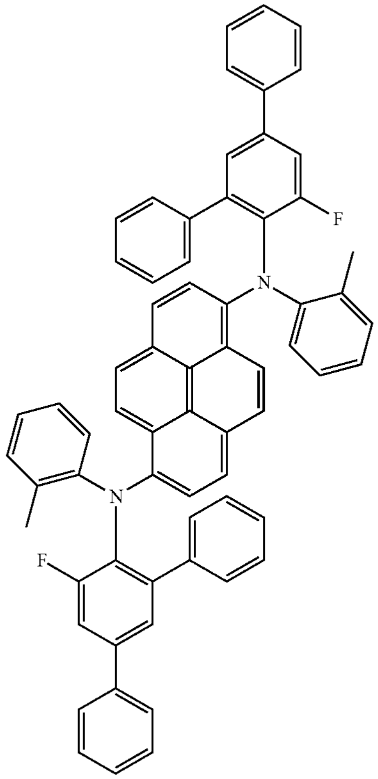

-continued
A-152
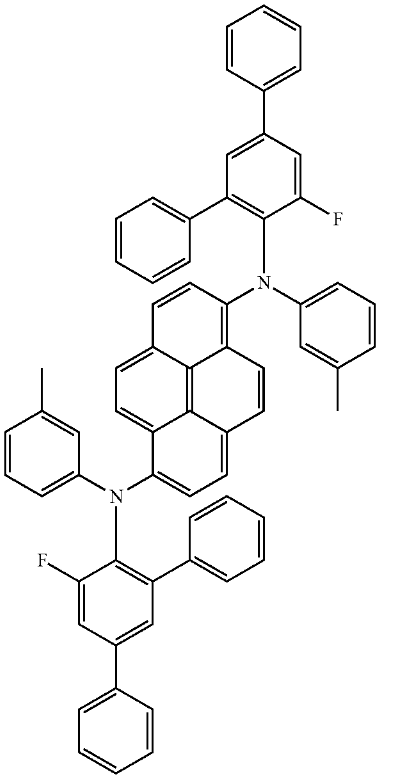
A-153
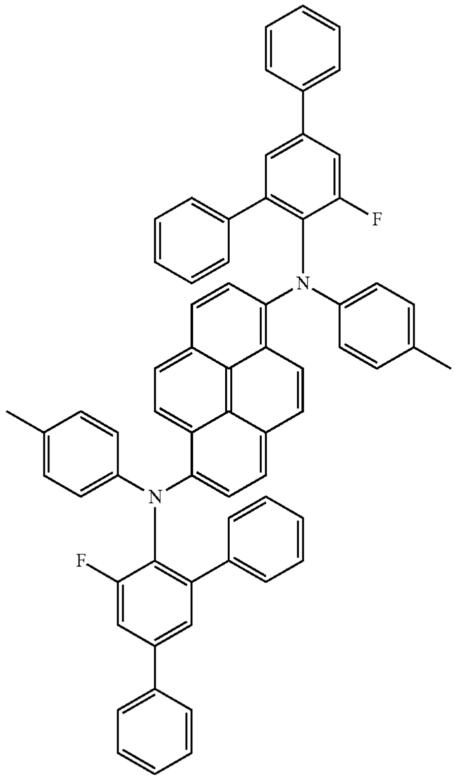
-continued
A-154
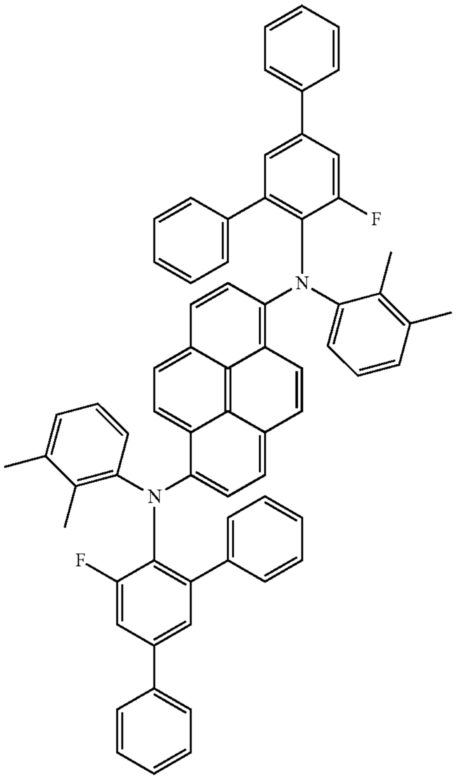
A-155
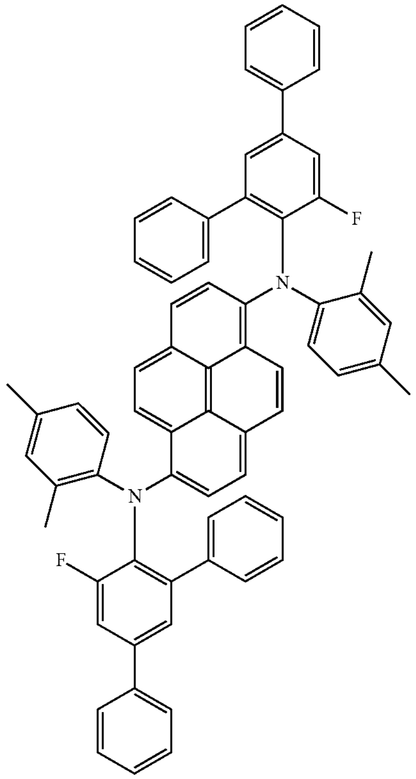

-continued
A-156
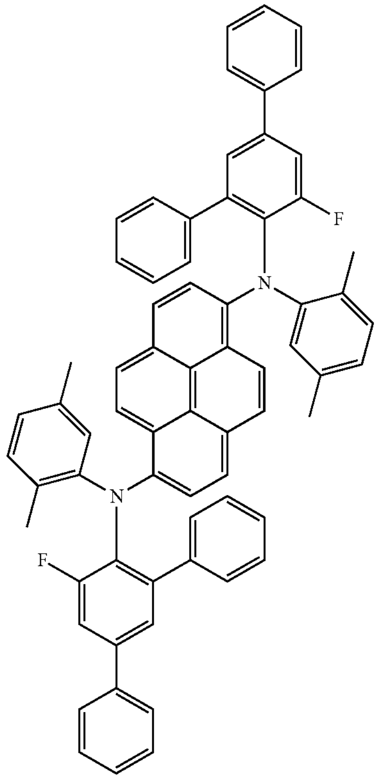
A-157
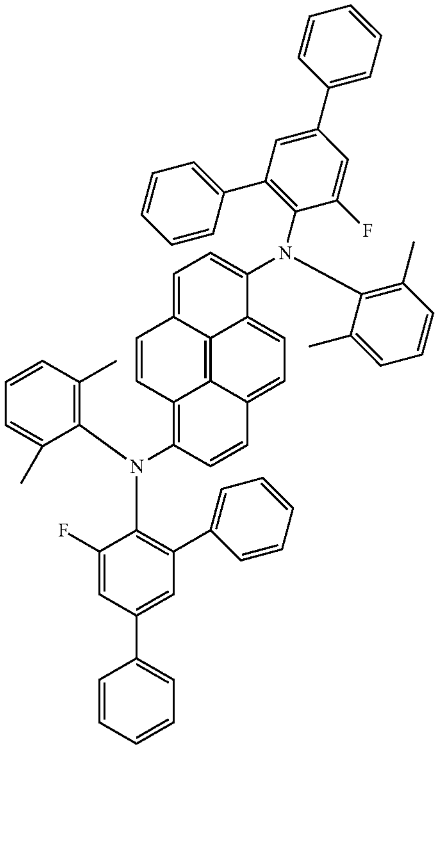
-continued
A-158
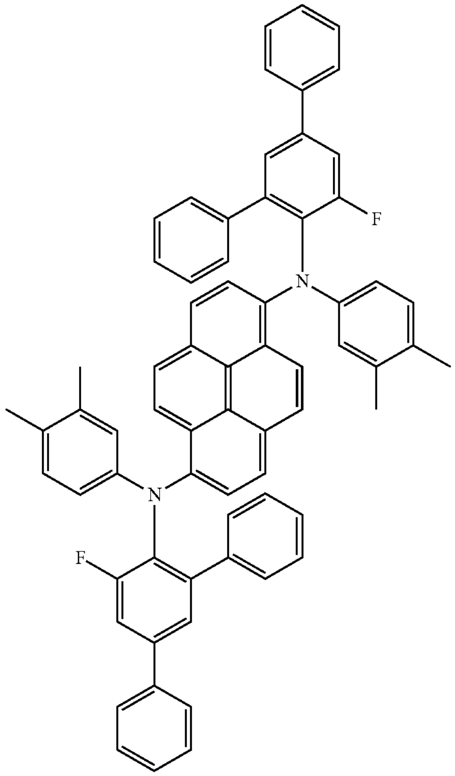
A-159
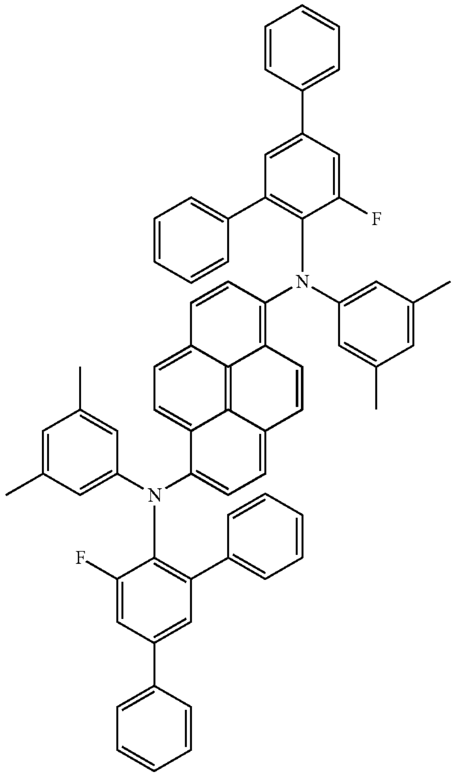

-continued
A-160
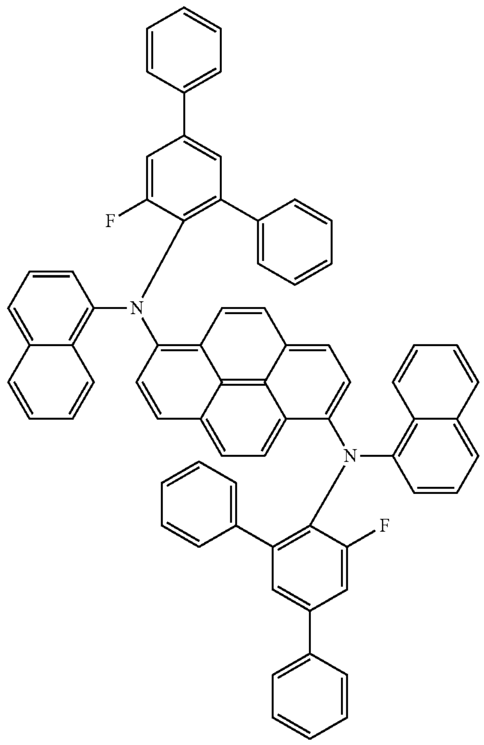
A-161
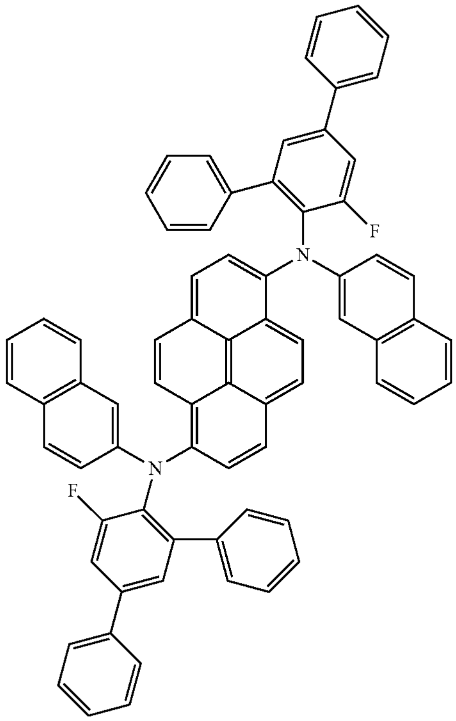
-continued
A-162
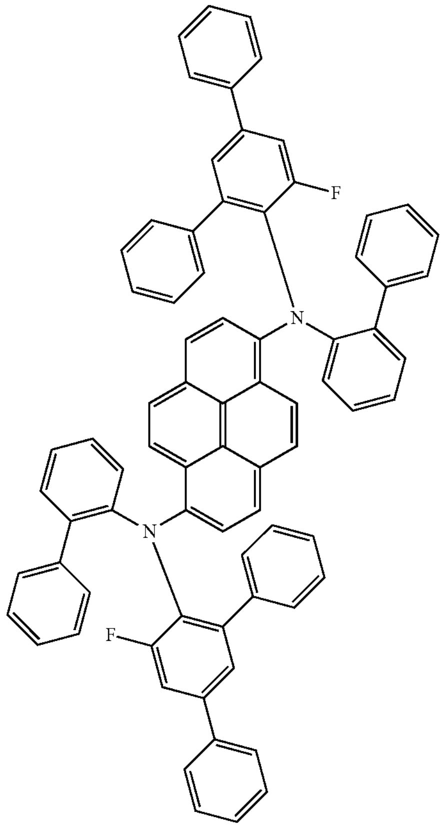
A-163
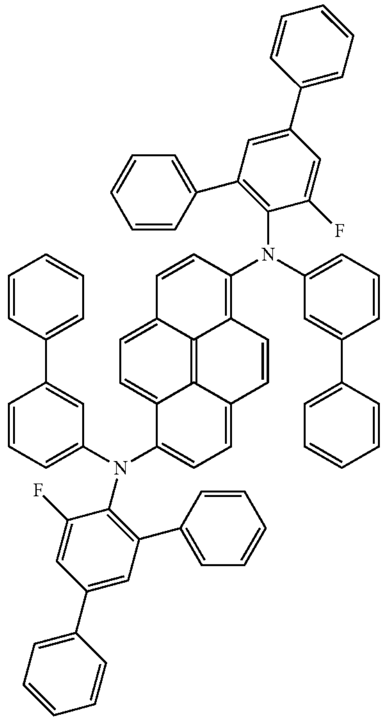

-continued
A-164
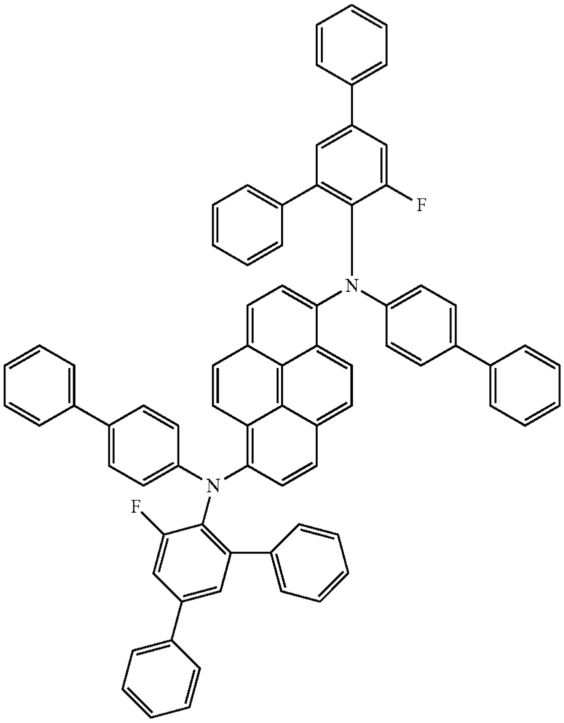
A-165
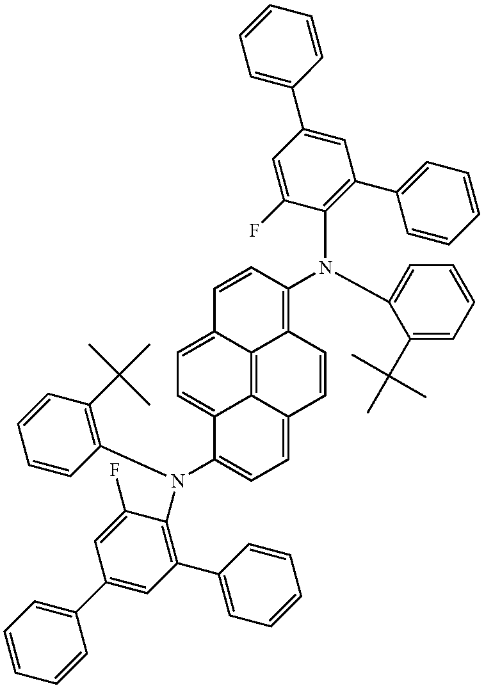
-continued
A-166
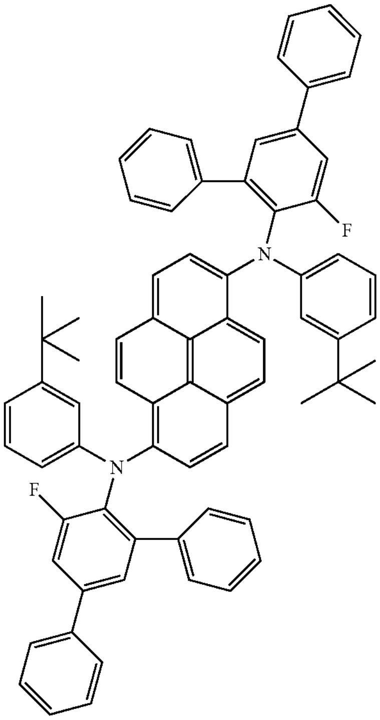
A-167
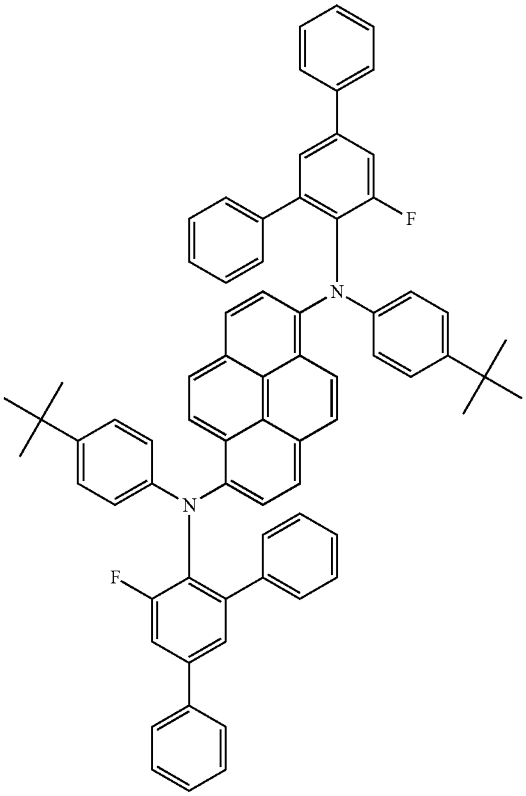

-continued
A-168
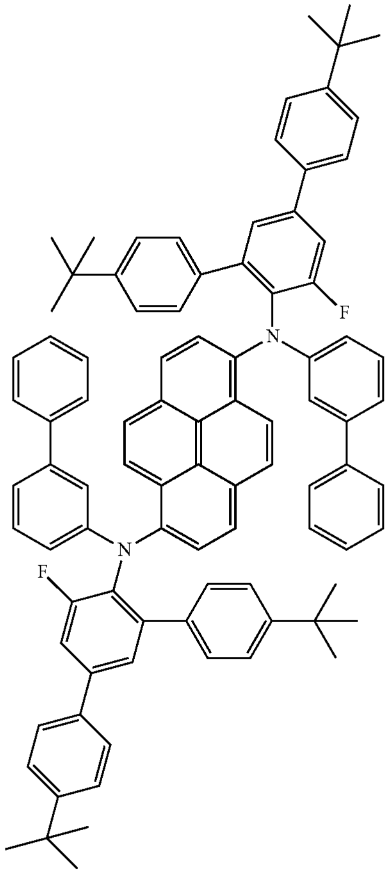
-continued
A-169
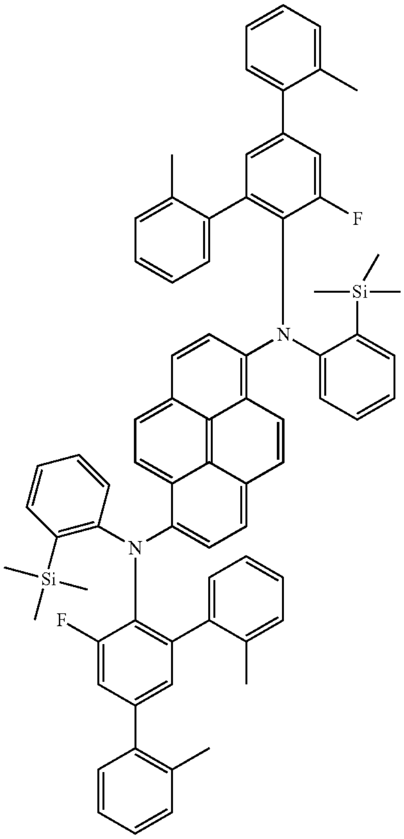
A-170
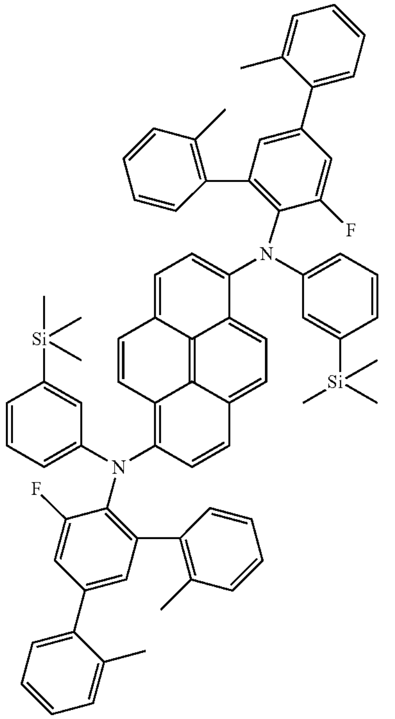

-continued
A-171
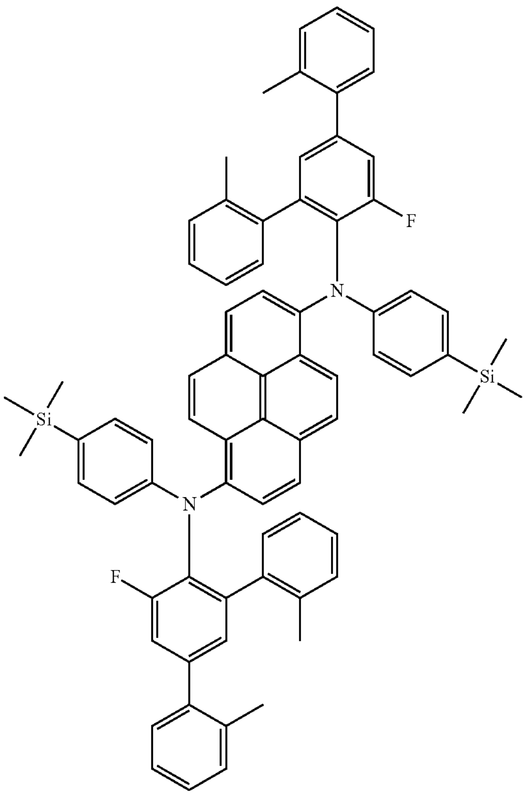
A-172
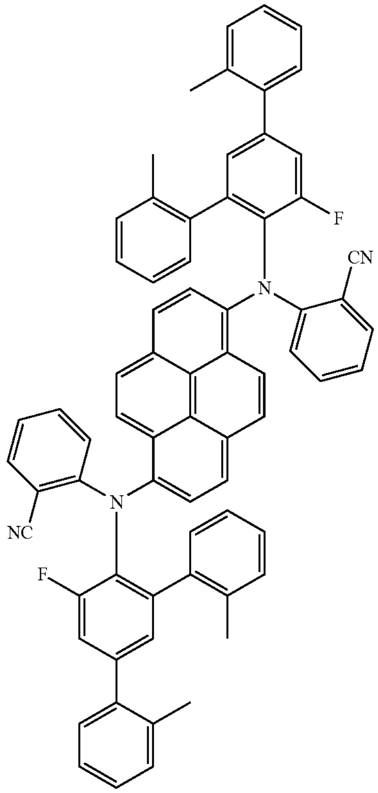
-continued
A-173
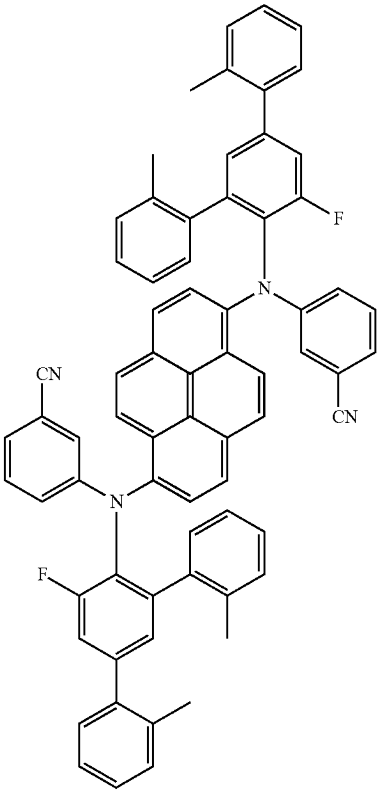
A-174
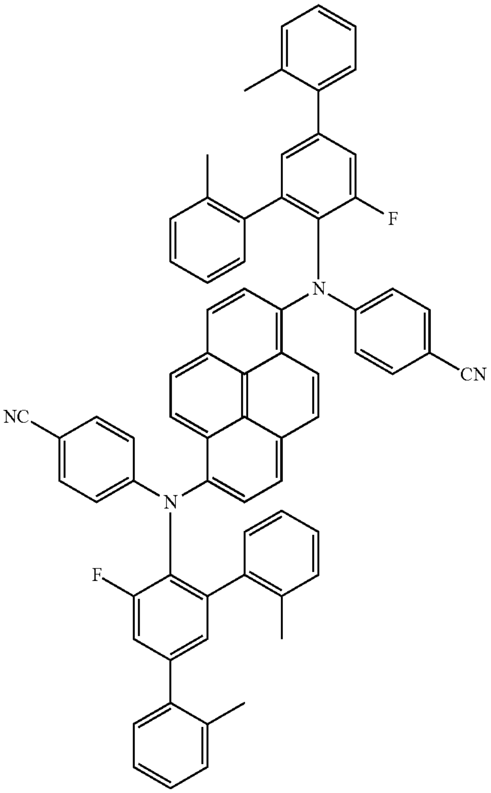

-continued
A-175
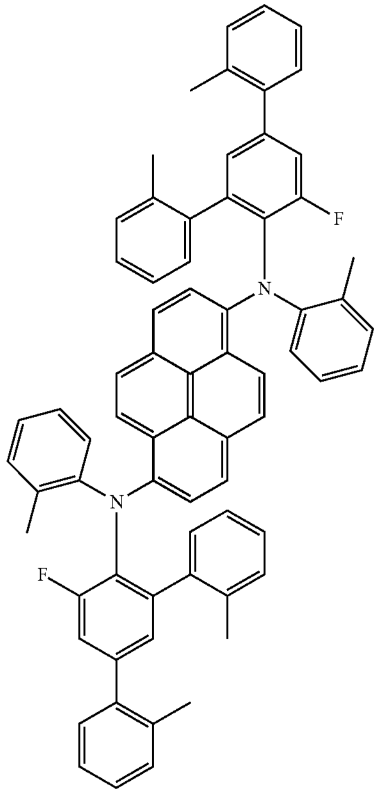
A-176
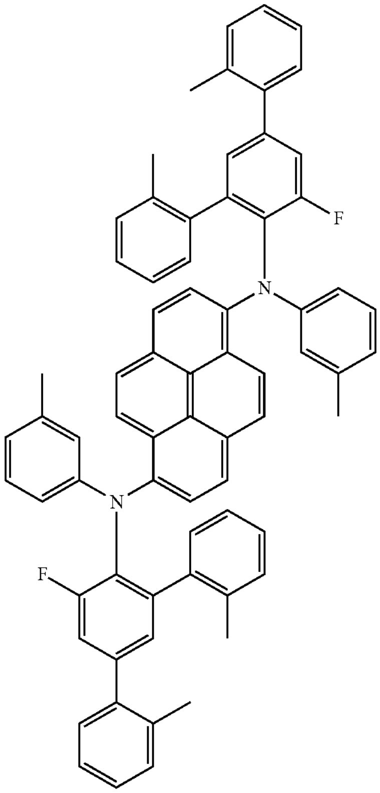
-continued
A-177
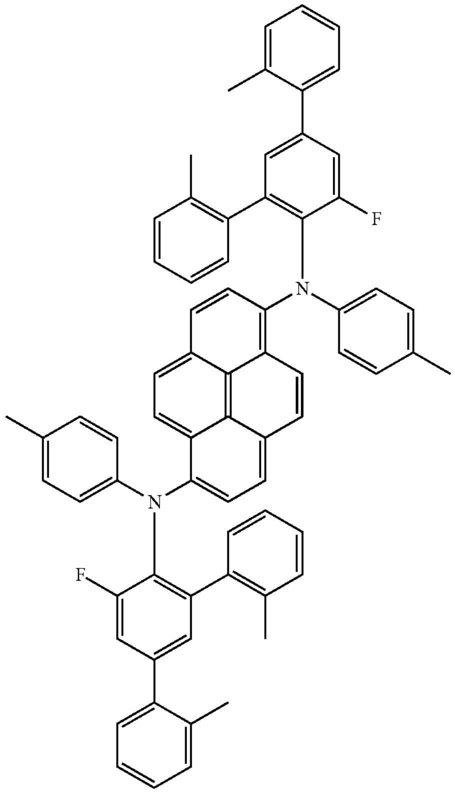
A-178
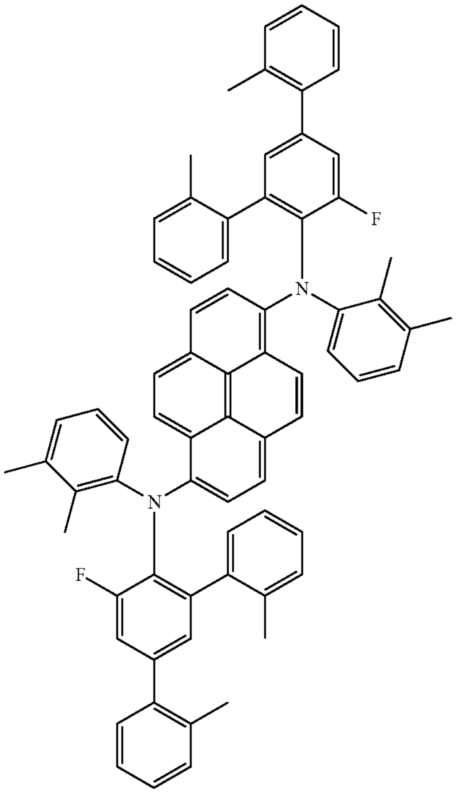

-continued
A-179
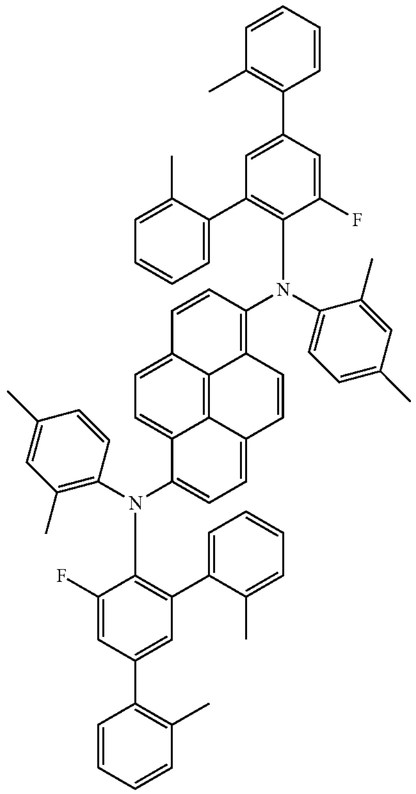
A-180
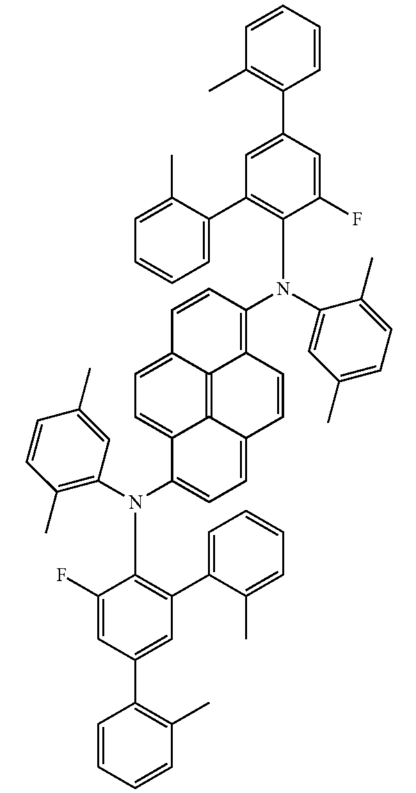
-continued
A-181
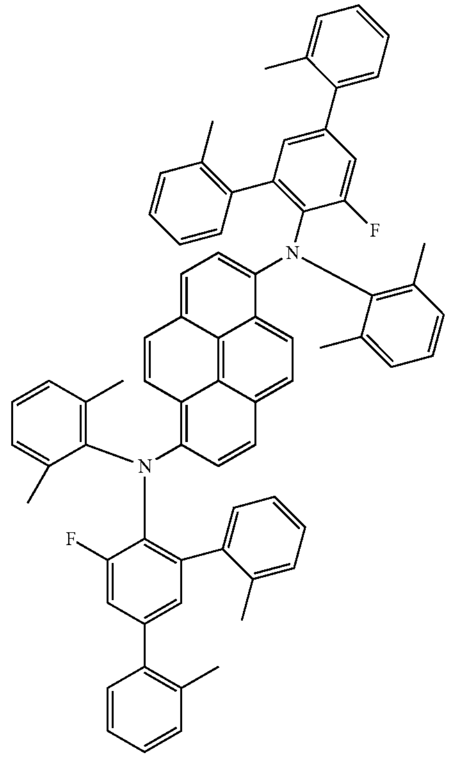
A-182
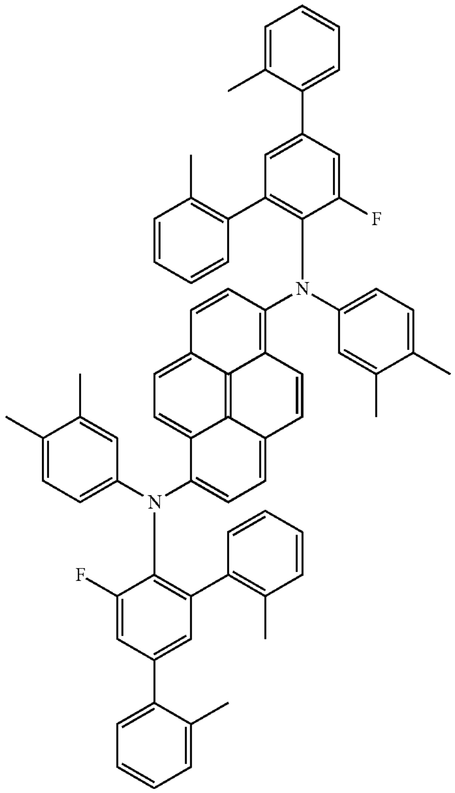

-continued
A-183
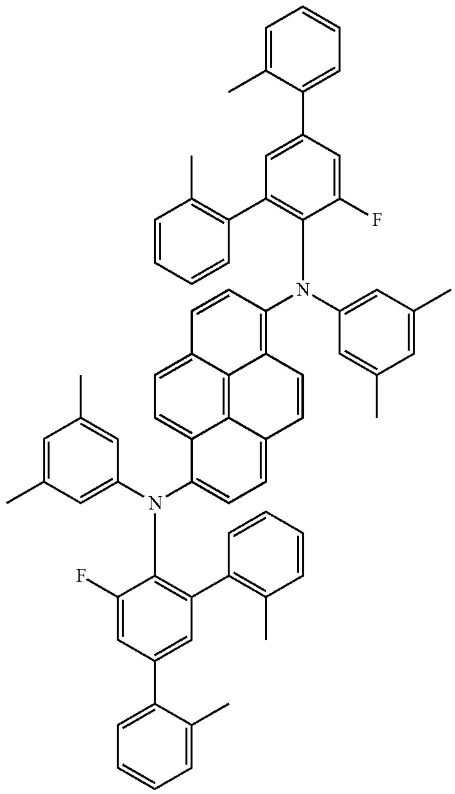
A-184
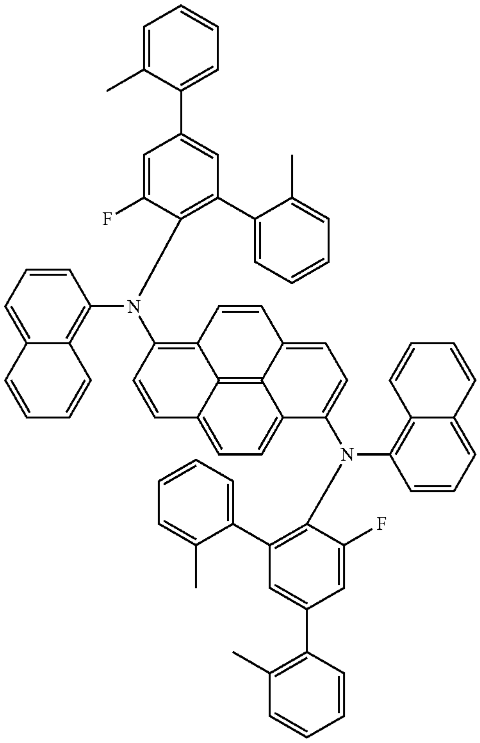
-continued
A-185
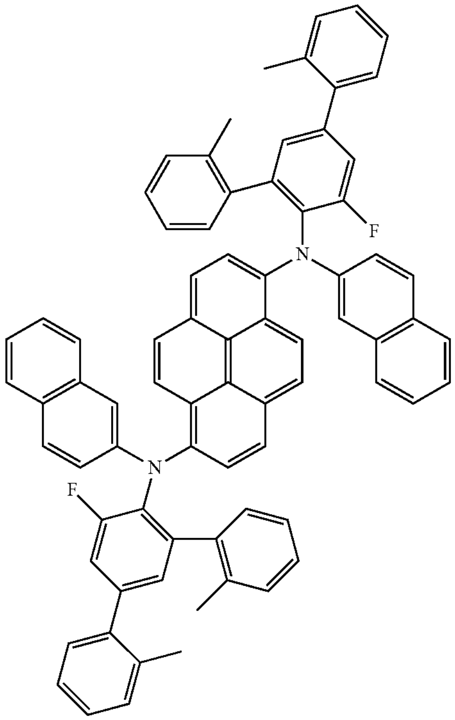
A-186
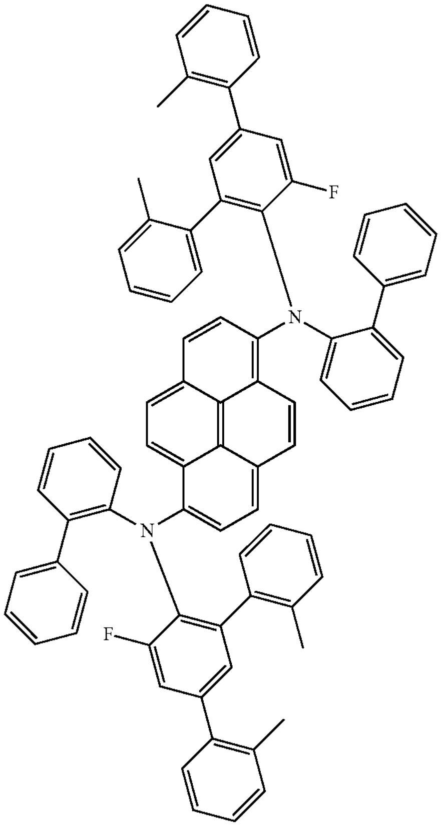

A-187
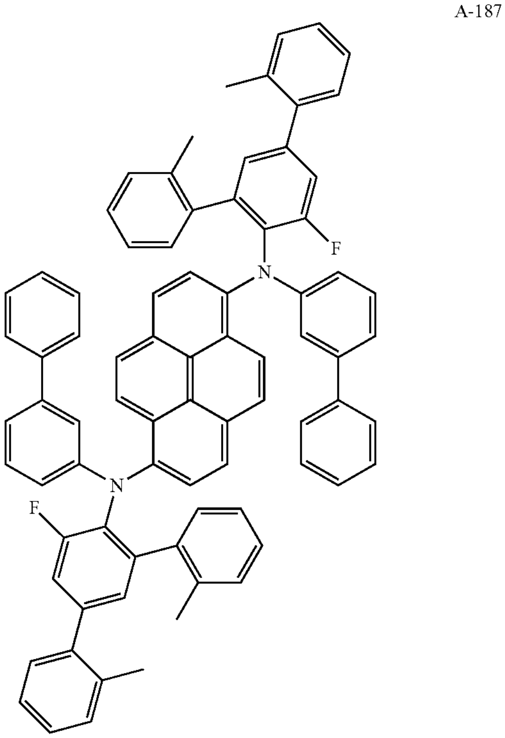
A-188
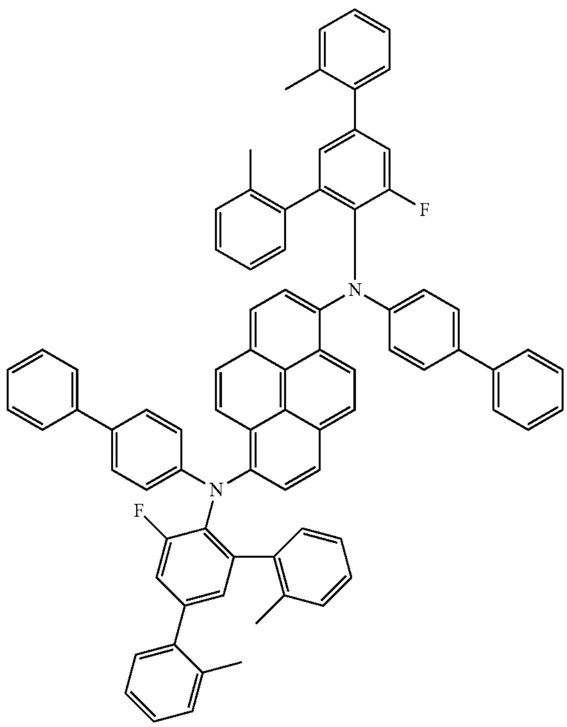
A-189
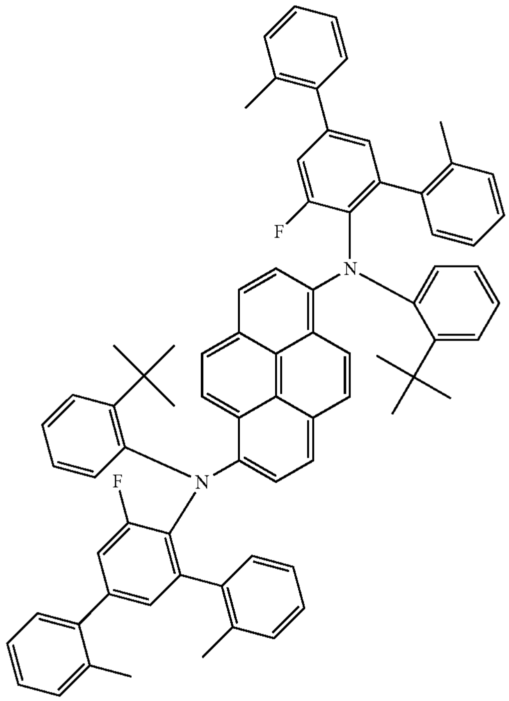
A-190
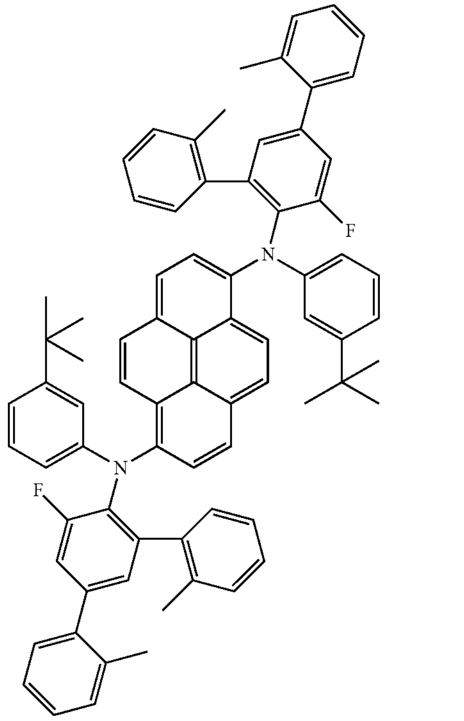

A-191
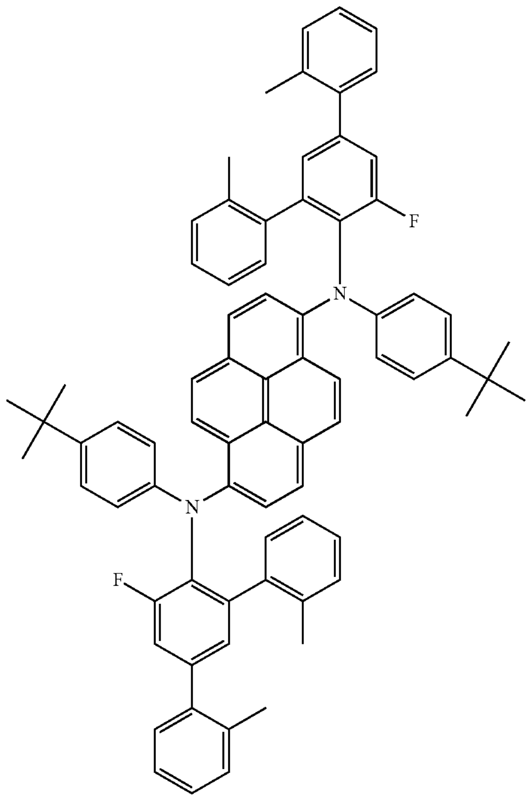
A-192
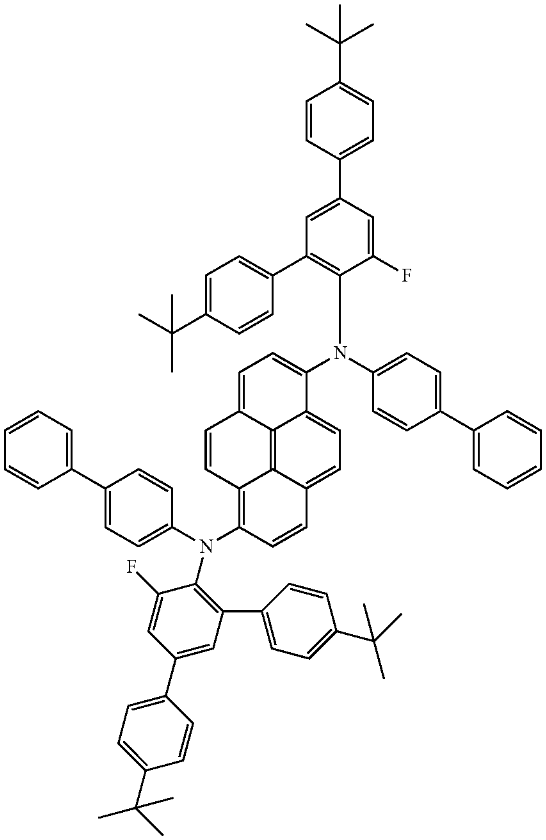
A-189
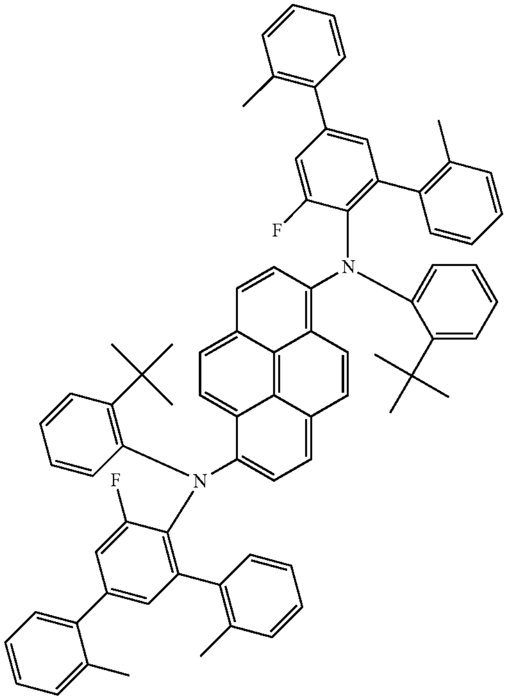
A-190
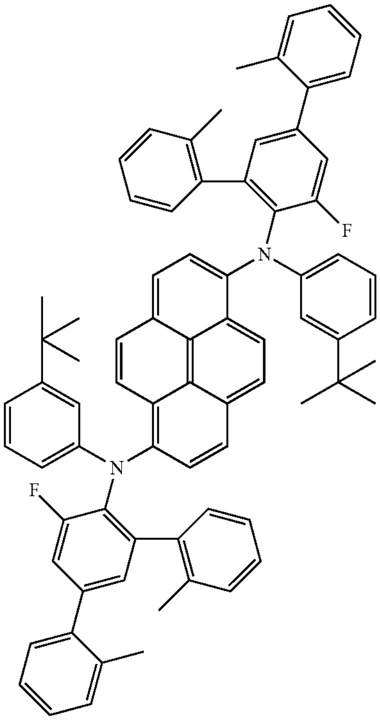

-continued
A-191
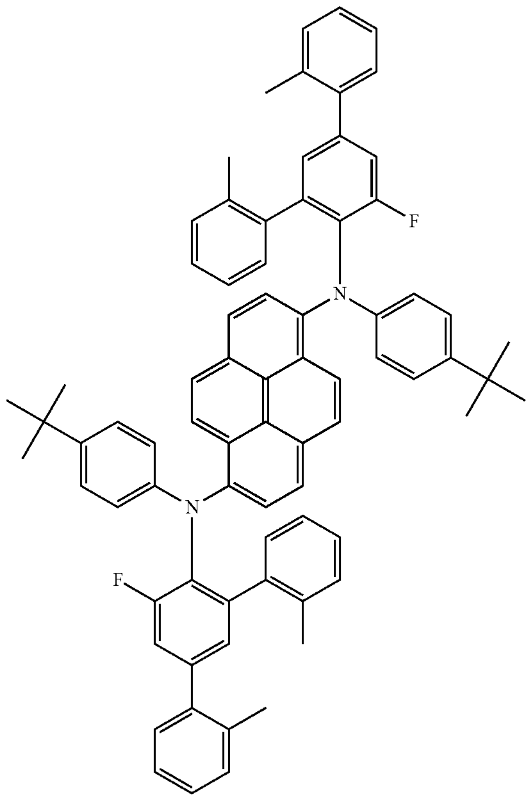
A-192
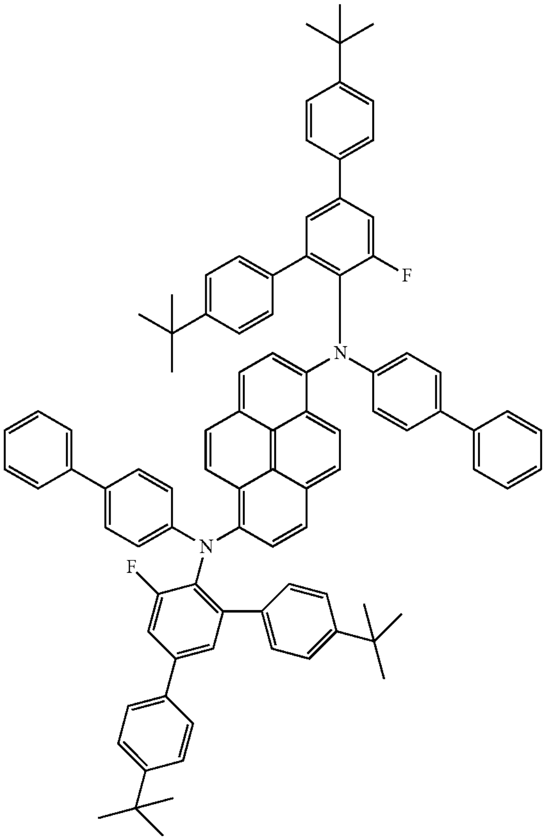
-continued
A-173
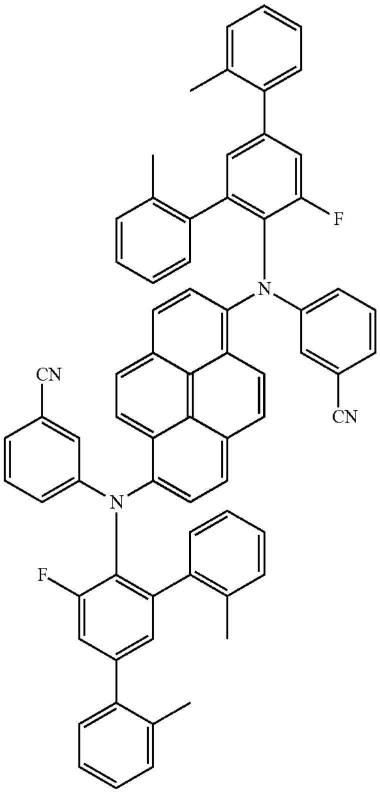
A-174
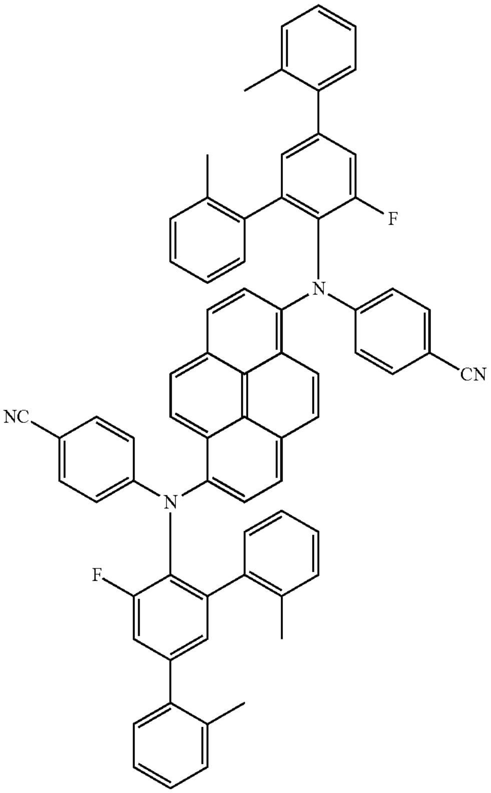

A-175
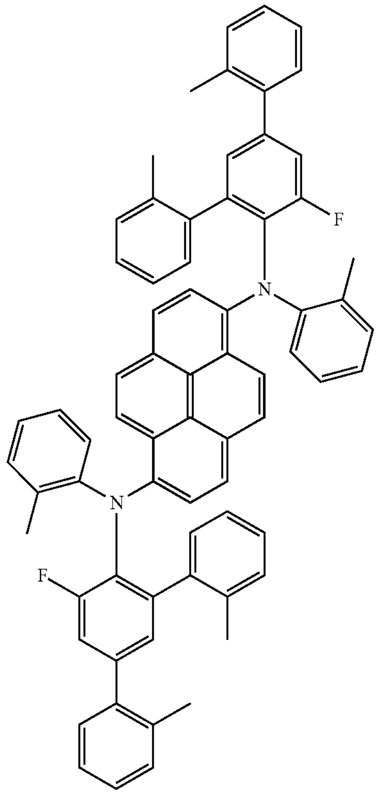
A-176
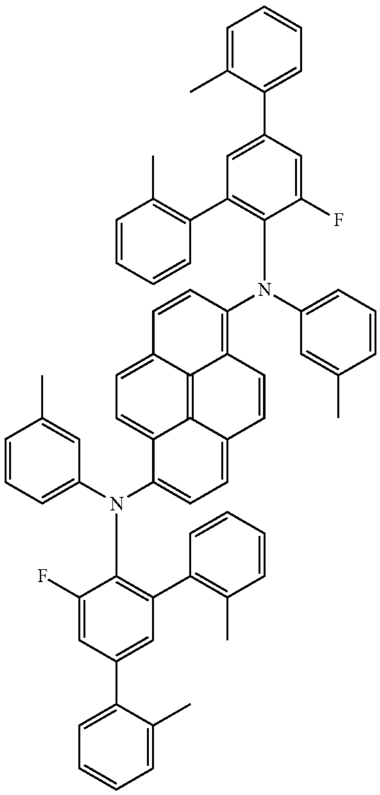
A-177
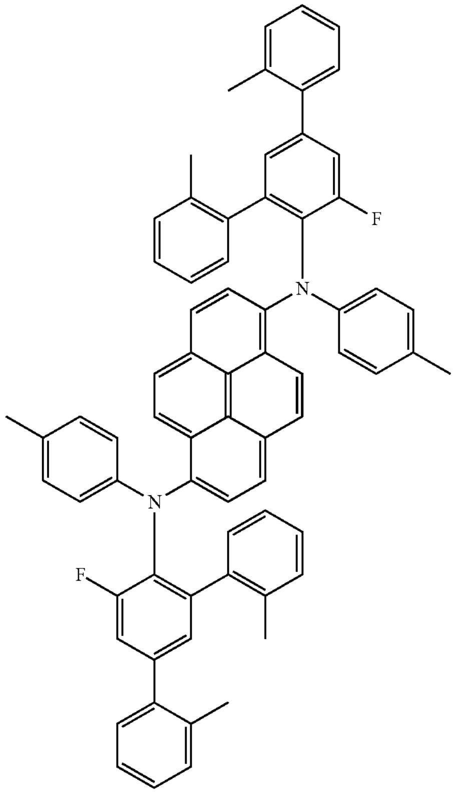
A-178
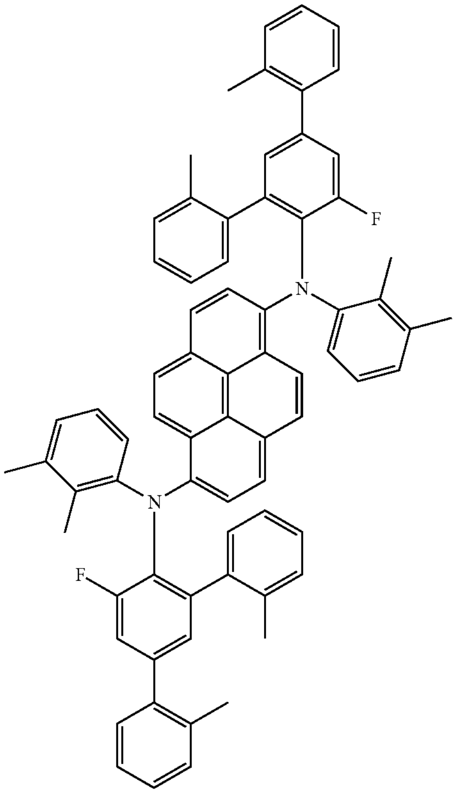

-continued
A-179
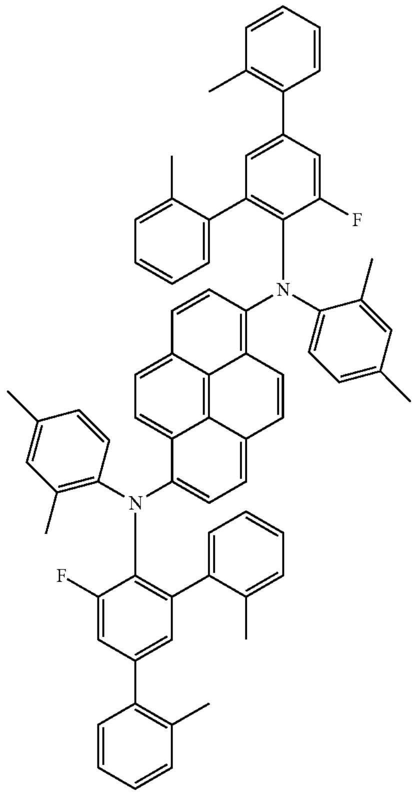
A-180
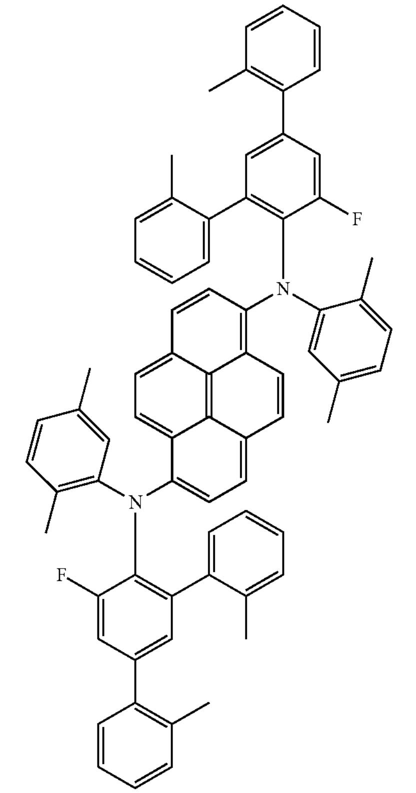
-continued
A-181
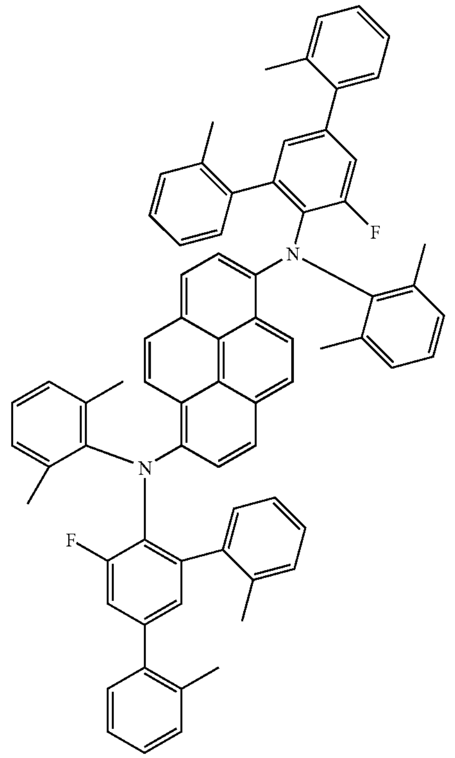
A-182
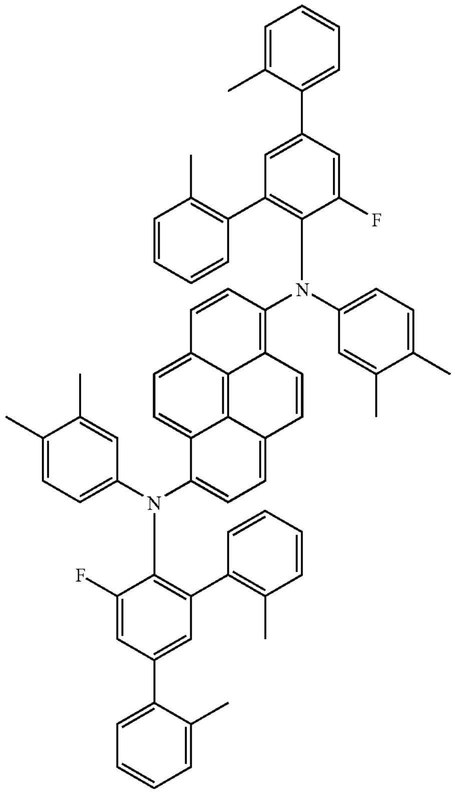

-continued
A-183
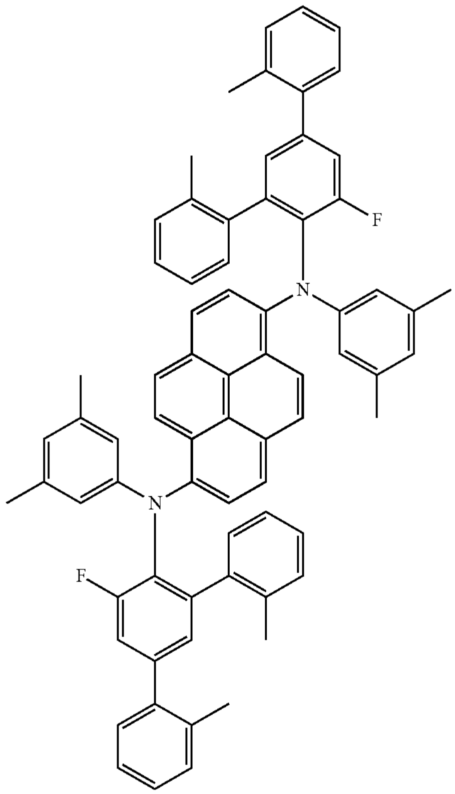
A-184
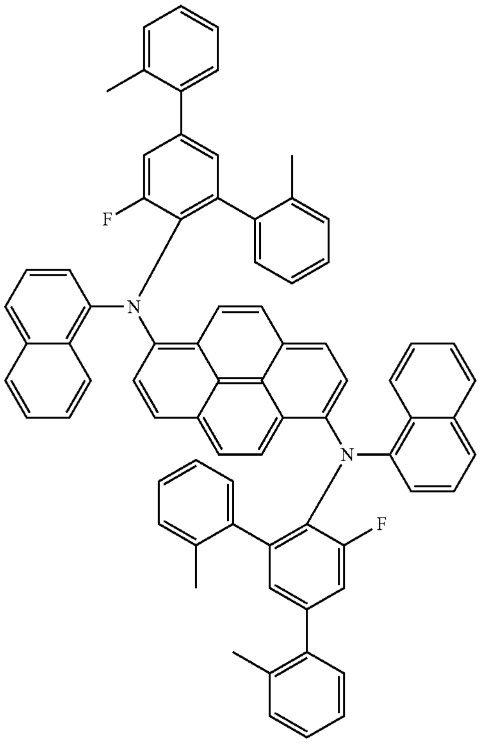
-continued
A-185
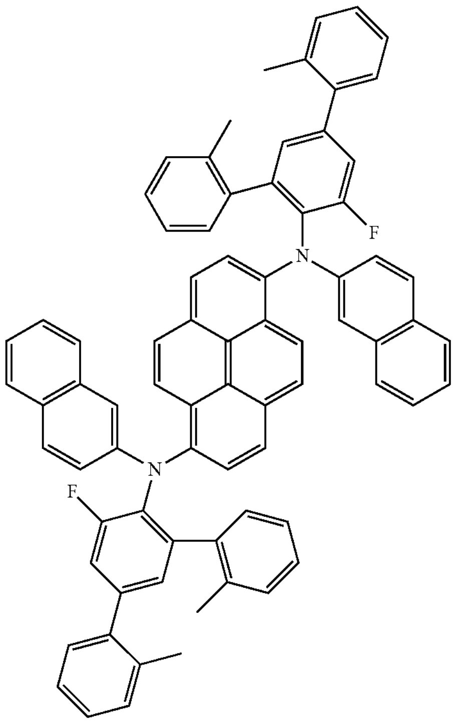
A-186
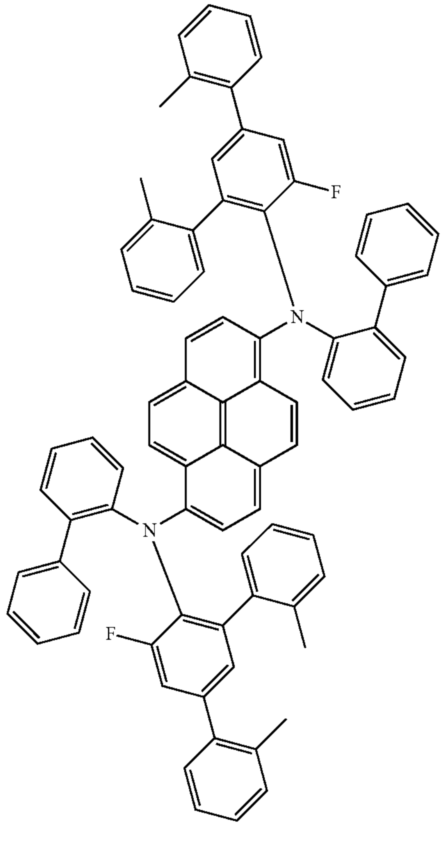

-continued
A-187
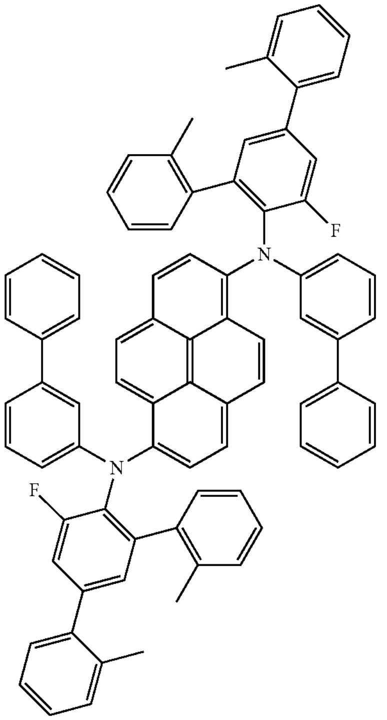
A-188
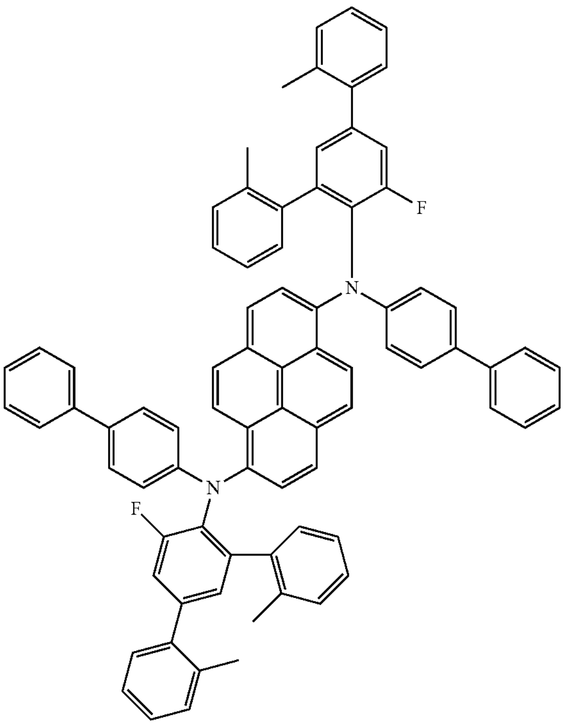
-continued
A-189
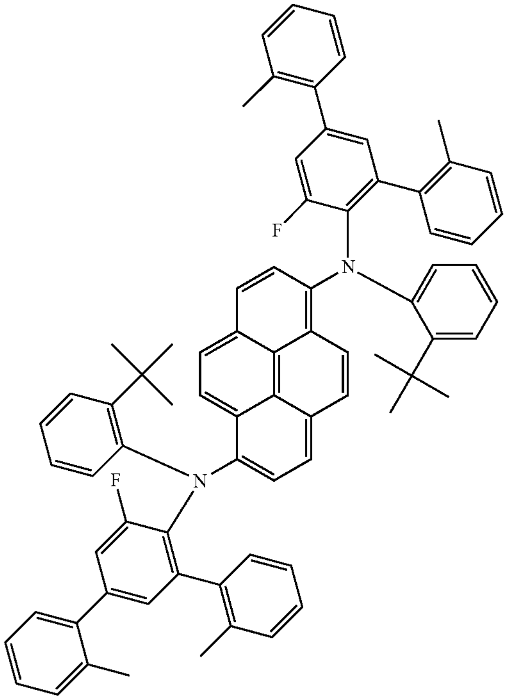
A-190
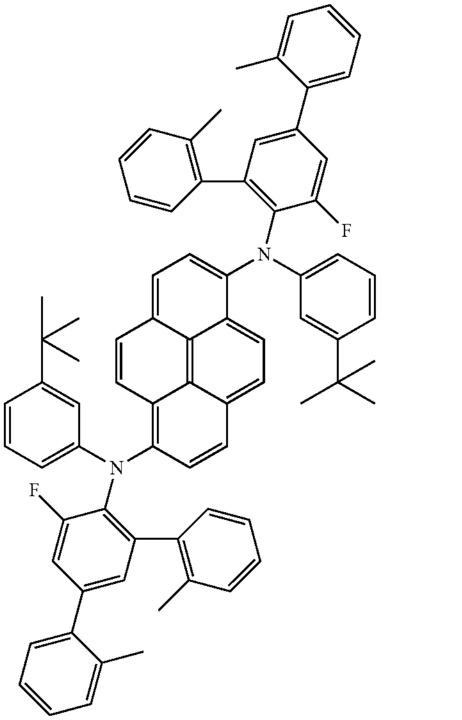

-continued
A-191
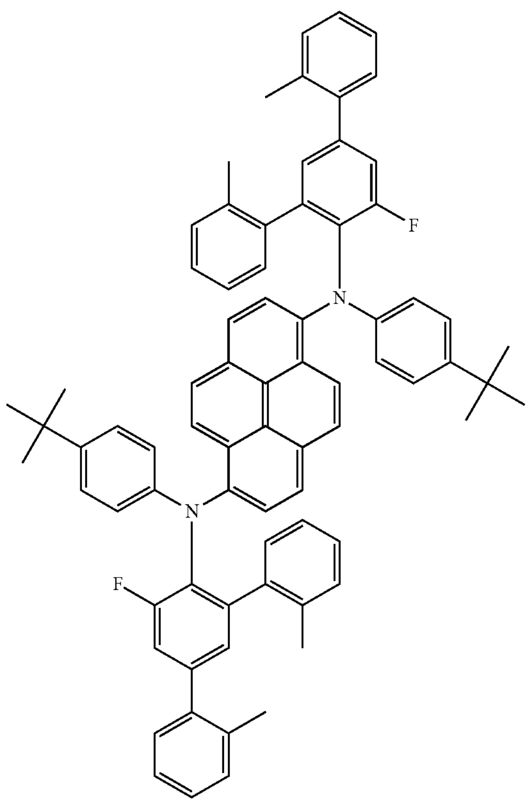
A-192
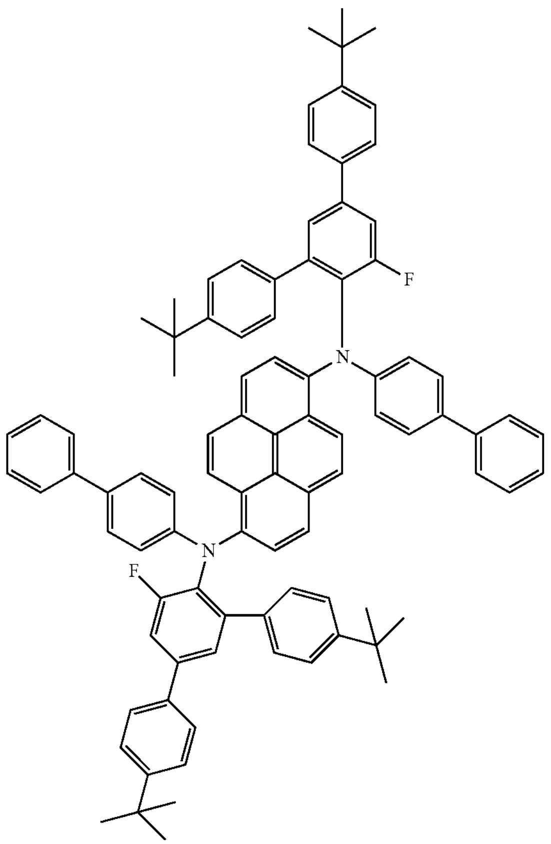
-continued
A-193
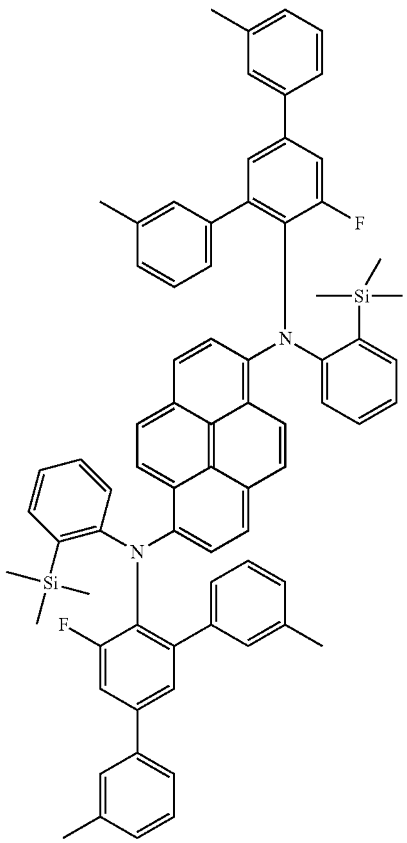
A-194
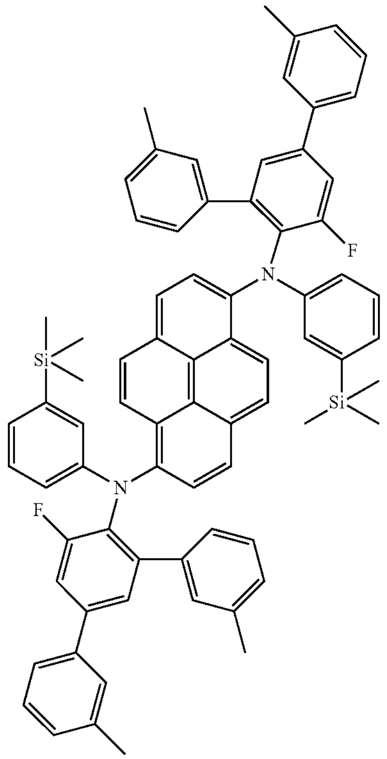

-continued
A-195
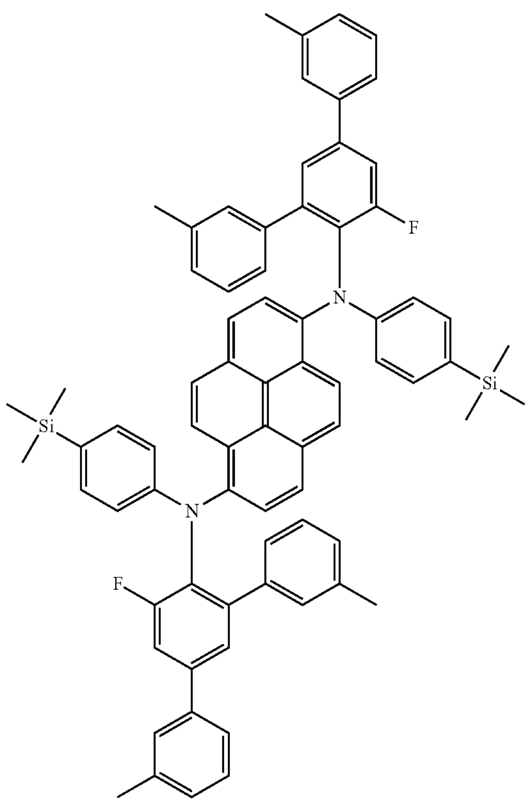
A-196
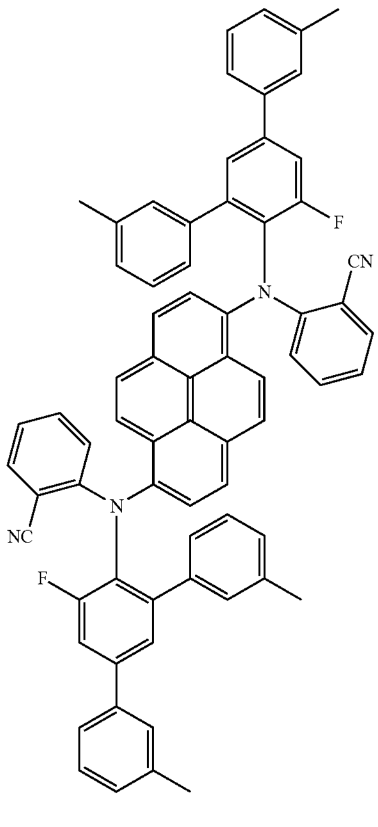
-continued
A-197
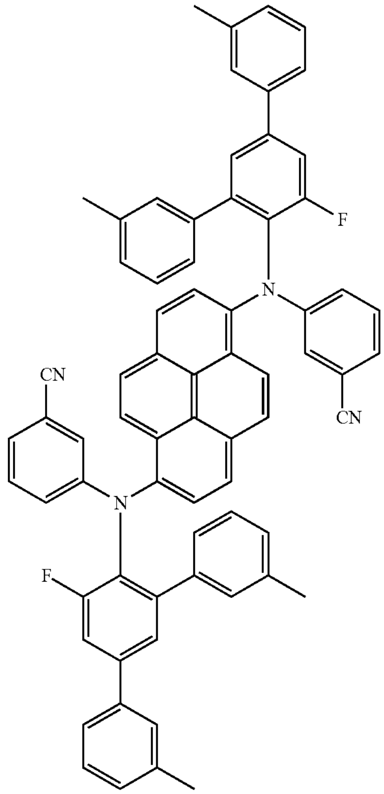
A-198
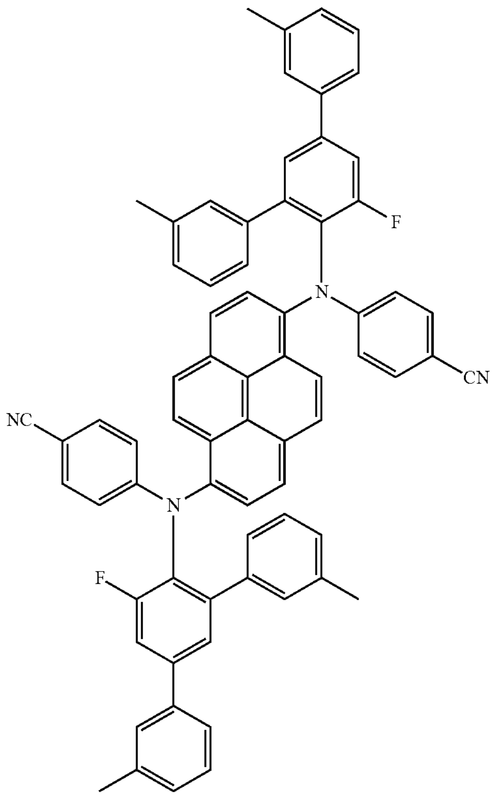

-continued
A-199
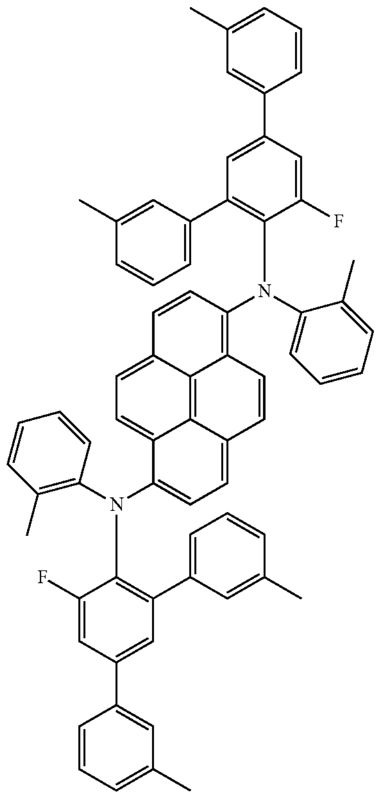
A-200
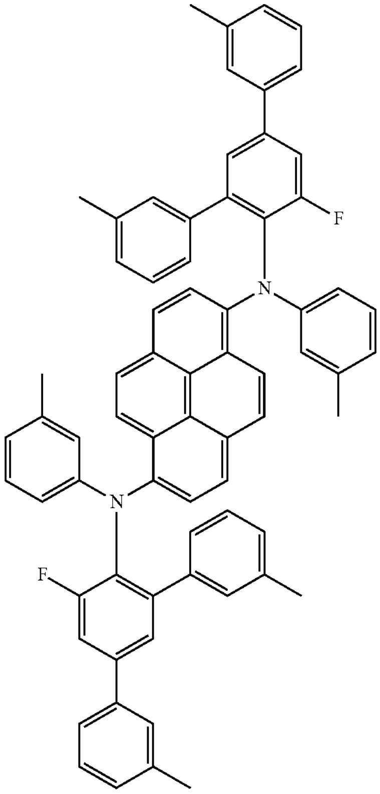
-continued
A-201
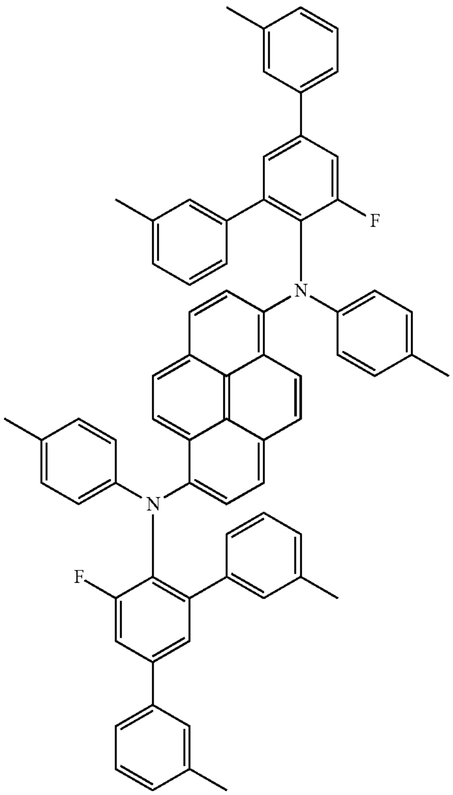
A-202
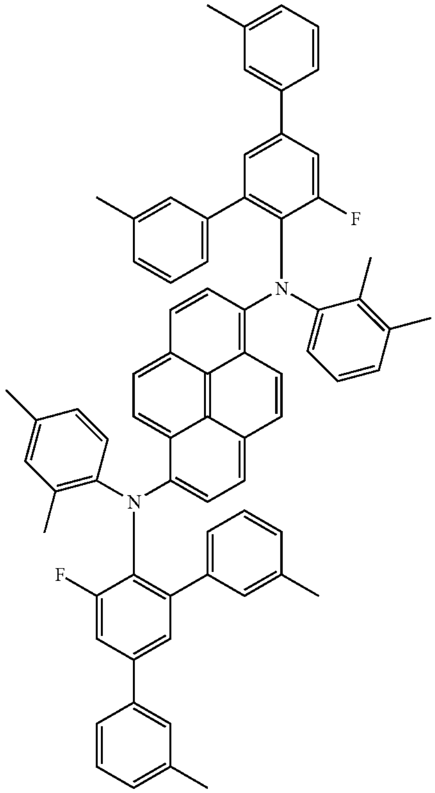

-continued
A-203
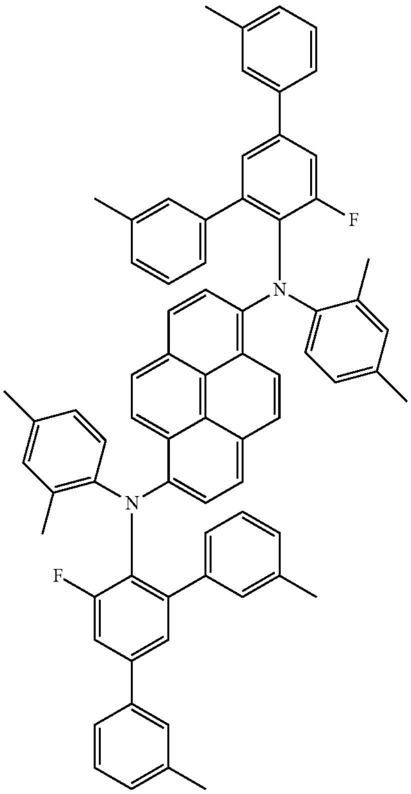
A-204
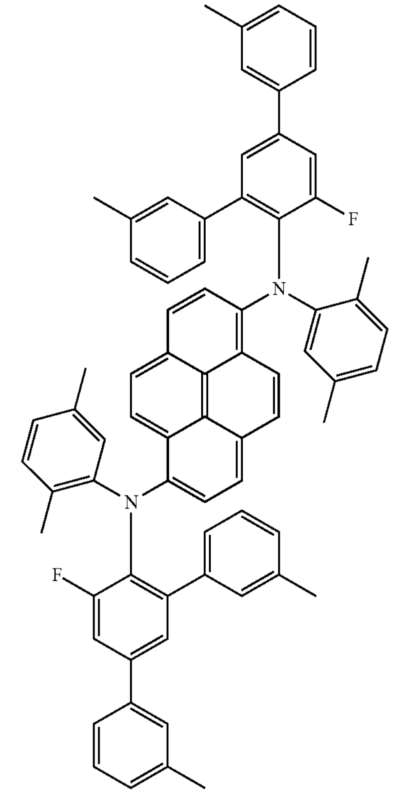
-continued
A-205
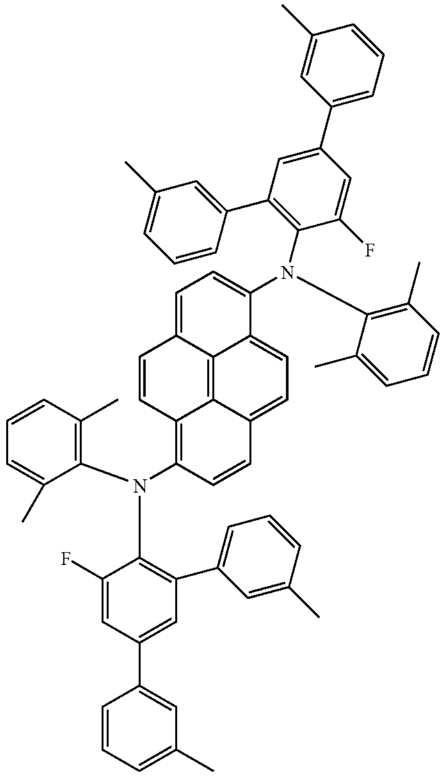
A-206
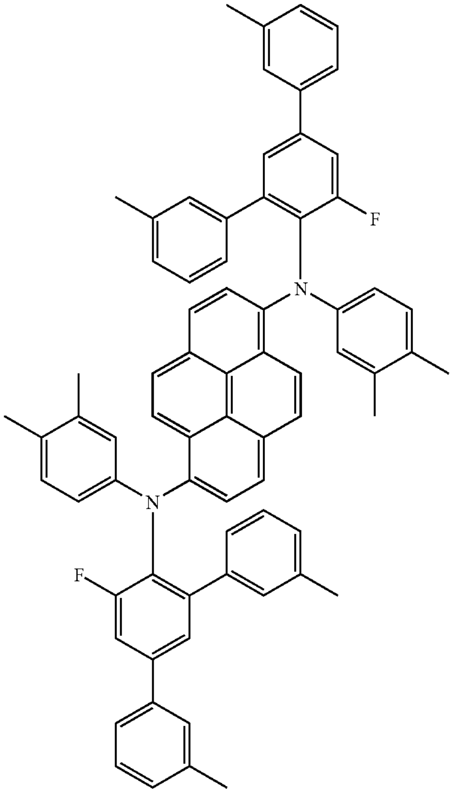

-continued
A-207
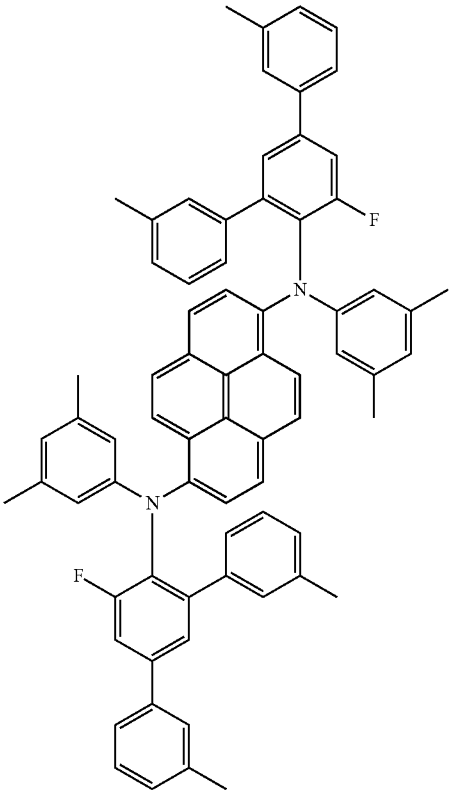
A-208
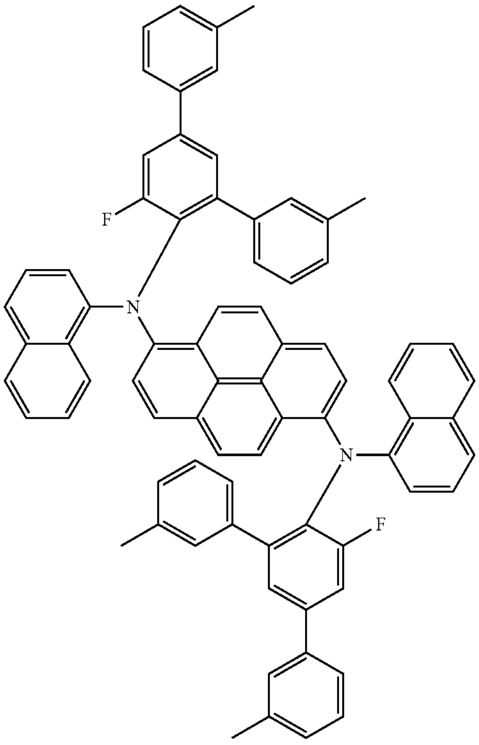
-continued
A-209
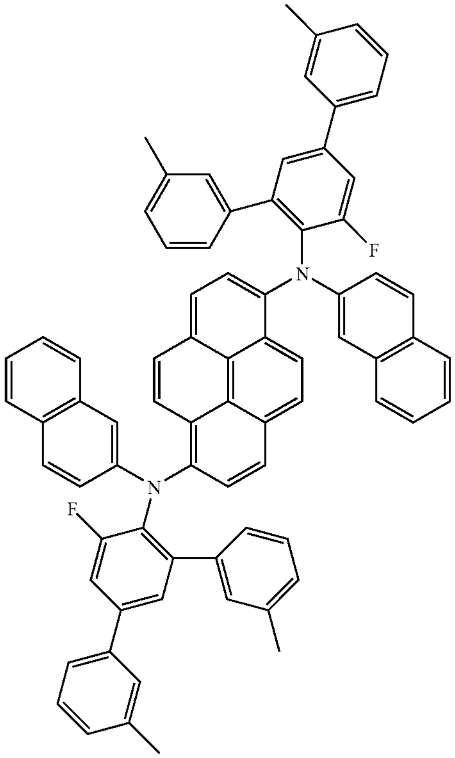
A-210
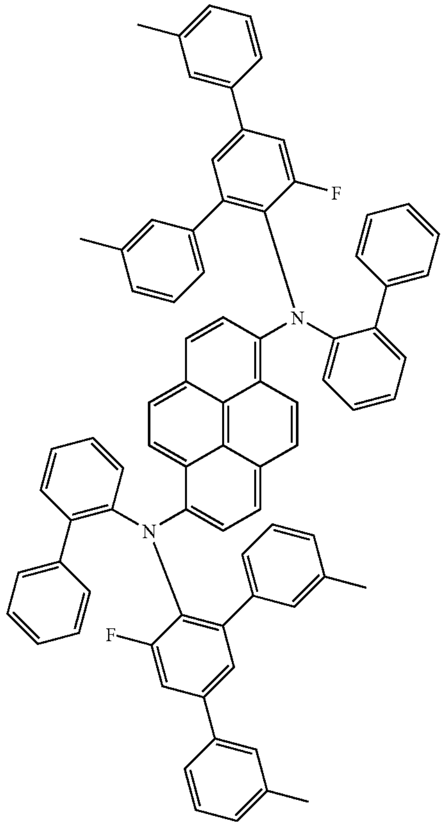

-continued
A-211
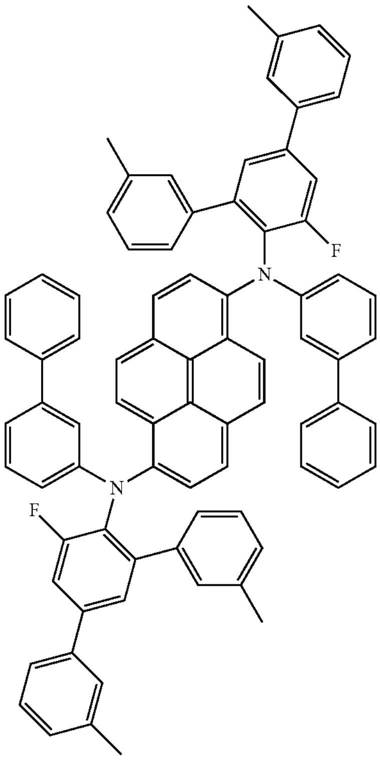
A-212
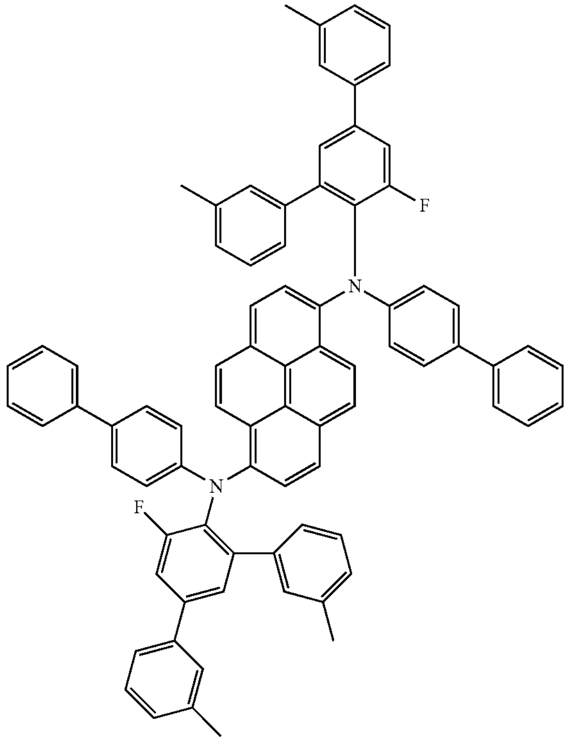
-continued
A-213
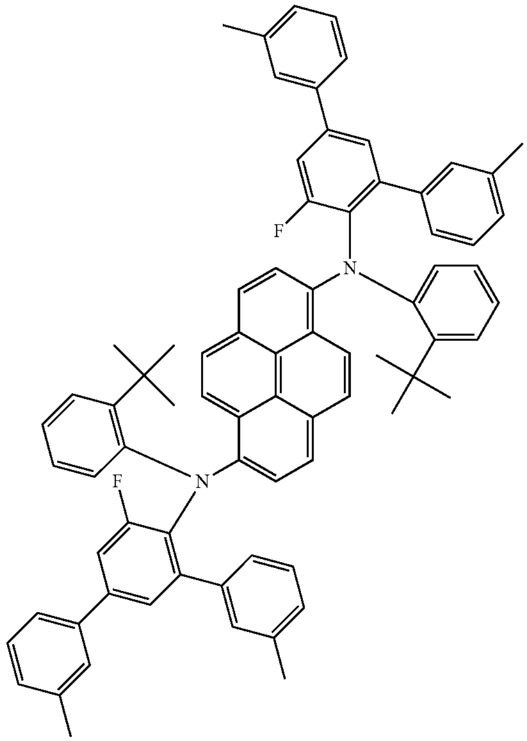
A-214
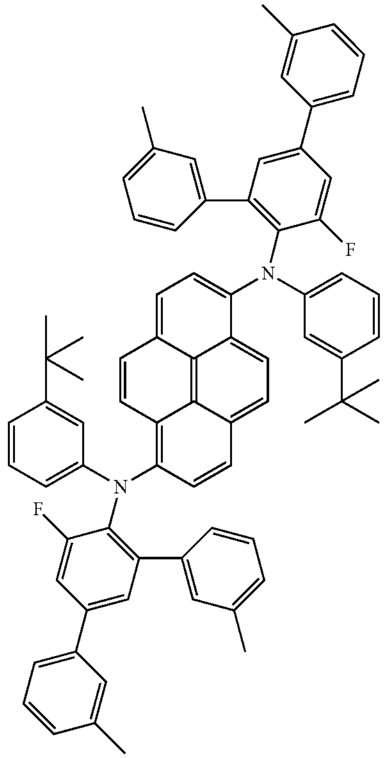

-continued
A-215
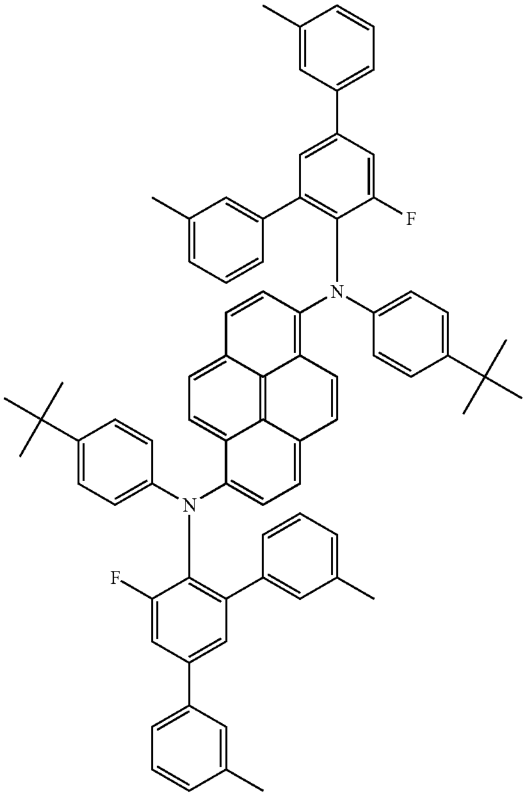
A-216
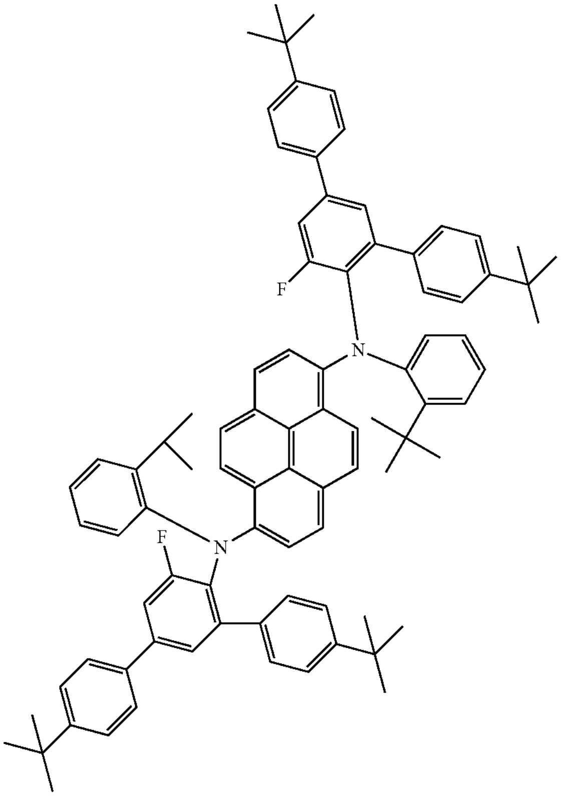
-continued
A-217
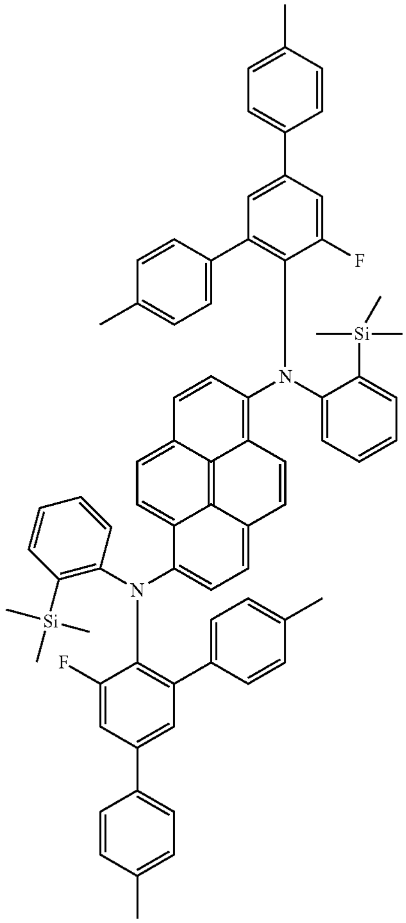

-continued
A-218
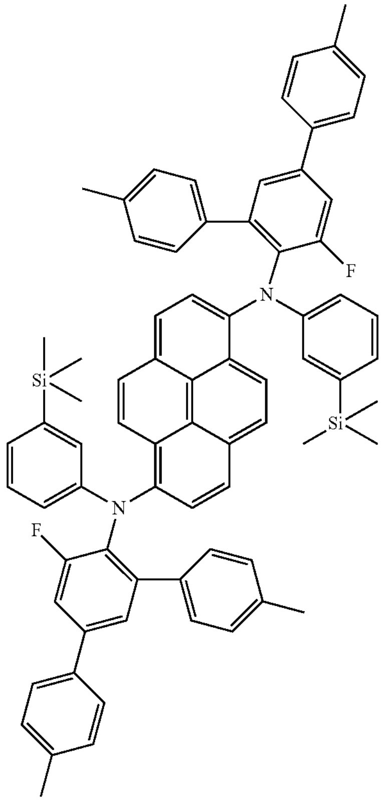
A-219
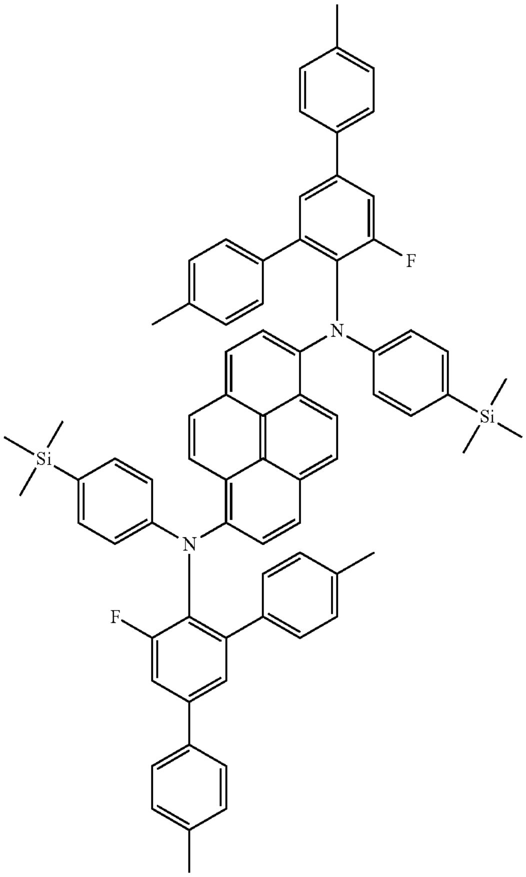
-continued
A-220
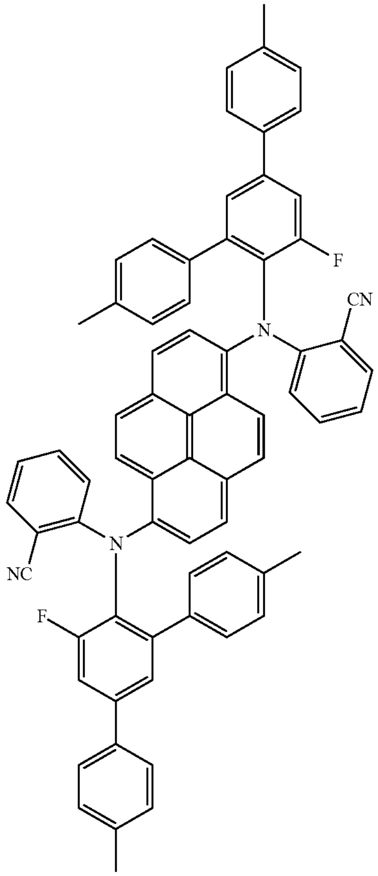

-continued
A-221
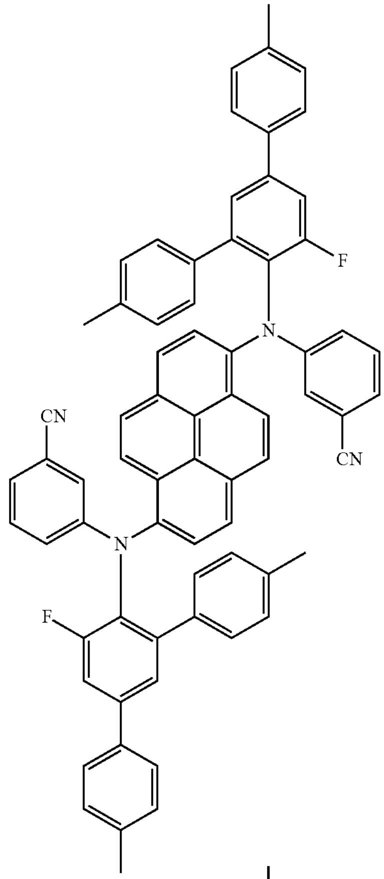
A-222
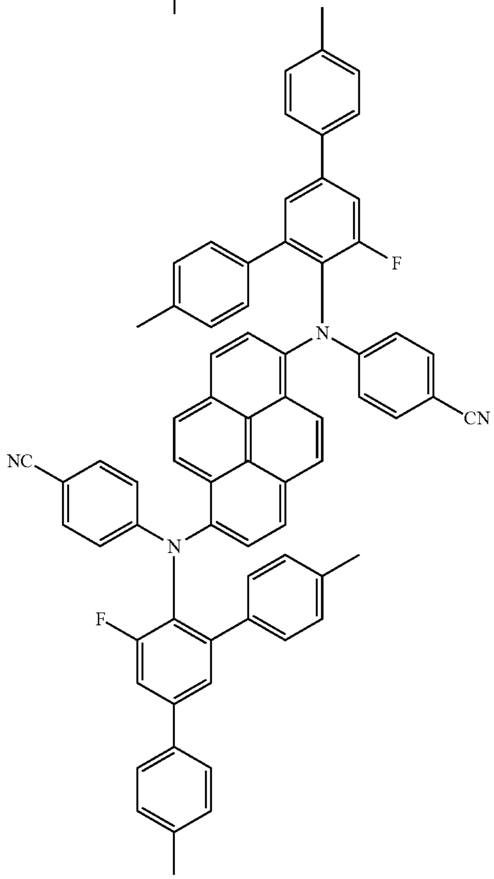
A-223
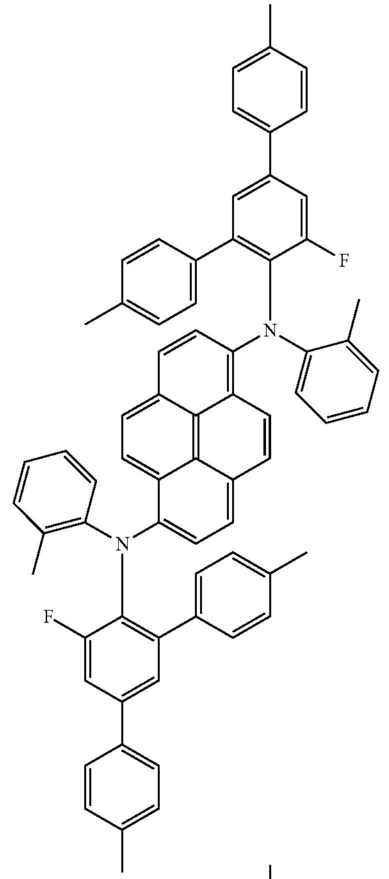
A-224
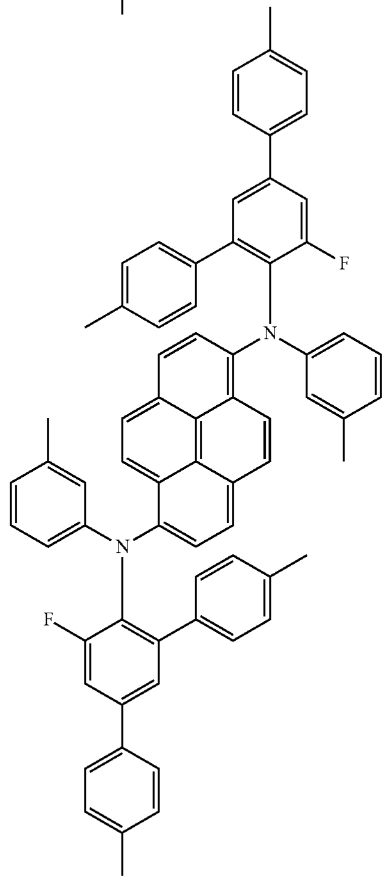

-continued
A-225
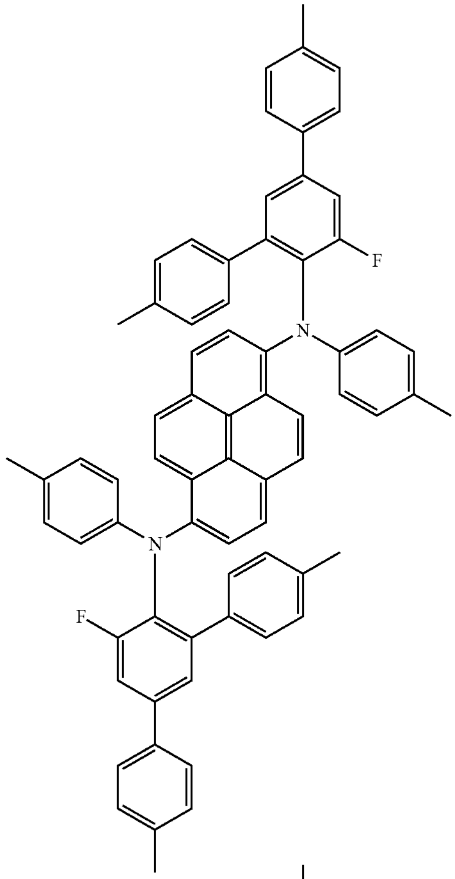
A-226
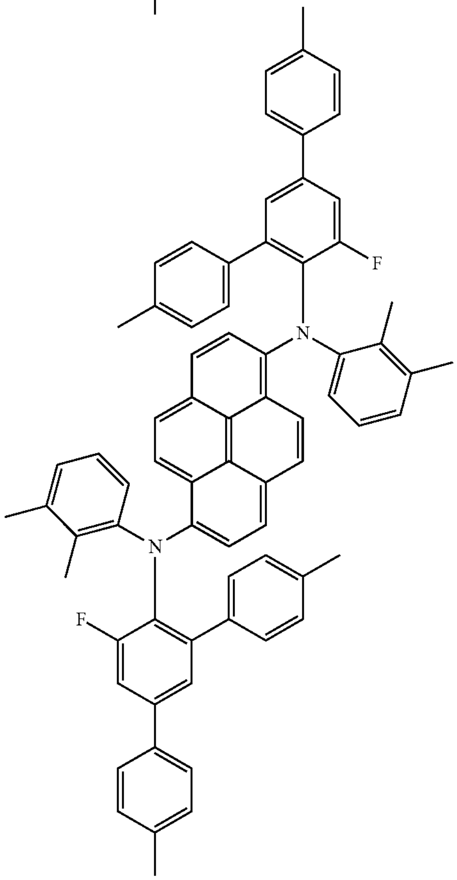
-continued
A-227
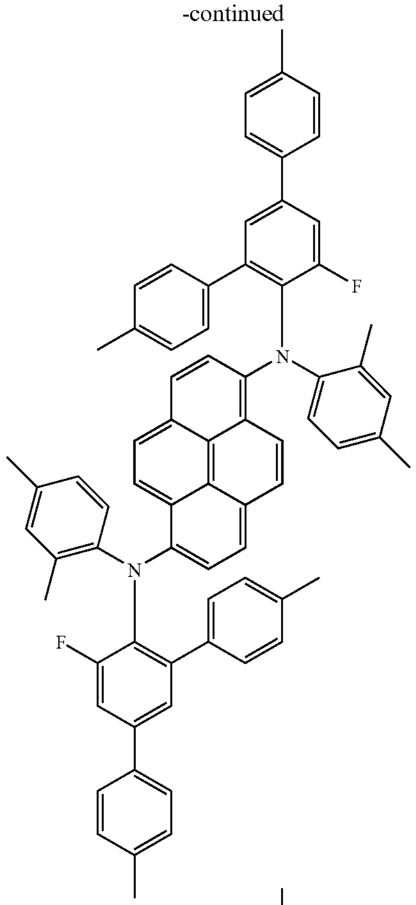
A-228
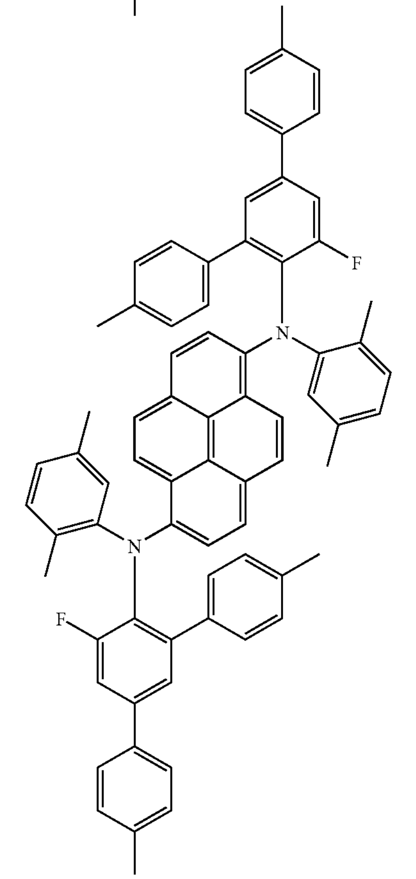

-continued
A-229
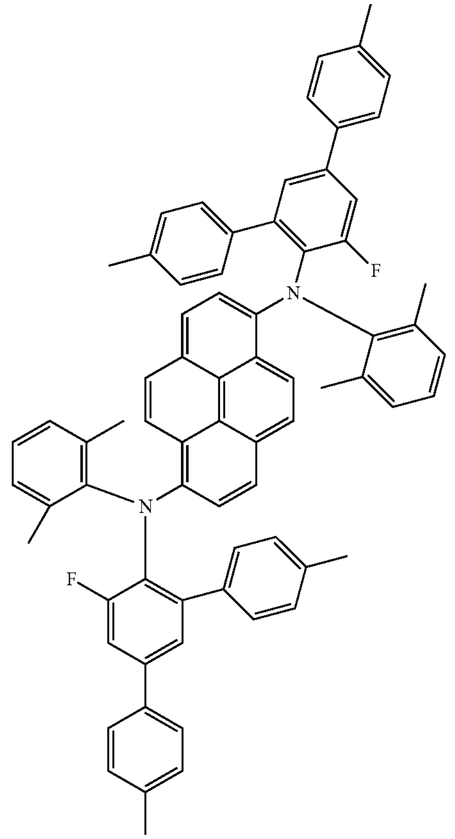
A-230
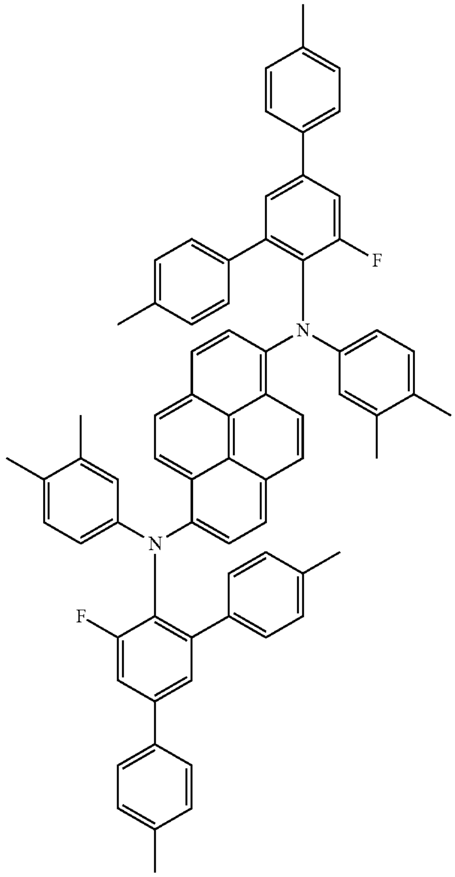
-continued
A-231
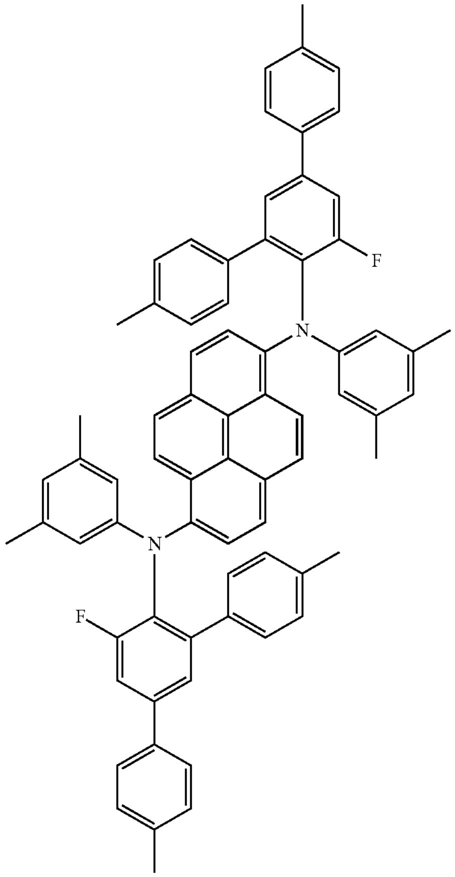
A-232
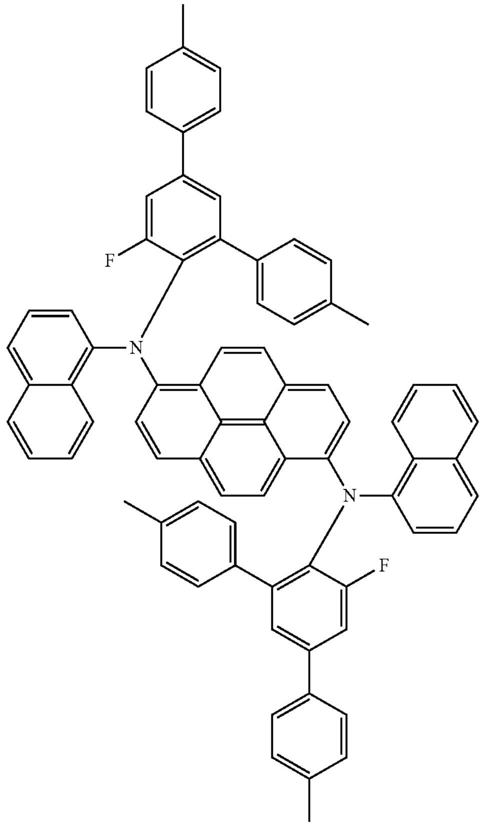

-continued
A-233
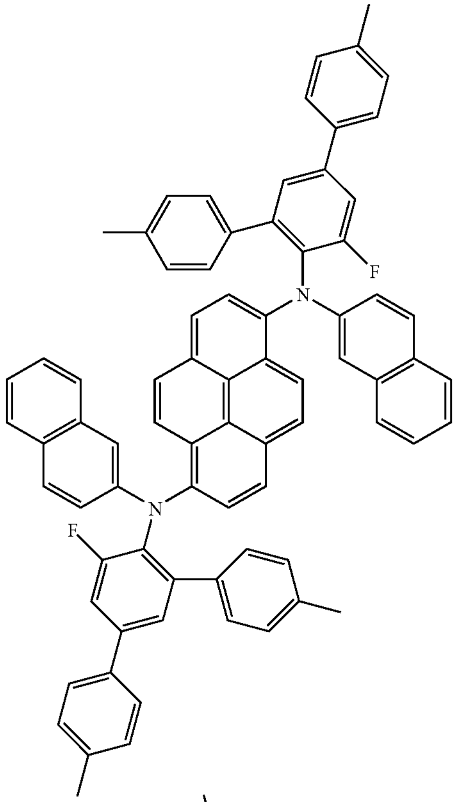
A-234
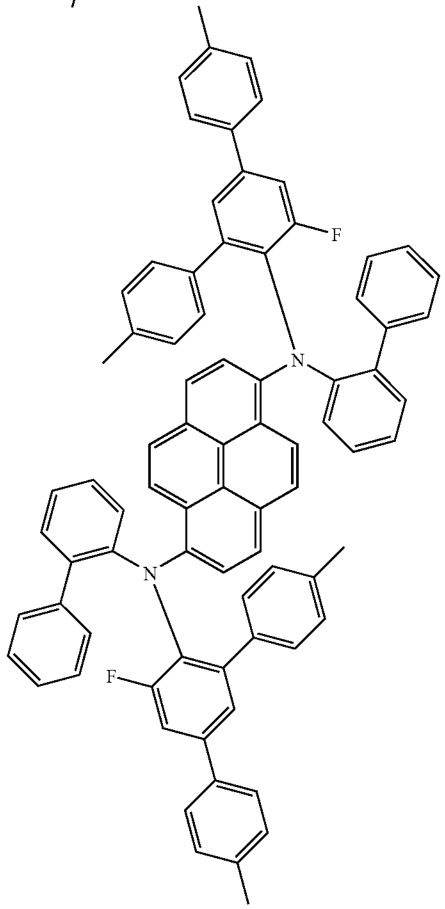
-continued
A-235
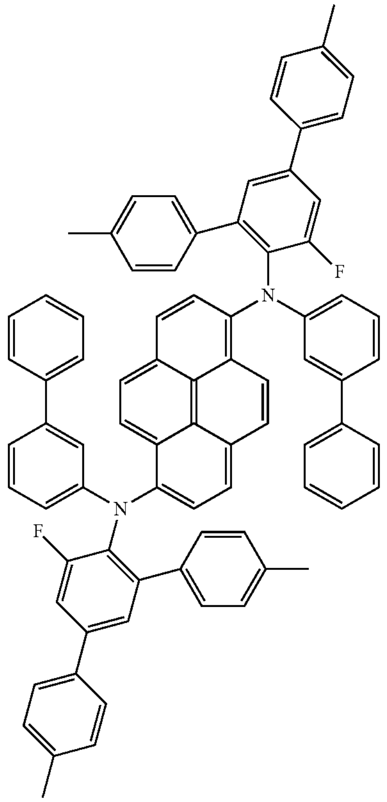
A-236
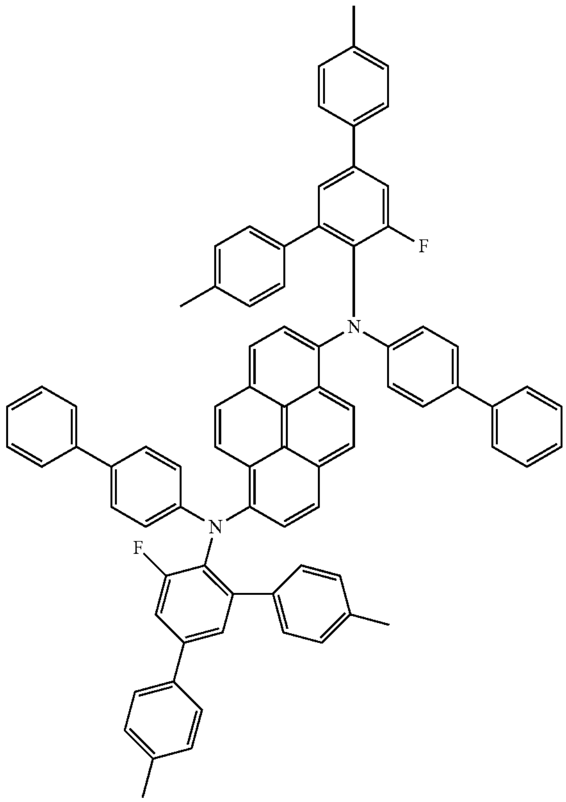

-continued
A-237
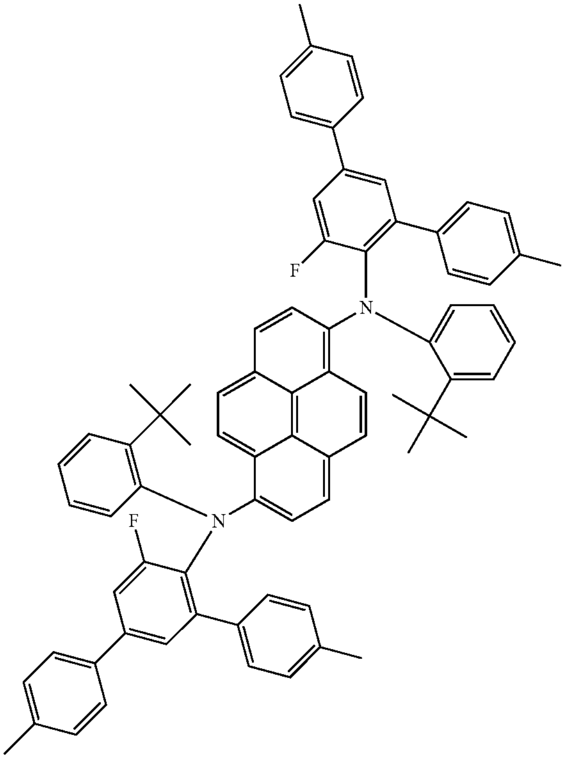
A-238
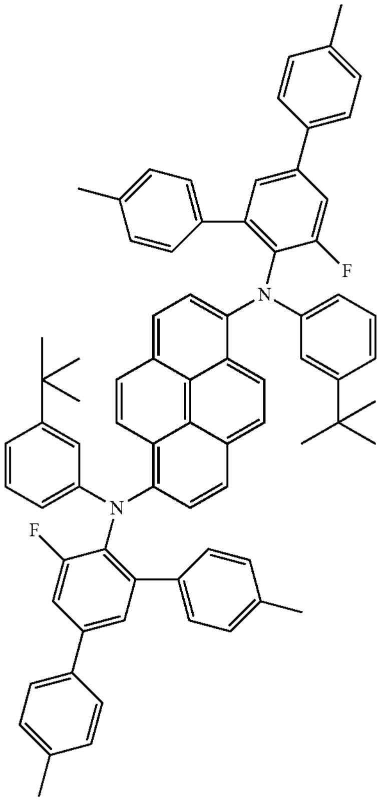
-continued
A-239
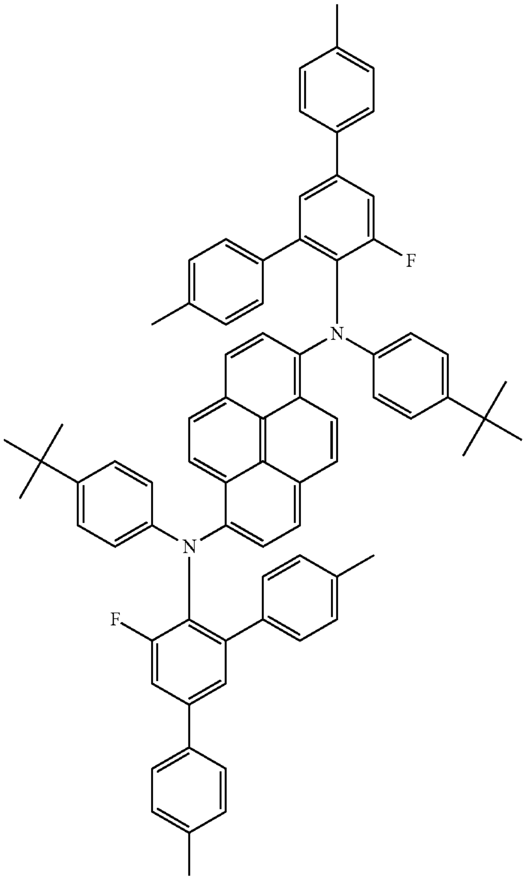

-continued
A-240
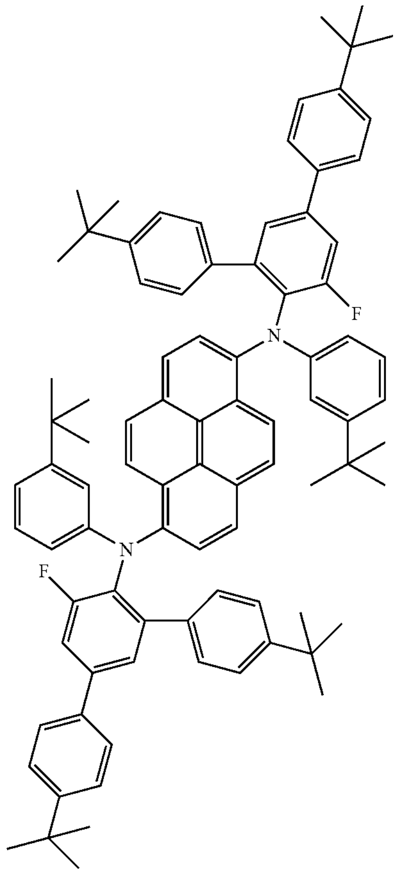
-continued
A-241
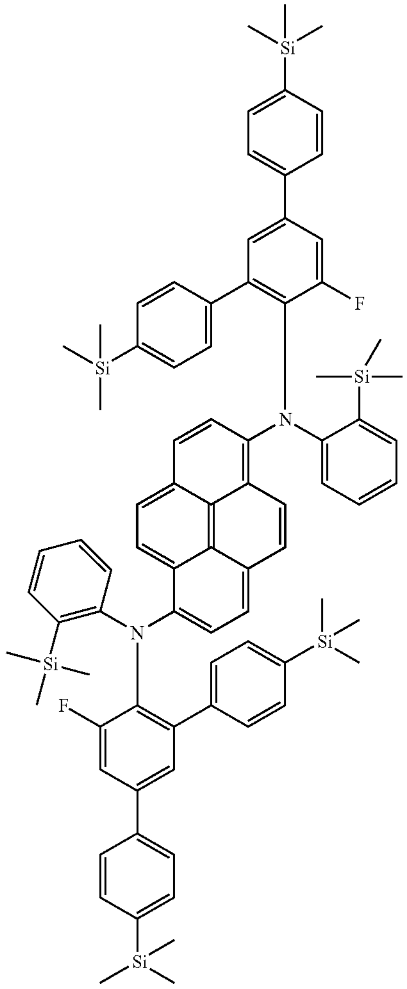

-continued
A-242
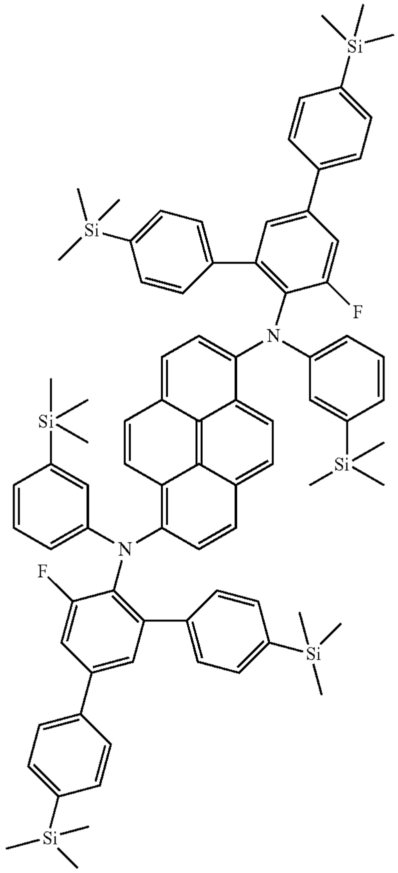
-continued
A-243
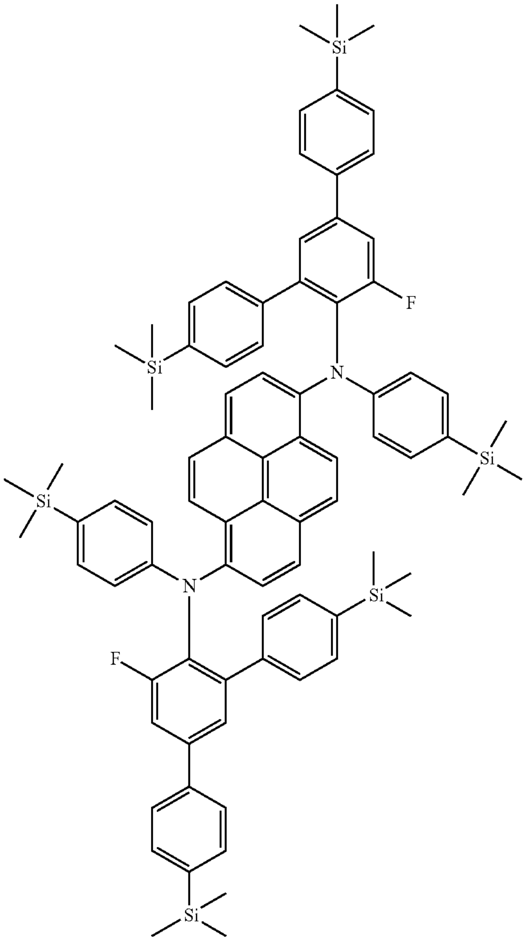

-continued
A-244
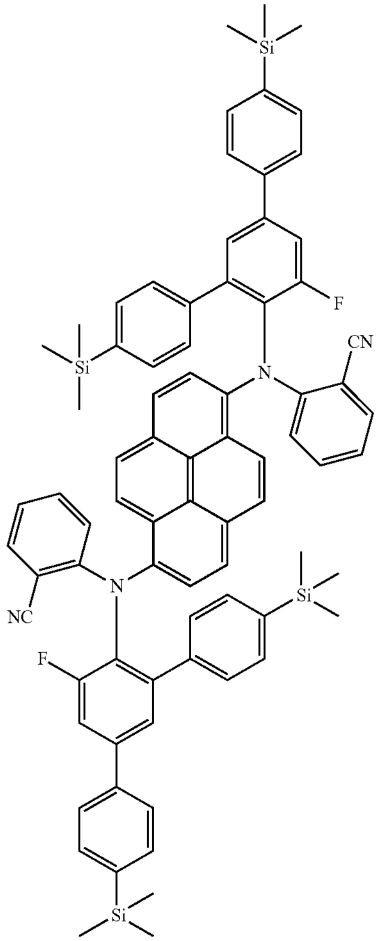
-continued
A-245
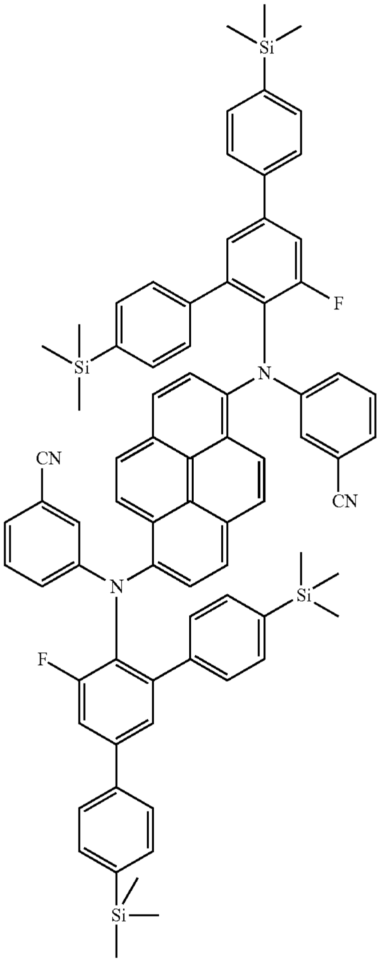

-continued
A-246
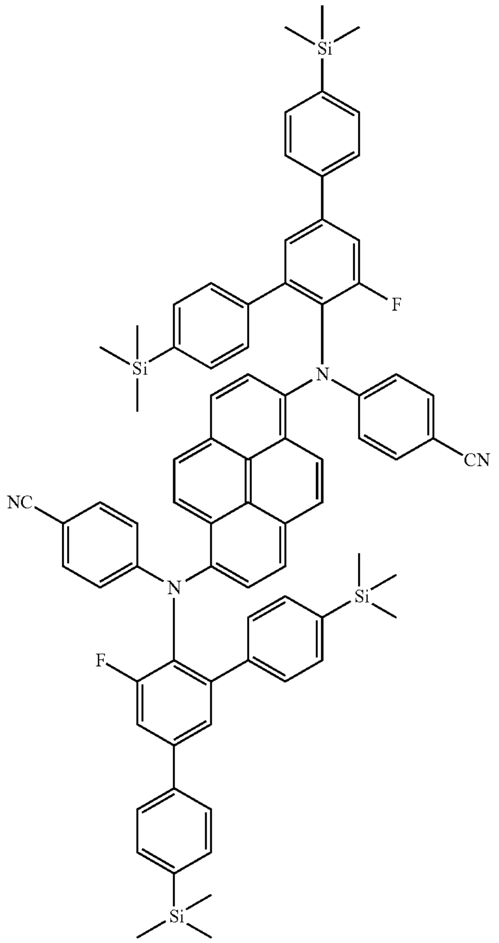
-continued
A-247
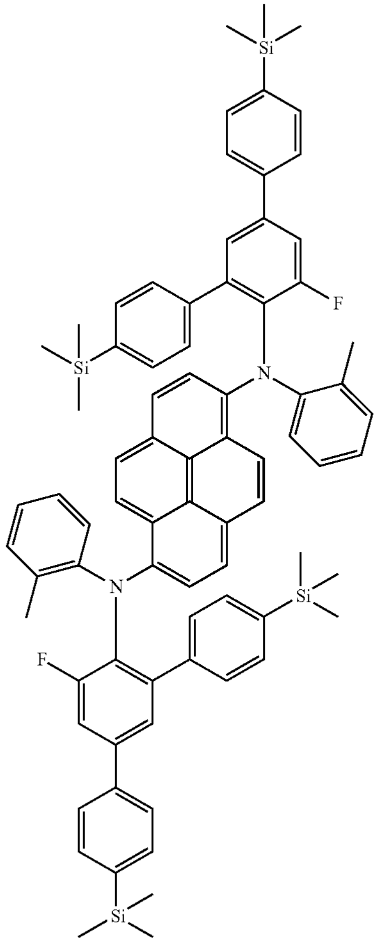

-continued
A-248
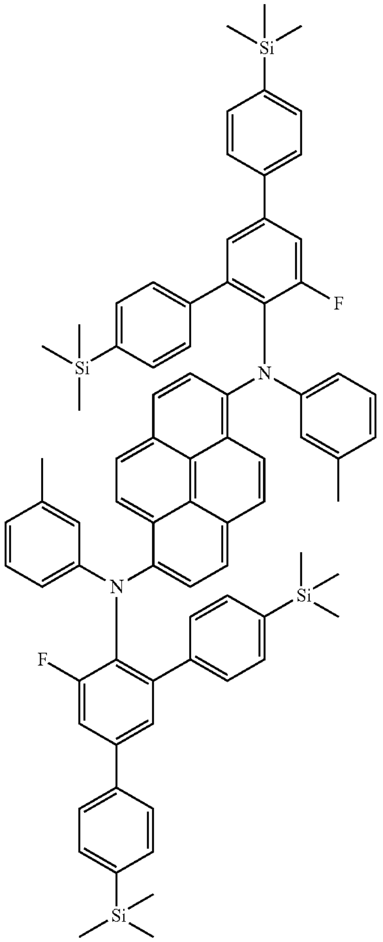
-continued
A-249
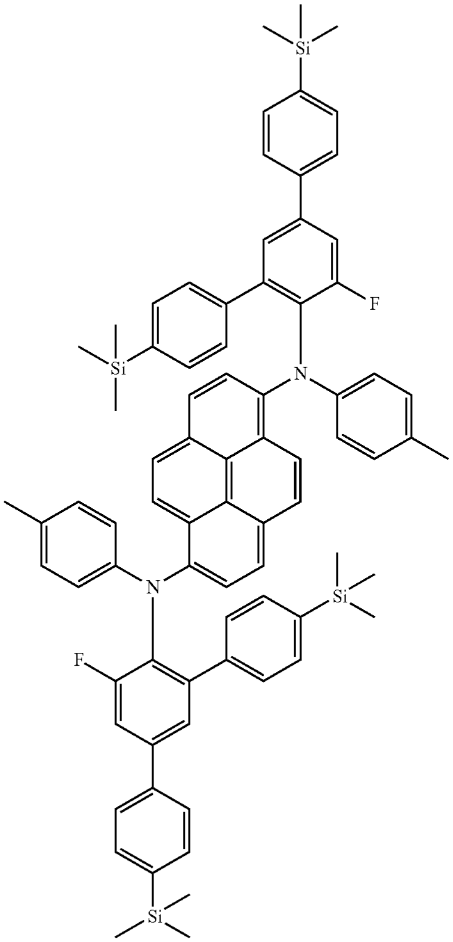

-continued
A-250
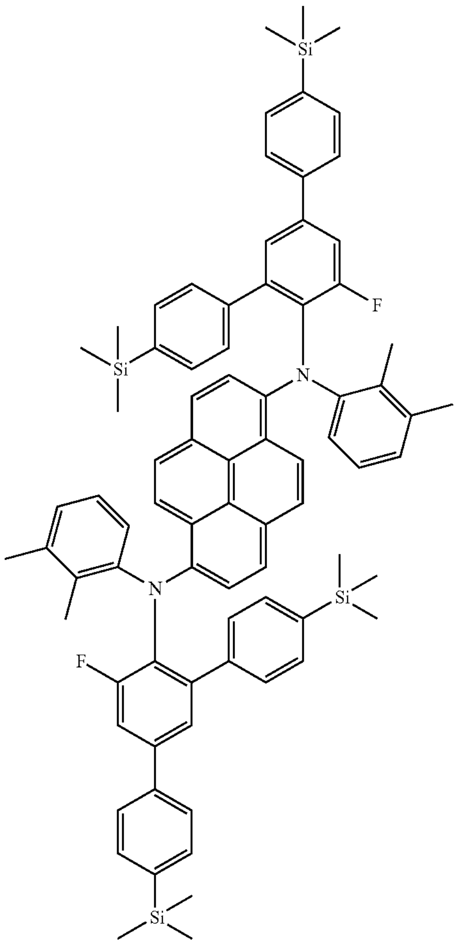
-continued
A-251
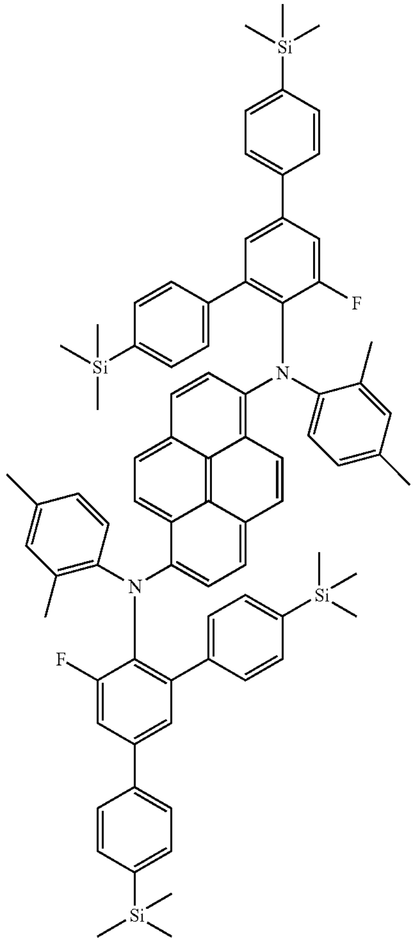

-continued
A-252
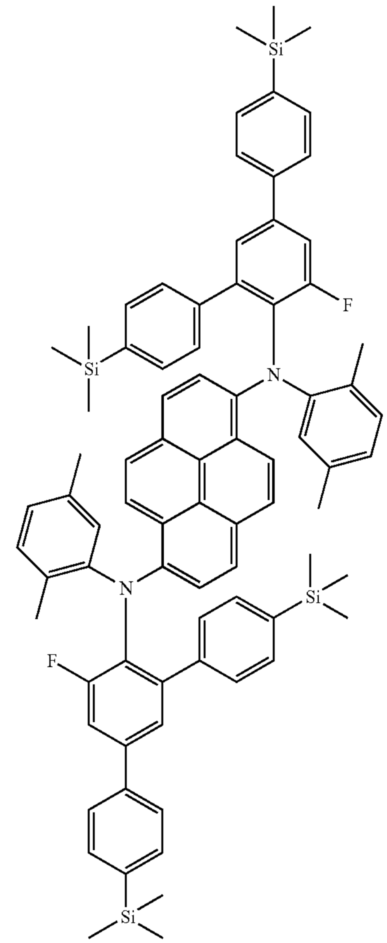
-continued
A-253
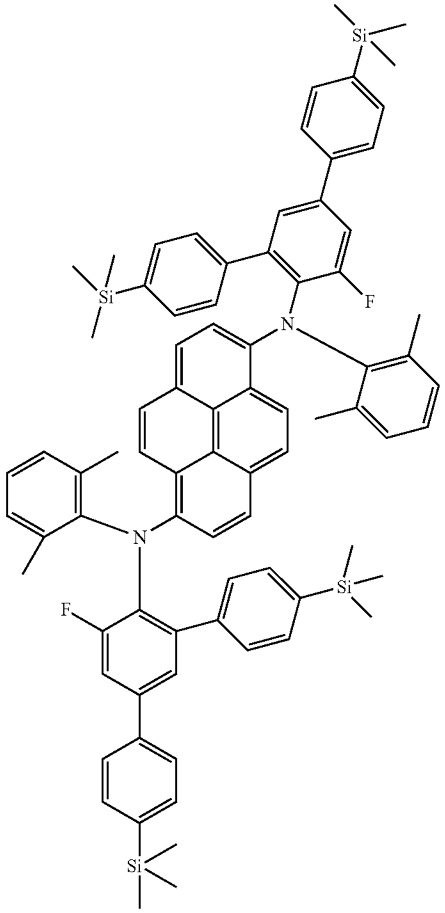

-continued
A-254
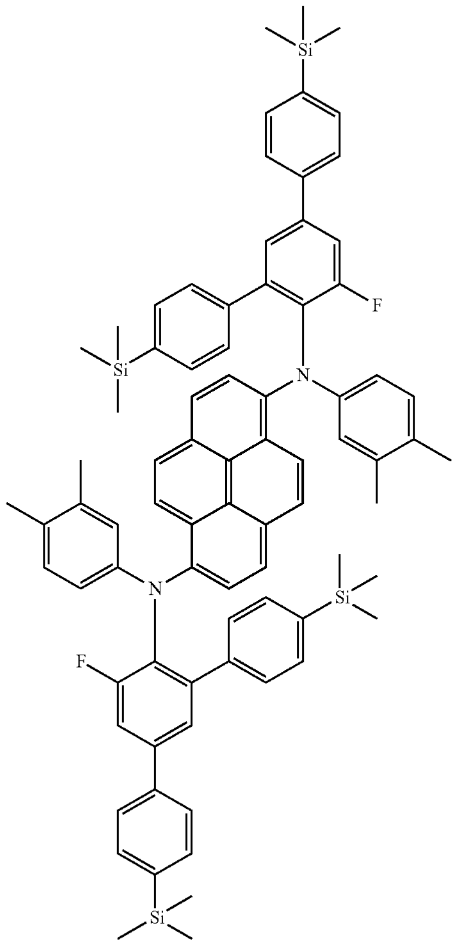
-continued
A-255
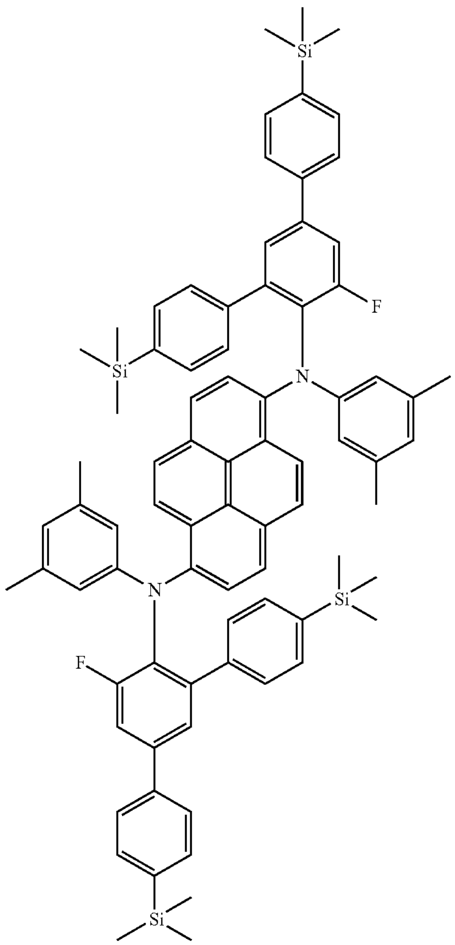

-continued
A-256
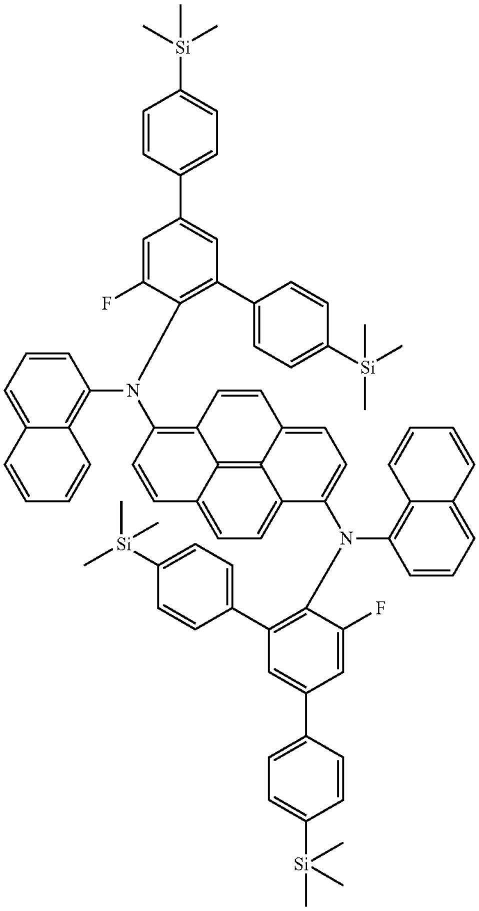
-continued
A-257
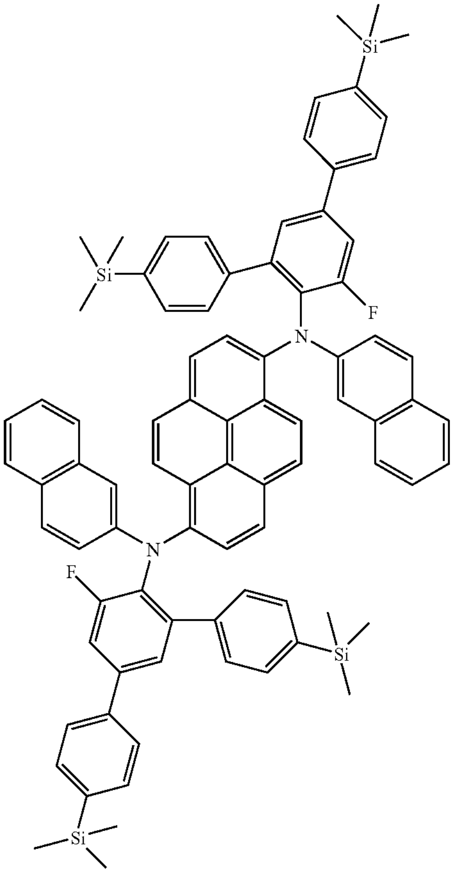

-continued
A-258
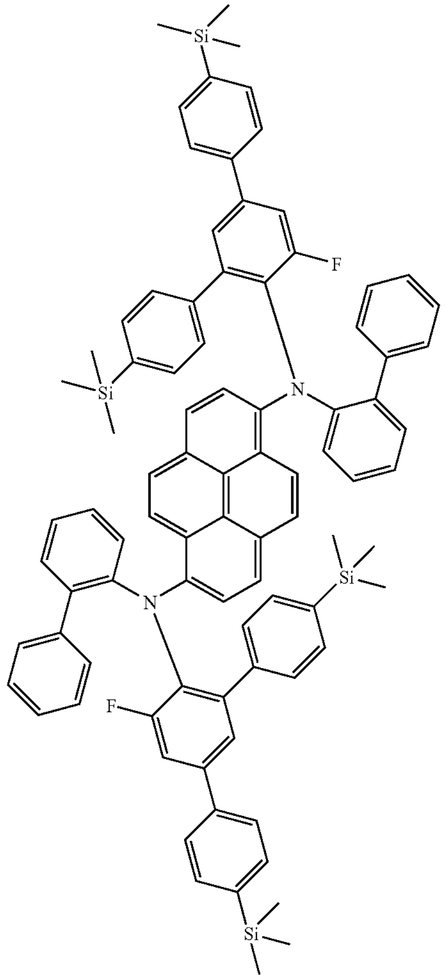
-continued
A-259
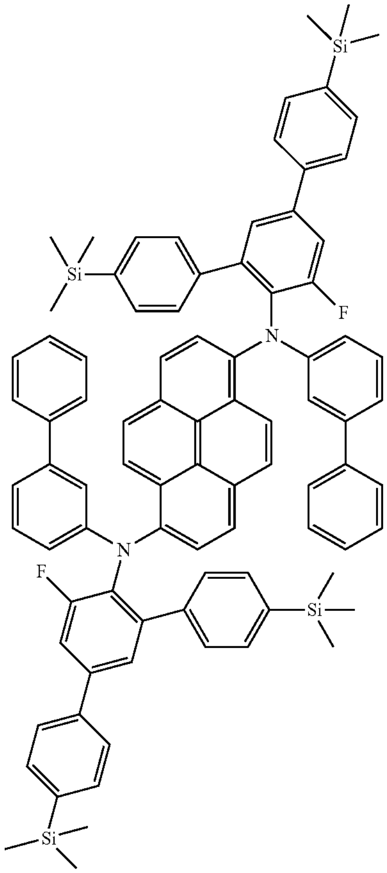

-continued
A-260
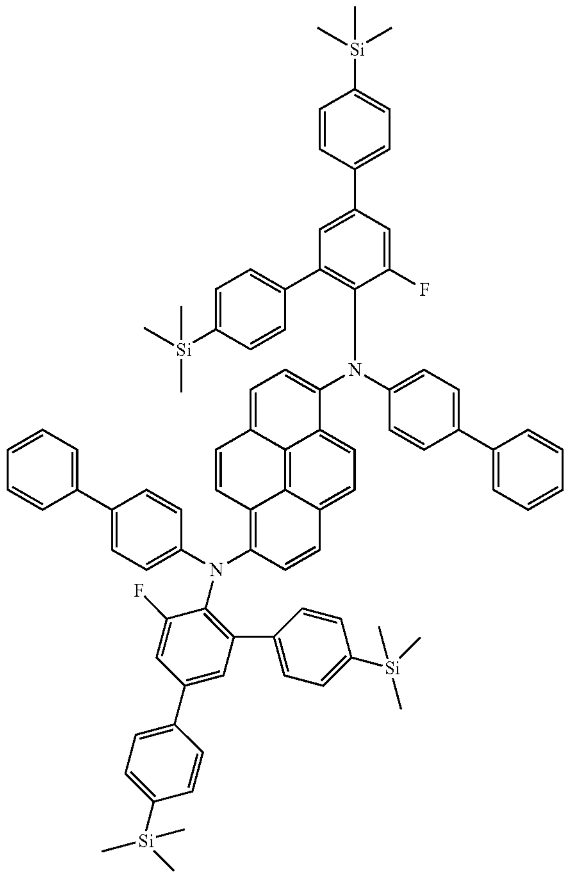
A-261
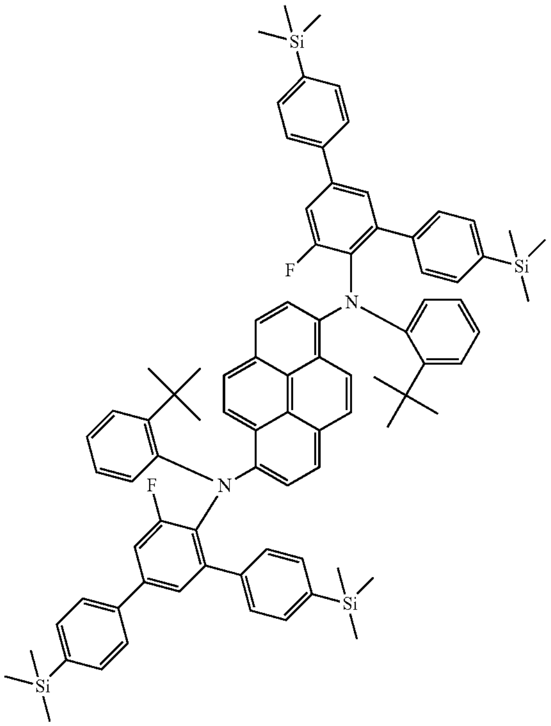
-continued
A-262
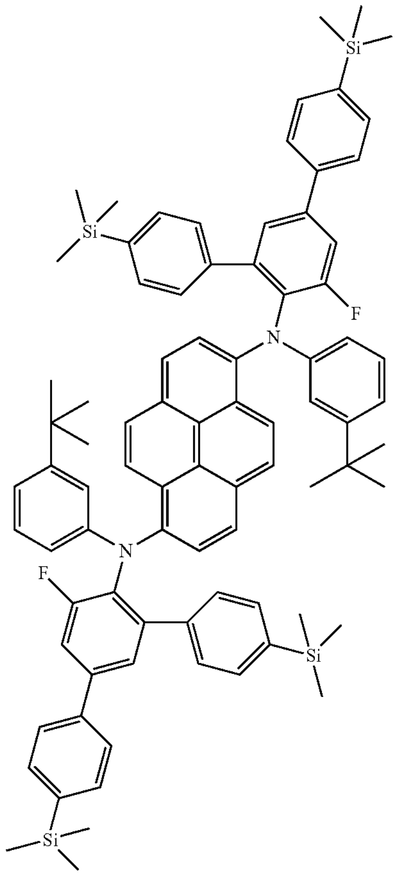

-continued
A-263
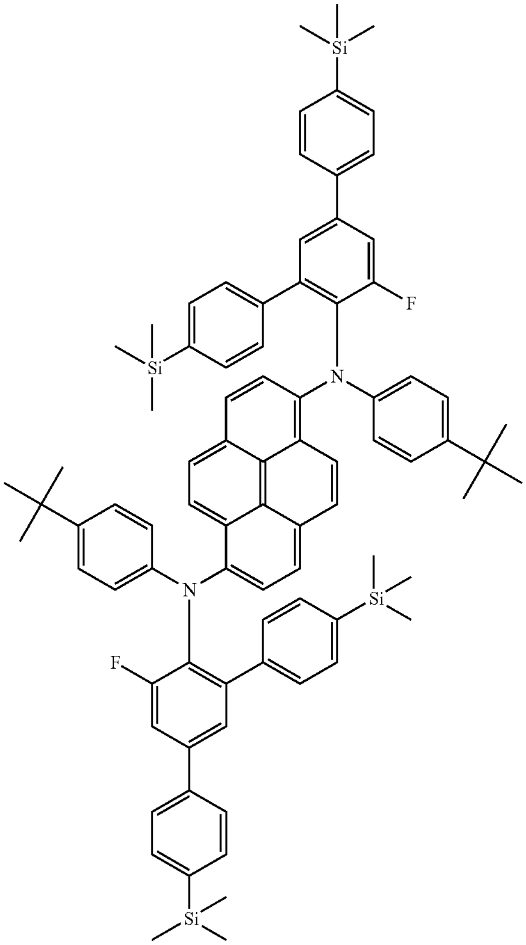
-continued
A-264
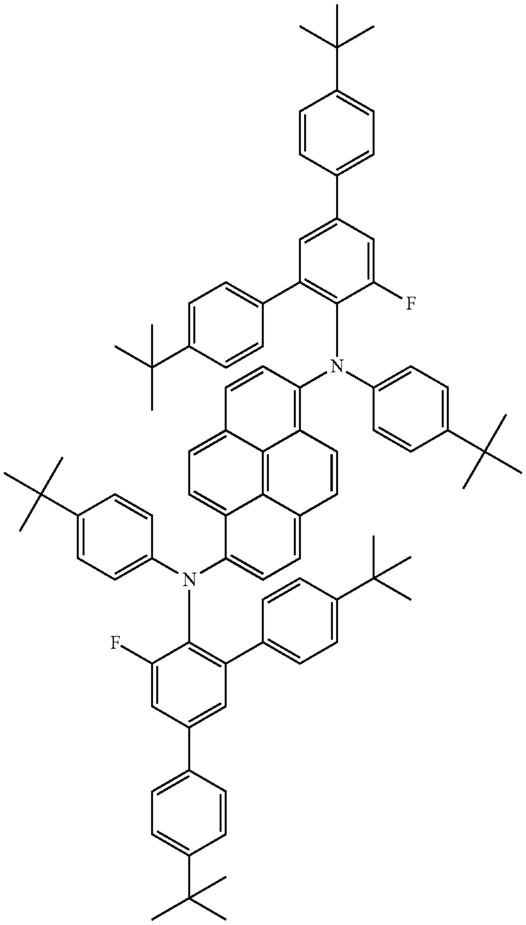

-continued
A-265
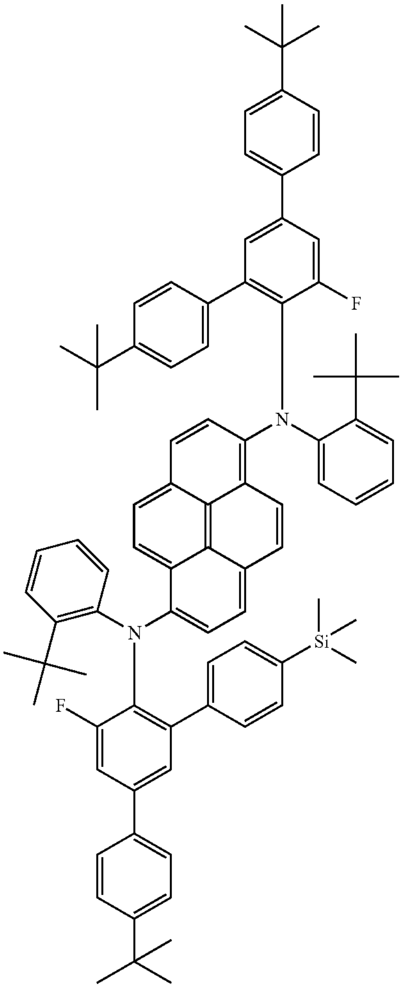
-continued
A-266
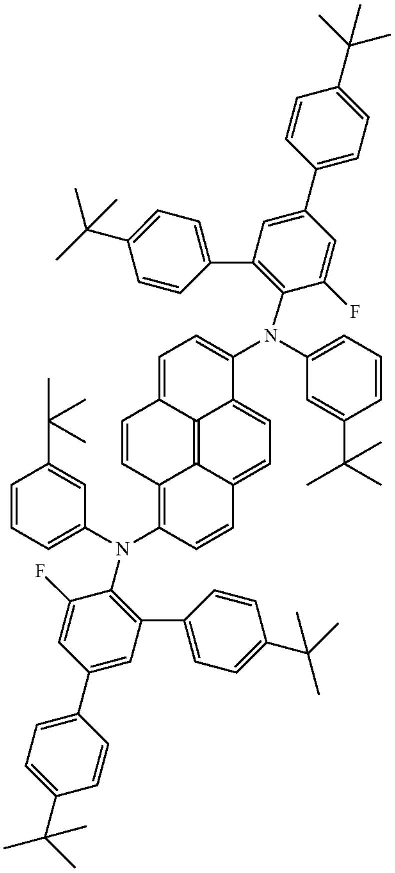

-continued
A-267
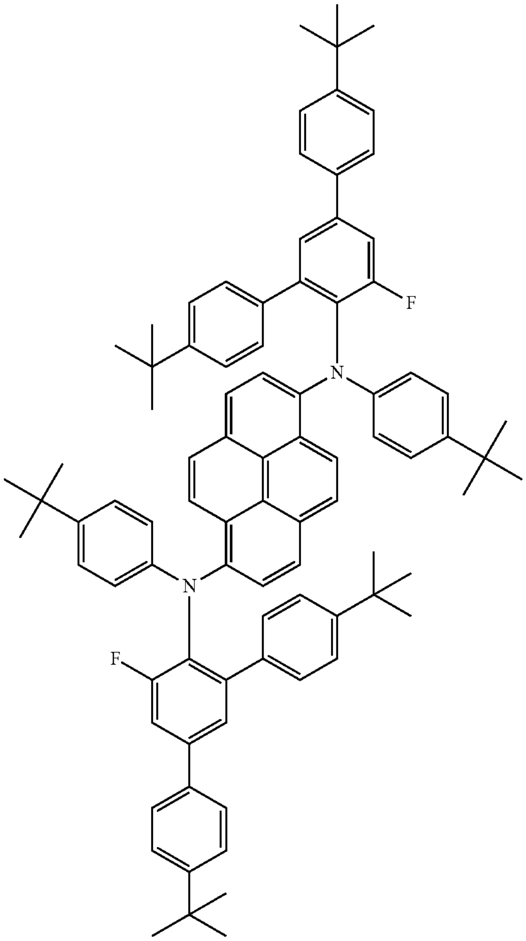
-continued
A-268
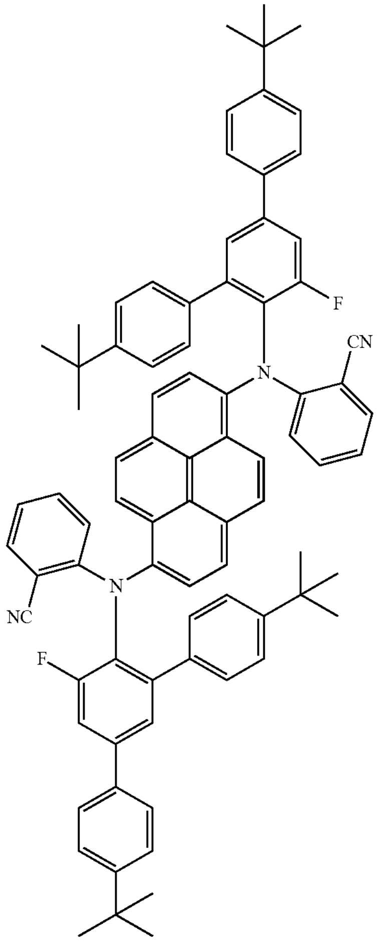

-continued
A-269
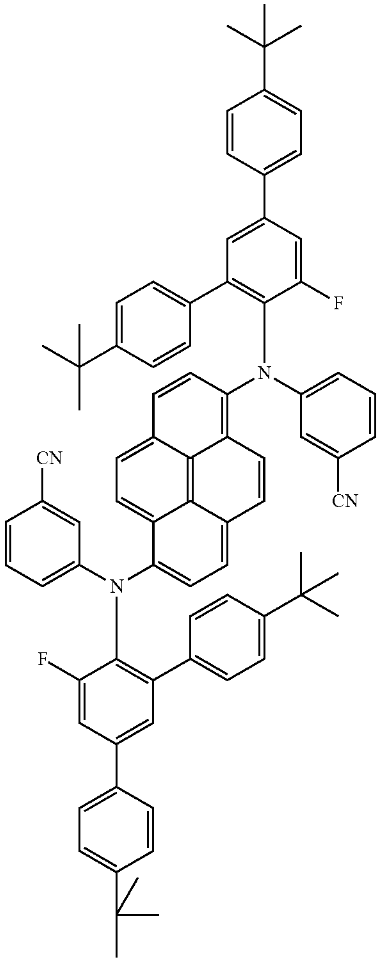
-continued
A-270
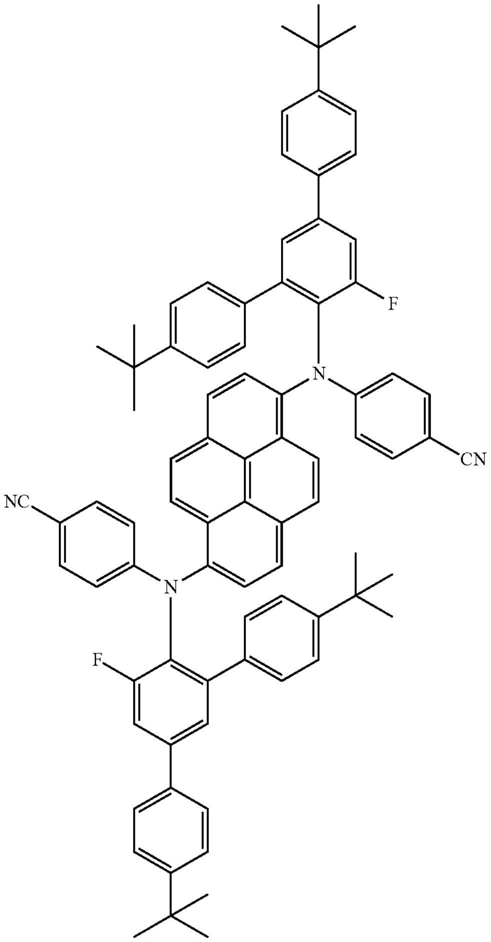

-continued
A-271
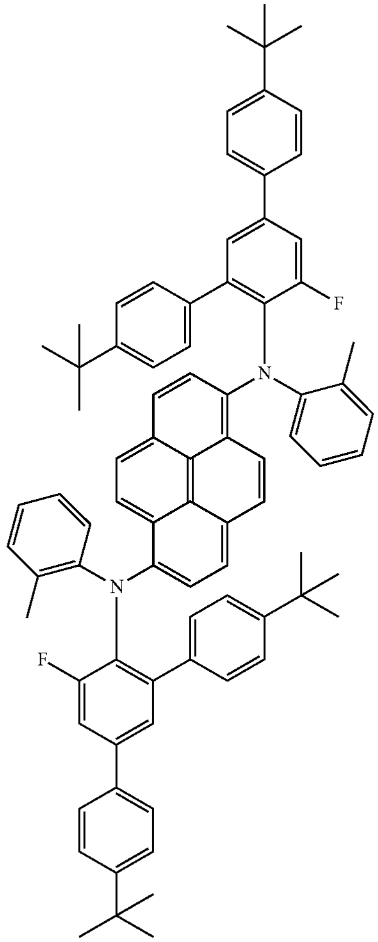
-continued
A-272
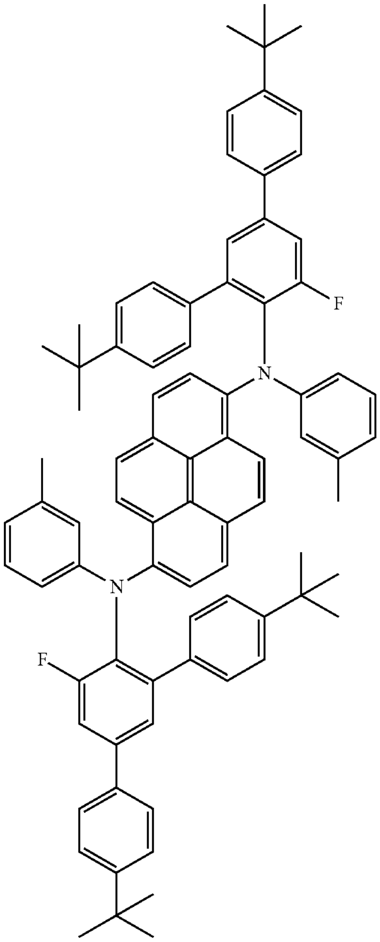

-continued
A-273
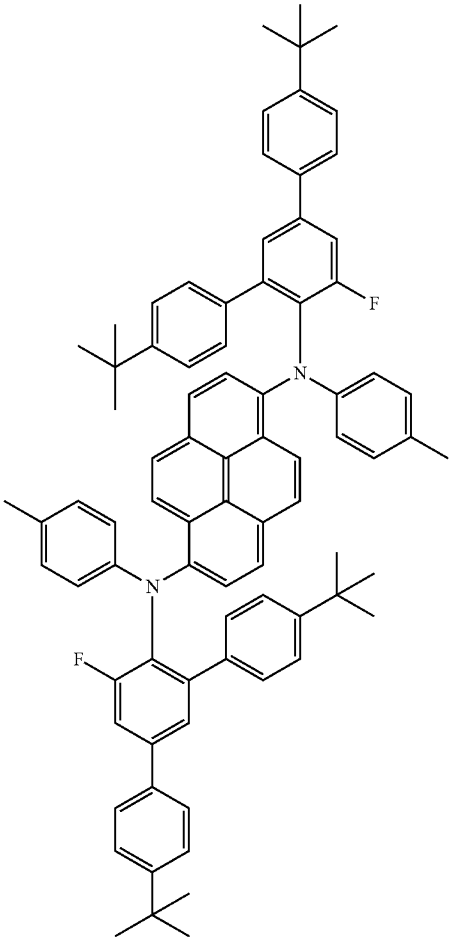
-continued
A-274
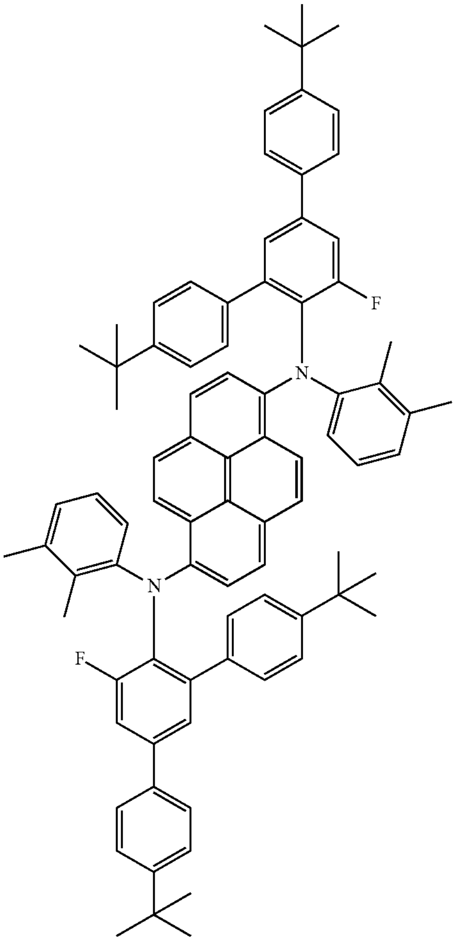

-continued
A-275
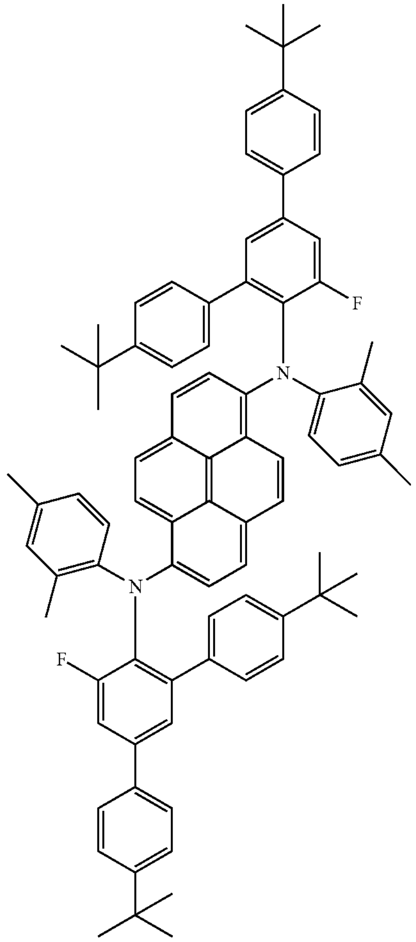
-continued
A-276
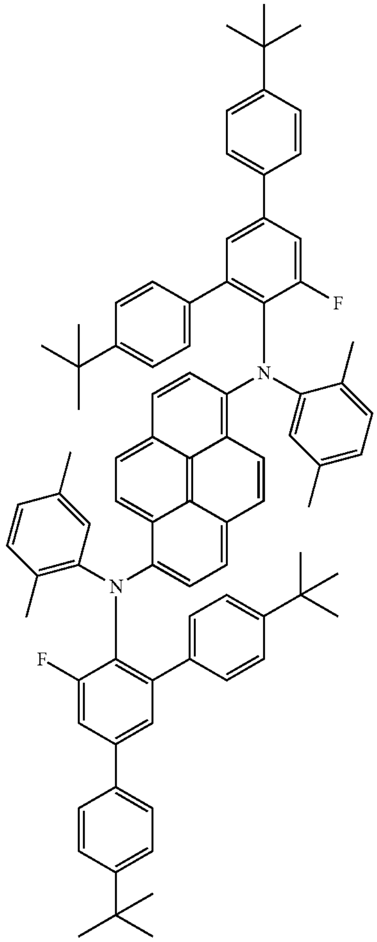

-continued
A-277
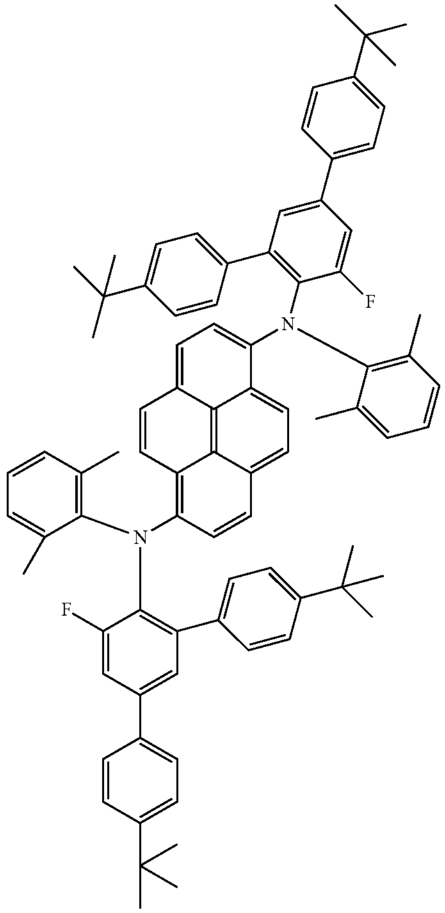
-continued
A-278
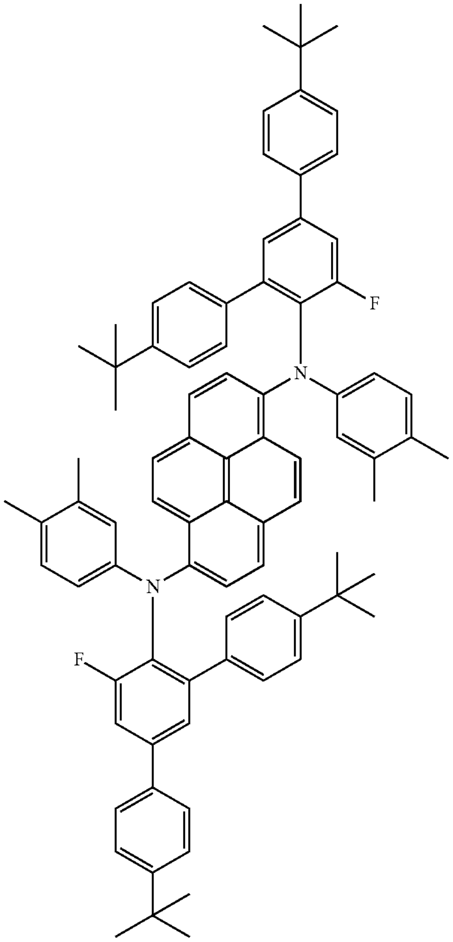

-continued
A-279
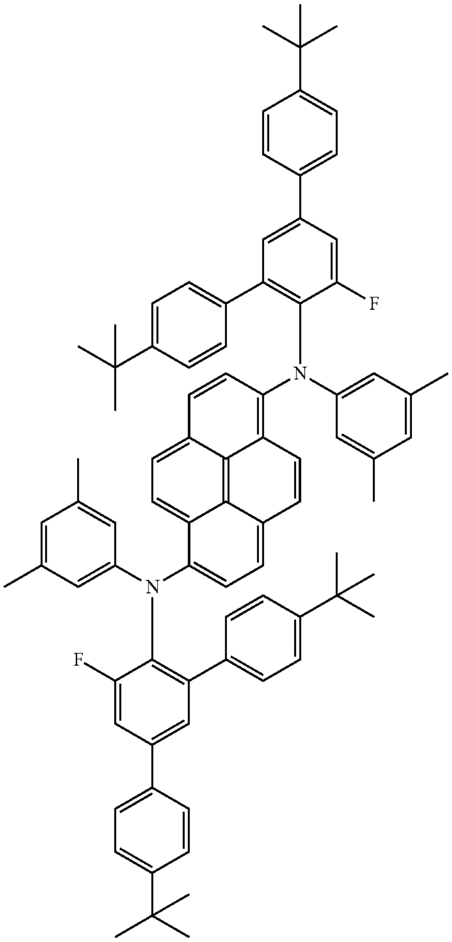
-continued
A-280
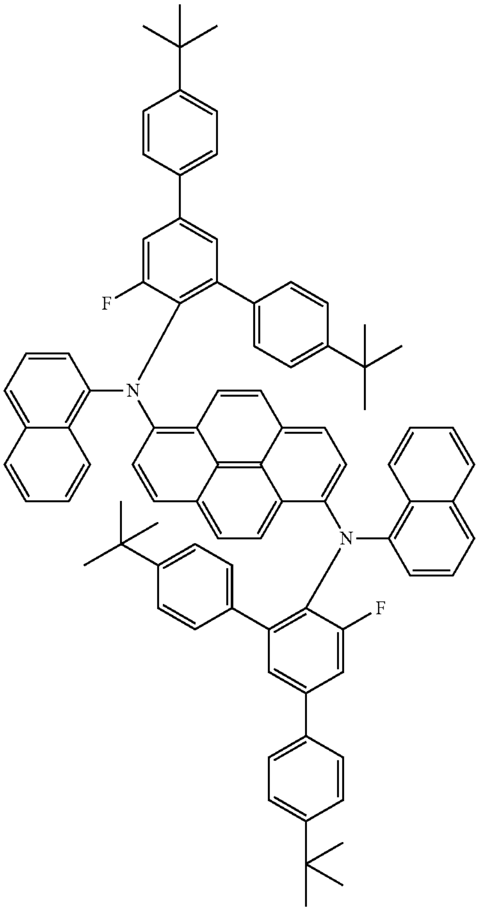

-continued
A-281
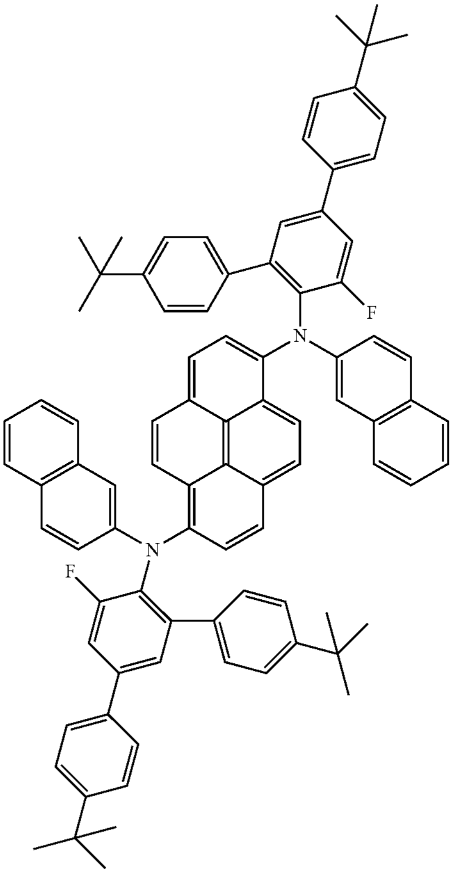
-continued
A-282
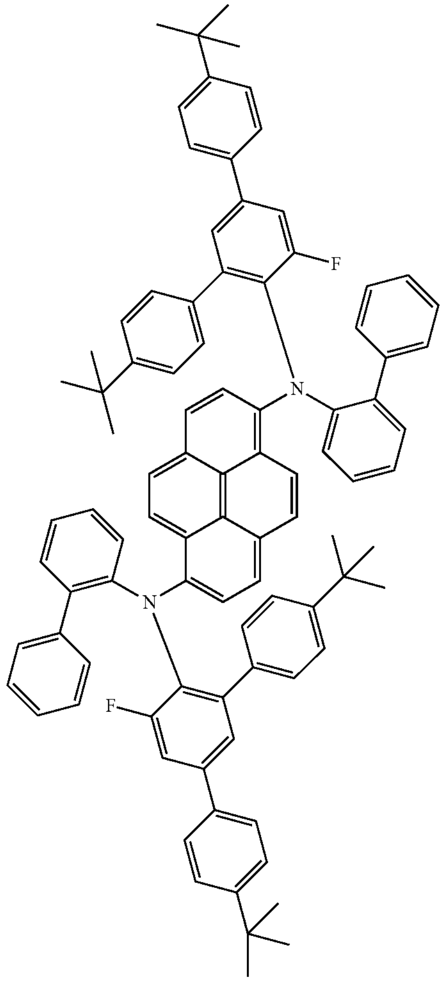
A synthesis example of the blue fluorescent compound marked by A-97 in the above Formula 3 is explained. The A-97 blue fluorescent compound is $N^1$,$N^6$-bis(2,4-diphenyl-6-fluorophenyl)-$N^1$,$N^6$-diphenylpyrene-1,6-diamine.
1. Synthesis of 2,4-diphenyl-6-fluoroaniline
2,4-diphenyl-6-fluoroaniline is synthesized by following Reaction Formula 1.
[Reaction Formula 1]
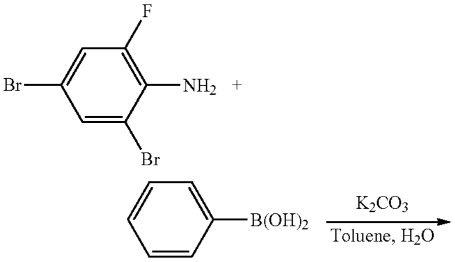

-continued

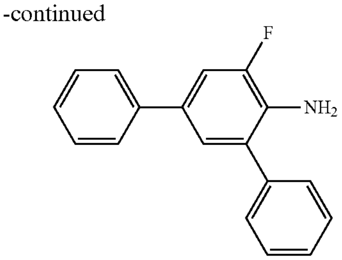

2,4-dibromo-6-fluoroaniline (10 mmol), benzeneboronic acid (24 mmol), tetrakis(triphenylphosphine)palladium(0) (1 mmol) and potassium carbonate (12 g) are put in a two-neck round-bottom flask and dissolved in toluene (30 mL) and $H_2O$ (10 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-diphenyl-6-fluoroaniline (2.1 g) is yielded.

2. Synthesis of 2,4-diphenyl-6-fluoro-N-phenylbenzenamine 2,4-diphenyl-6-fluoro-N-phenylbenzenamine is synthesized by following Reaction Formula 2.

[Reaction Formula 2]

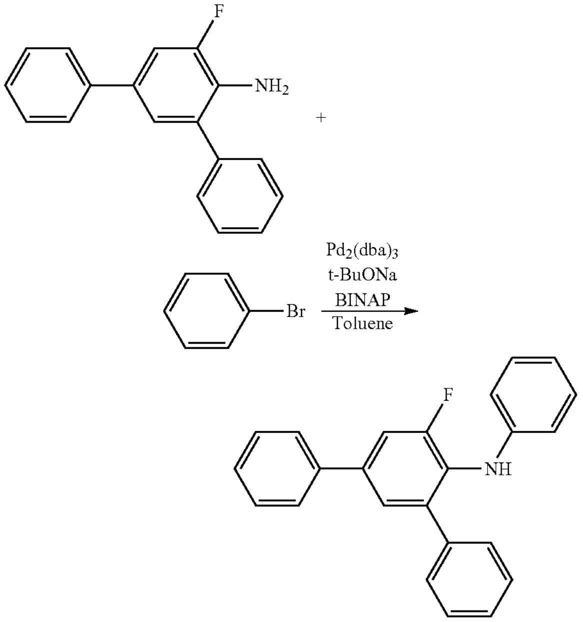

2,4-diphenyl-6-fluoroaniline (12 mmol), bromobenzene (10 mmol), tris(dibenzylideneacetone)dipalladium(0) (0.15 mmol), (±)-2,2'-bis(diphenylphosphine)-1,1'-binaphthalene (0.3 mmol) and sodium tert-butoxie (14 mmol) are put in a two-neck round-bottom flask and dissolved in toluene (30 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-diphenyl-6-fluoro-N-phenylbenzenamine (2.5 g) is yielded.

3. Synthesis of $N^1$,$N^6$-bis(2,4-diphenyl-6-fluorophenyl)-$N^1$,$N^6$-diphenylpyrene-1,6-diamine $N^1$,$N^6$-bis(2,4-diphenyl-6-fluorophenyl)-$N^1$,$N^6$-diphenylpyrene-1,6-diamine is synthesized by following Reaction Formula 3.

[Reaction Formula 3]

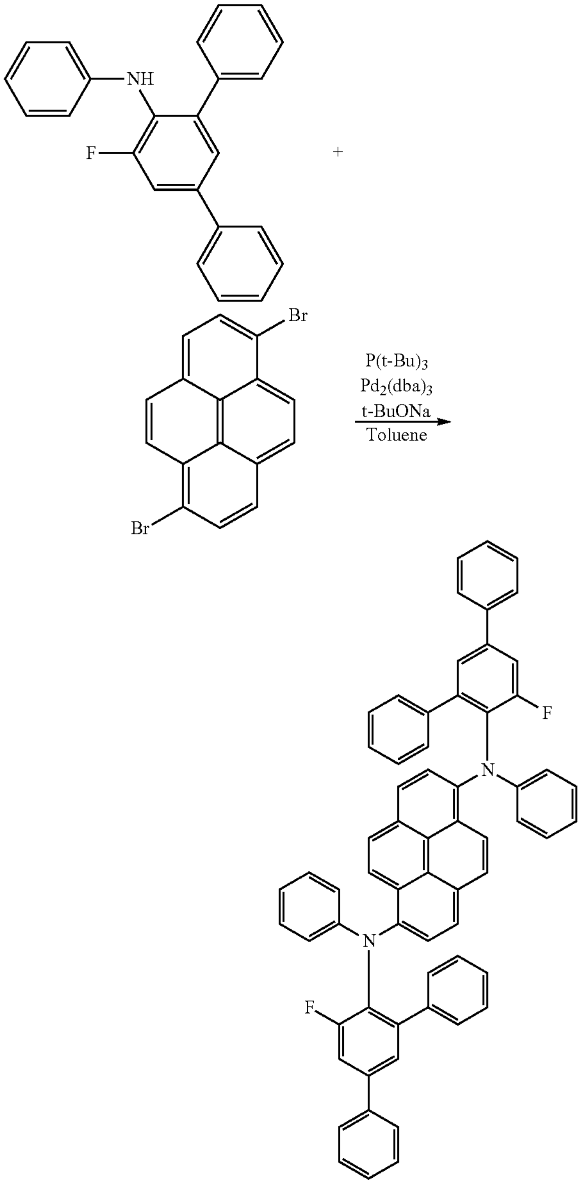

2,4-diphenyl-6-fluoro-N-phenylbenzenamine (6 mmol), 1,6-dibromopyrene (5 mmol), tris(dibenzylideneacetone)dipalladium(0) (0.075 mmol), tri-tert-butylphosphine (0.15 mmol) and sodium tert-butoxie (7 mmol) are put in a two-neck round-bottom flask and dissolved in toluene (15 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, after re-crystallizing and filtering with dichloromethane and acetone, and then being thermally refined to yield $N^1$,$N^6$-bis(2,4-diphenyl-6-fluorophenyl)-$N^1$, $N^6$-diphenylpyrene-1,6-diamine is yielded.

Hereinafter, a detailed description will be made of preferred examples associated with the OELD according to the present invention. More specifically, the examples relate to an OELD including an emission material layer which uses the blue fluorescent compound of Formula 2 as a dopant.

EXAMPLES

Example 1

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), 4,4'-bis[N-(1-naphtyl)-N-phenylamino]-biphenyl (NPD) (about 400 angstroms), an emitting layer (about 200 angstroms) including DPVBi as a host and a compound represented by A-97 in the above Formula 3 as a dopant (about 5 weight %), Alq3 (about 350 angstroms), fluorolithium (LiF) (about 5 angstroms) and aluminum (Al) (about 1000 angstroms) are sequentially formed on the ITO layer such that an OELD is fabricated.

The OELD produces a brightness of 606 $cd/m^2$ at an electric current of 10 mA and a voltage of 4.36 V. At this time, the X index and Y index of CIE color coordinates are 0.136 and 0.142, respectively.

Example 2

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ ton. CuPC (about 200 angstroms), NPD (about 400 angstroms), an emitting layer (about 200 angstroms) including DPVBi as a host and a compound represented by A-147 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 618 $cd/m^2$ at an electric current of 10 mA and a voltage of 4.45 V. At this time, the X index and Y index of CIE color coordinates are 0.135 and 0.133, respectively.

Example 3

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and a compound represented by A-164 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 683 $cd/m^2$ at an electric current of 10 mA and a voltage of 4.46 V. At this time, the X index and Y index of CIE color coordinates are 0.131 and 0.157, respectively.

Example 4

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and a compound represented by A-171 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 583 $cd/m^2$ at an electric current of 10 mA and a voltage of 4.49 V. At this time, the X index and Y index of CIE color coordinates are 0.137 and 0.136, respectively.

Example 5

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and a compound represented by A-257 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 641 $cd/m^2$ at an electric current of 10 mA and a voltage of 4.54 V. At this time, the X index and Y index of CIE color coordinates are 0.137 and 0.176, respectively.

Comparative Example 1

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and BD-a represented by the above Formula 1-3 as a dopant (about 1 weight %), Alq3 (about 350 angstroms), LiF (about 5 angstroms) and Al (about 1000 angstroms) are sequentially formed on the ITO layer such that an OELD is fabricated.

The OELD produces a brightness of 526 $cd/m^2$ at an electric current of 10 mA and a voltage of 6.7 V. At this time, the X index and Y index of CIE color coordinates are 0.136 and 0.188, respectively.

Herein, CuPC and DPVBi are respectively represented by the above Formulas 1-1 and 1-2. NPD and Alq3 are represented by following Formulas 4-1 and 4-2, respectively.

[Formula 4-1]

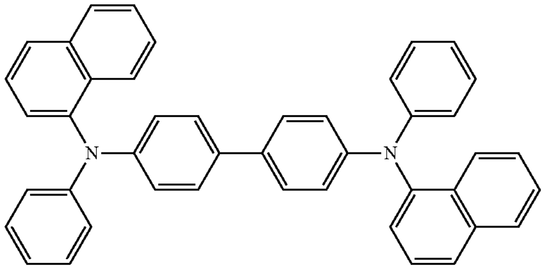

[Formula 4-2]

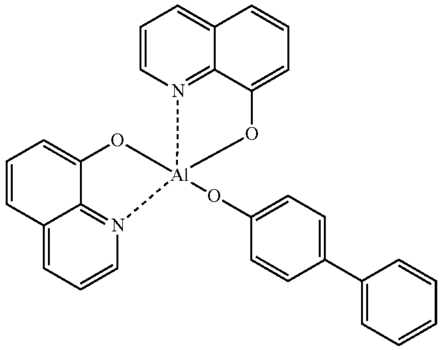

The OELD fabricated in Examples 1 to 5 and Comparative Example 1 is evaluated for efficiency, brightness, and so on. A voltage has a dimension of [V], an electric current has a dimension of [mA], and a brightness has a dimension of [cd/m2. The evaluated results are shown in Table 1.

TABLE 1

| | voltage | Electric current | Brightness | CIE(X) | CIE(Y) |
|---|---|---|---|---|---|
| Ex. 1 | 4.36 | 10 | 606 | 0.136 | 0.142 |
| Ex. 2 | 4.45 | 10 | 618 | 0.135 | 0.133 |
| Ex. 3 | 4.46 | 10 | 683 | 0.131 | 0.157 |
| Ex. 4 | 4.49 | 10 | 583 | 0.137 | 0.136 |
| Ex. 5 | 4.54 | 10 | 641 | 0.137 | 0.176 |
| Com. Ex. 1 | 6.7 | 10 | 526 | 0.136 | 0.188 |

As shown in Table 1, the OELD in Examples 1 to 5 has high color purity and low driving voltage such that power consumption for the OELD is reduced. As a result, a lifetime of the OELD using the blue fluorescent compound according to the present invention is improved.

-Second Embodiment-

A blue fluorescent compound according to the second embodiment of the present invention includes 1,6-pyrene and 6-fluorophenylamine derivative. Namely, each of 1 and 6 positions of pyrene are substituted by 6-fluorophenylamine derivative. In addition, at least one of at 2 to 5 positions of 6-fluorophenylamine derivative and one position of nitrogen (N) of 6-fluorophenylamine derivative is substituted by aromatic group including deuterium (D). Furthermore, at least two of 2 to 5 positions of 6-fluorophenylamine derivative are substituted by one of hydrogen (H), substituted or non-substituted aromatic group, or substituted or non-substituted heterocyclic group. Moreover, one position of nitrogen (N) of 6-fluorophenylamine derivative is substituted by one substituted or non-substituted aromatic group, and substituted or non-substituted heterocyclic group.

The blue fluorescent compound according to the second embodiment of the present invention is represented by following Formula 5.

[Formula 5]

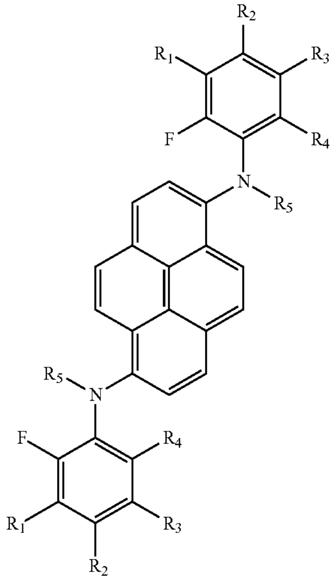

In the above Formula 5, at least one of R1, R2, R3, R4, and R5 is selected from aromatic group substituted by deuterium (D), and at least two of R1 to R4 is selected from hydrogen (H), substituted or non-substituted aromatic group, or substituted or non-substituted heterocyclic group. In addition, R5 is selected from substituted or non-substituted aromatic group or substituted or non-substituted heterocyclic group.

For example, each of R1 to R5 is one of aromatic group including phenyl, byphenyl, naphthyl, phenanthrene, terphenyl and fluorenyl and their substitution products. In addition, each of R1 to R5 is one of heterocyclic group including furan, thiophene, pyrrole, pyridine and pyrimidine and their substitution products. The aromatic group substituted by deuterium (D) may be deuterium(D)-substituted phenyl.

A substituent for aromatic group or heterocyclic group is selected from C1 to C6 alkyl group including methyl, ethyl, propyl, i-propyl, and t-butyl. Alternatively, the substituent may be cyano group, silyl group or fluorine.

Namely, in the second embodiment, two 6-fluorophenylamine derivatives, where at least one D-substituted aromatic, at least two substituents, such as H, substituted or non-substituted aromatic and substituted or non-substituted heterocyclic, and at least one substituent, such as substituted or non-substituted aromatic and substituted or non-substituted heterocyclic, are introduced, are symmetrically introduced at 1 and 6 position of pyrene such that the blue fluorescent compound has improved color purity and luminescent efficiency.

For example, the blue fluorescent compound represented by Formula 5 is one of compounds in following Formula 6. For convenience, B-1 to B-170 are respectively marked to compounds.

[Formula 6]
B-1
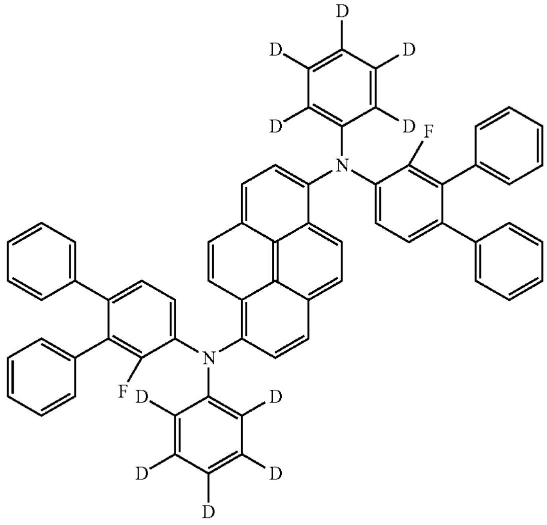
B-2
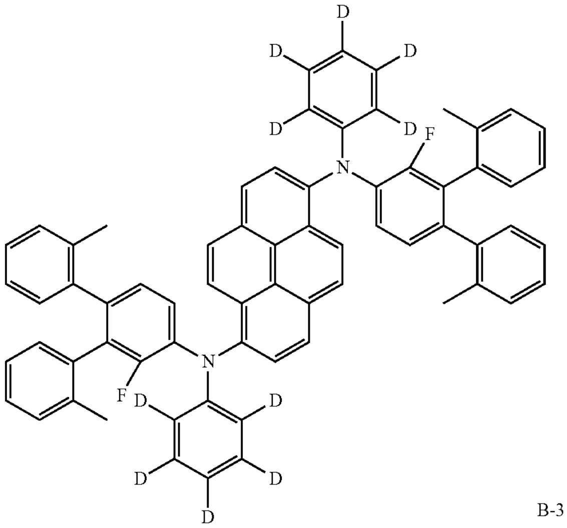
B-3
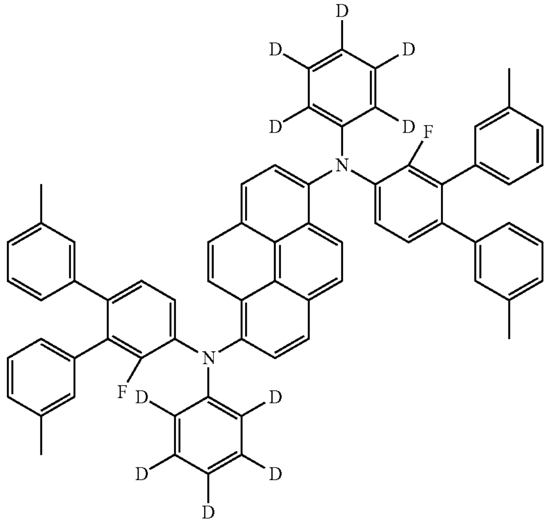
-continued
B-4
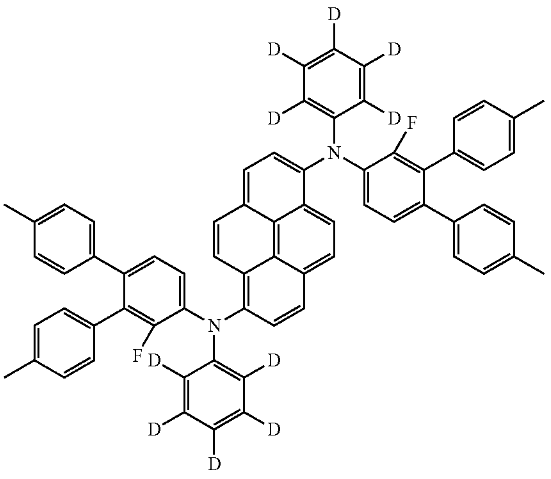
B-5
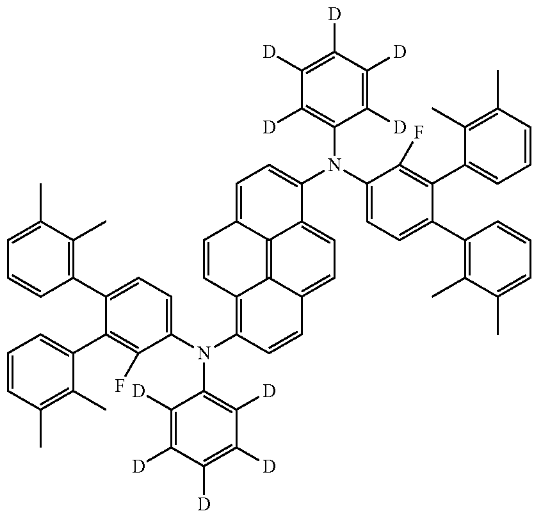
B-6
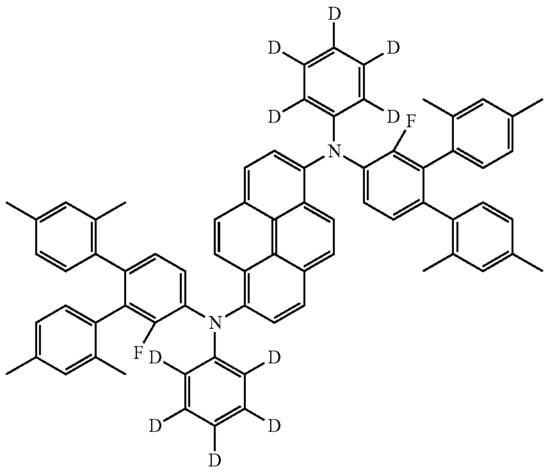

-continued
B-7
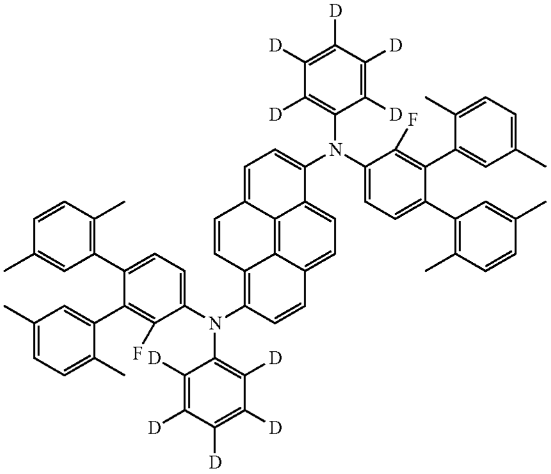
B-8
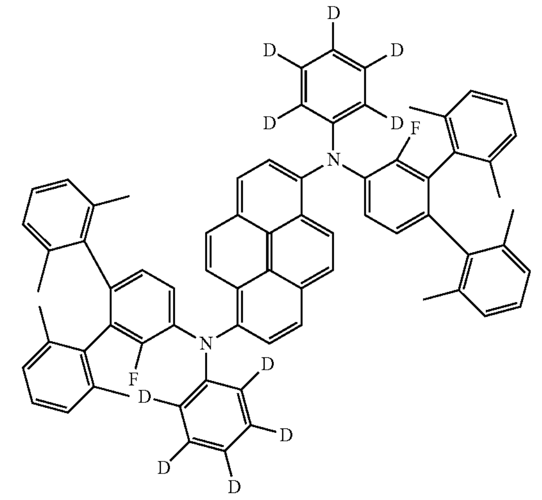
B-9
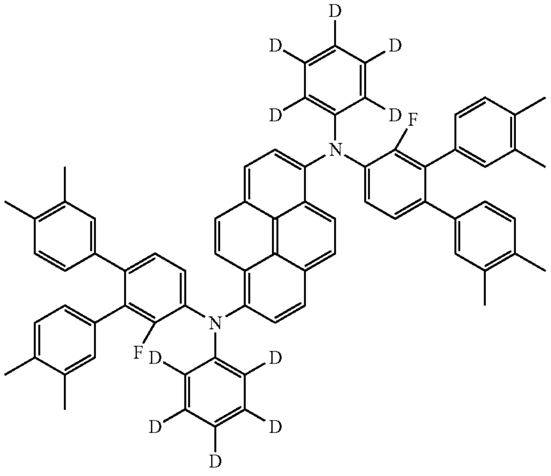
-continued
B-10
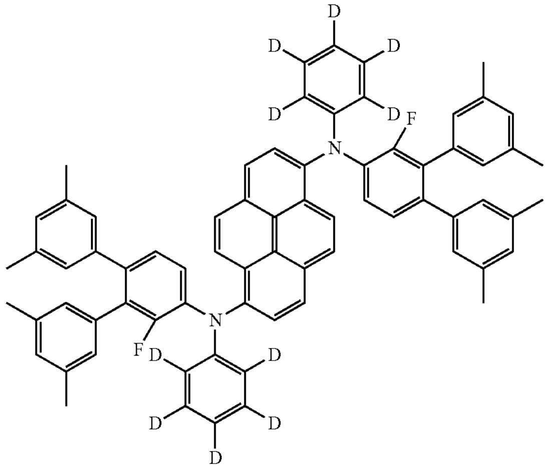
B-11
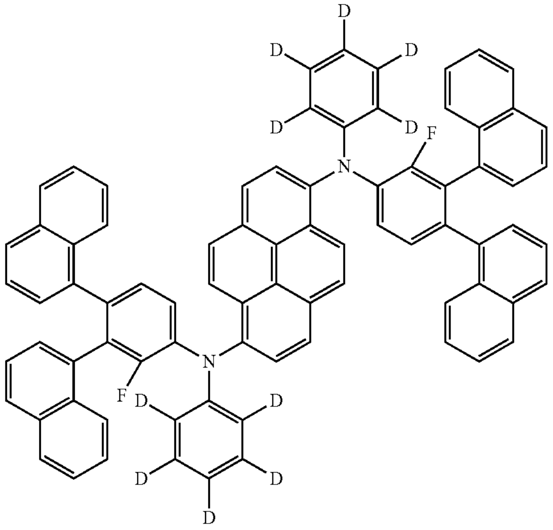
B-12
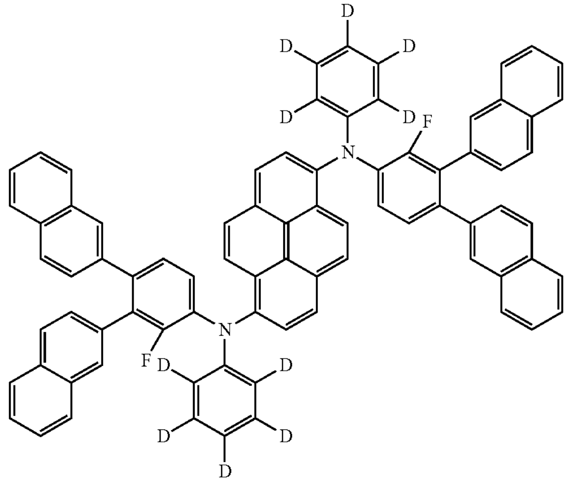

-continued
B-13
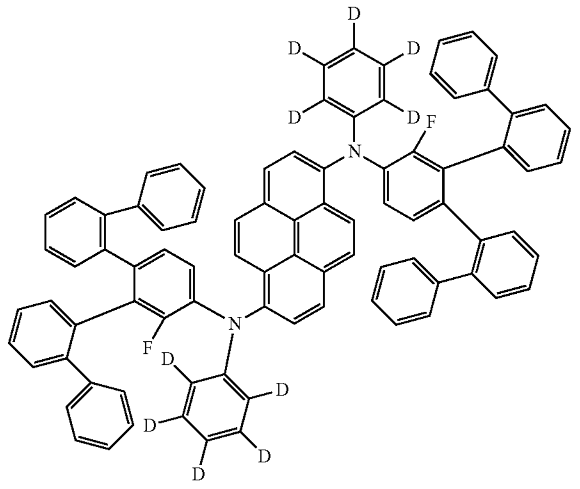
B-14
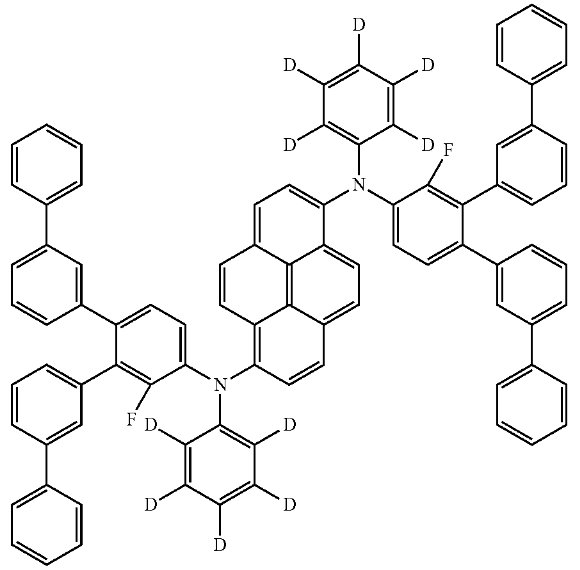
B-15
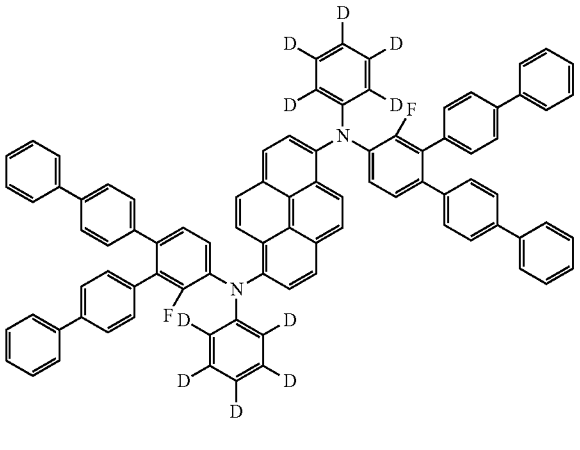
-continued
B-16
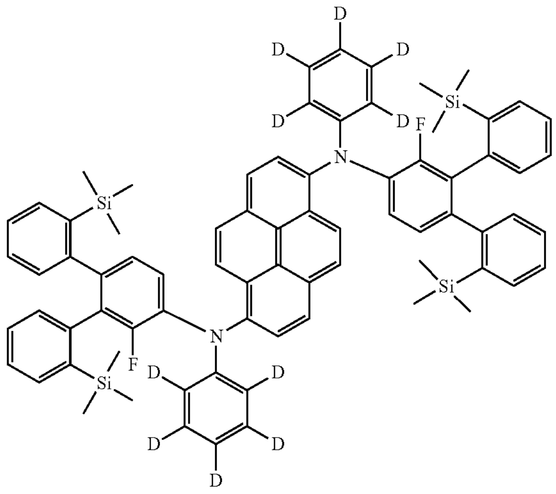
B-17
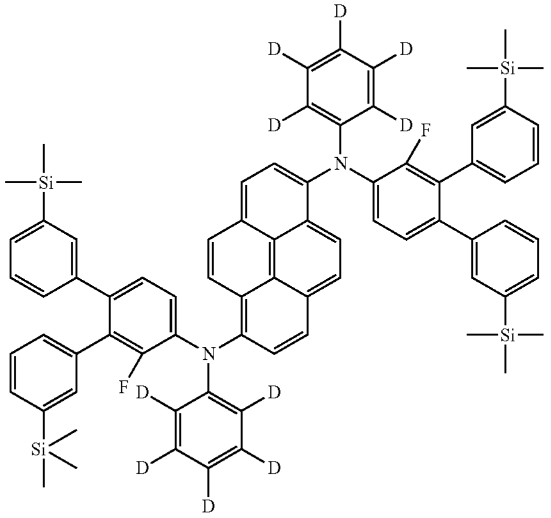
B-18
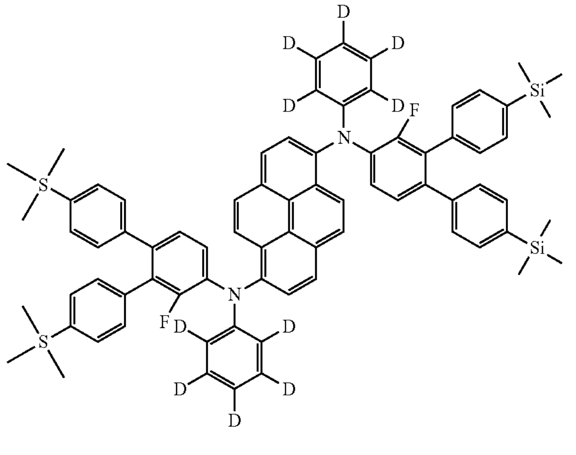

-continued
B-19
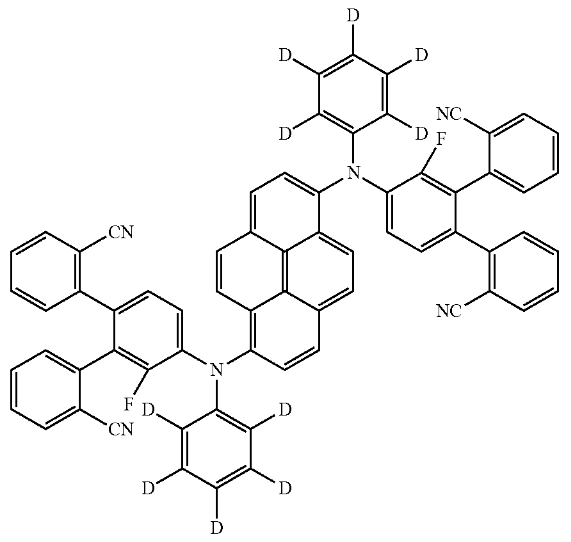
B-20
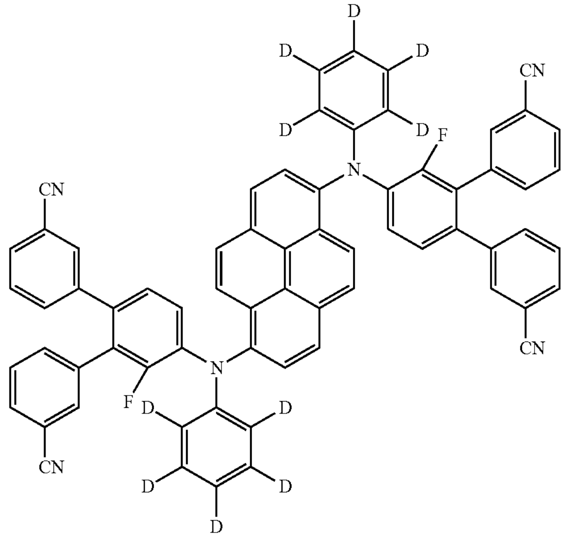
B-21
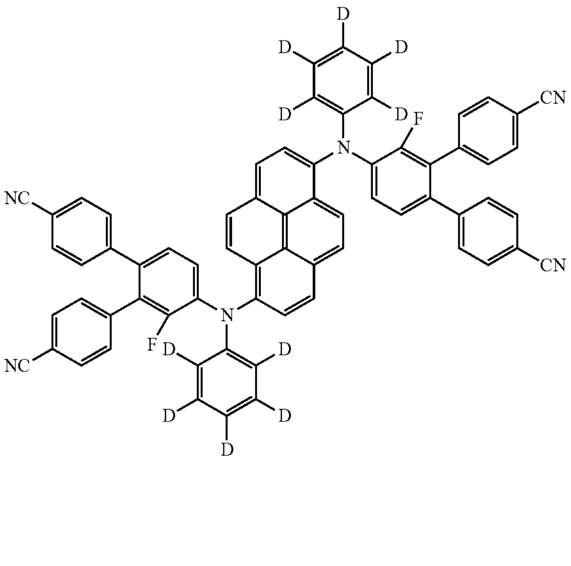
-continued
B-22
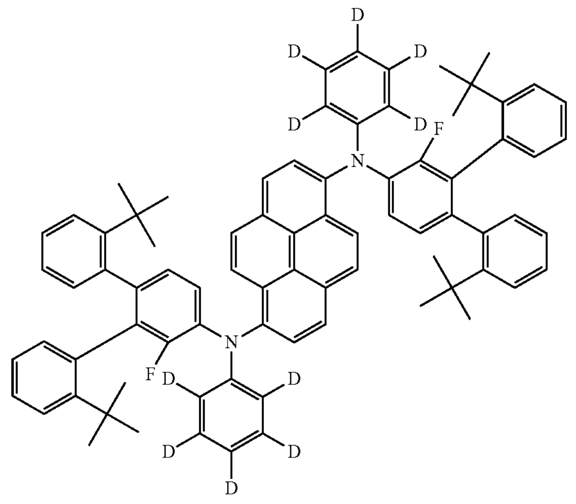
B-23
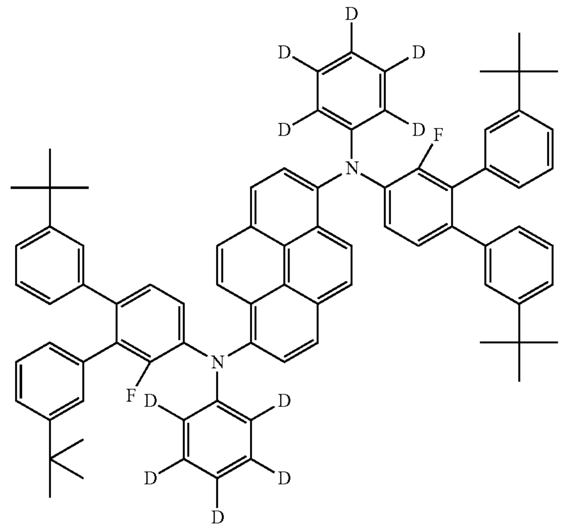
B-24
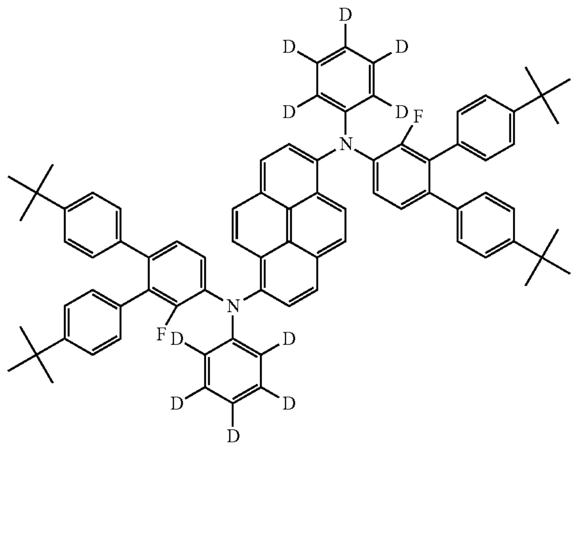

-continued
B-25
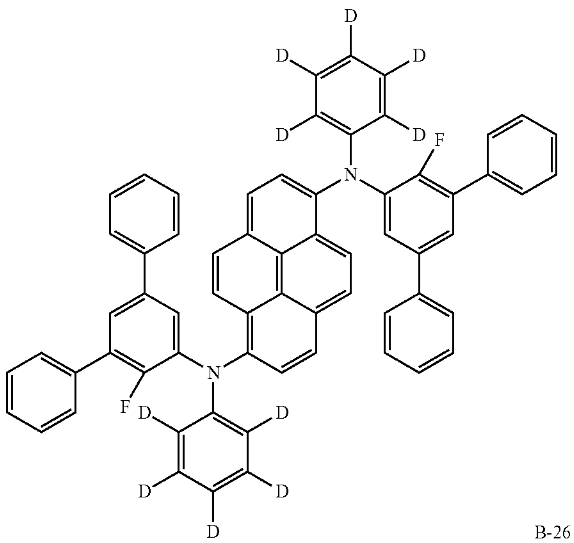
B-26
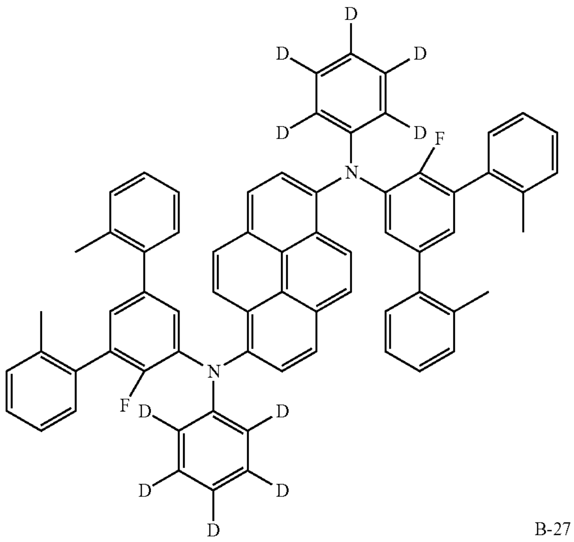
B-27
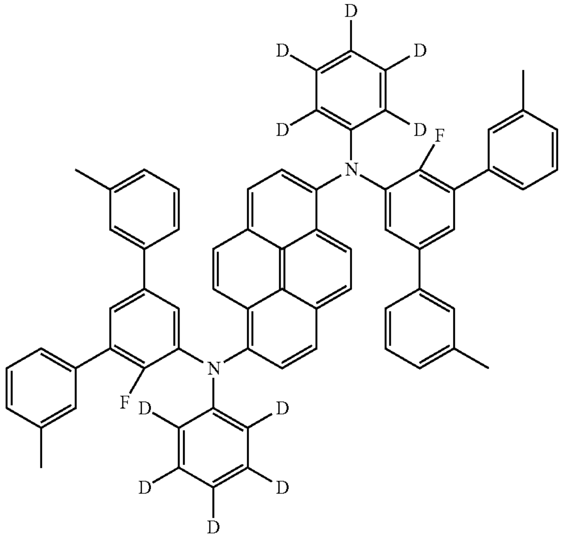
-continued
B-28
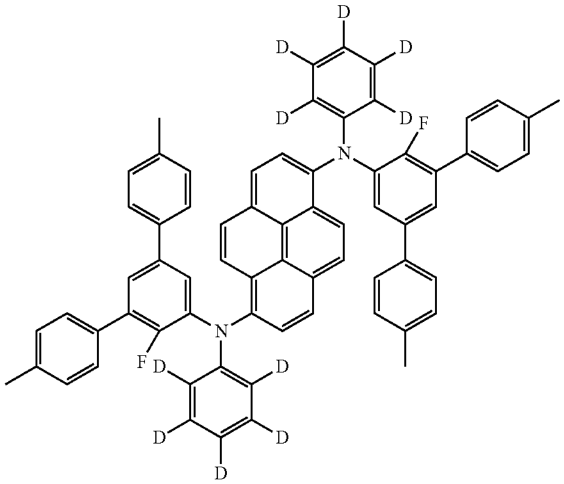
B-29
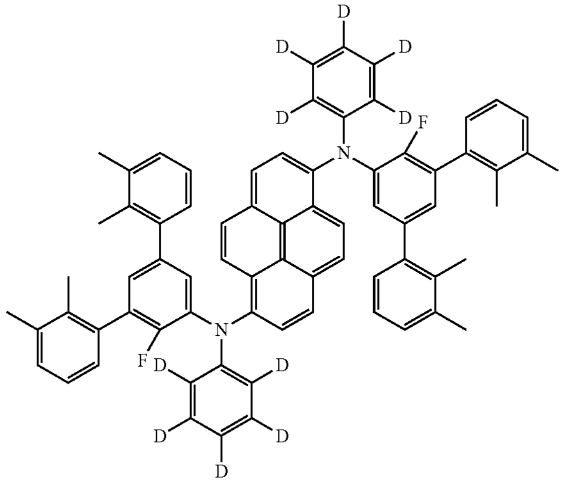
B-30
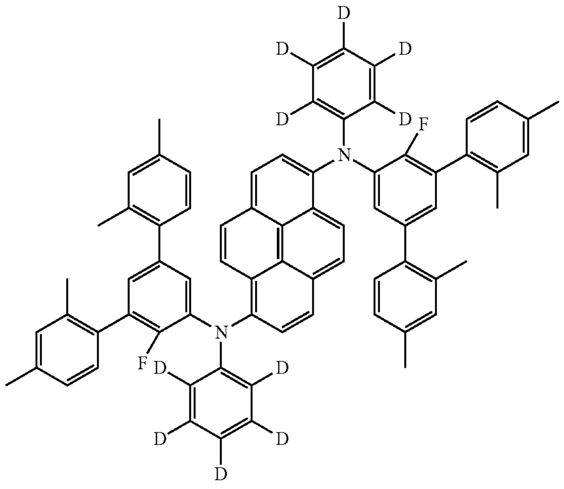

B-31
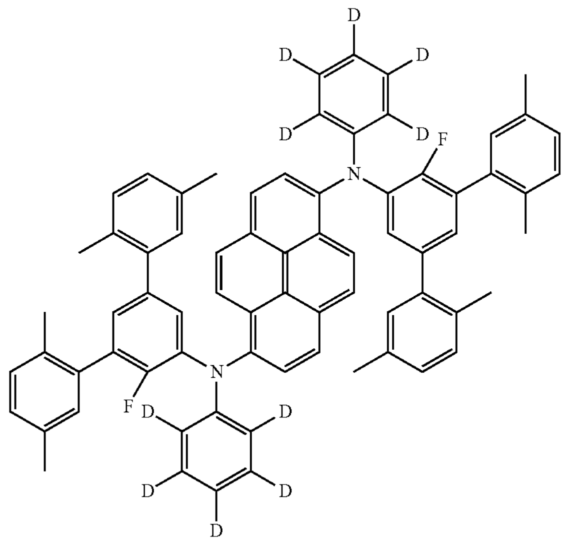
B-32
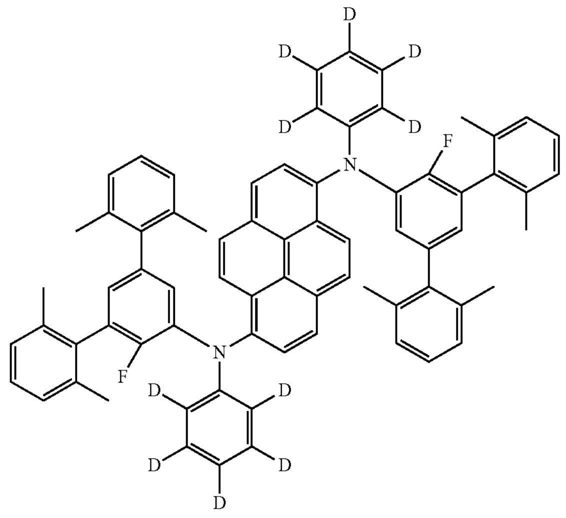
B-33
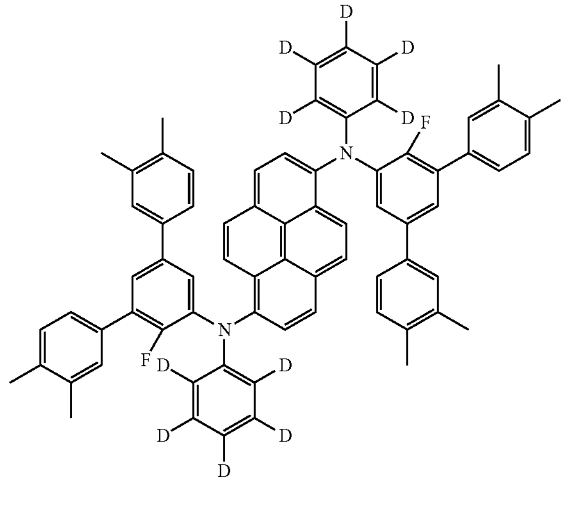
B-34
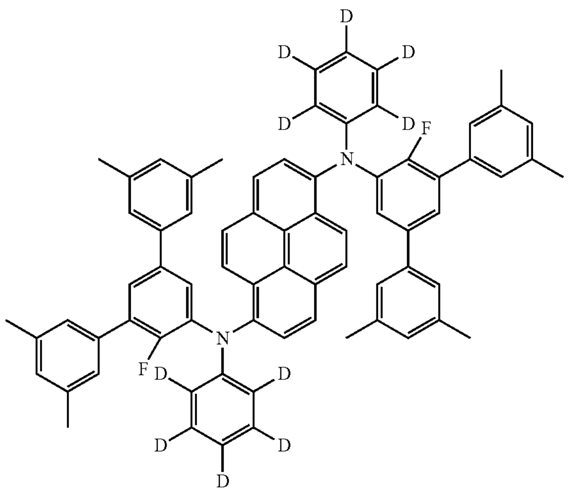
B-35
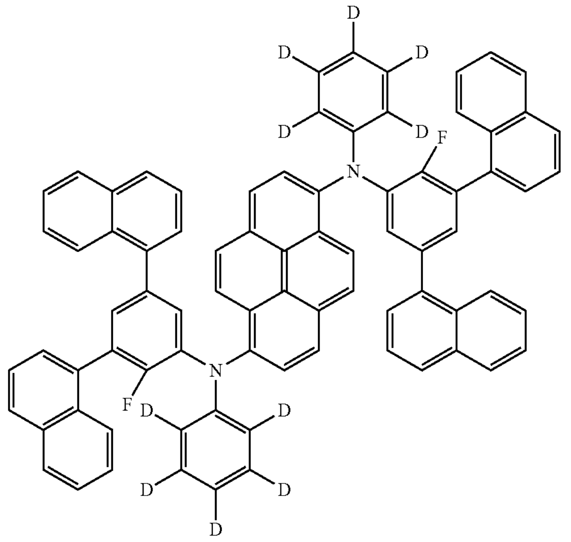
B-36
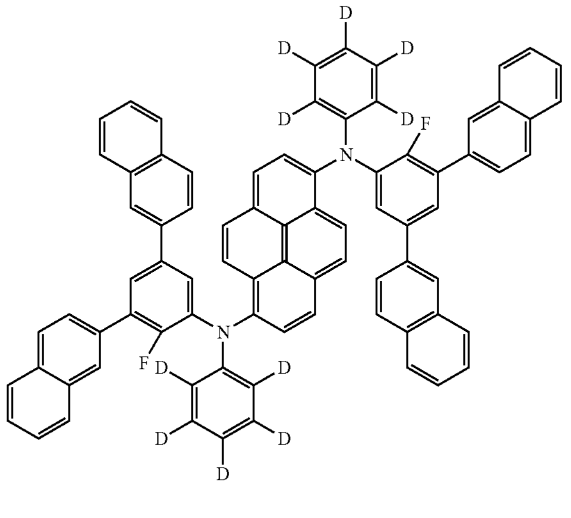

-continued
B-37
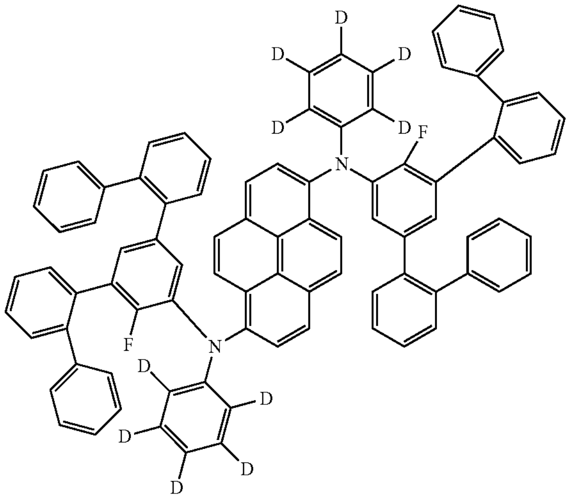
B-38
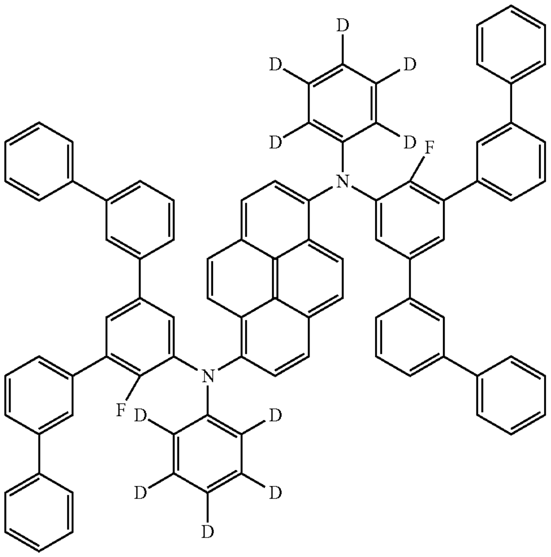
B-39
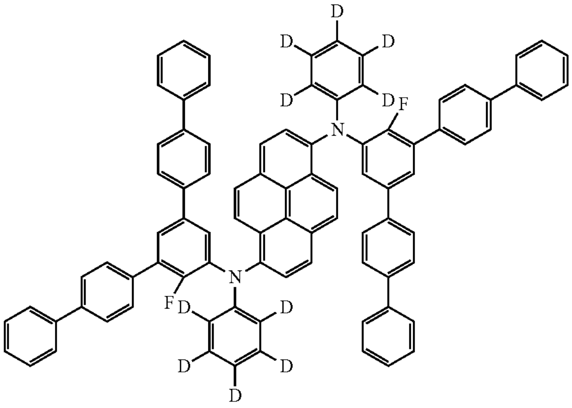
-continued
B-40
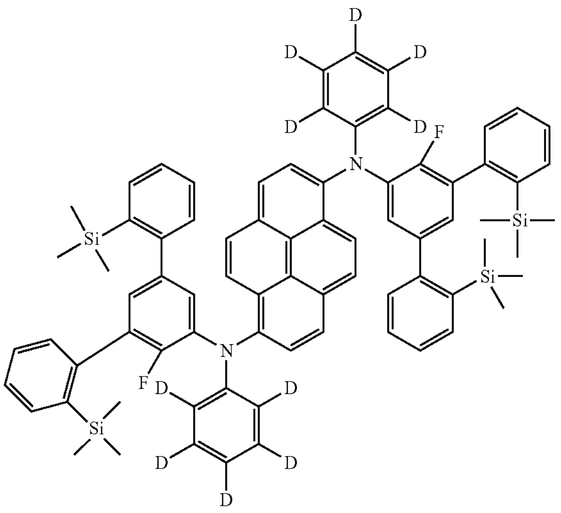
B-41
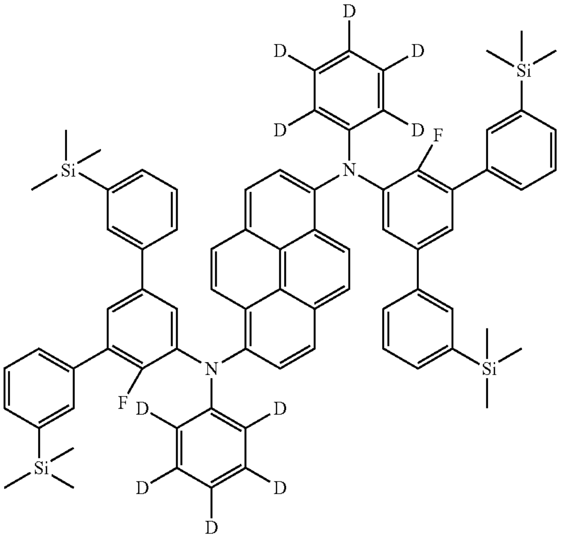
B-42
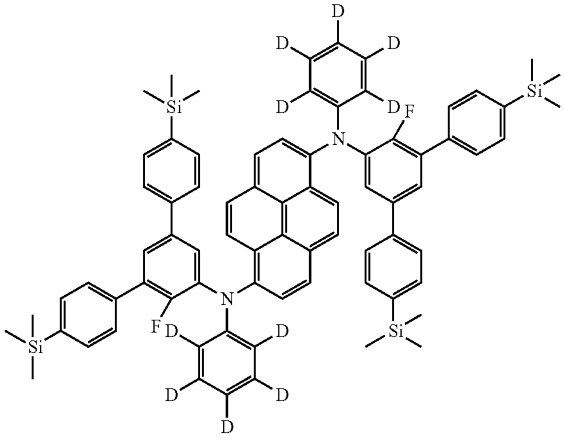

-continued
B-43
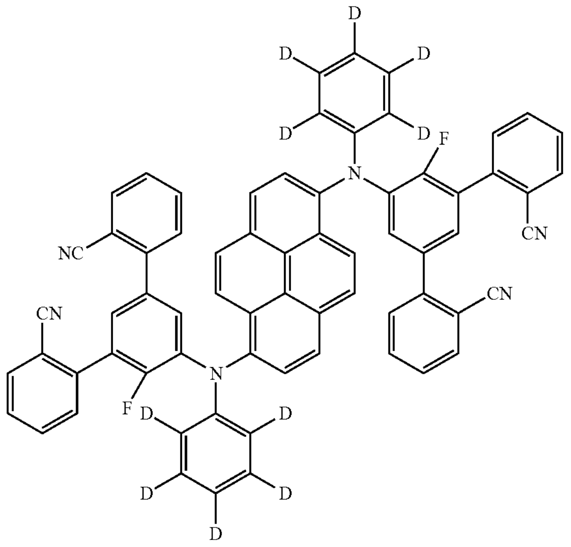
B-44
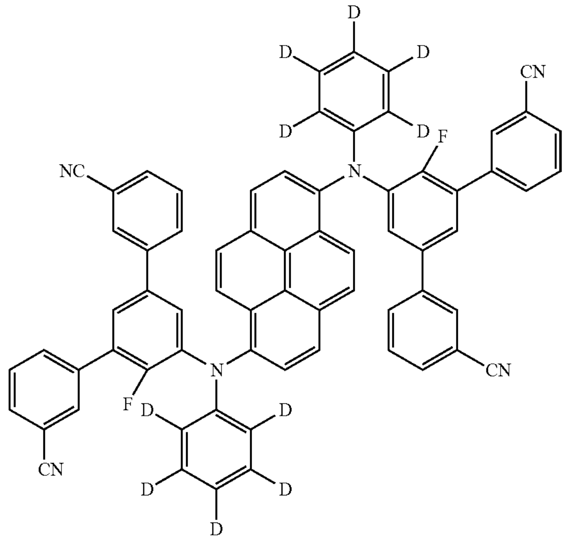
B-45
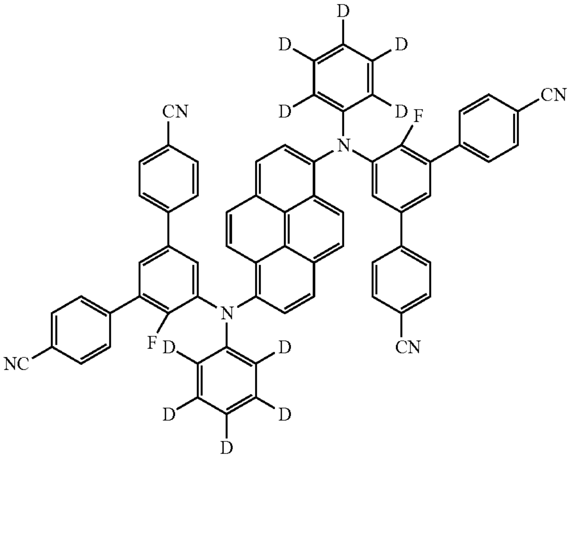
-continued
B-46
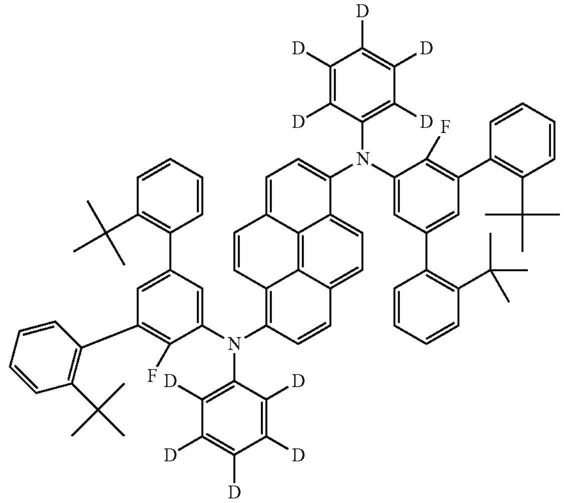
B-47
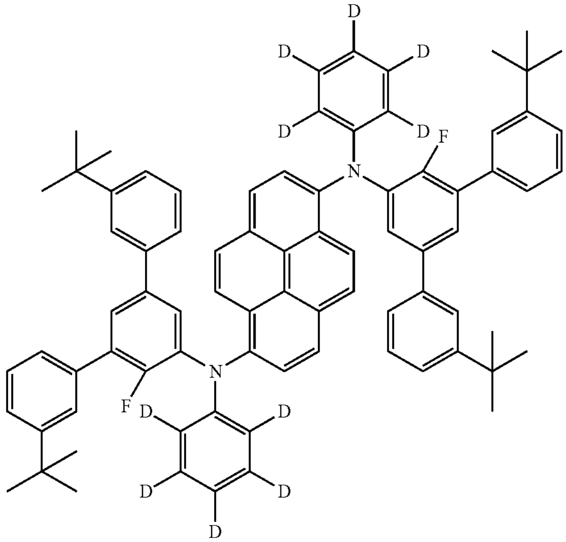
B-48
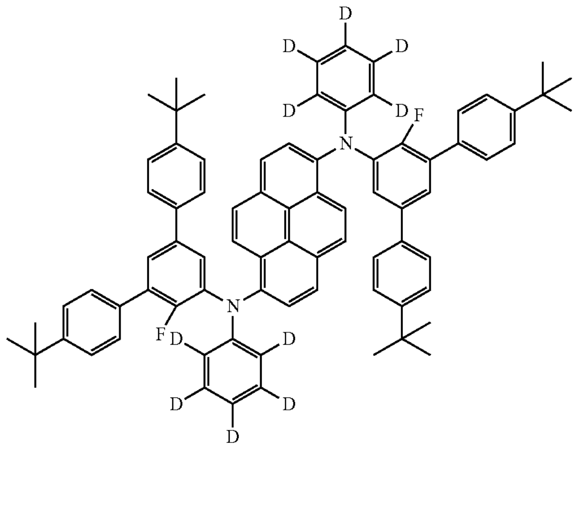

-continued
B-49
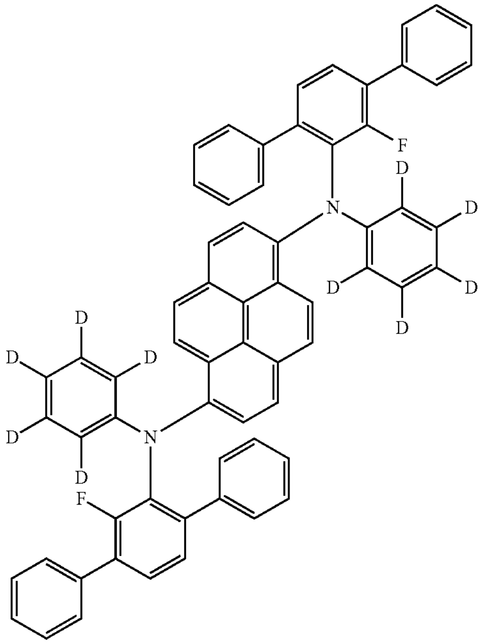
B-50
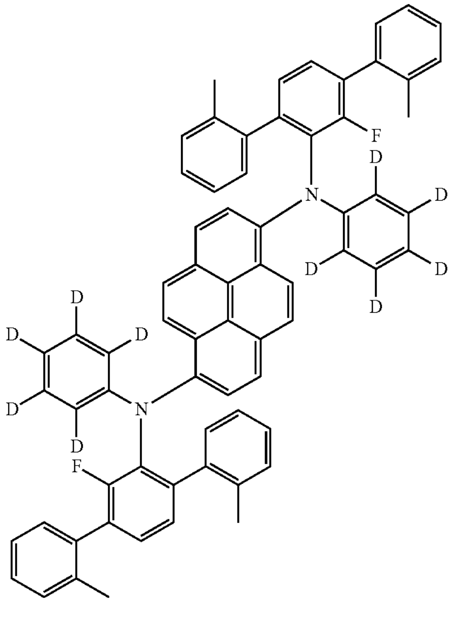
-continued
B-51
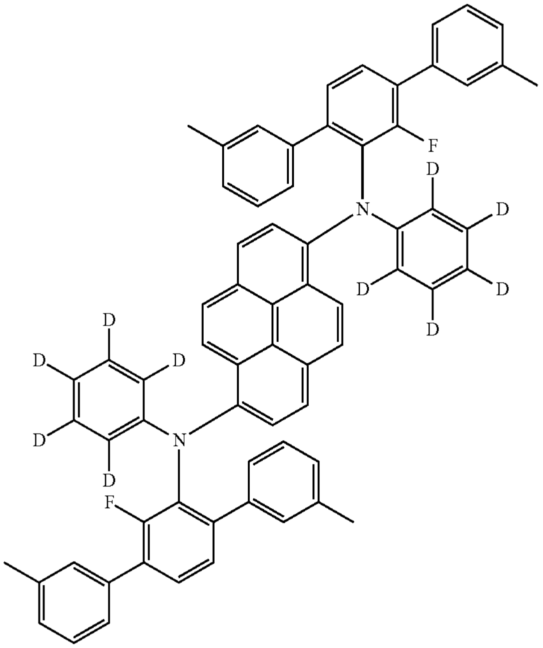
B-52
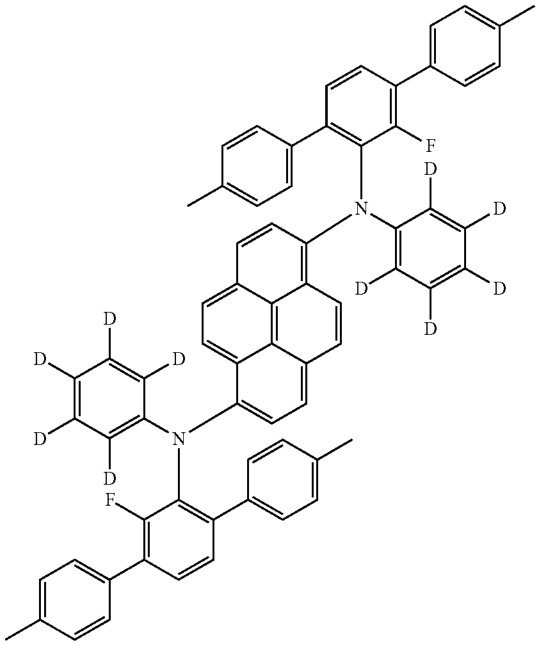

-continued
-continued
B-53
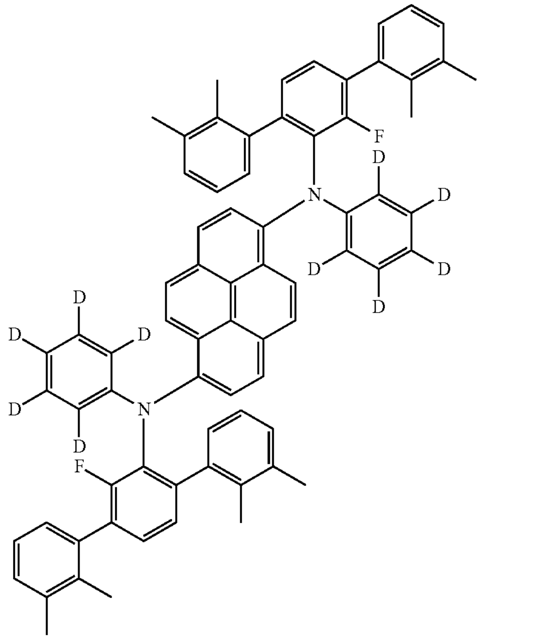
B-55
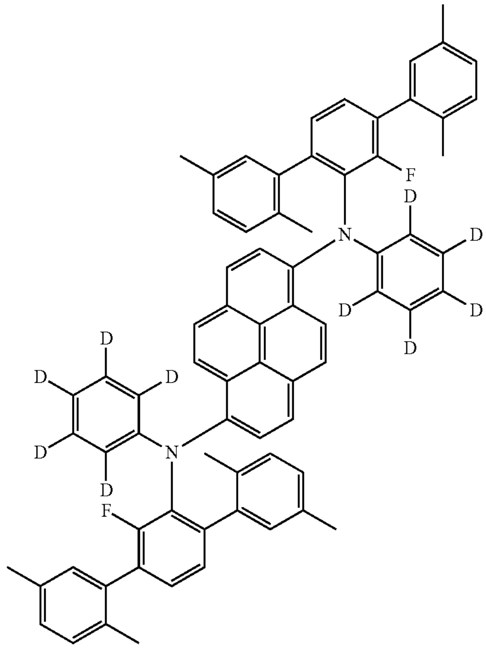
B-54
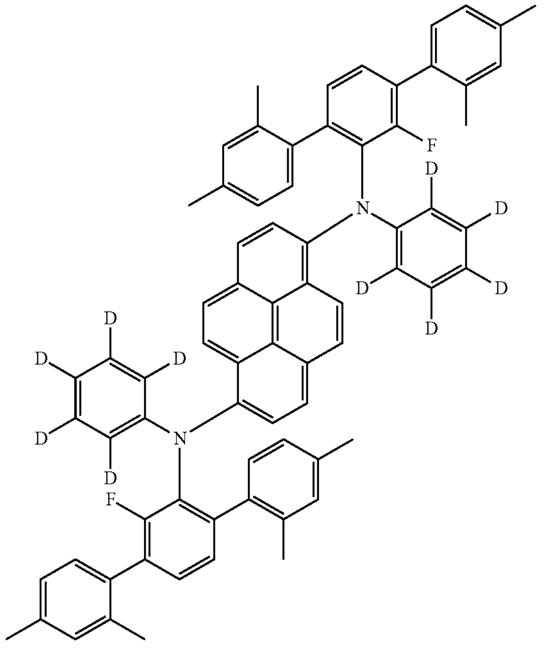
B-56
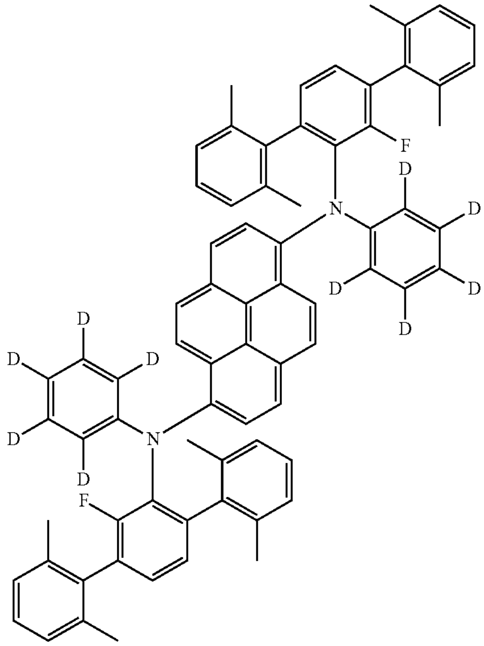

B-57
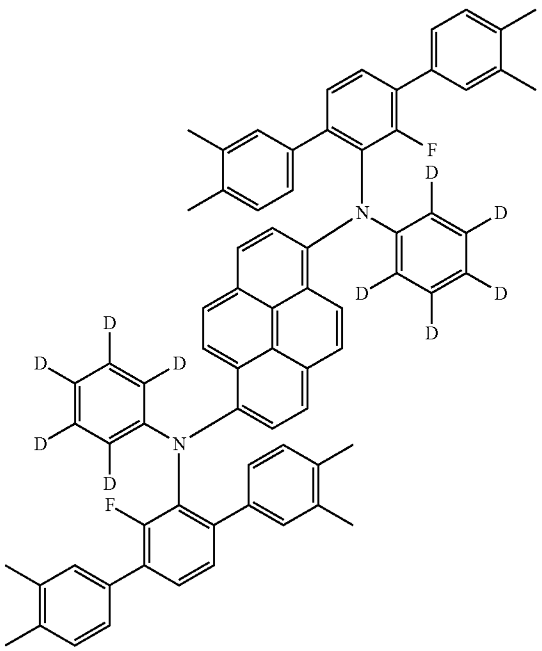
B-58
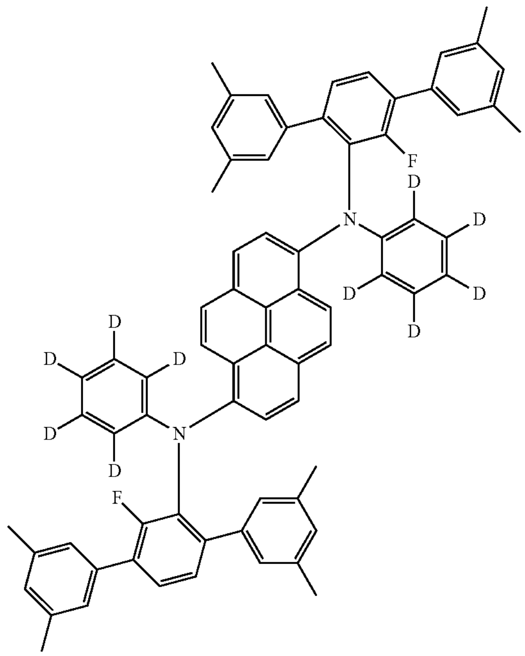
B-59
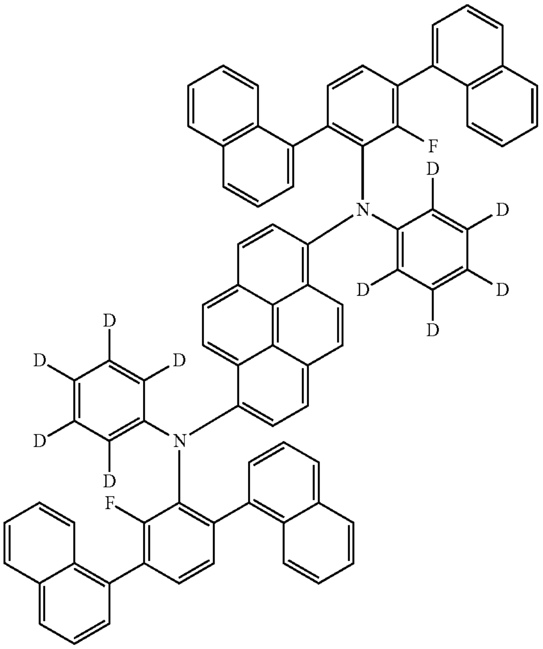
B-60
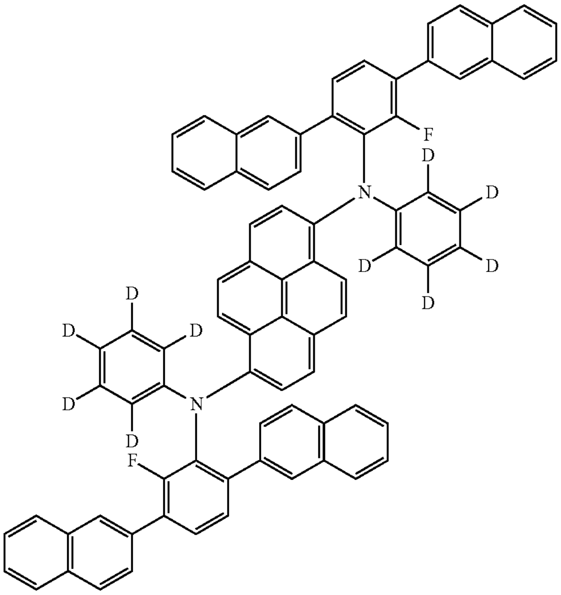

-continued
B-61
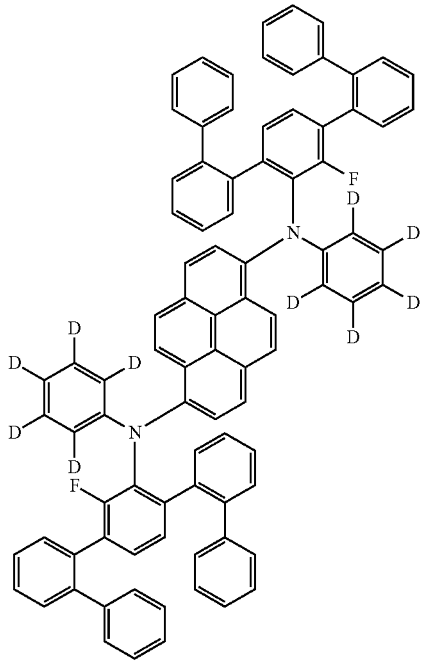
B-62
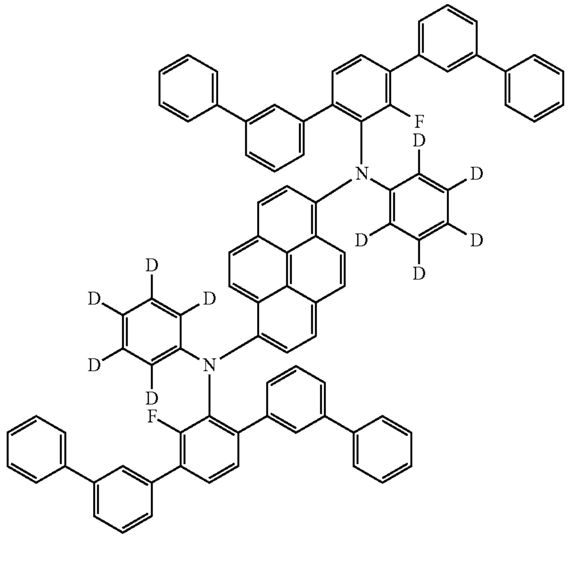
-continued
B-63
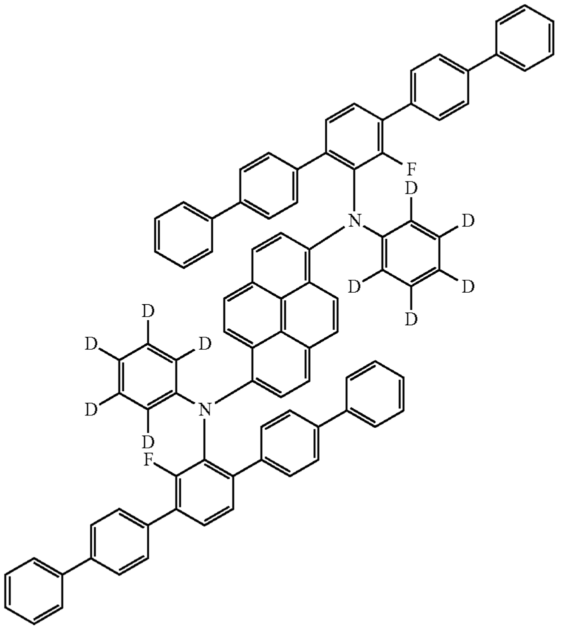
B-64
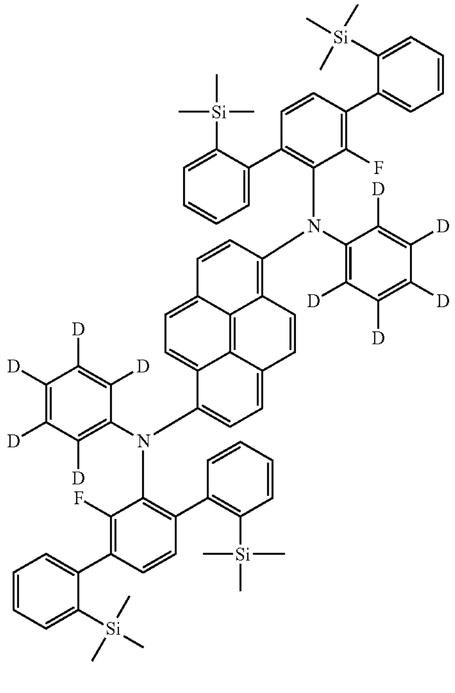

-continued
B-65
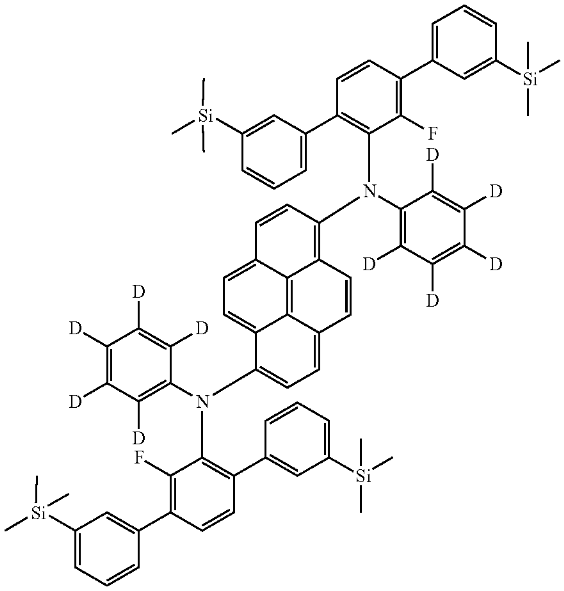
B-66
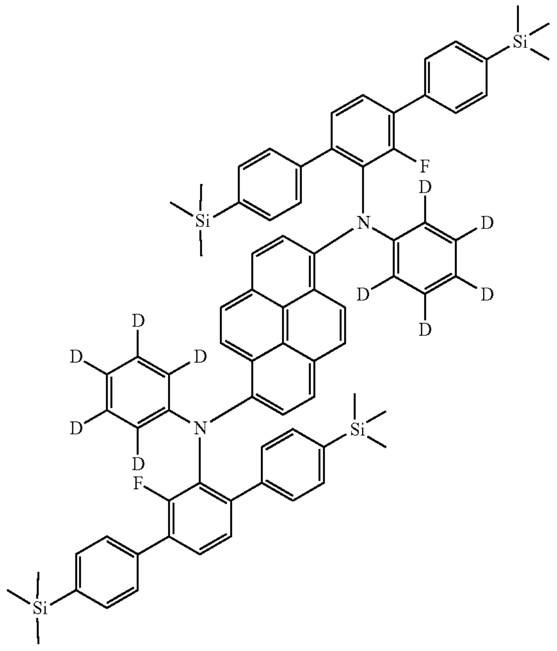
-continued
B-67
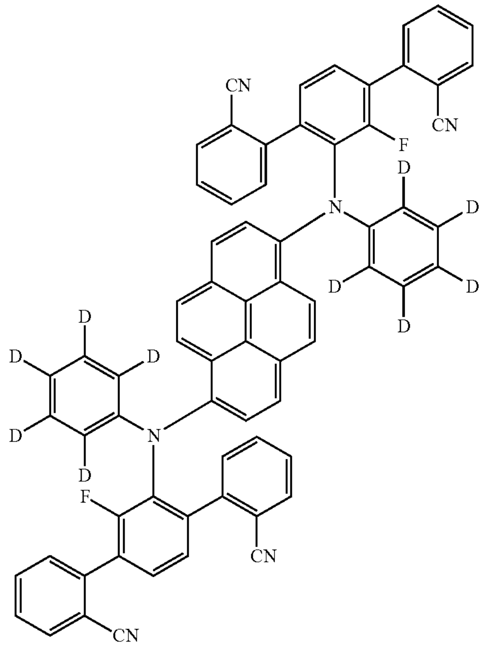
B-68
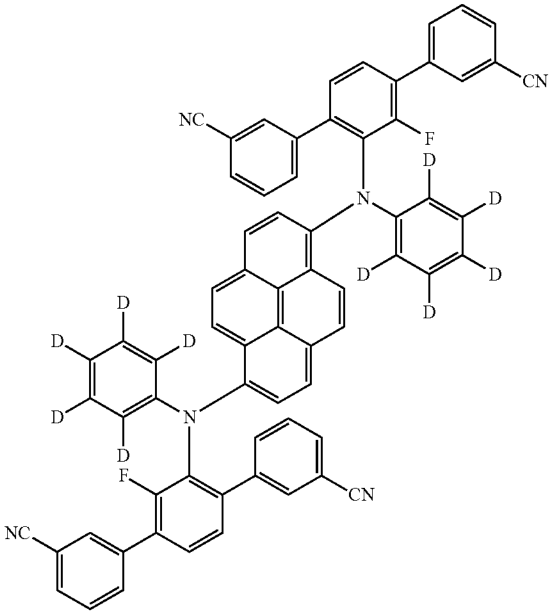

-continued
B-69
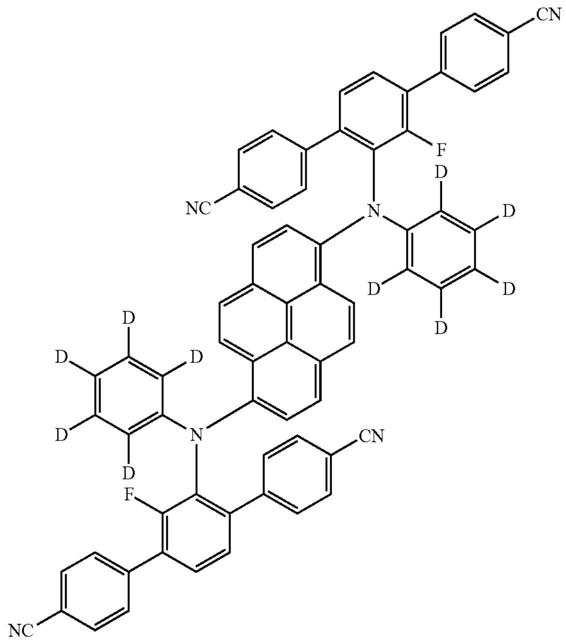
B-70
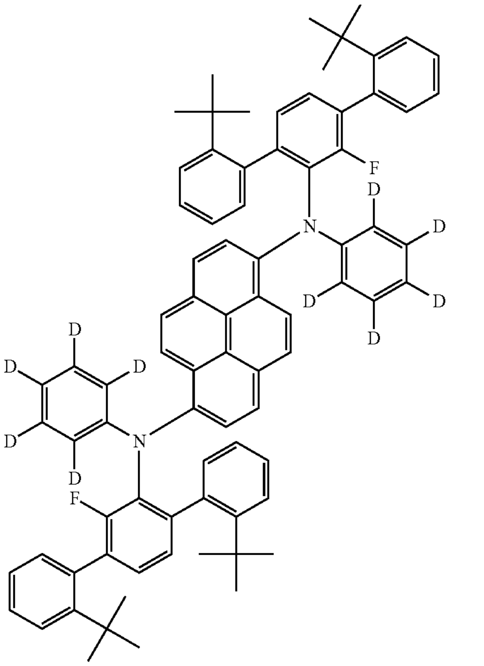
-continued
B-71
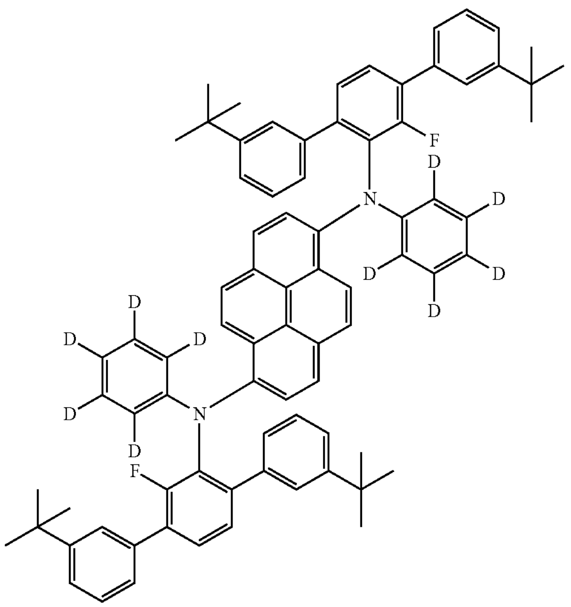
B-72
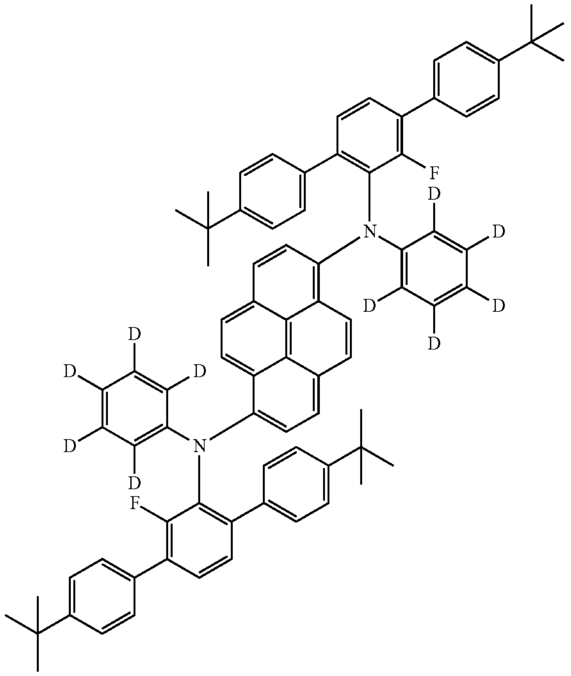

-continued
B-73
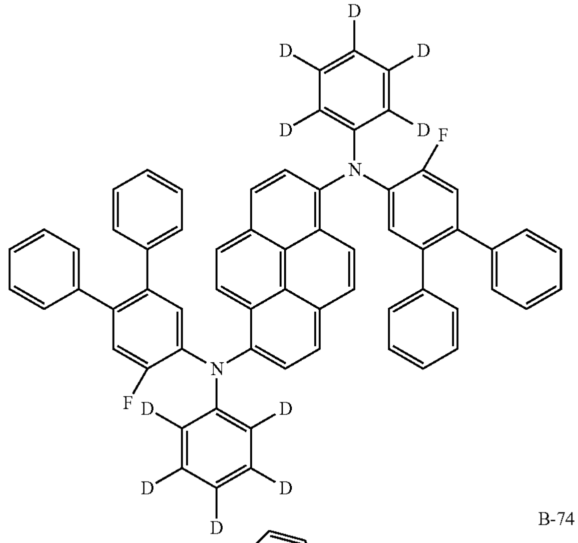
B-74
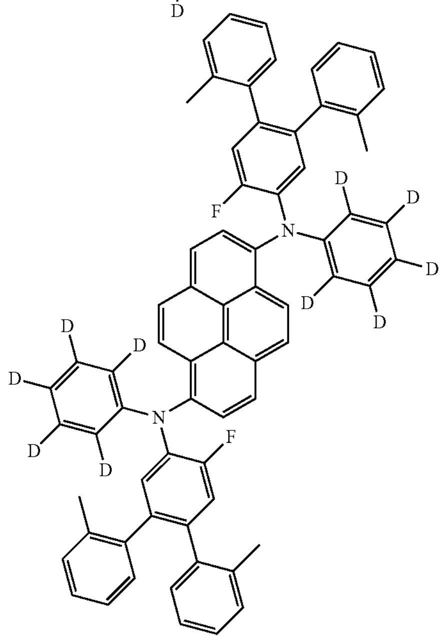
B-75
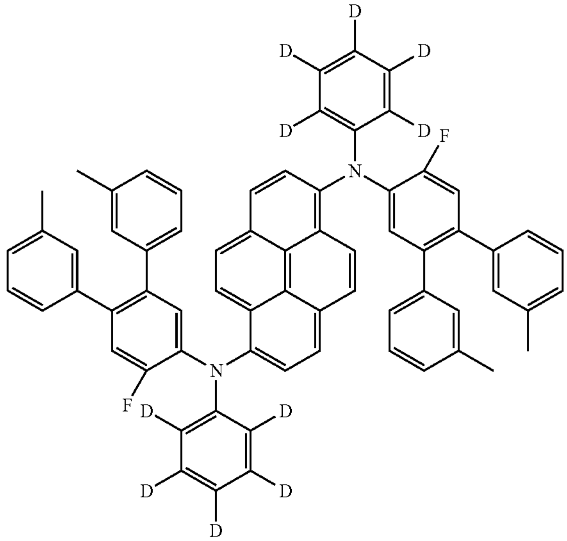
-continued
B-76
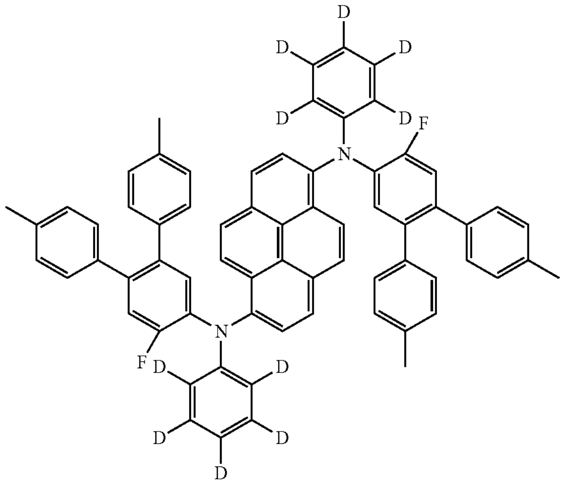
B-77
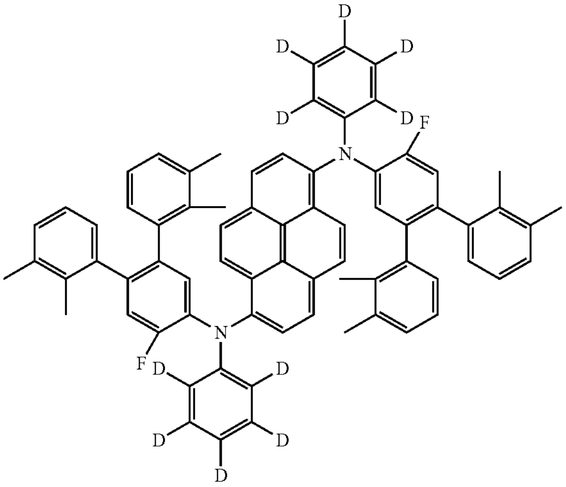
B-78
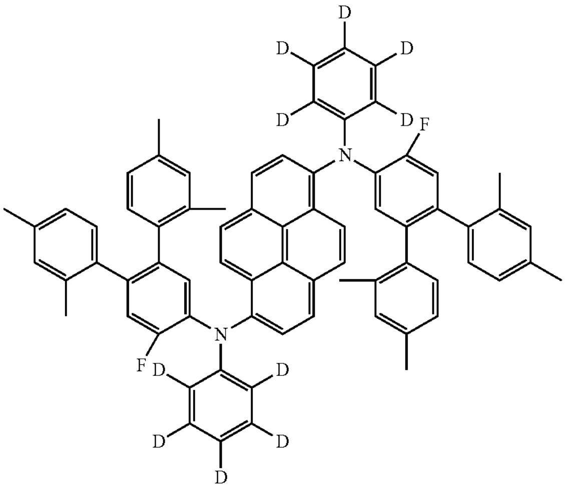

B-79
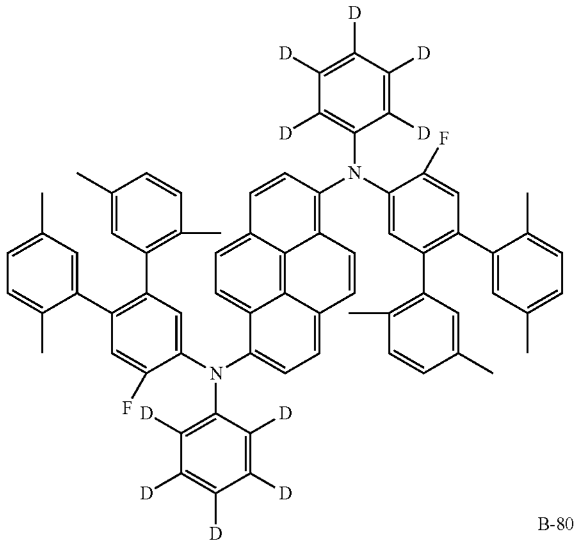
B-80
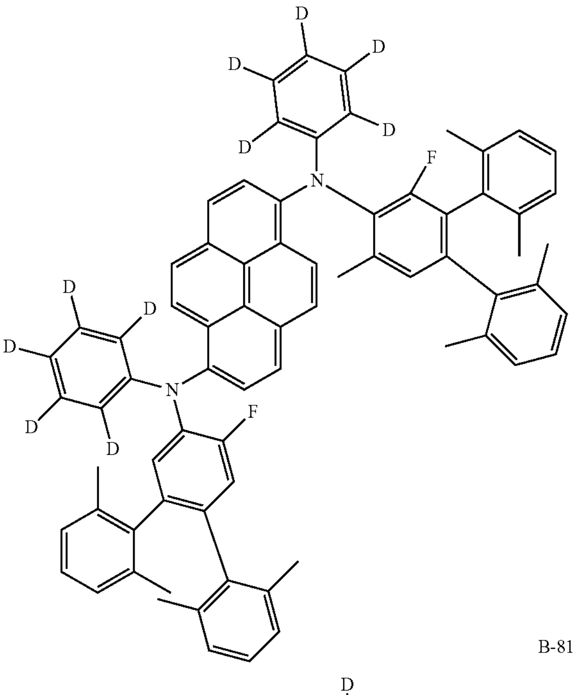
B-81
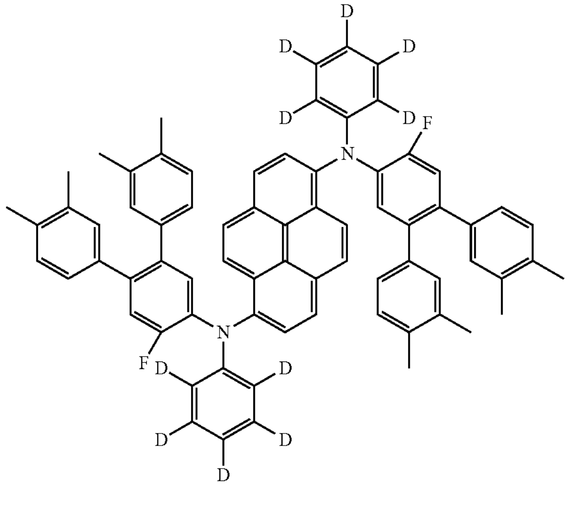
B-82
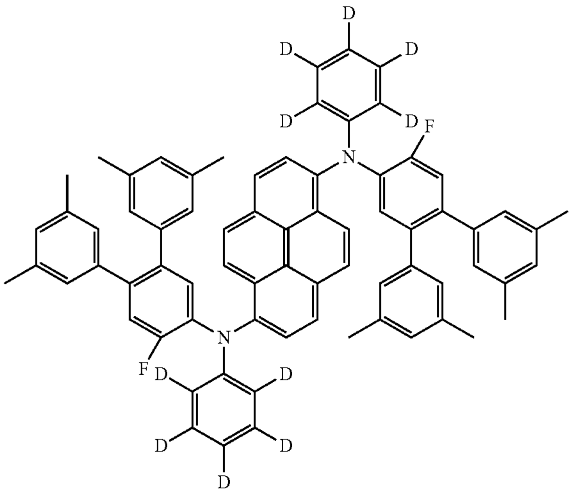
B-83
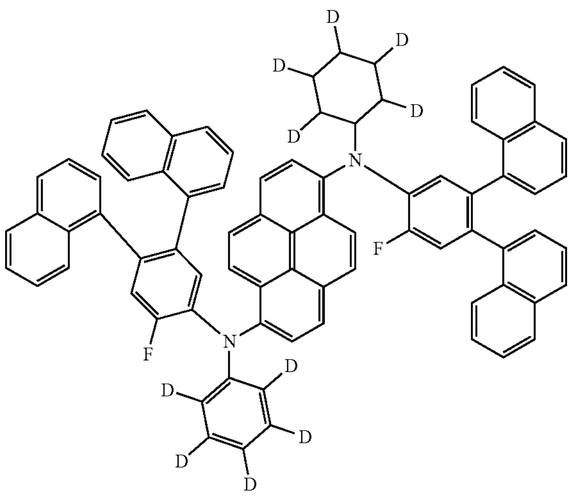
B-84
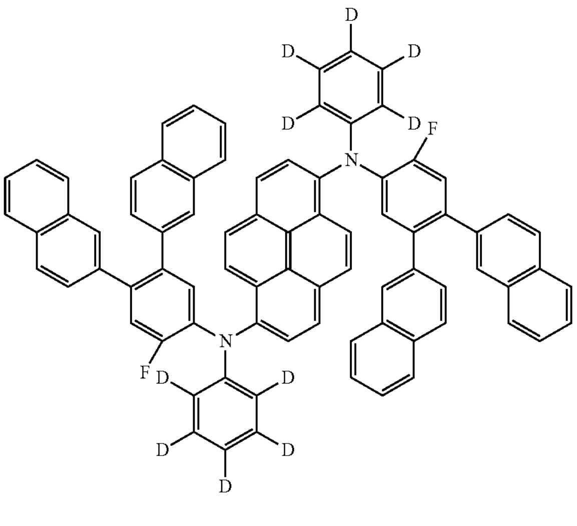

-continued
B-85
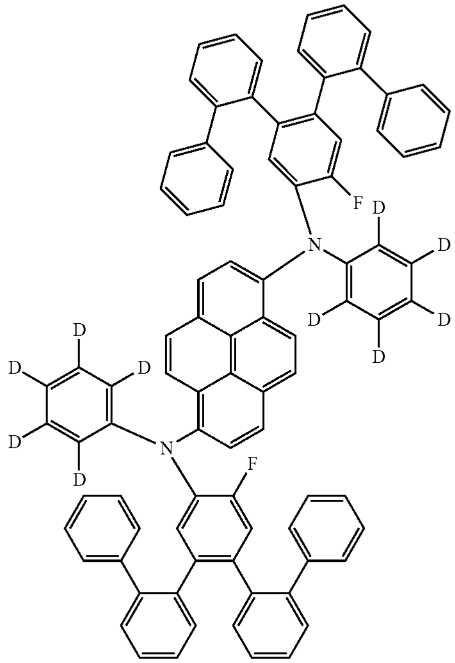
B-86
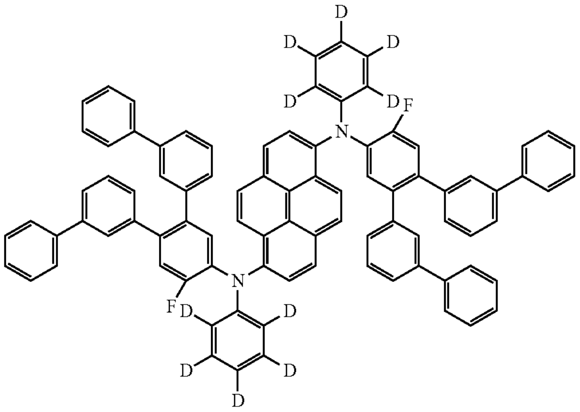
B-87
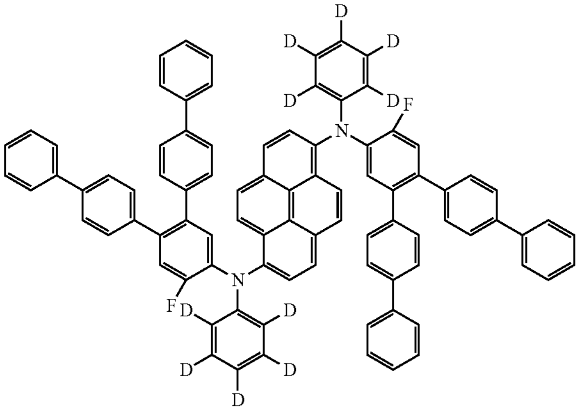
-continued
B-88
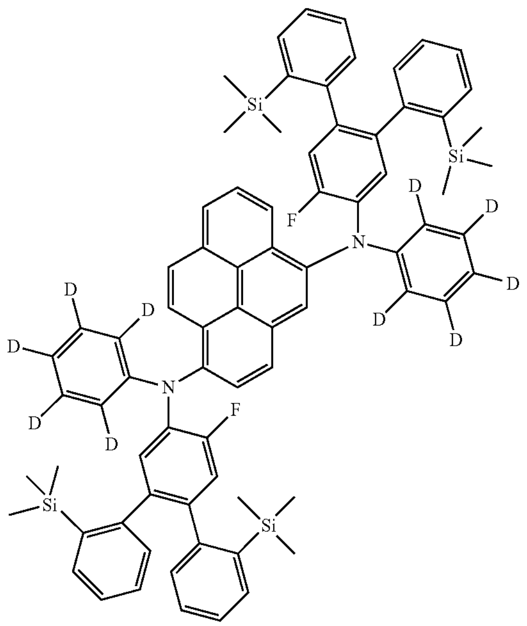
B-89
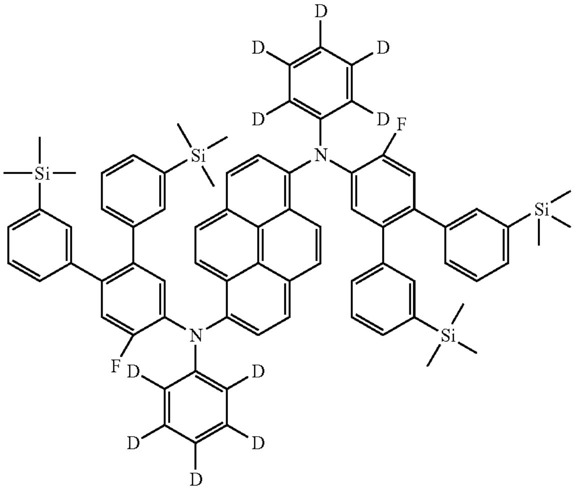
B-90
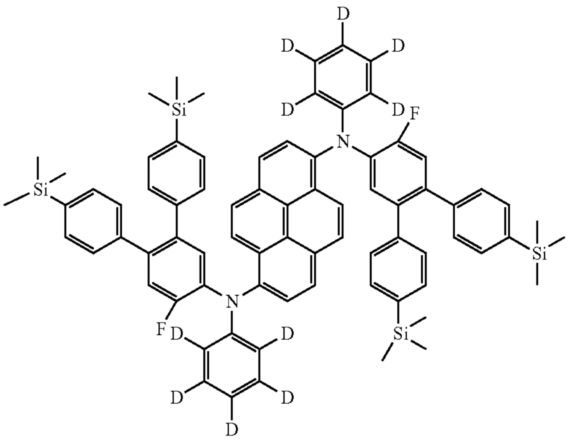

-continued
B-91
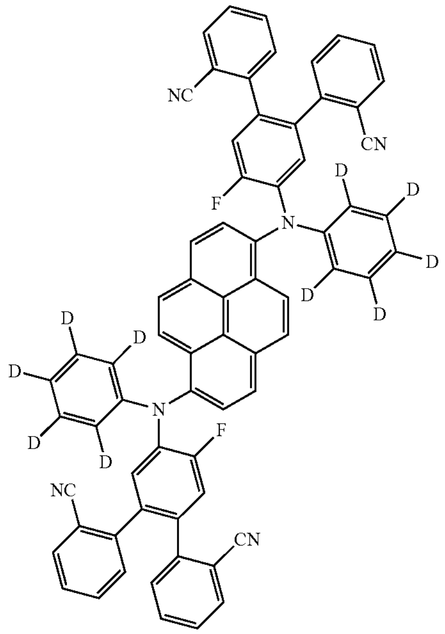
B-92
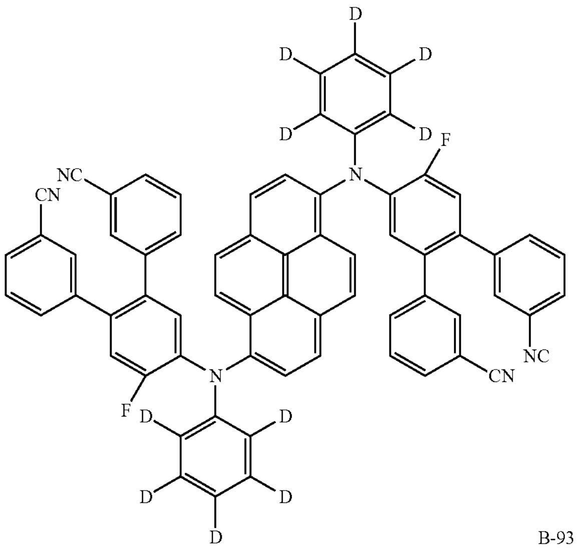
B-93
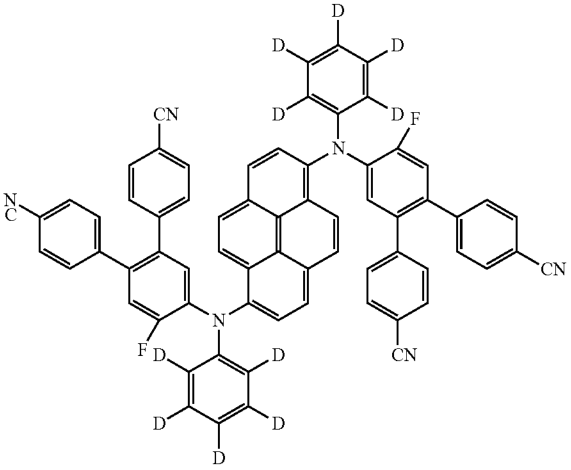
-continued
B-94
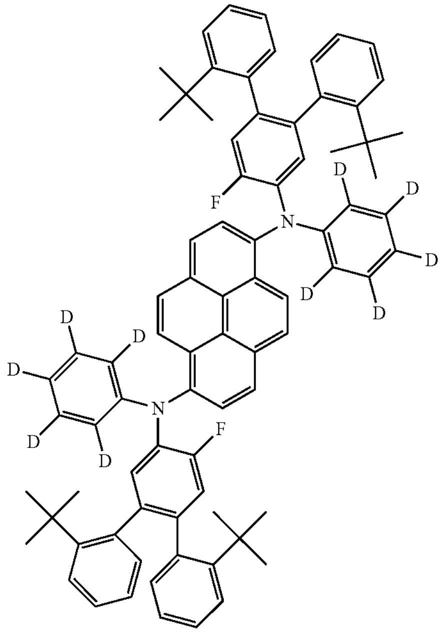
B-95
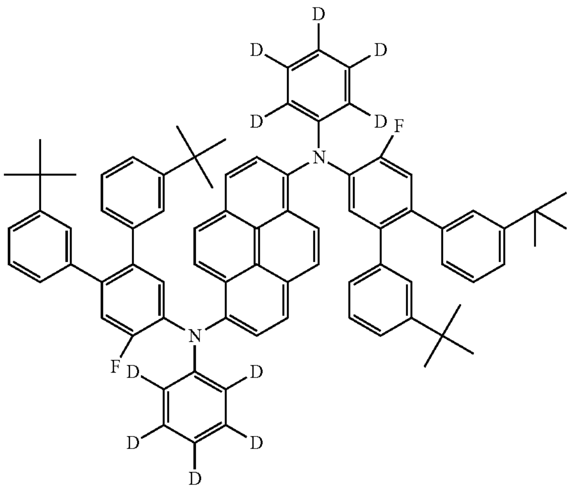
B-96
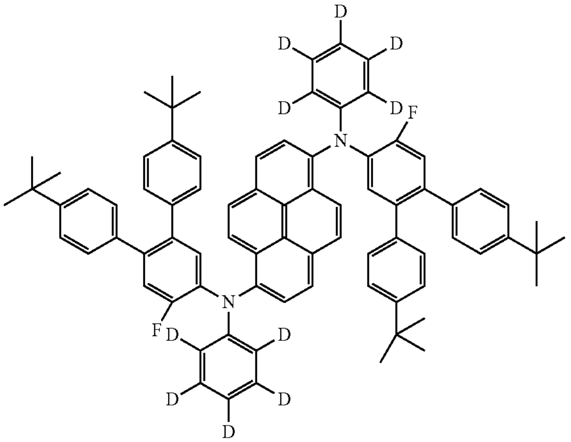

-continued
B-97
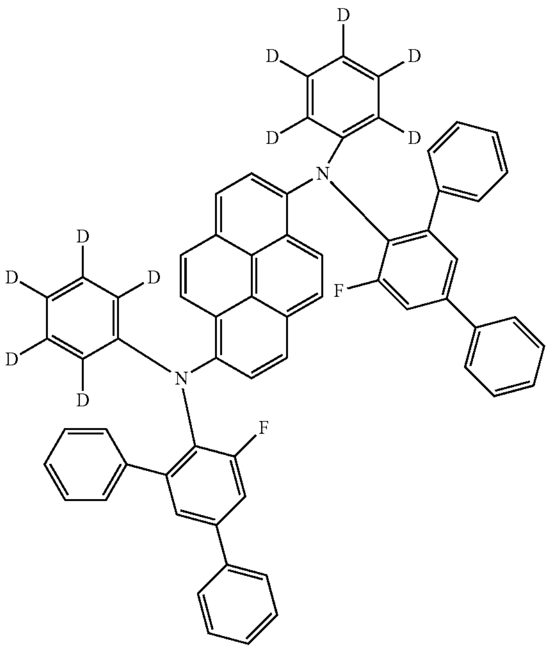
B-98
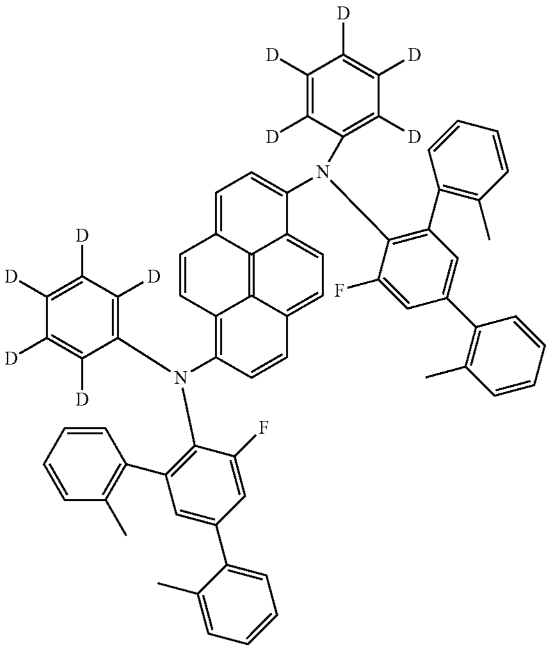
-continued
B-99
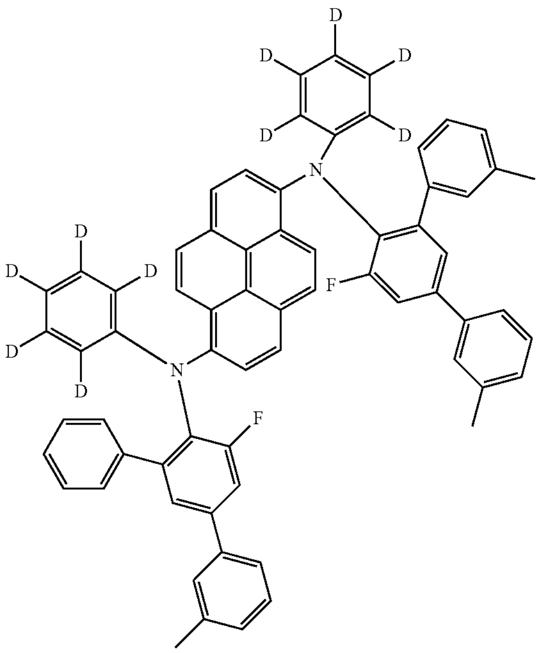
B-100
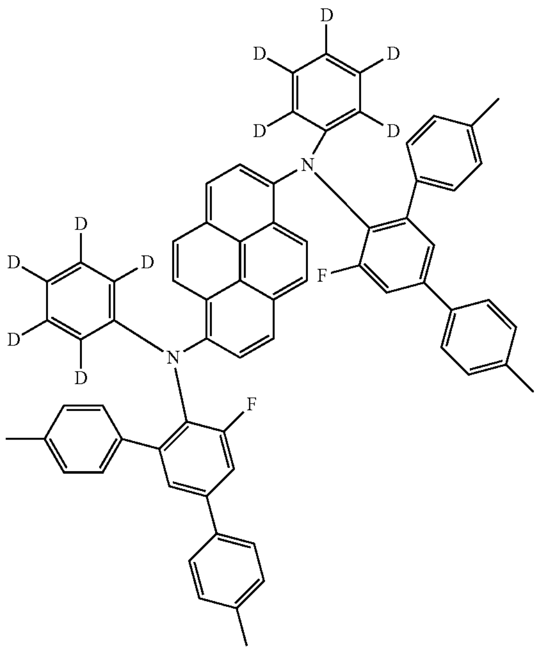

-continued
B-101
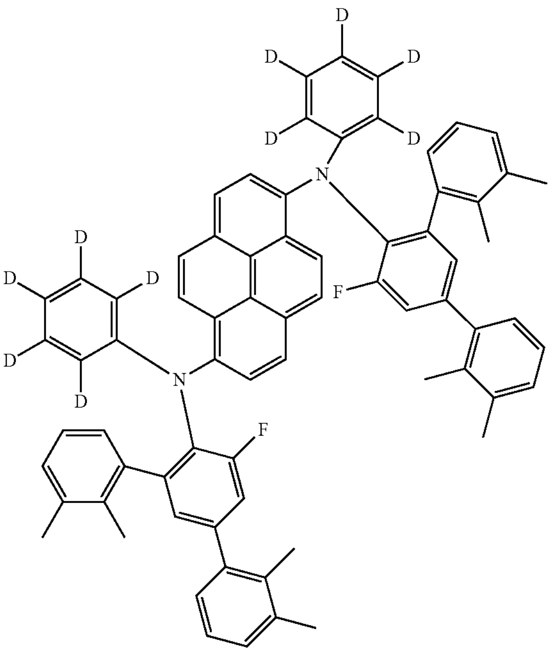
B-102
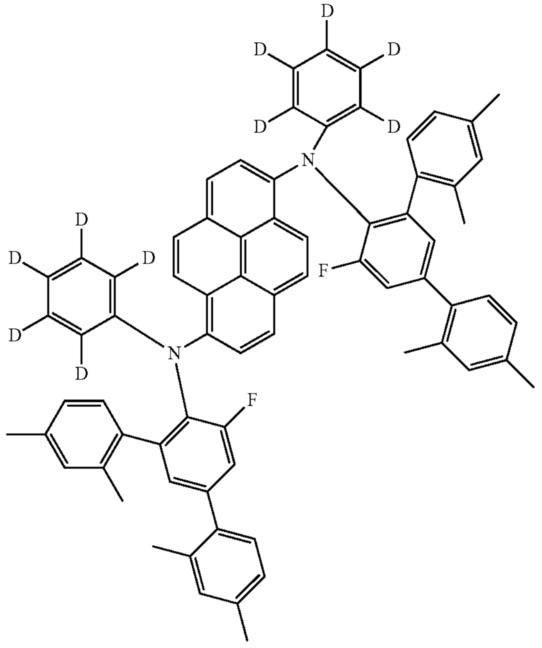
-continued
B-103
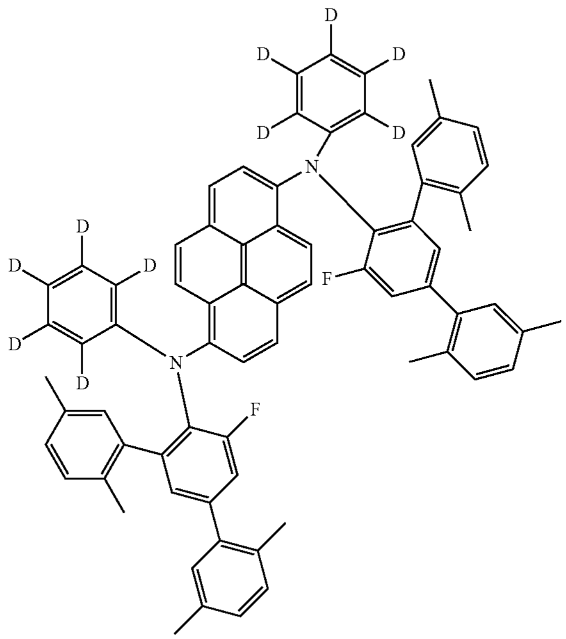
B-104
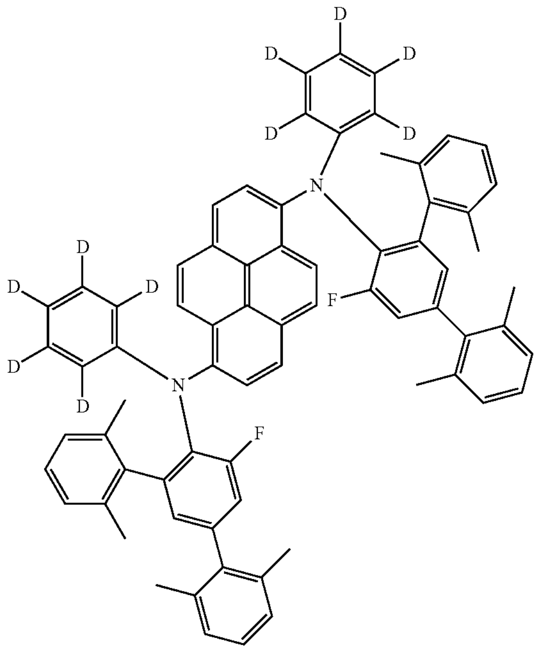

-continued
B-105
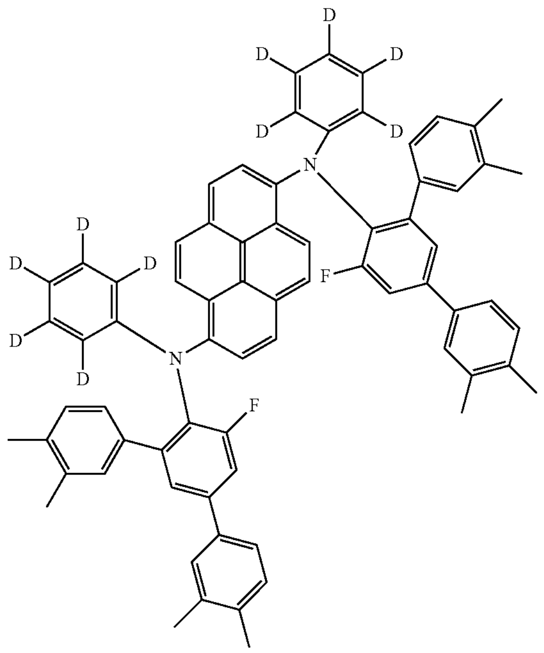
B-106
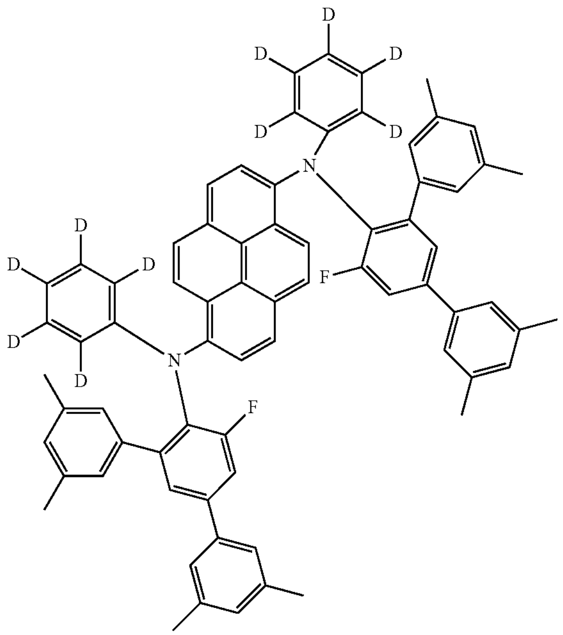
-continued
B-107
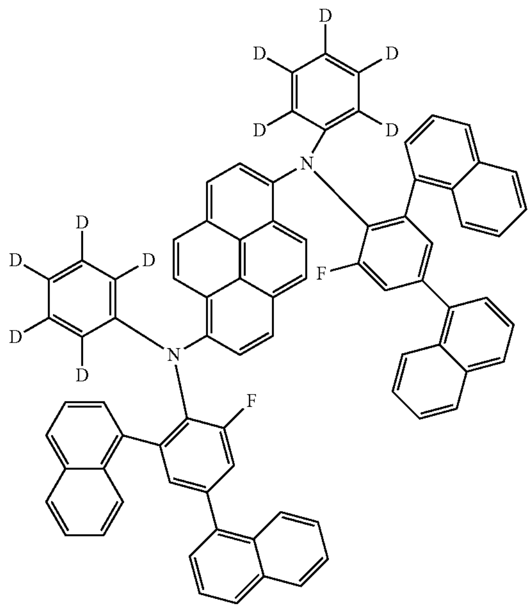
B-108
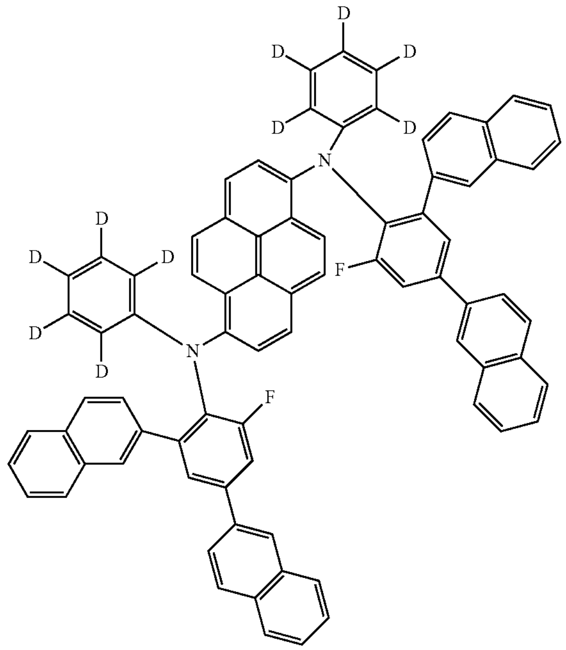

-continued
B-109
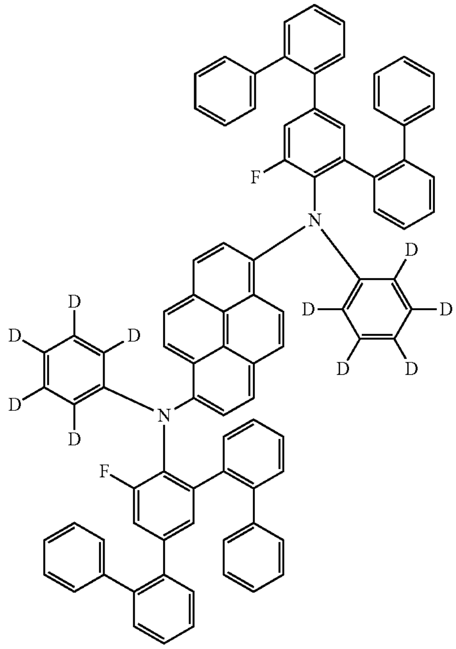
B-110
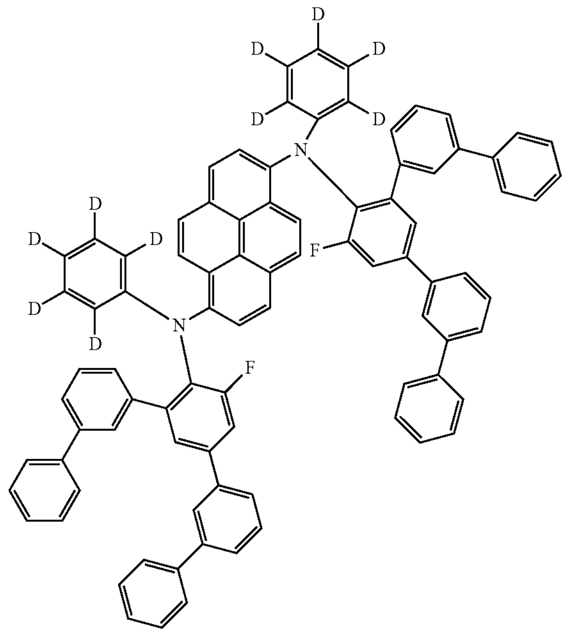
-continued
B-111
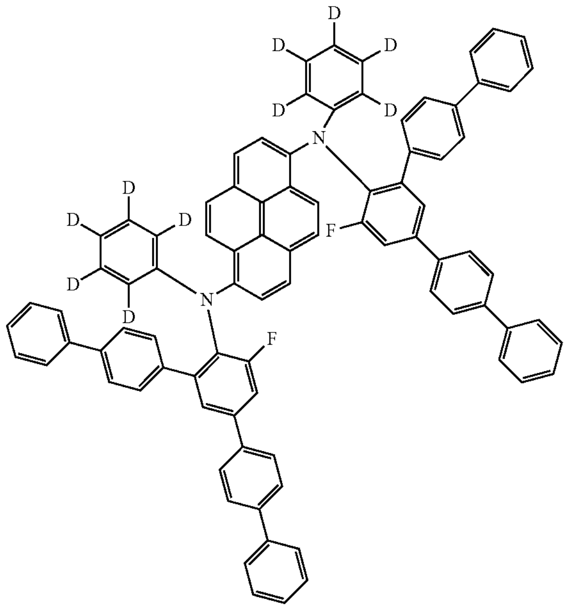
B-112
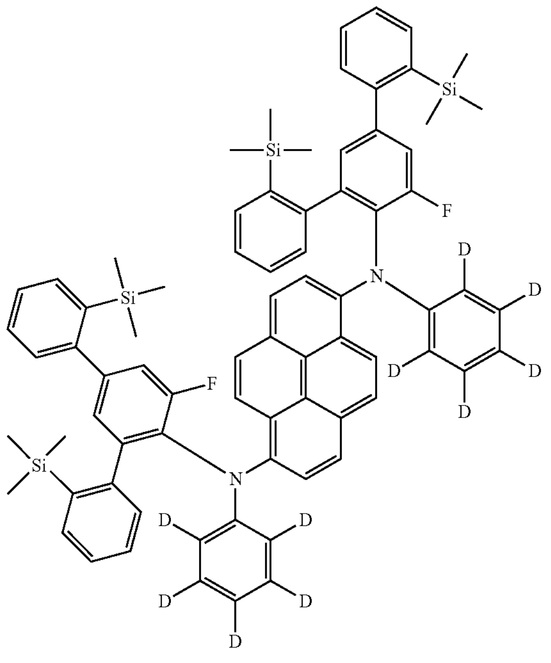

-continued
B-113
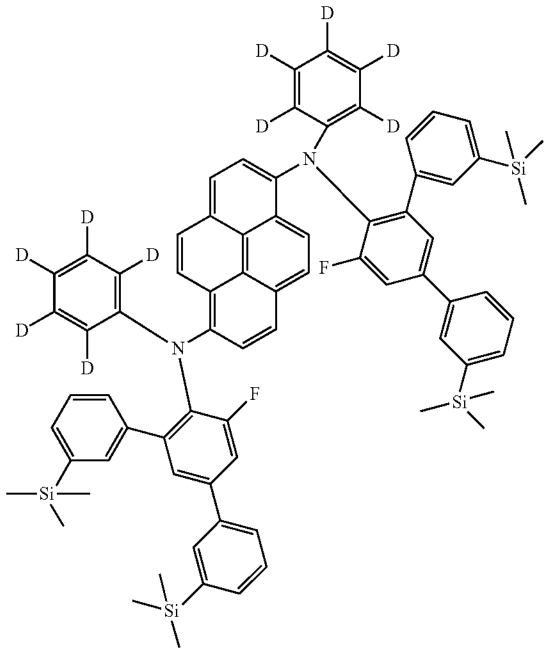
B-114
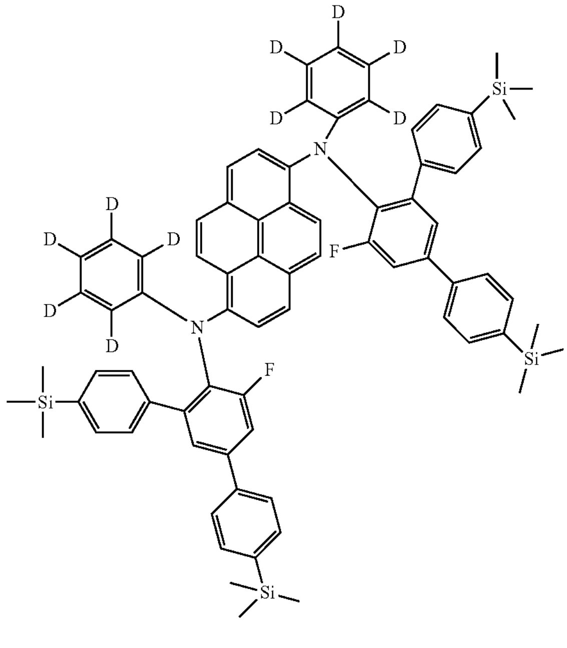
-continued
B-115
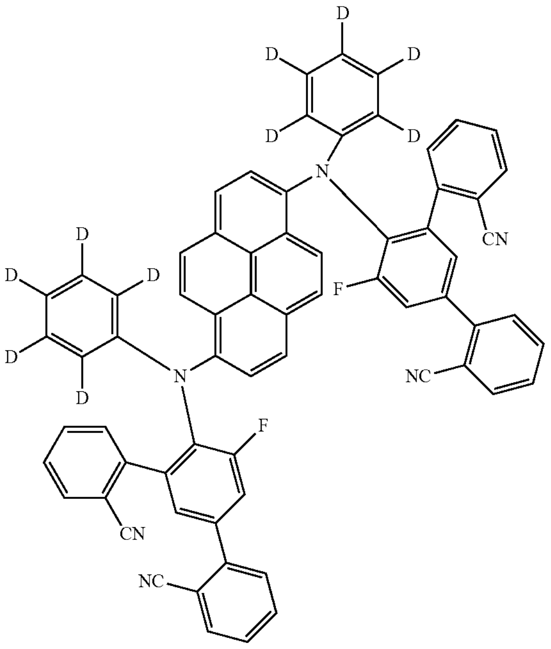
B-116
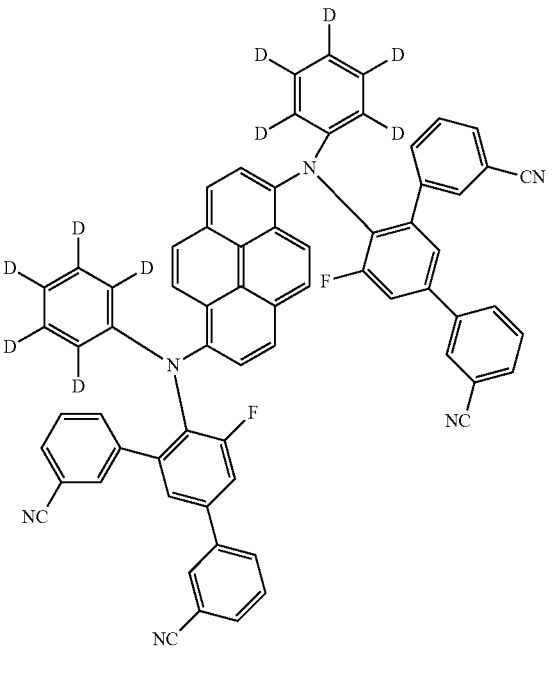

-continued
B-117
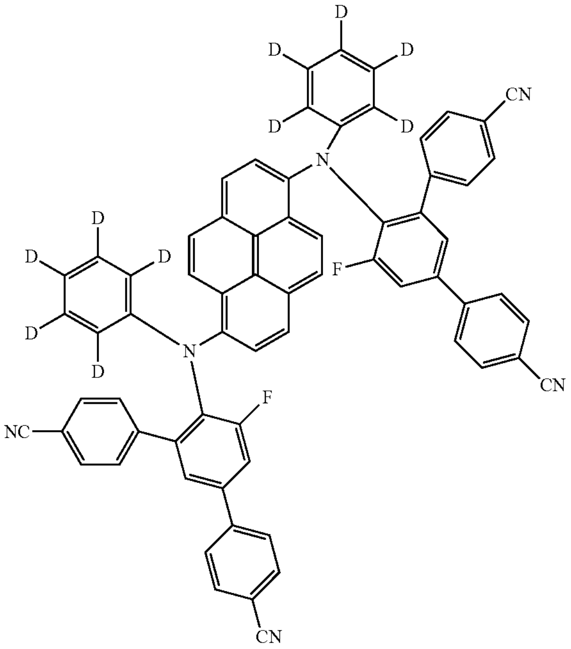
B-118
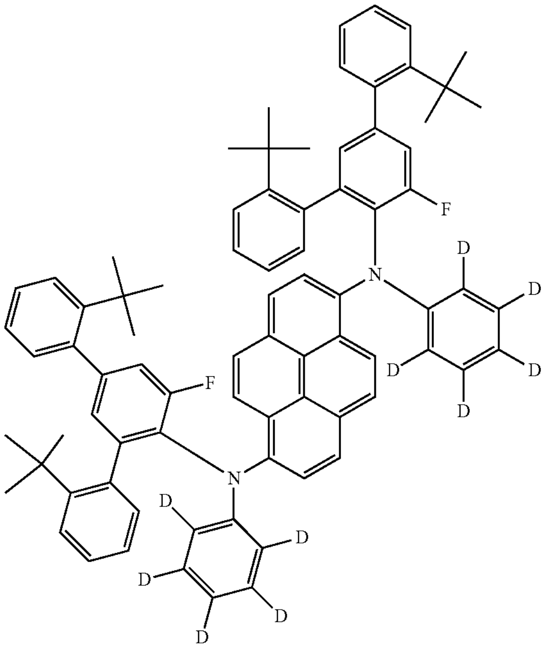
-continued
B-119
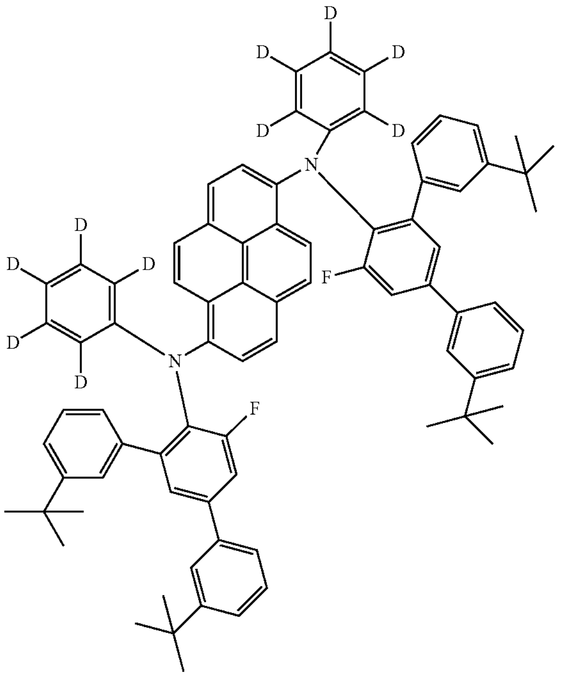
B-120
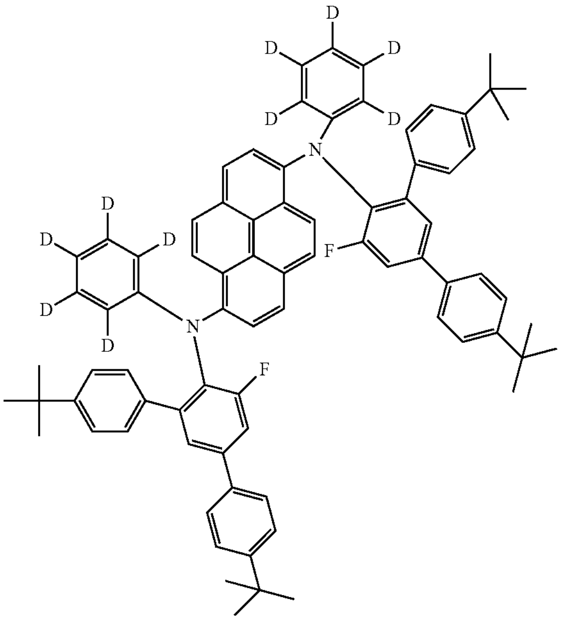

-continued
B-121
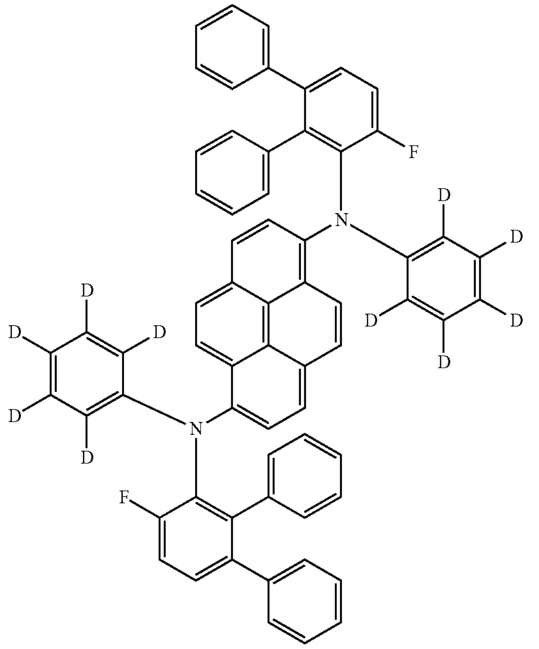
B-122
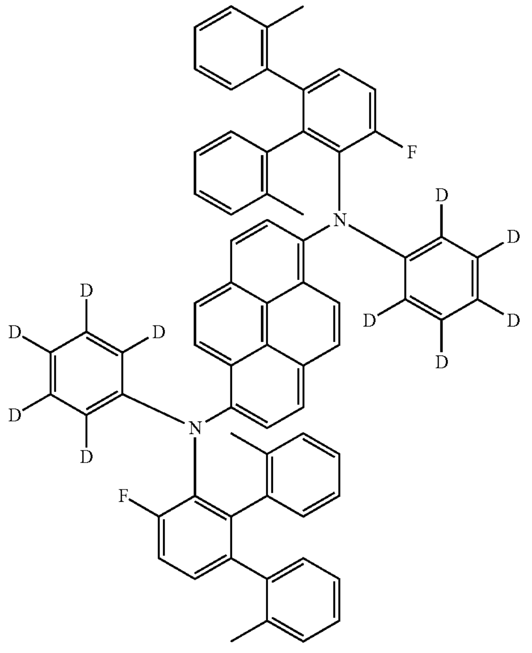
-continued
B-123
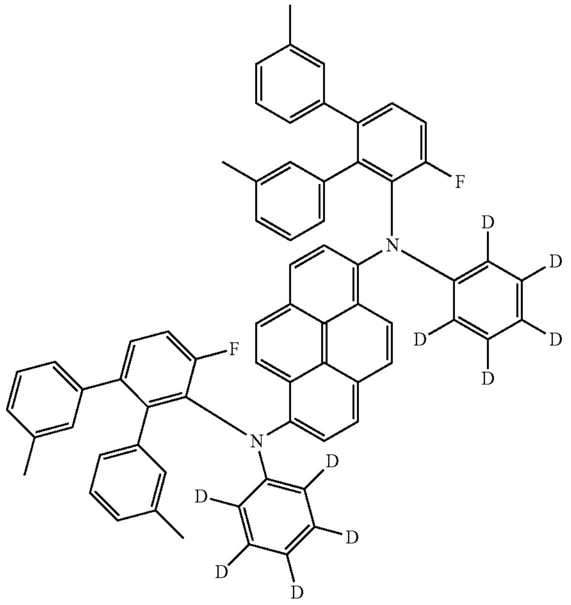
B-124
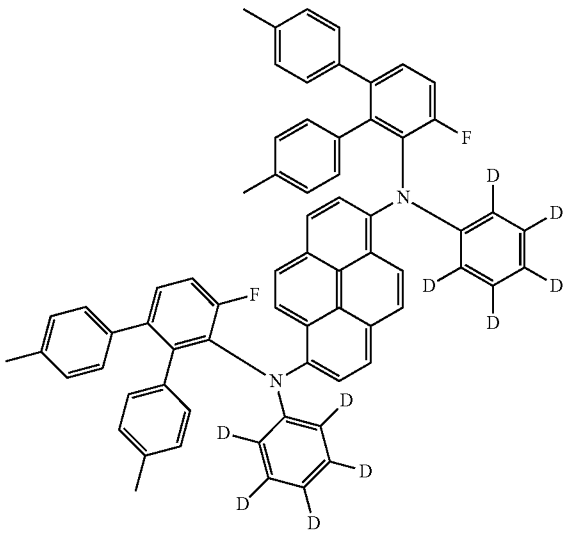

-continued
B-125
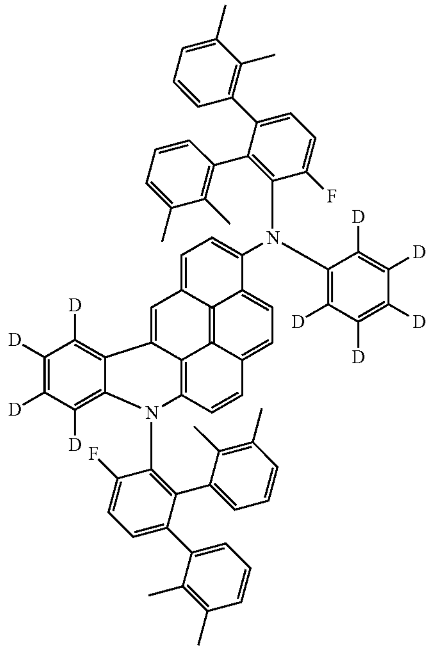
B-127
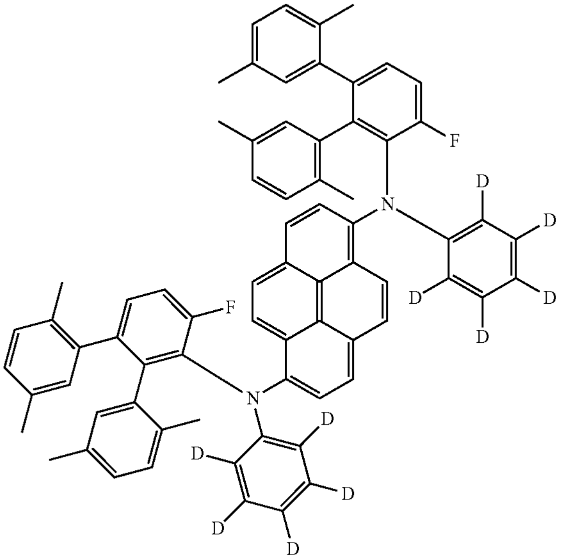
B-126
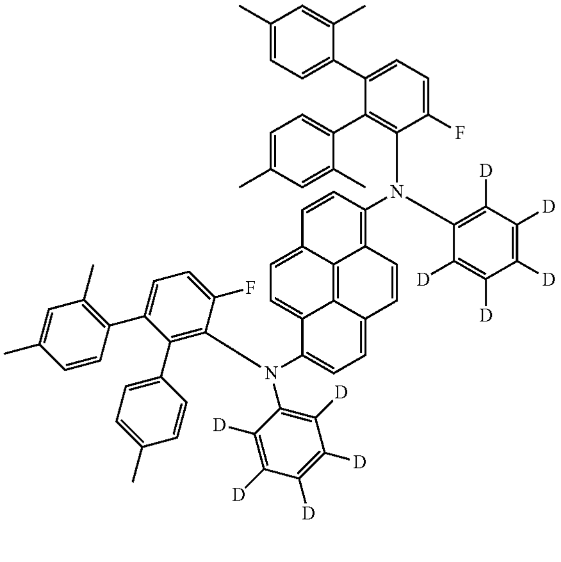
B-128
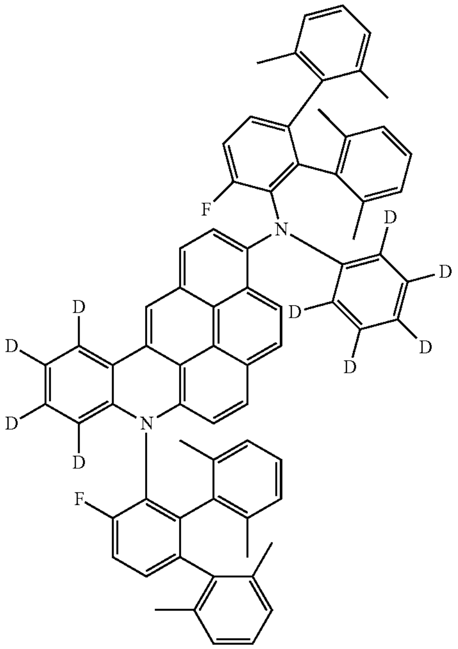

-continued
B-129
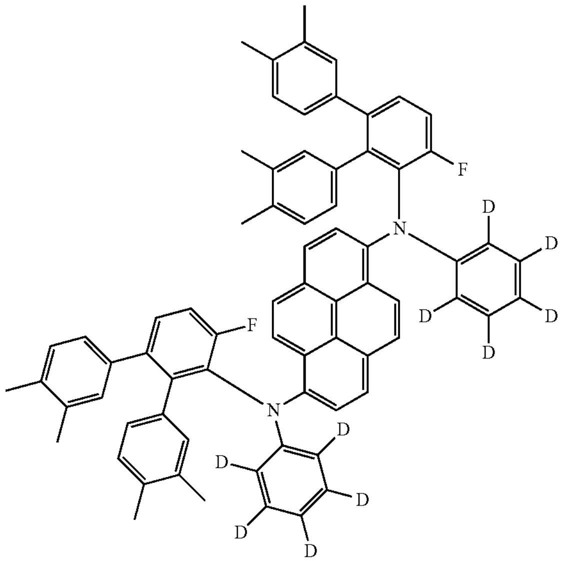
B-130
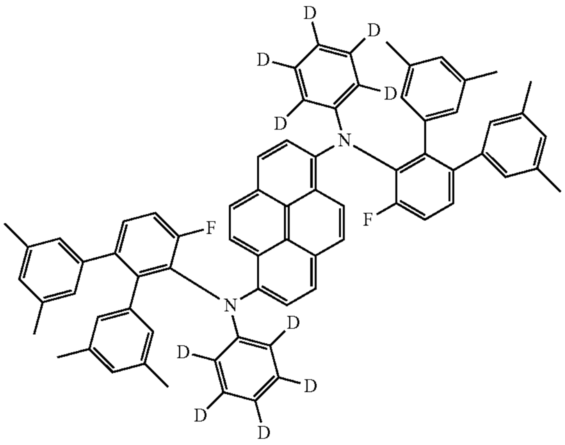
-continued
B-131
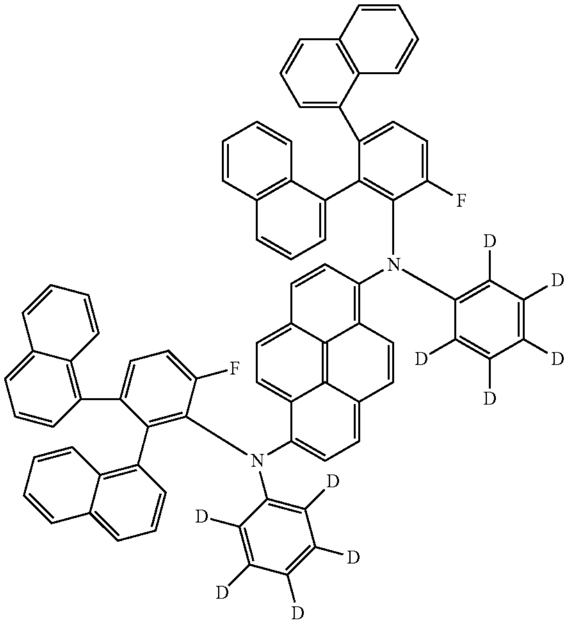
B-132
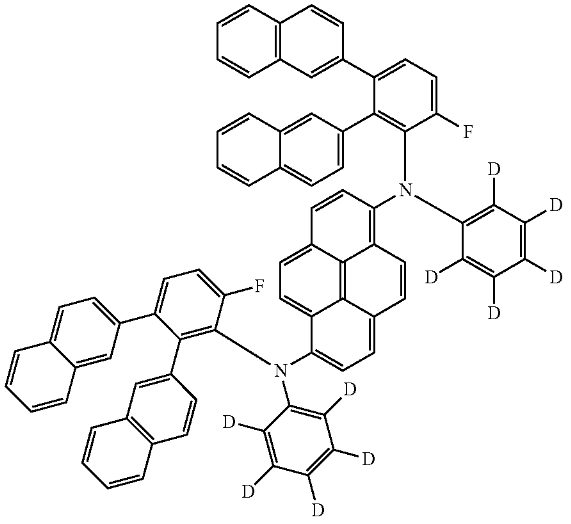

-continued
B-133
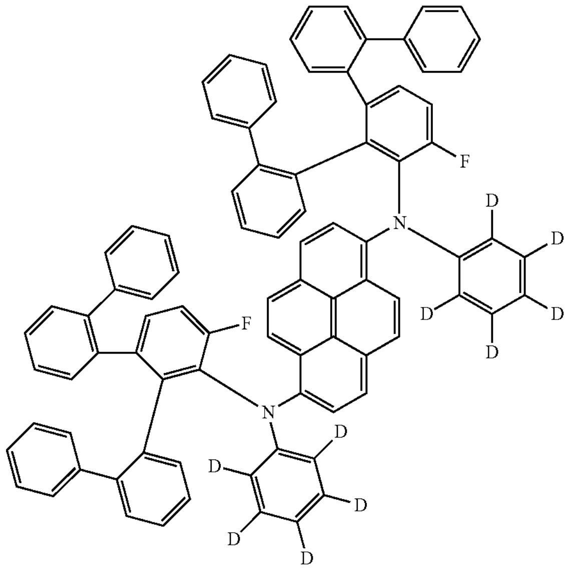
B-134
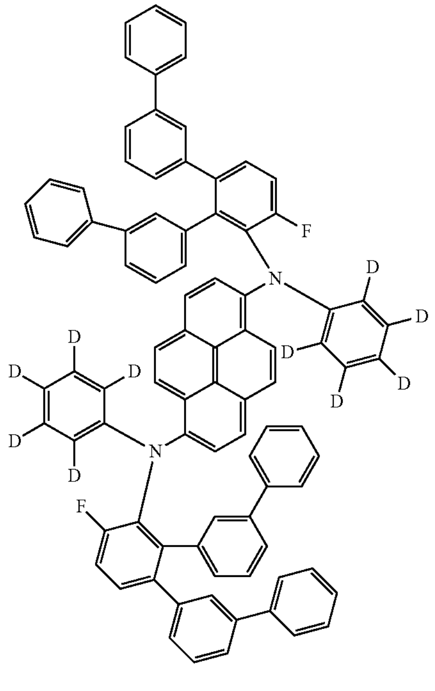
-continued
B-135
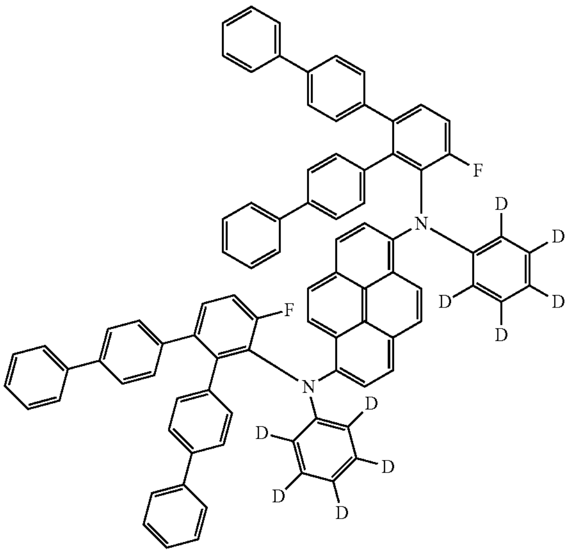
B-136
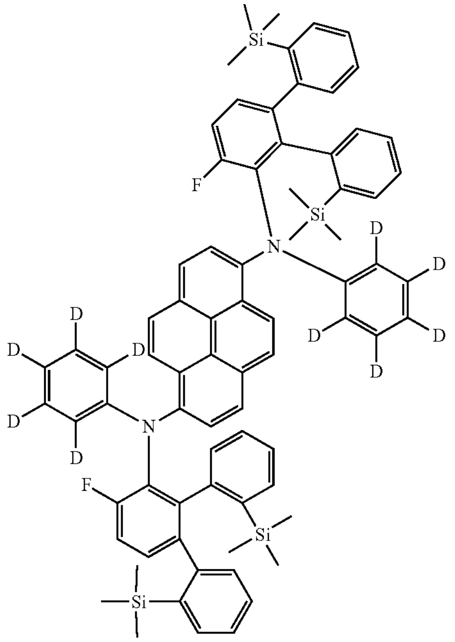
B-137
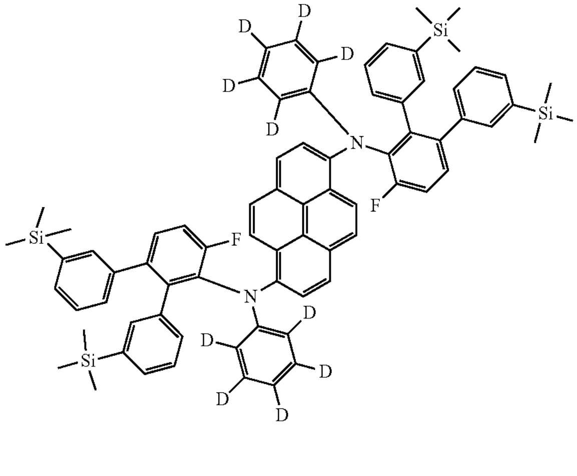

-continued
B-138
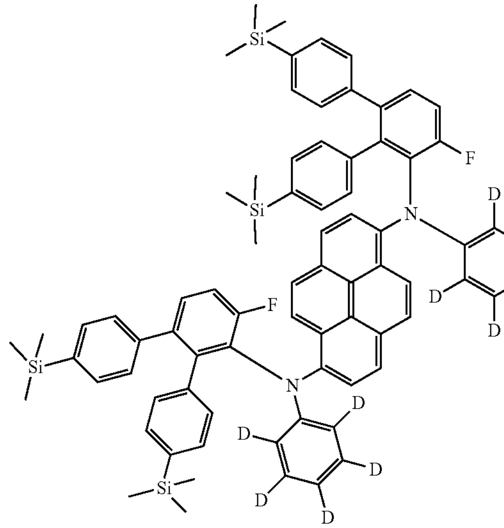
B-139
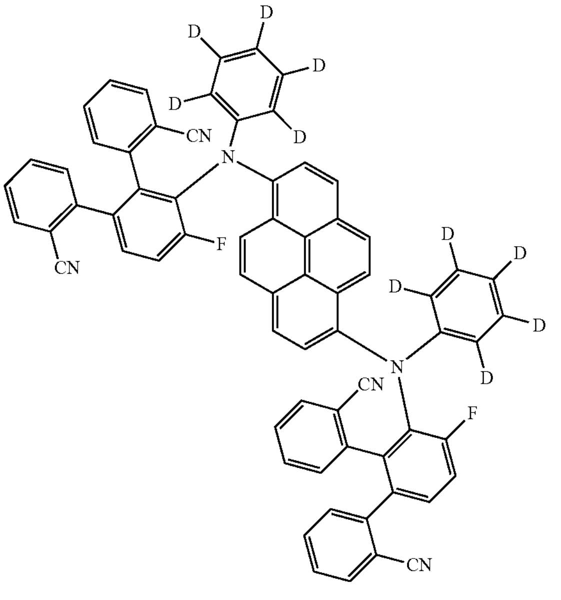
-continued
B-140
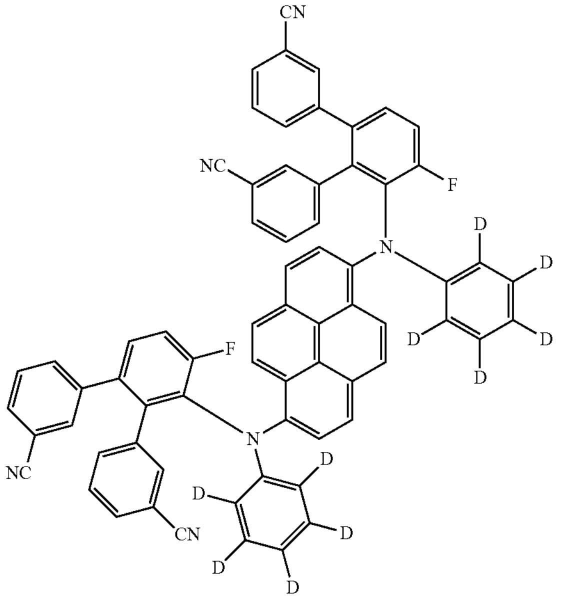
B-141
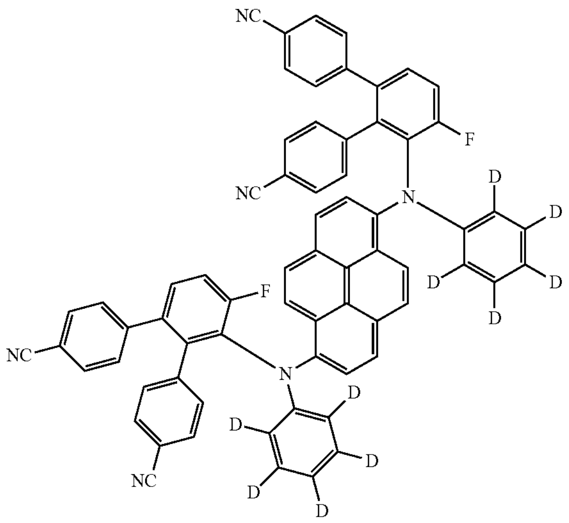

-continued
B-142
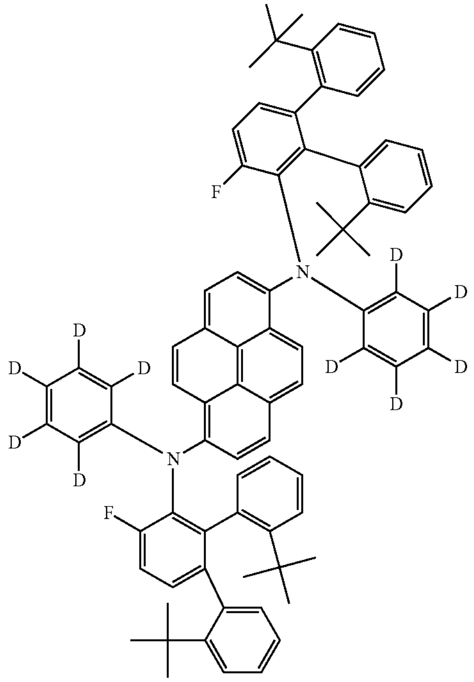
B-143
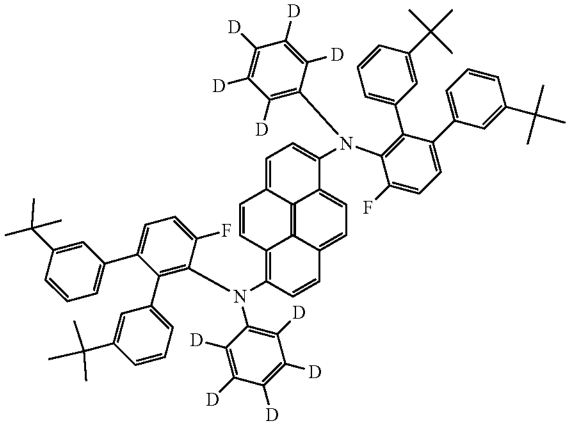
B-144
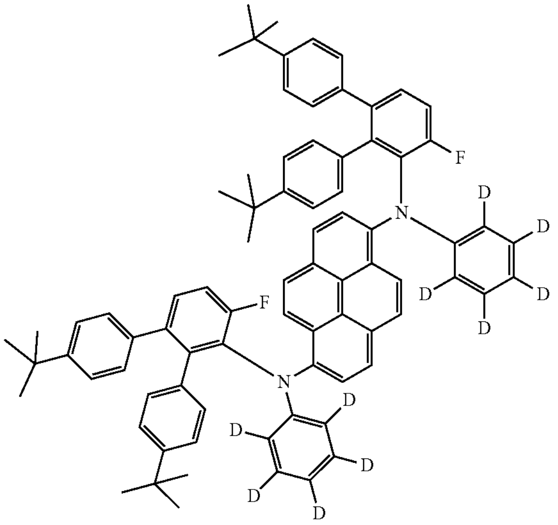
-continued
B-145
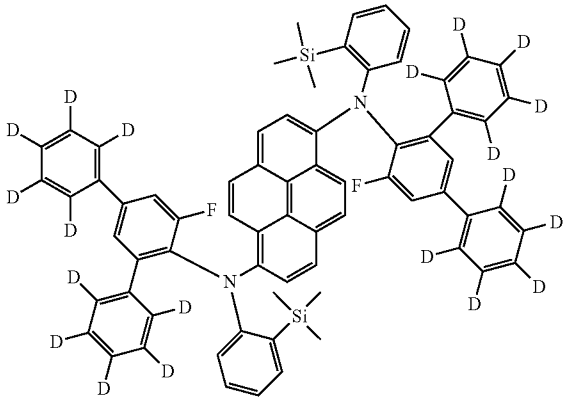
B-146
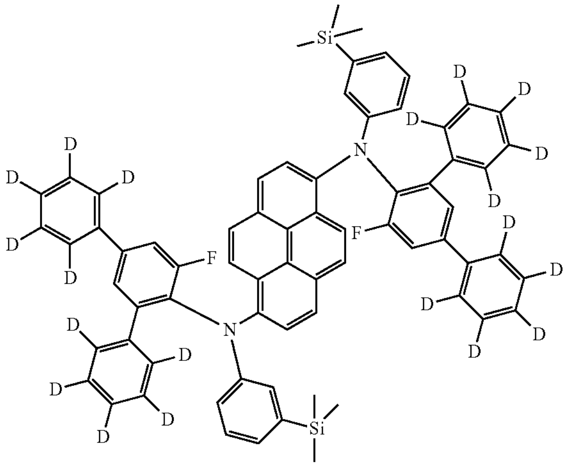
B-147
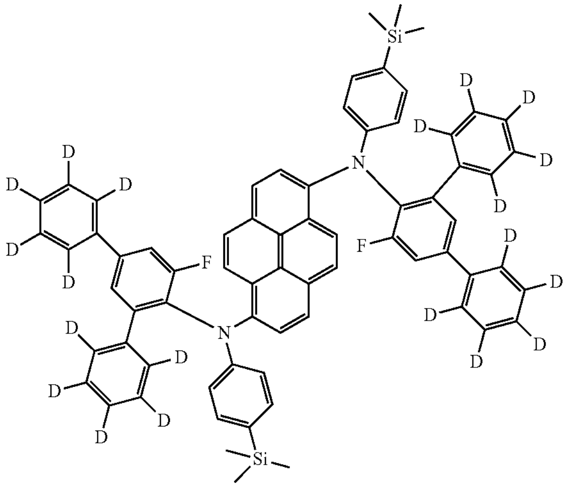

-continued
B-148
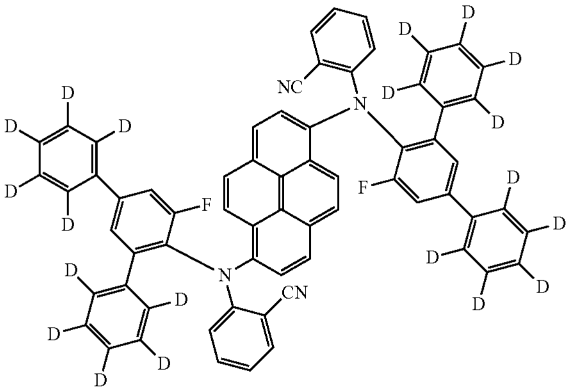
B-149
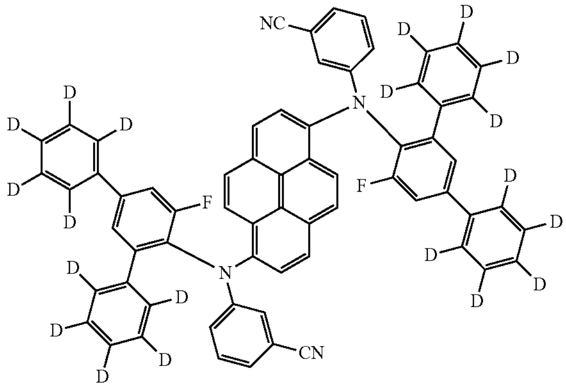
B-150
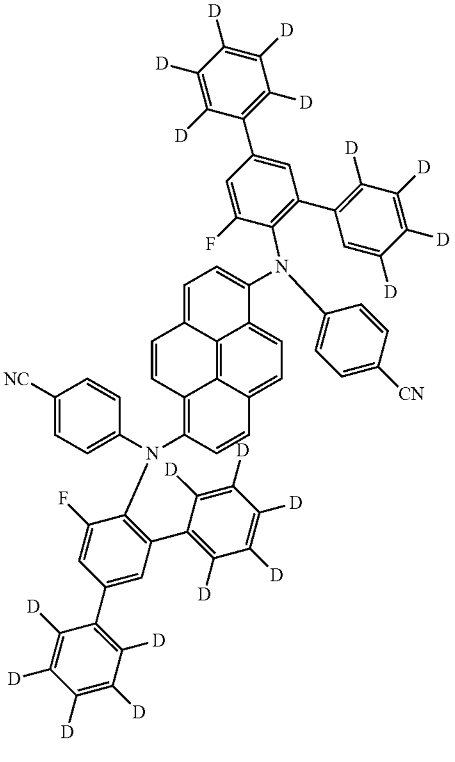
-continued
B-151
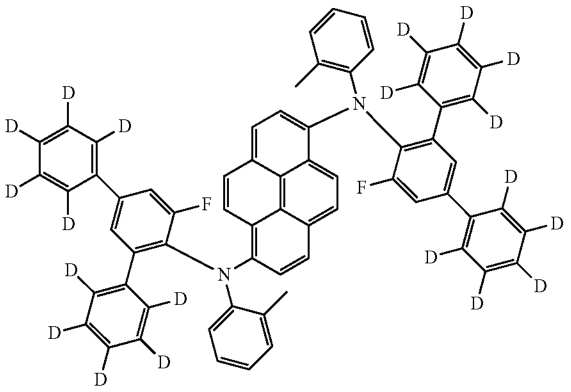
B-152
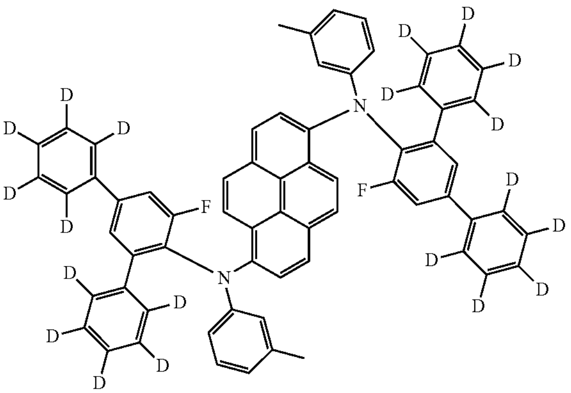
B-153
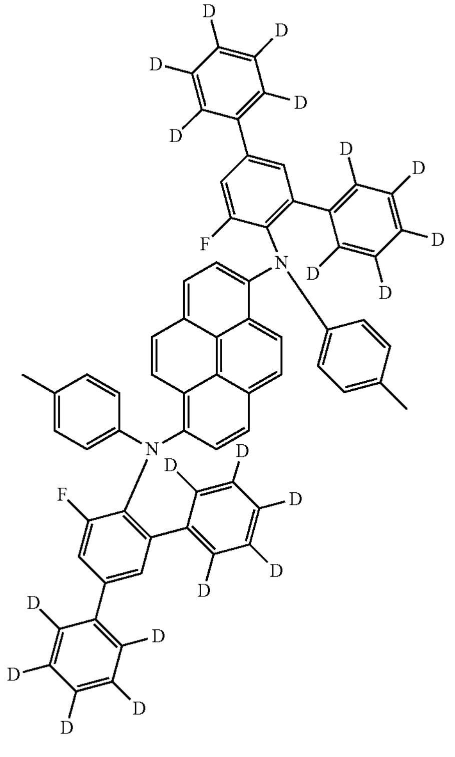

-continued
B-154
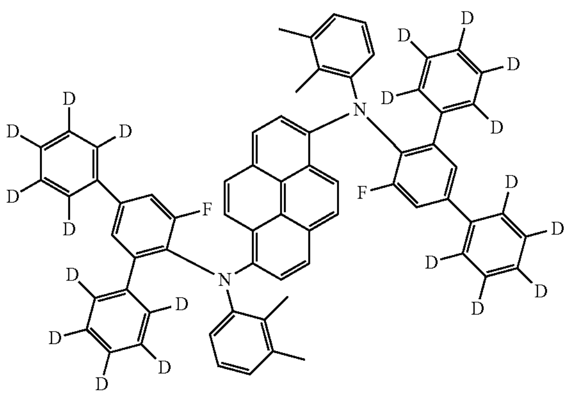
B-155
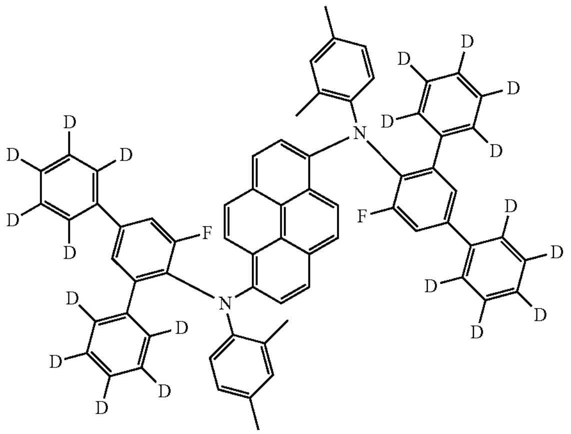
B-156
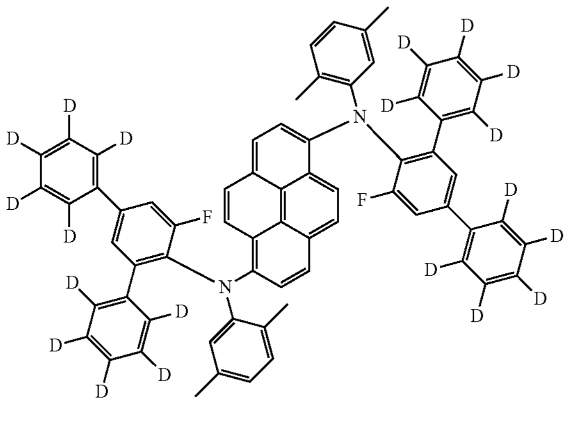
-continued
B-157
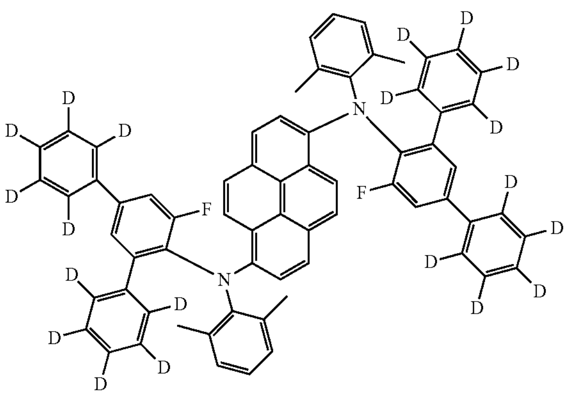
B-158
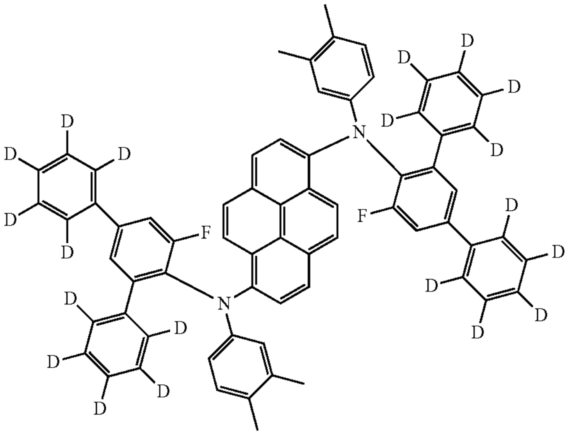
B-159
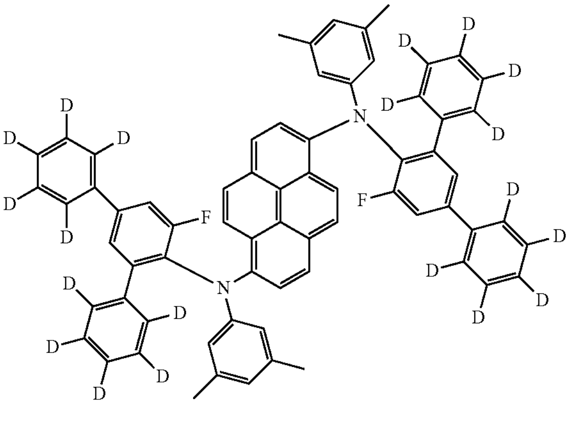

-continued
B-160
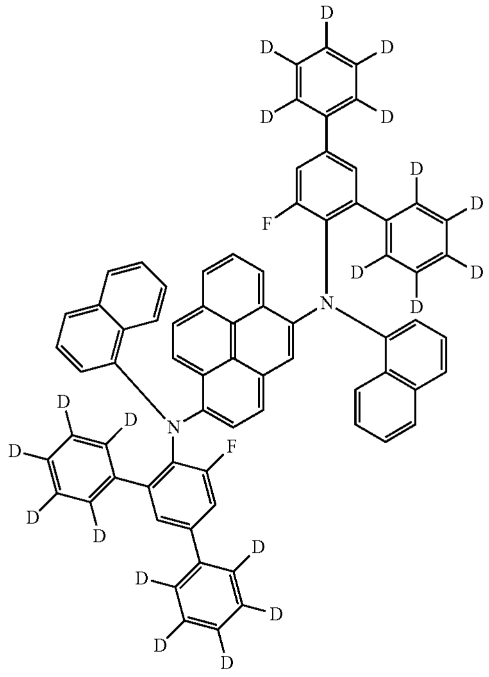
B-161
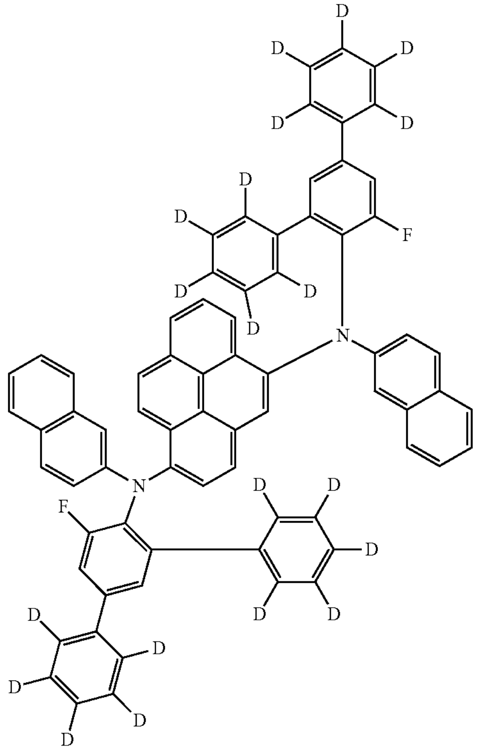
-continued
B-162
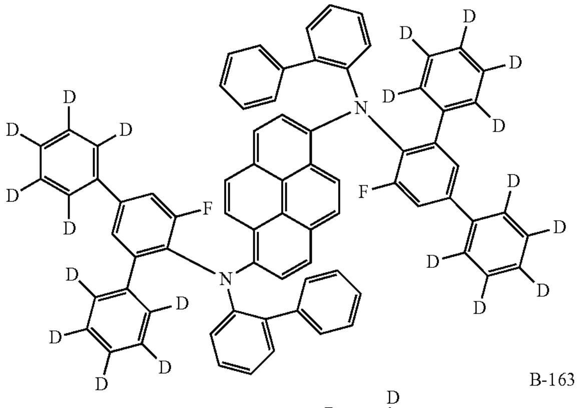
B-163
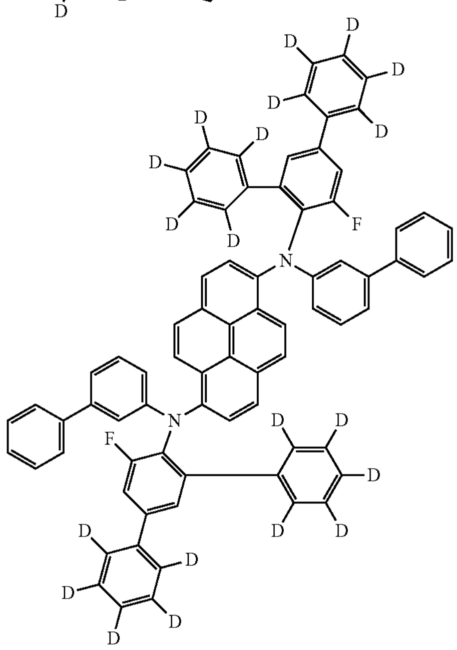
B-164
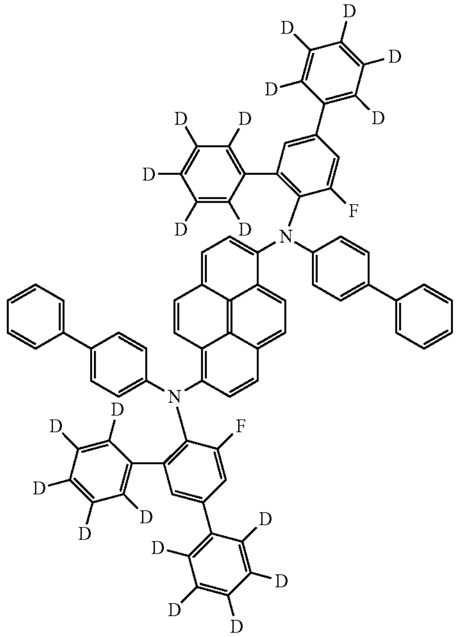

B-165
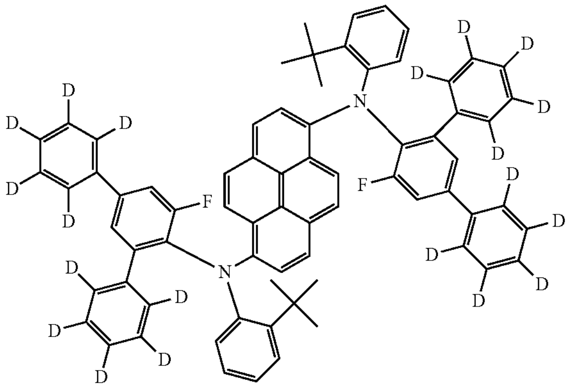
B-166
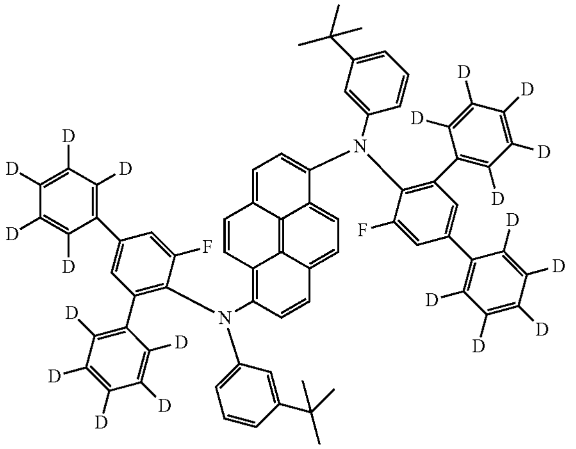
B-167
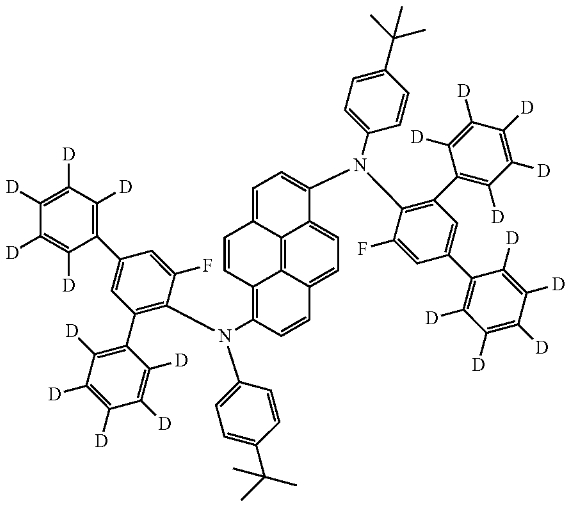
B-168
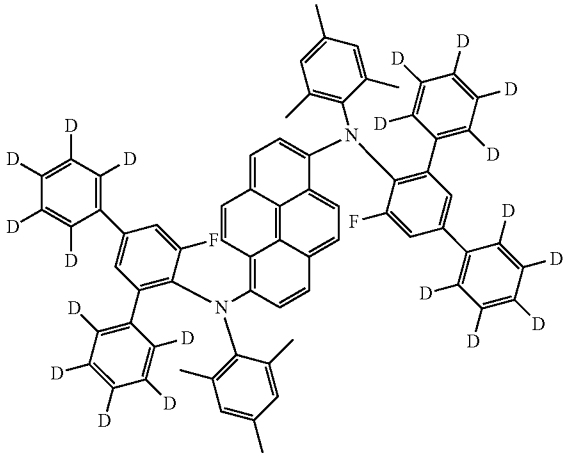
B-169
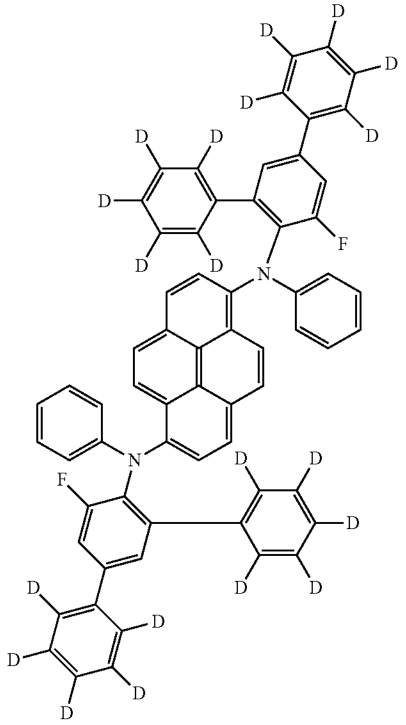

-continued

B-170

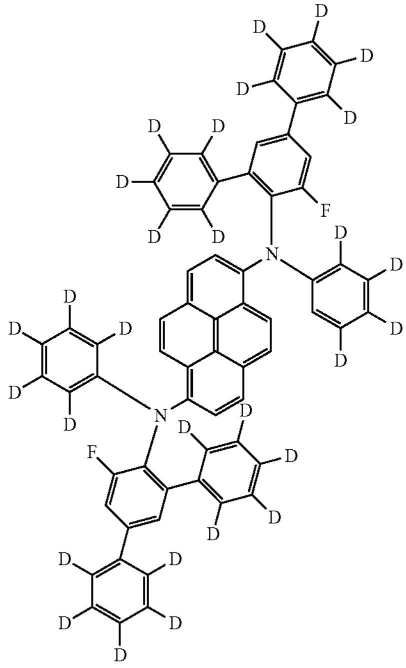

A synthesis example of the blue fluorescent compound marked by B-169 in the above Formula 6 is explained. The B-169 blue fluorescent compound is $N^1$,$N^6$-bis(2,4-di(2,3,4,5,6-pentadeuterium)phenyl-6-fluorophenyl)-$N^1$,$N^6$-diphenylpyrene-1,6-diamine.

1. Synthesis of 2,4-di(2,3,4,5,6-pentadeuterium)phenyl-6-fluoroaniline 2,4-di(2,3,4,5,6-pentadeuterium)phenyl-6-fluoroaniline is synthesized by following Reaction Formula 4.

[Reaction Formula 4]

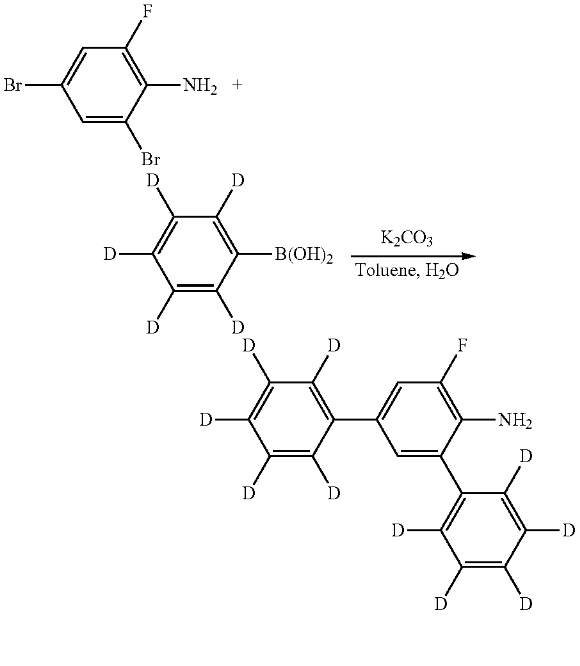

2,4-dibromo-6-fluoroaniline (10 mmol), 2,3,4,5,6-pentadeuteriumbenzeneboronic acid (24 mmol), tetrakis(triphenylphosphine)palladium(0) (1 mmol) and potassium carbonate (12 g) are put in a two-neck round-bottom flask and dissolved in toluene (30 mL) and $H_2O$ (10 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-di(2,3,4,5,6-pentadeuterium)phenyl-6-fluoroaniline (2.2 g) is yielded.

2. Synthesis of 2,4-di(2,3,4,5,6-pentadeuterium)phenyl-6-fluoro-N-phenylbenzenamine 2,4-di(2,3,4,5,6-pentadeuterium)phenyl-6-fluoro-N-phenylbenzenamine is synthesized by following Reaction Formula 5.

[Reaction Formula 5]

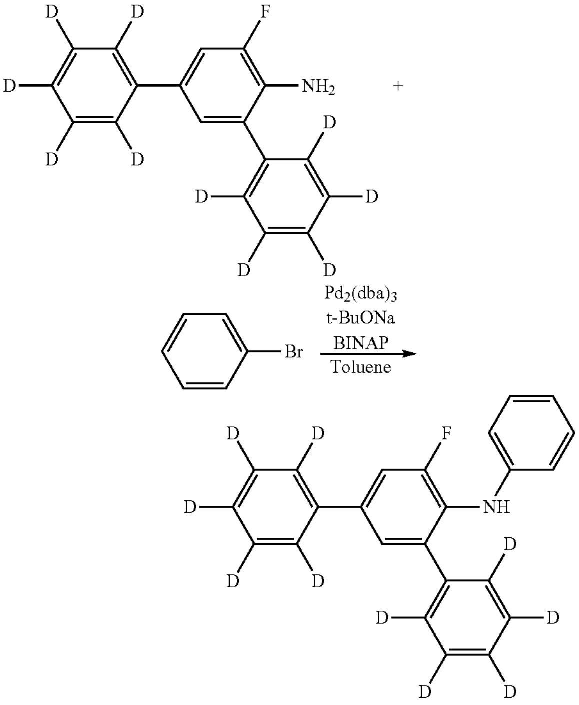

2,4-di(2,3,4,5,6-pentadeuterium)phenyl-6-fluoroaniline (12 mmol), bromobenzene (10 mmol), tris(dibenzylideneacetone)dipalladium(0) (0.15 mmol), (±)-2,2'-bis(diphenylphosphine)-1,1'-binaphthalene (0.3 mmol) and sodium tert-butoxie (14 mmol) are put in a two-neck round-bottom flask and dissolved in toluene (30 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-di(2,3,4,5,6-pentadeuterium)phenyl-6-fluoro-N-phenylbenzenamine (2.6 g) is yielded.

3. Synthesis of $N^1$,$N^6$-bis(2,4-di(2,3,4,5,6-pentadeuterium)phenyl-6-fluorophenyl)-$N^1$,$N^6$-diphenylpyrene-1,6-diamine $N^1$,$N^6$-bis(2,4-di(2,3,4,5,6-pentadeuterium)phenyl-6-fluorophenyl)-$N^1$,$N^6$-diphenylpyrene-1,6-diamine is synthesized by following Reaction Formula 6.

[Reaction Formula 6]

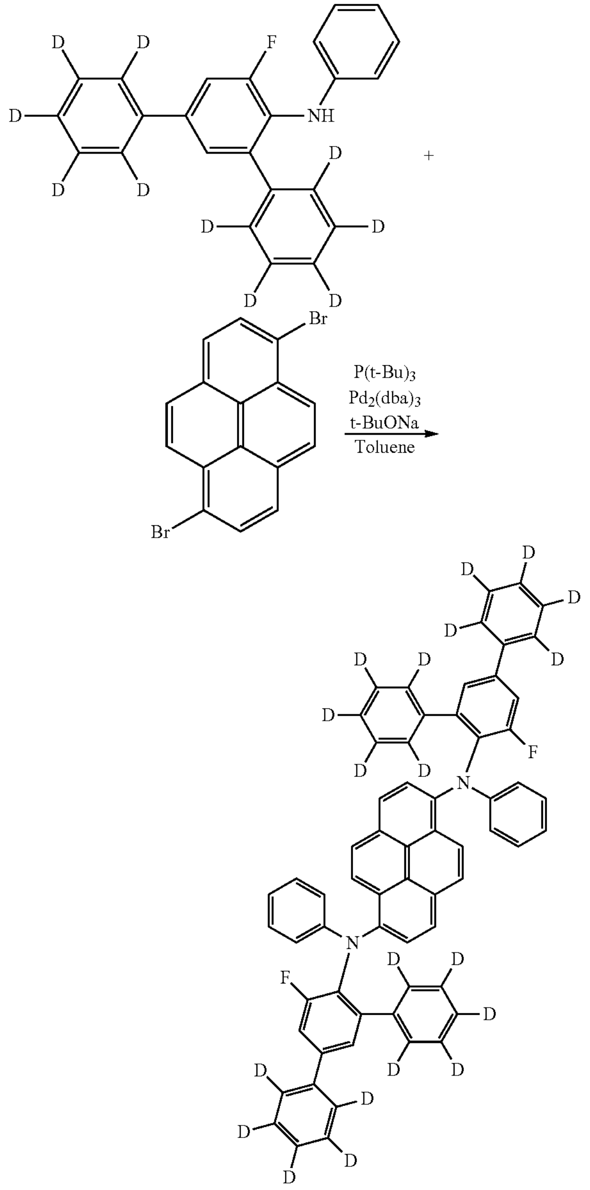

2,4-di(2,3,4,5,6-pentadeuterium)phenyl-6-fluoro-N-phenylbenzenamine (6 mmol), 1,6-dibromopyrene (5 mmol), tris(dibenzylideneacetone)dipalladium(0) (0.075 mmol), tri-tert-butylphosphine (0.15 mmol) and sodium tert-butoxie (7 mmol) are put in a two-neck round-bottom flask and dissolved in toluene (15 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, after re-crystallizing and filtering with dichloromethane and acetone, and then being thermally refined to yield $N^1$,$N^6$-bis(2,4-di(2,3,4,5,6-pentadeuterium)phenyl-6-fluorophenyl)-$N^1$,$N^6$-diphenylpyrene-1,6-diamine is yielded.

Hereinafter, a detailed description will be made of preferred examples associated with the OELD according to the present invention. More specifically, the examples relate to an OELD including an emission material layer which uses the blue fluorescent compound of Formula 5 as a dopant.

EXAMPLES

Example 6

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), 4,4'-bis[N-(1-naphtyl)-N-phenylamino]-biphenyl (NPD) (about 400 angstroms), an emitting layer (about 200 angstroms) including DPVBi as a host and a compound represented by B-97 in the above Formula 6 as a dopant (about 5 weight %), Alq3 (about 350 angstroms), fluorolithium (LiF) (about 5 angstroms) and aluminum (Al) (about 1000 angstroms) are sequentially formed on the ITO layer such that an OELD is fabricated.

The OELD produces a brightness of 614 cd/m$^2$ at an electric current of 10 mA and a voltage of 4.73 V. At this time, the X index and Y index of CIE color coordinates are 0.139 and 0.130, respectively.

Example 7

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and a compound represented by B-114 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 628 cd/m$^2$ at an electric current of 10 mA and a voltage of 4.61 V. At this time, the X index and Y index of CIE color coordinates are 0.140 and 0.131, respectively.

Example 8

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and a compound represented by B-147 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 659 cd/$m^2$ at an electric current of 10 mA and a voltage of 4.42 V. At this time, the X index and Y index of CIE color coordinates are 0.139 and 0.143, respectively.

Example 9

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torn CuPC (about 200 angstroms), NPD (about 400 angstroms), an emitting layer (about 200 angstroms) including DPVBi as a host and a compound represented by B-169 in the above Formula 3 as a dopant (about 5 weight %), Alq3 (about 350 angstroms), LiF (about 5 angstroms) and Al (about 1000 angstroms) are sequentially formed on the ITO layer such that an OELD is fabricated.

The OELD produces a brightness of 602 cd/$m^2$ at an electric current of 10 mA and a voltage of 4.65 V. At this time, the X index and Y index of CIE color coordinates are 0.132 and 0.136, respectively.

Comparative Example 2

An ITO layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 200 angstroms), NPD (about 400 angstroms), an emitting layer (about 200 angstroms) including DPVBi as a host and BD-a represented by the above Formula 1-3 as a dopant (about 1 weight %), Alq3 (about 350 angstroms), LiF (about 5 angstroms) and Al (about 1000 angstroms) are sequentially formed on the ITO layer such that an OELD is fabricated.

The OELD produces a brightness of 526 cd/$m^2$ at an electric current of 10 mA and a voltage of 6.7 V. At this time, the X index and Y index of CIE color coordinates are 0.136 and 0.188, respectively.

Herein, CuPC and DPVBi are respectively represented by the above Formulas 1-1 and 1-2. NPD and Alq3 are represented by the above Formulas 4-1 and 4-2, respectively.

The OELD fabricated in Examples 6 to 9 and Comparative Example s is evaluated for efficiency, brightness, and so on. A voltage has a dimension of [V], an electric current has a dimension of [mA], and a brightness has a dimension of [cd/m2. The evaluated results are shown in Table 2.

TABLE 2

| | voltage | Electric current | Brightness | CIE(X) | CIE(Y) |
|---|---|---|---|---|---|
| Ex. 6 | 4.73 | 10 | 614 | 0.139 | 0.130 |
| Ex. 7 | 4.61 | 10 | 628 | 0.140 | 0.131 |
| Ex. 8 | 4.42 | 10 | 659 | 0.139 | 0.143 |
| Ex. 9 | 4.65 | 10 | 602 | 0.132 | 0.136 |
| Com. Ex. 2 | 6.7 | 10 | 526 | 0.136 | 0.188 |

As shown in Table 2, the OELD in Examples 6 to 9 has high color purity and low driving voltage such that power consumption for the OELD is reduced. As a result, a lifetime of the OELD using the blue fluorescent compound according to the present invention is improved.

-Third Embodiment-

A blue fluorescent compound according to the third embodiment of the present invention includes 1,6-pyrene and fluorophenylamine derivative. Namely, each of 1 and 6 positions of pyrene are substituted by 6-fluorophenylamine derivative. Each 6-fluorophenylamine has first and second phenyl parts. At least one of fluorine, cyanine and tri-fluoromethyl is introduced into the first phenyl part, and at least two aryl are introduced into the second phenyl art. As a result, the blue fluorescent compound according to the third embodiment of the present invention has improved color purity and luminescent efficiency.

The blue fluorescent compound according to the second embodiment of the present invention is represented by following Formula 7.

[Formula 7]

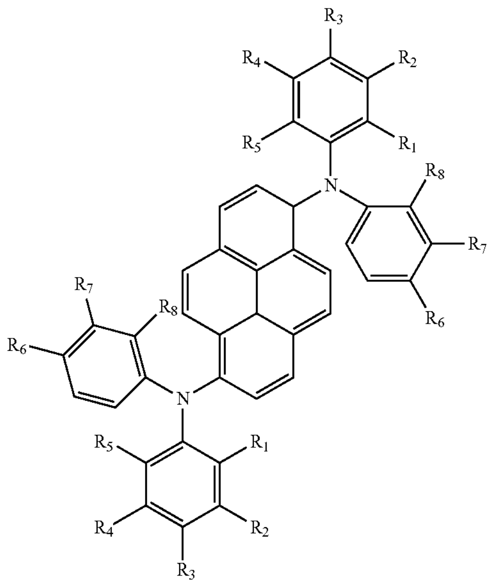

In the above Formula 7, each of R1 to the R5 is selected from hydrogen (H), C1 to C6 alkyl, or substituted or non-substituted aryl having at least six carbons (C). At least two of R1 to R5 are selected from the substituted or non-substituted aryl having at least six carbons. Each of R6 to R8 is selected from hydrogen (H), C1 to C6 alkyl, substituted or non-substituted aryl having at least six carbons, fluorine, cyanide, or tri-fluoromethyl. At least one of R6 to R8 is selected from fluorine, cyanide, or tri-fluoromethyl.

For example, C1 to C6 alkyl is one of methyl, ethyl, n-propyl, i-propyl, n-butyl, i-butyl and t-butyl. The aryl is one of phenyl, o-toluoyl, m-toluoyl, p-toluoyl, o-xylyl, m-xylyl, p-xylyl, 1-naphthyl, 2-naphthyl, and trimethylsilyl, and their substitution products. For example, the substituted aryl may be 2,3,4,5,6-pentadeuteriumphenyl.

Namely, in the third embodiment, two phenylamine derivatives, each of which includes first and second phenyl parts, are introduced into 1 and 6 positions of pyrene. At least one of fluorine, cyanine and tri-fluoromethyl is introduced into the first phenyl part, and at least two aryl are introduced into the second phenyl art such that the blue fluorescent compound according to the third embodiment of the present invention has improved color purity and luminescent efficiency.

For example, the blue fluorescent compound represented by Formula 7 is one of compounds in following Formula 8. For convenience, C-1 to C-152 are respectively marked to compounds.

[Formula 8]
C-1
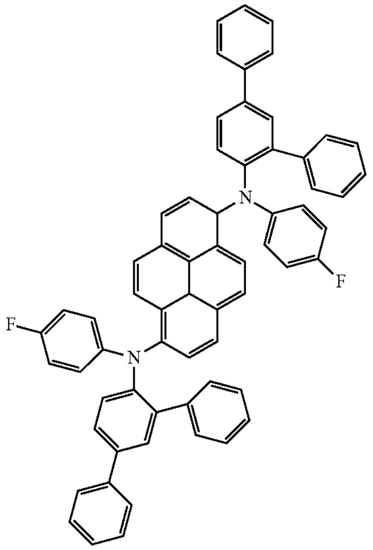
C-2
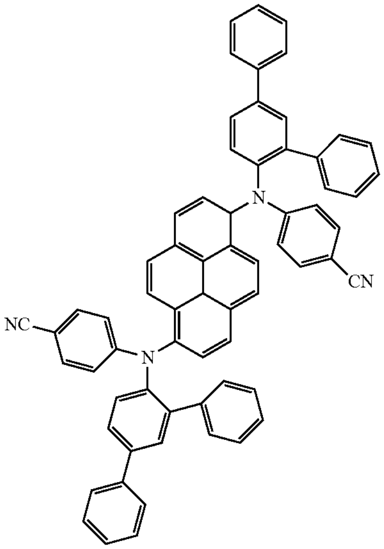
C-3
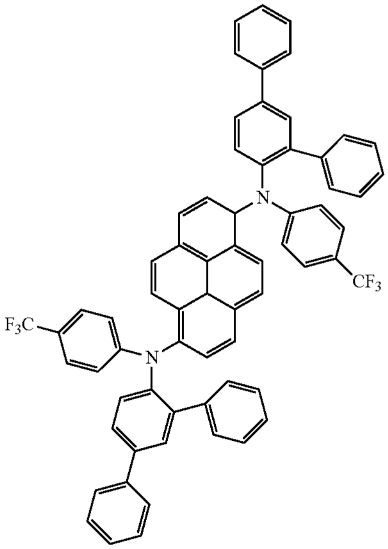
-continued
C-4
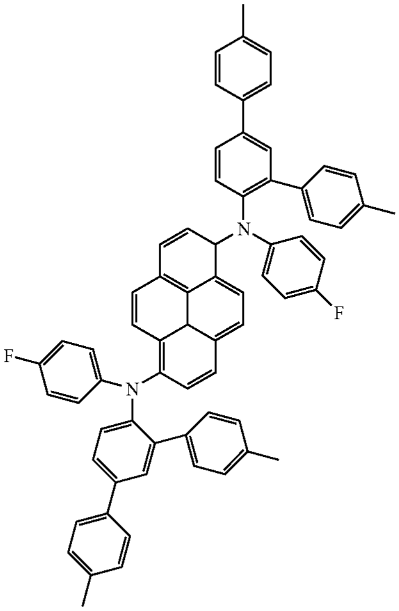
C-5
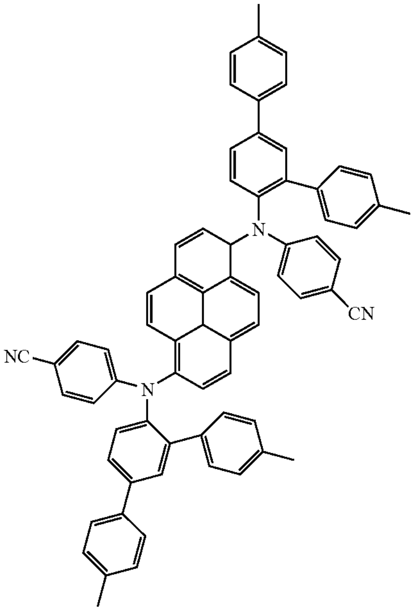

-continued
C-6
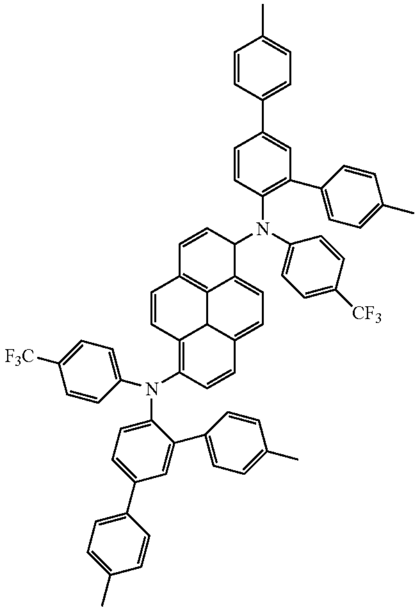
C-7
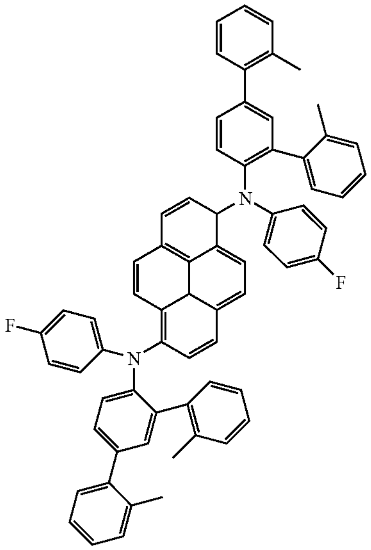
C-8
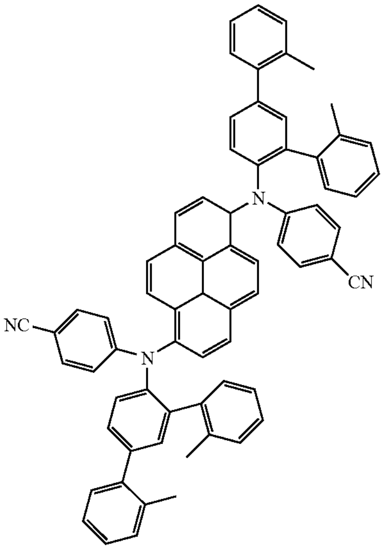
-continued
C-9
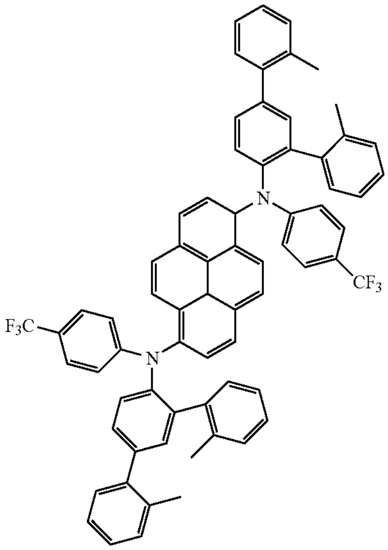
C-10
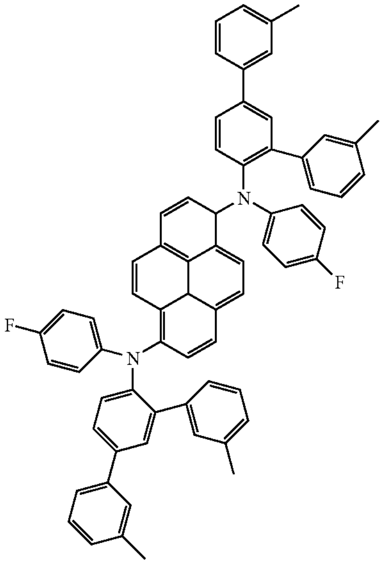
C-11
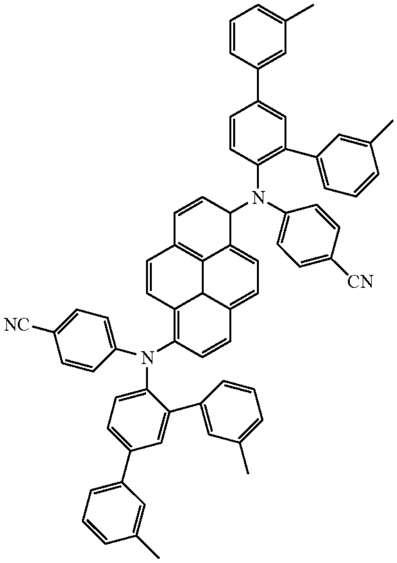

-continued
C-12
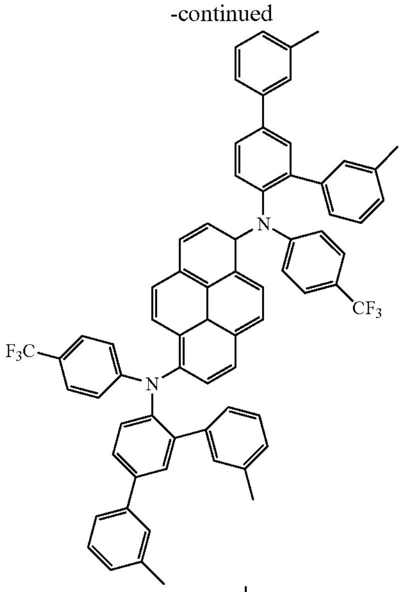
C-13
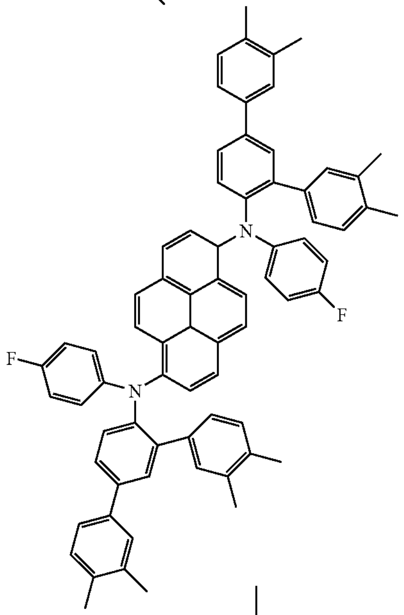
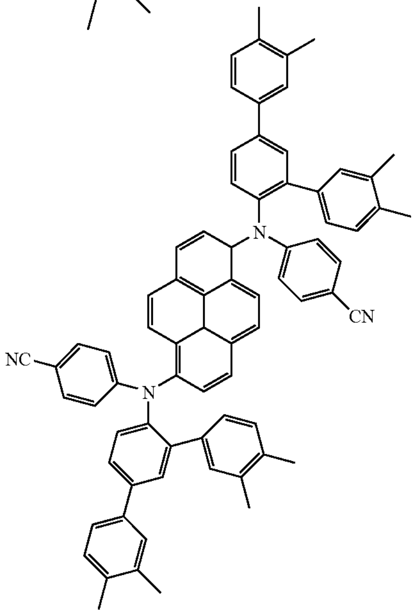
-continued
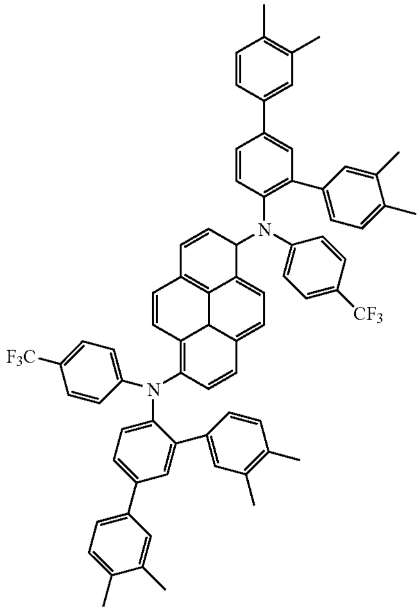
C-16
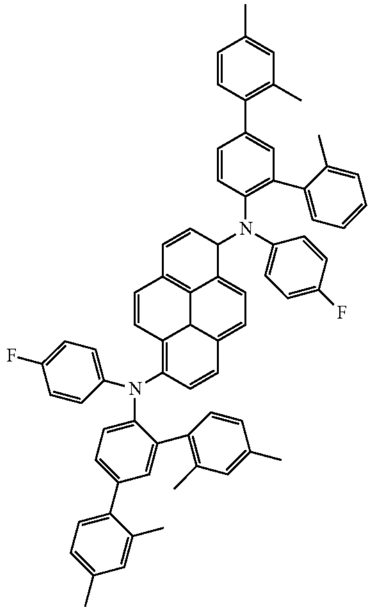

-continued
C-17
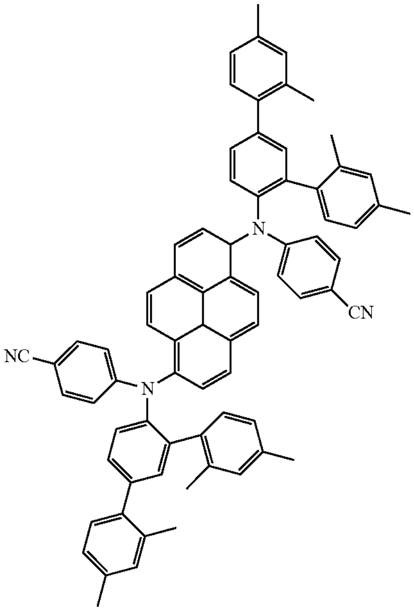
C-18
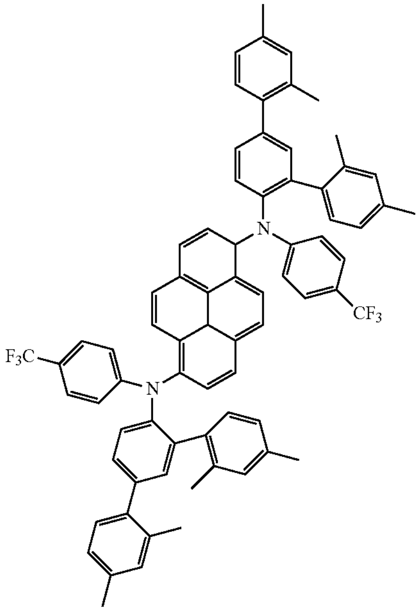
-continued
C-19
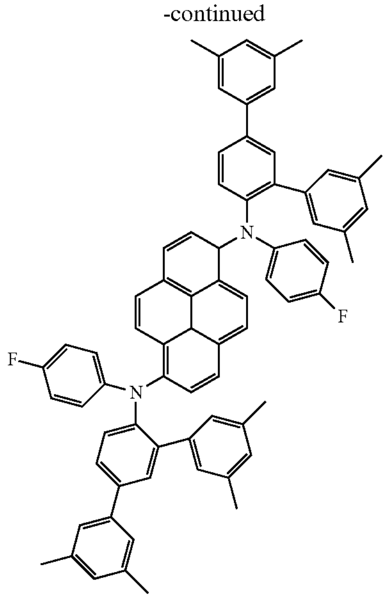
C-20
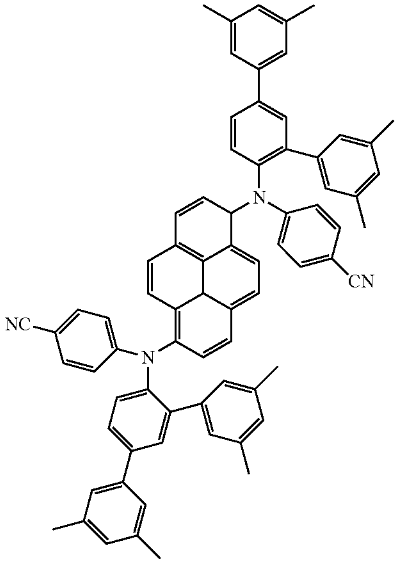
C-21
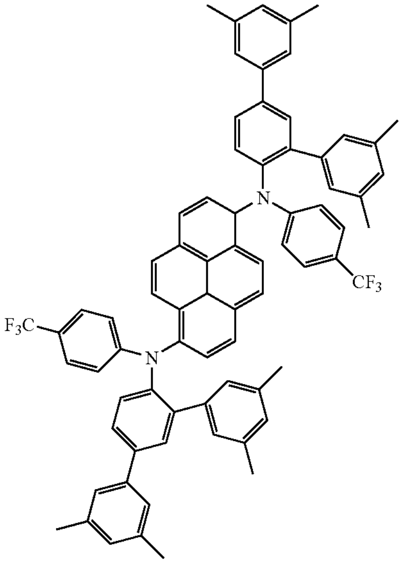

-continued
C-22
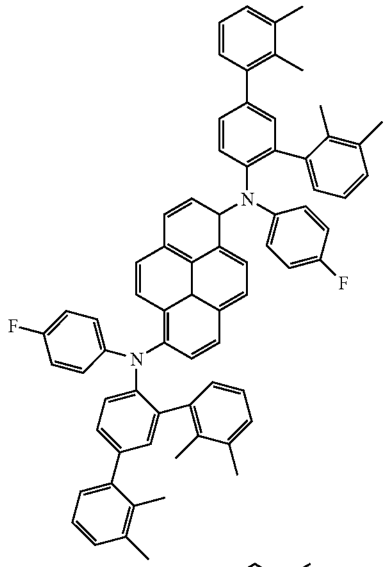
C-23
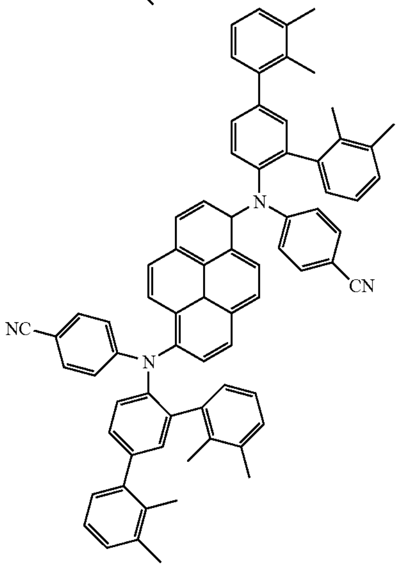
C-24
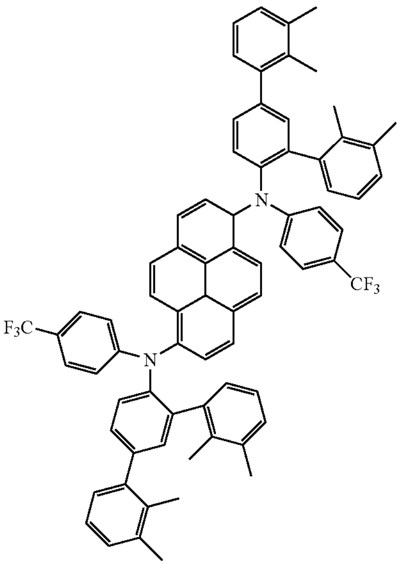
-continued
C-25
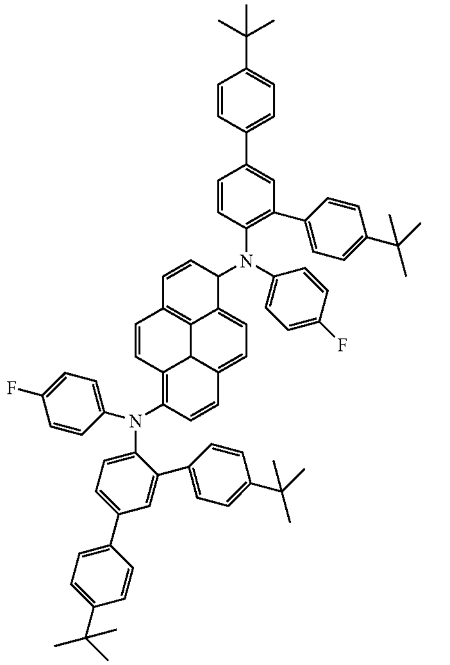
C-26
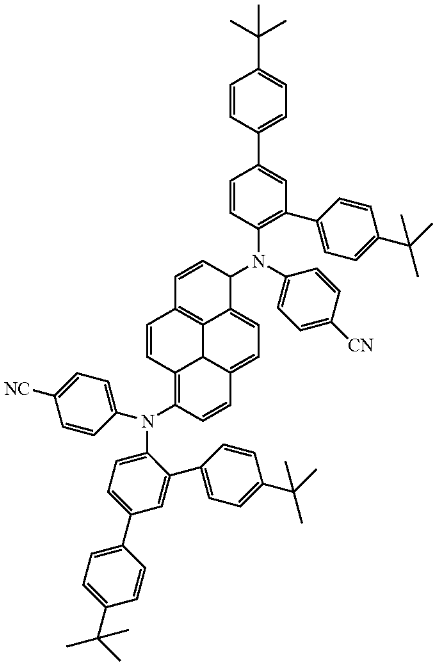

C-27
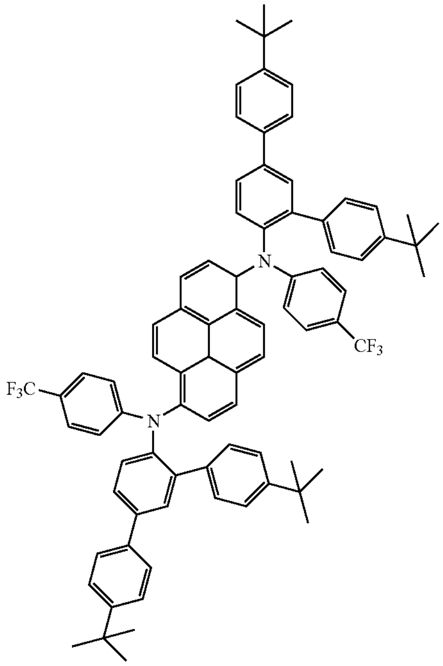
C-28
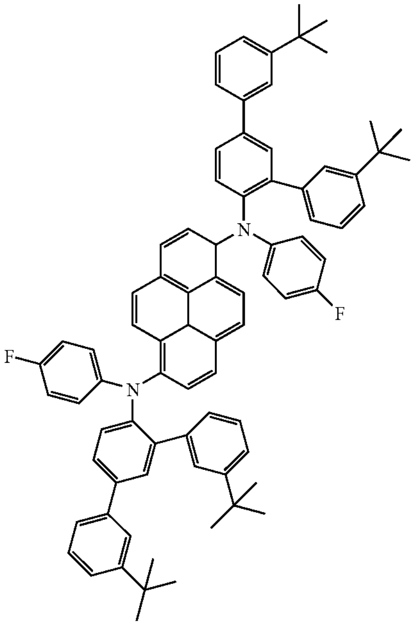
C-29
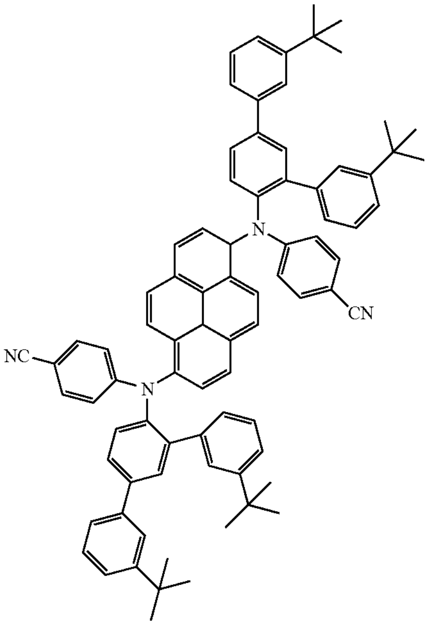
C-30
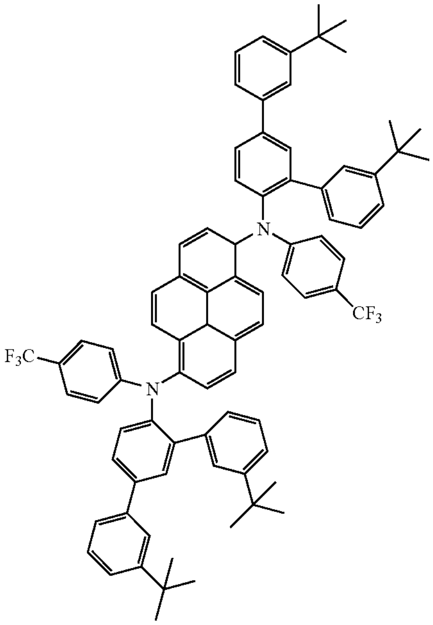

-continued
C-31
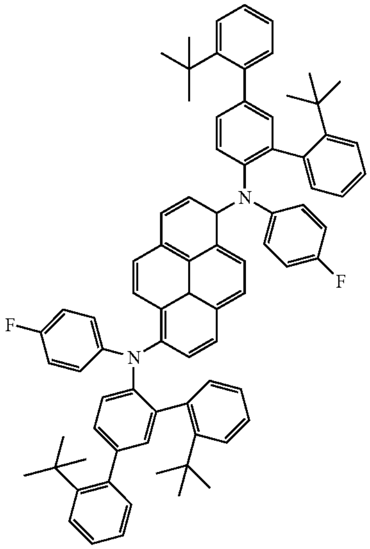
C-32
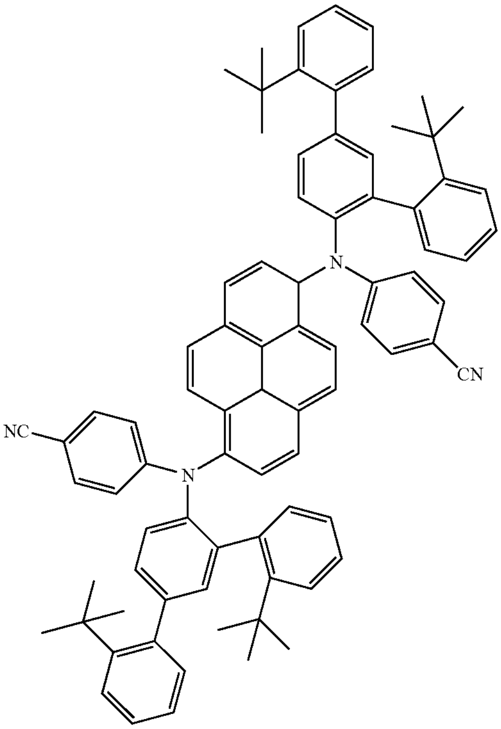
-continued
C-33
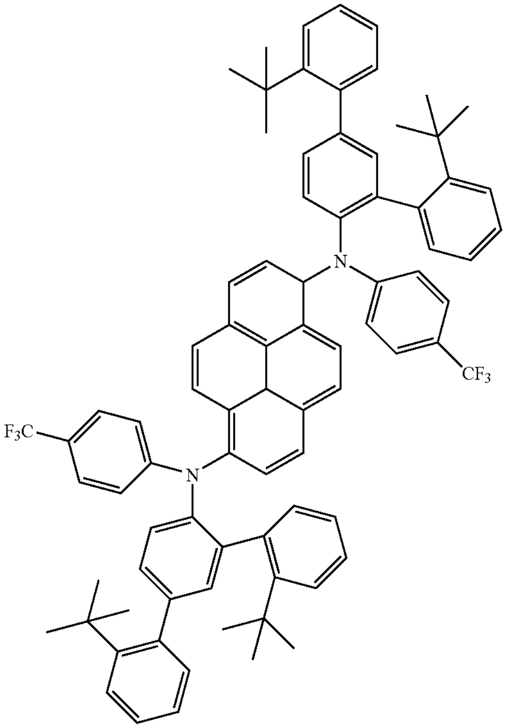
C-34
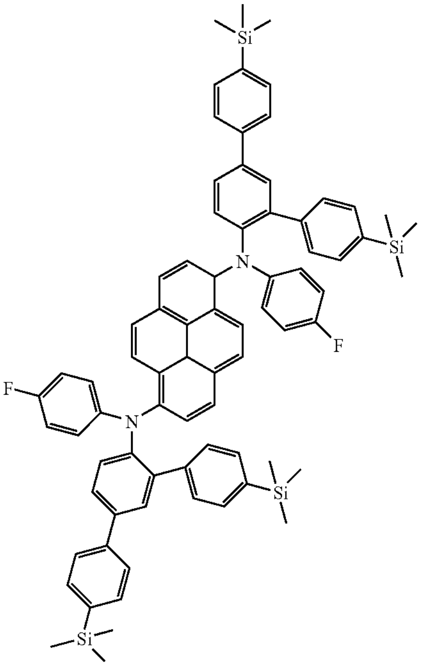

-continued
C-35
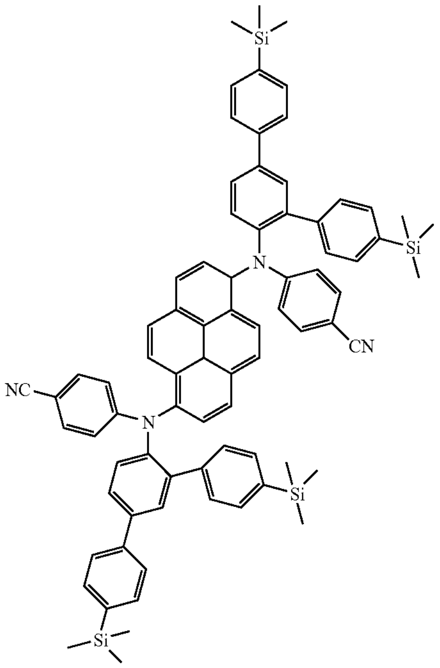
C-36
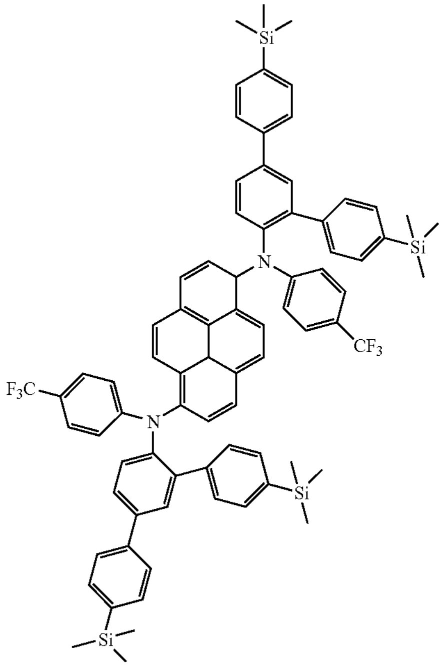
-continued
C-37
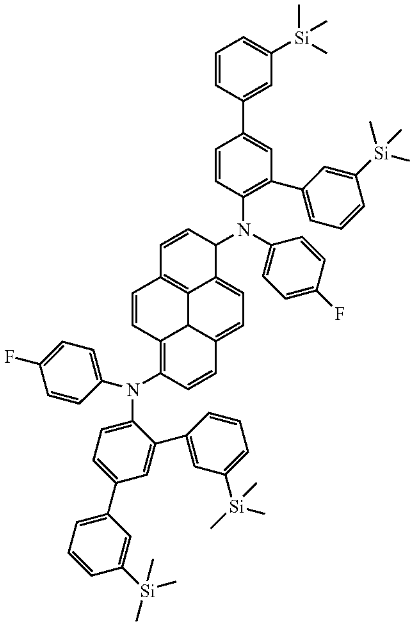
C-38
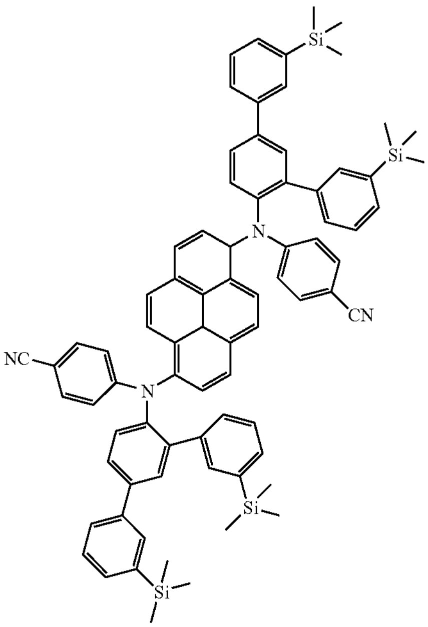

-continued
C-39
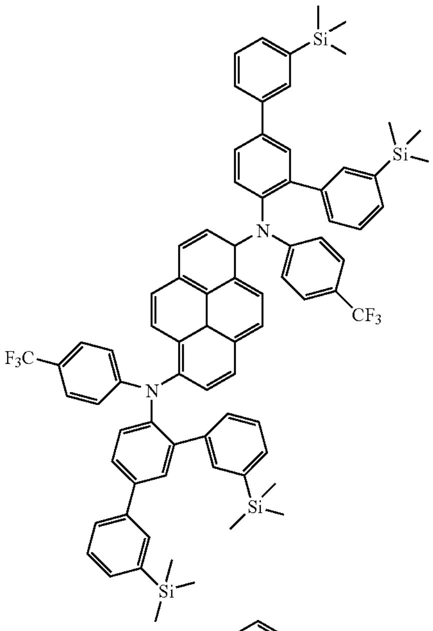
C-40
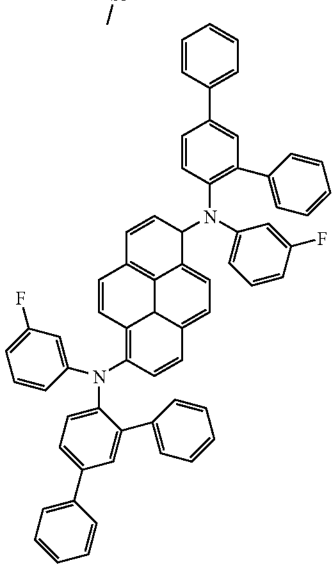
C-41
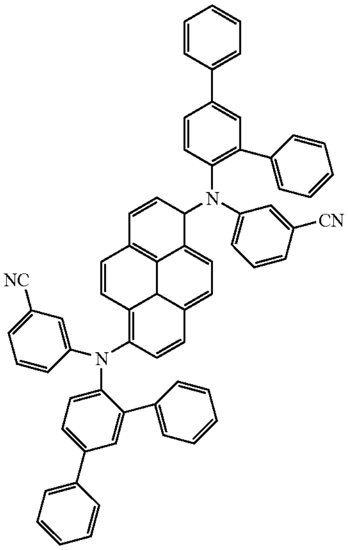
-continued
C-42
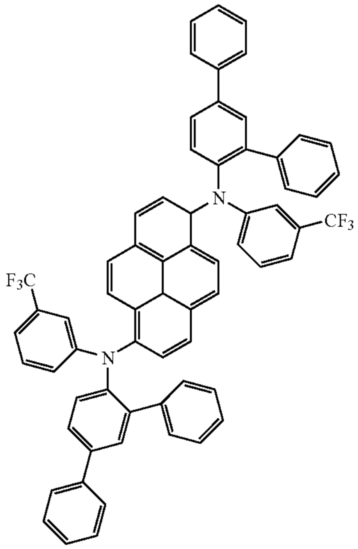
C-43
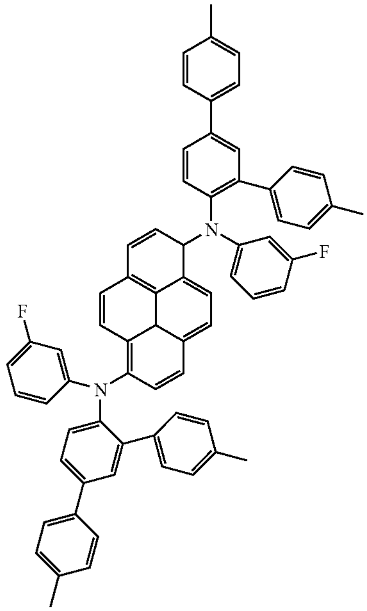

C-44
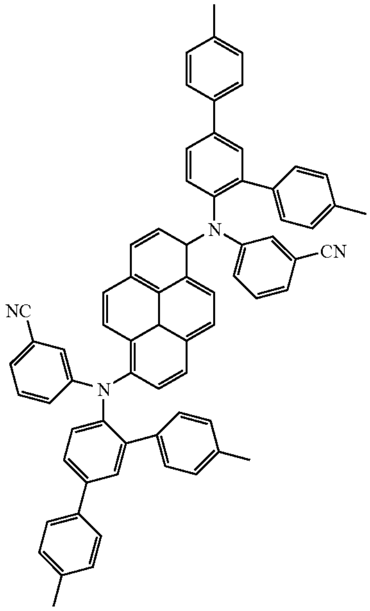
C-45
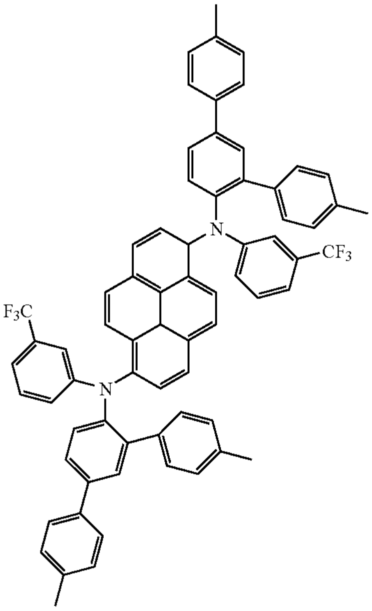
C-46
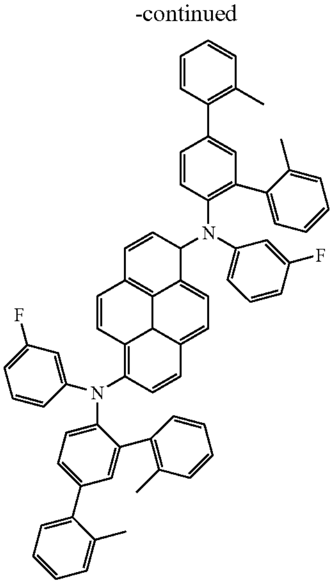
C-47
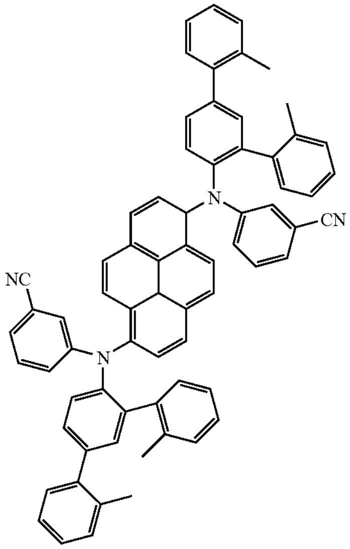
C-48
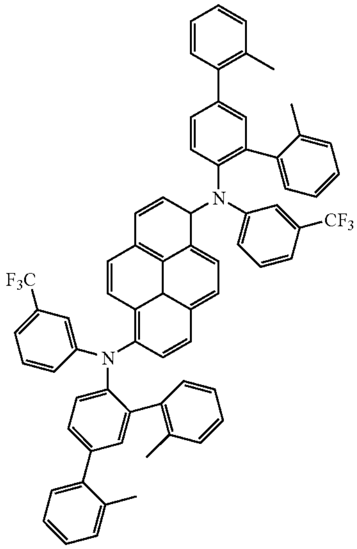

-continued
C-49
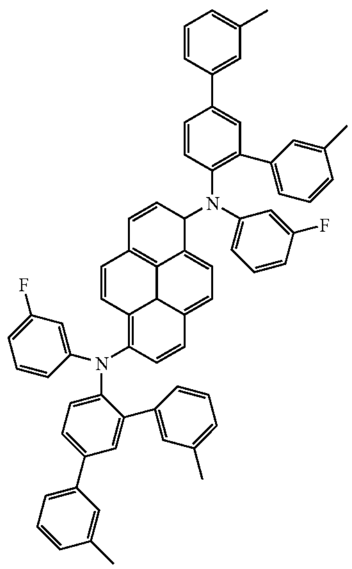
C-50
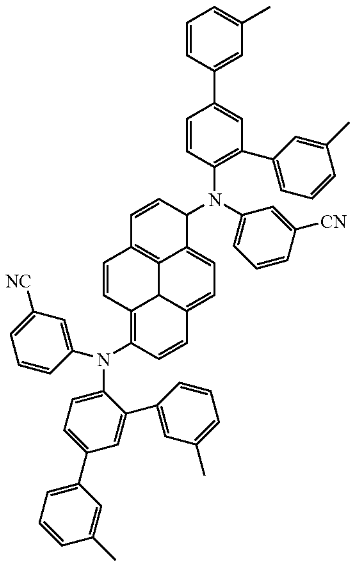
C-51
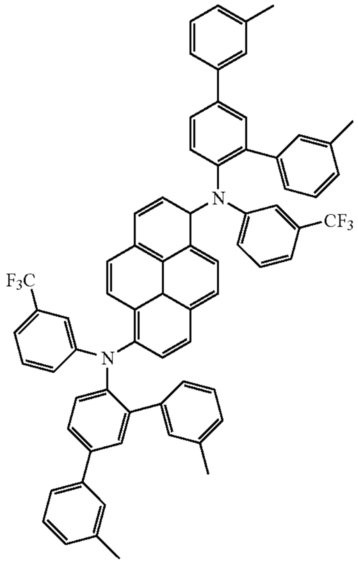
-continued
C-52
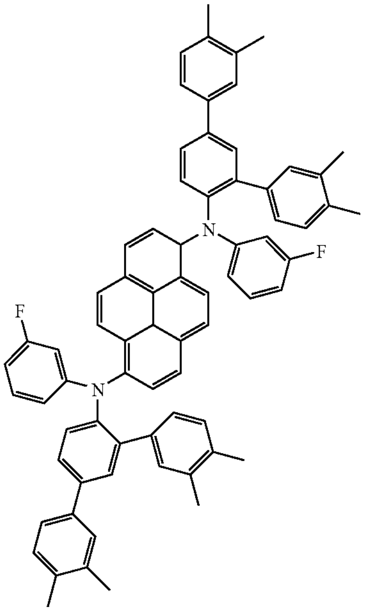
C-53
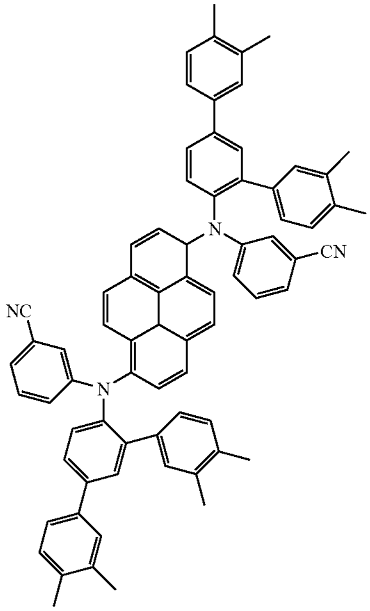

-continued
C-54
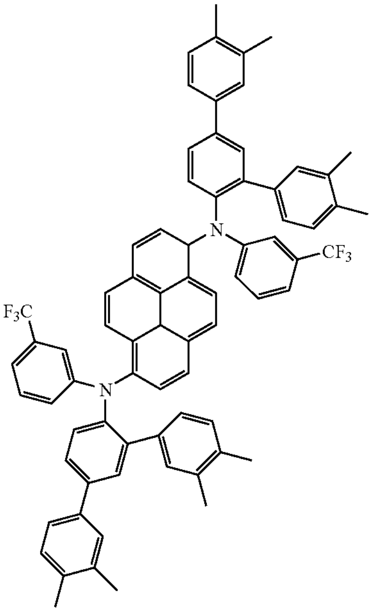
C-55
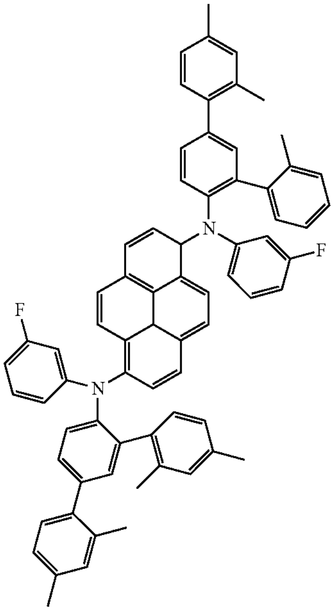
-continued
C-56
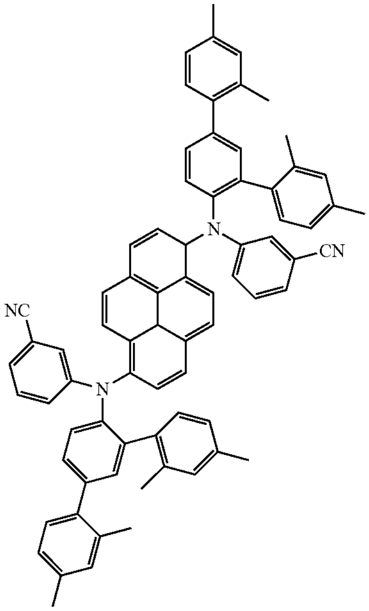
C-57
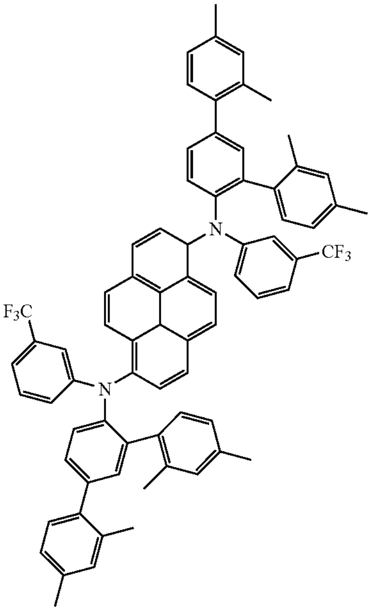

-continued
C-58
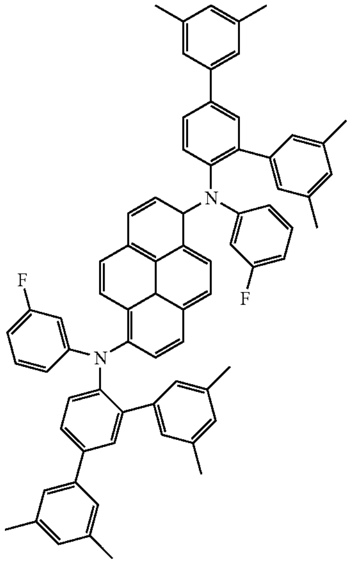
C-59
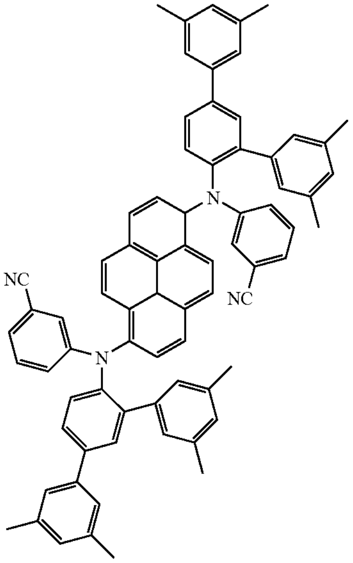
-continued
C-60
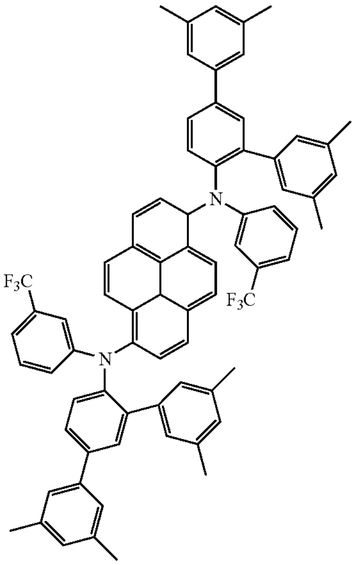
C-61
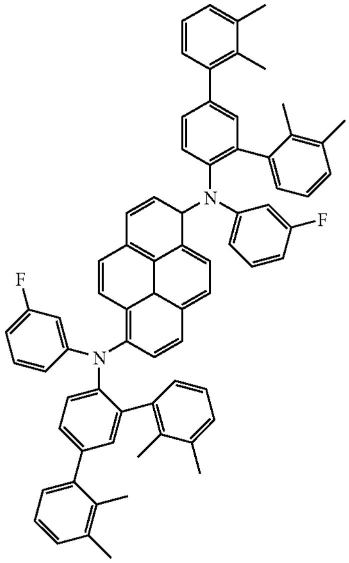

-continued
C-62
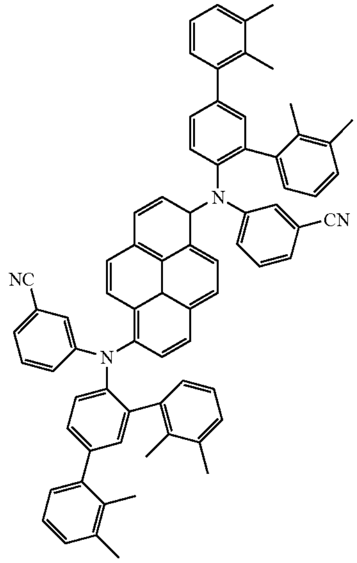
C-63
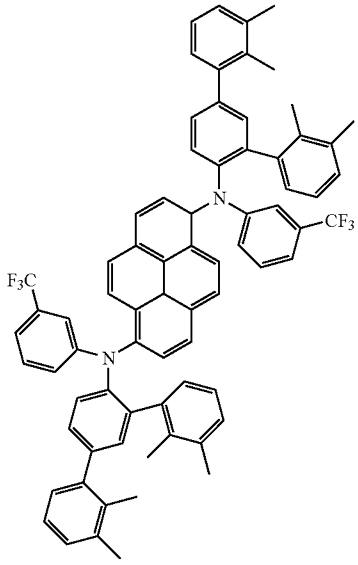
-continued
C-64
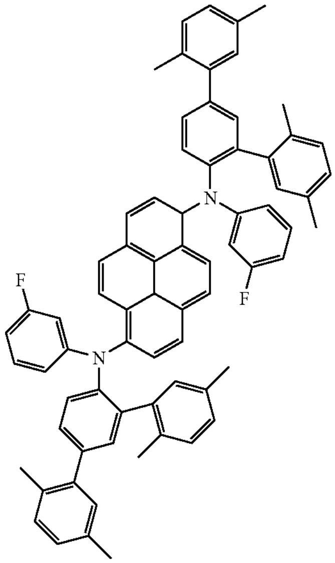
C-65
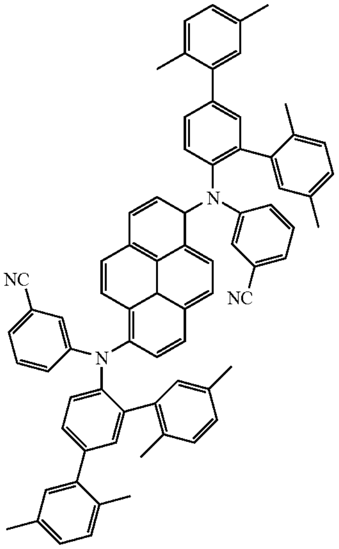

-continued
C-66
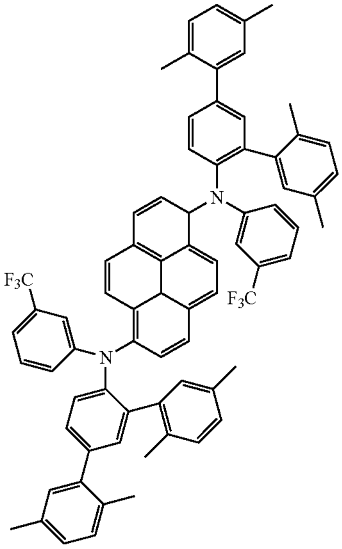
C-67
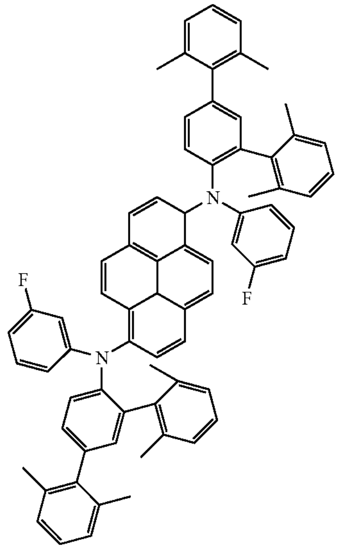
-continued
C-68
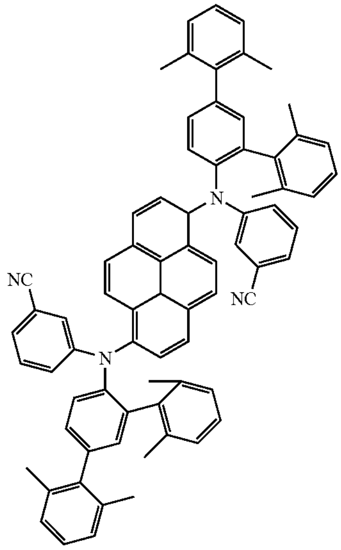
C-69
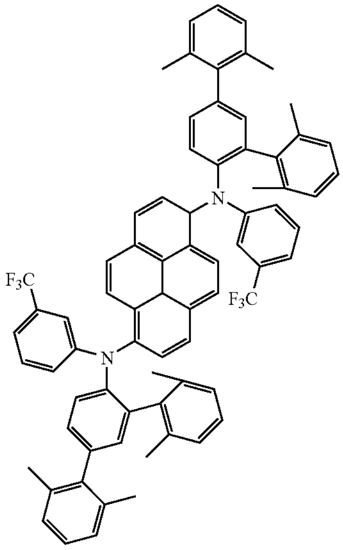

-continued
C-70
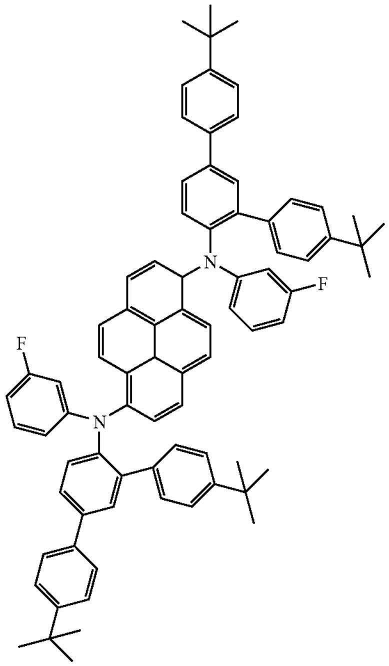
C-71
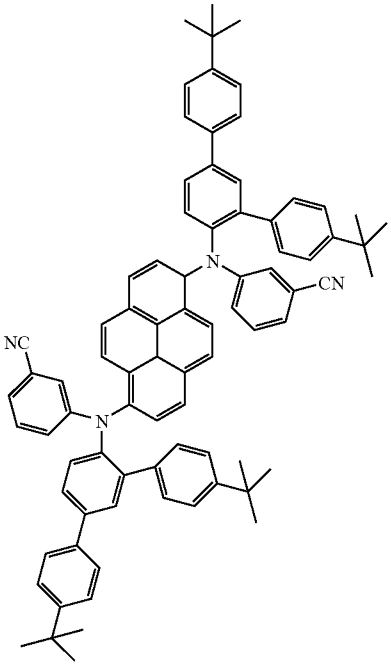
-continued
C-72
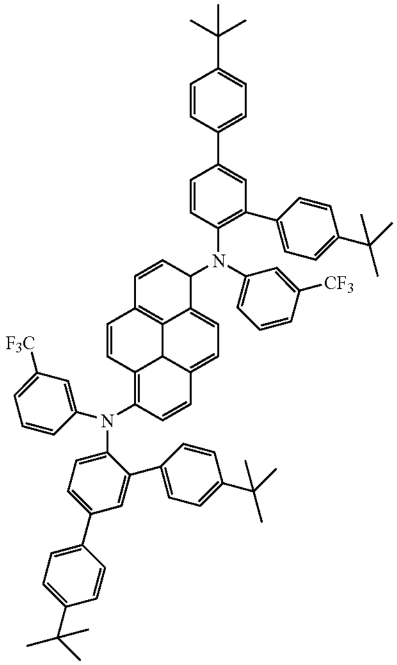
C-73
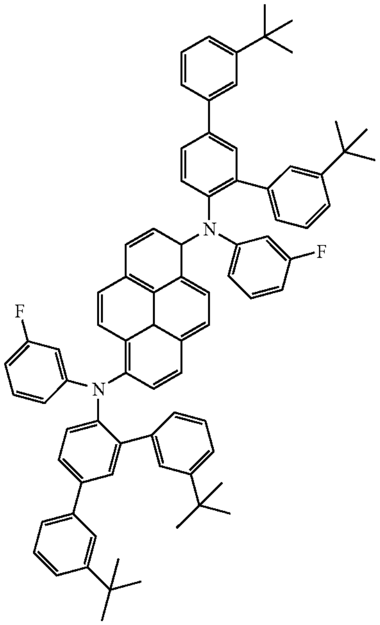

-continued
C-74
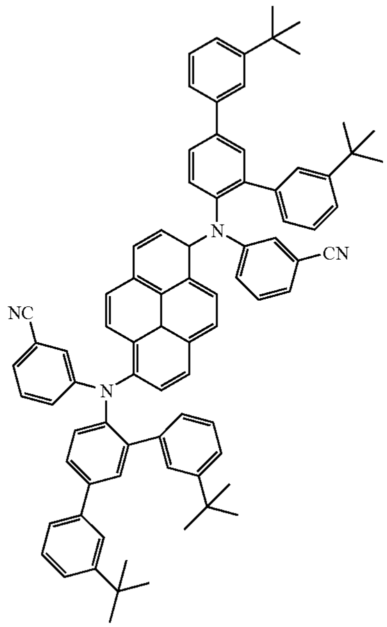
C-75
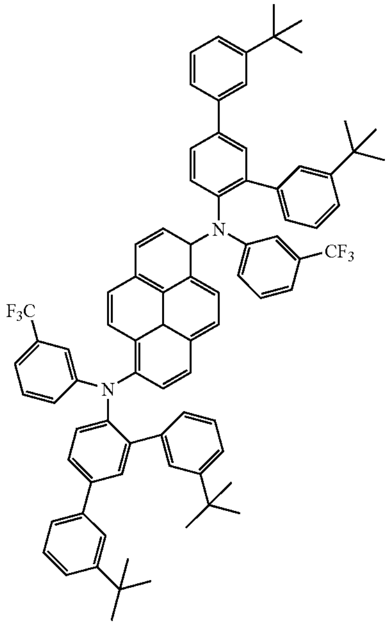
-continued
C-76
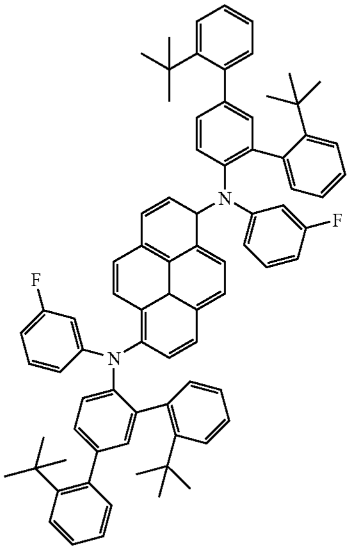
C-77
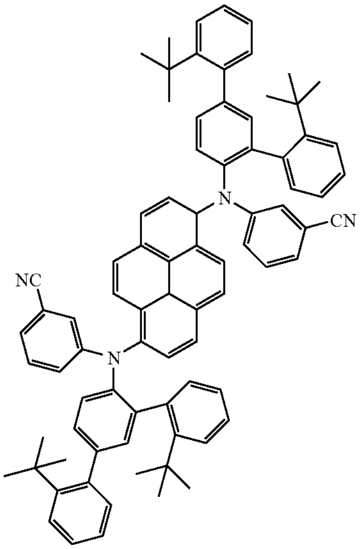

C-78
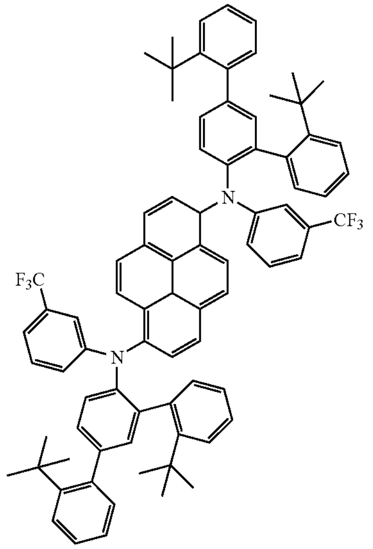
C-79
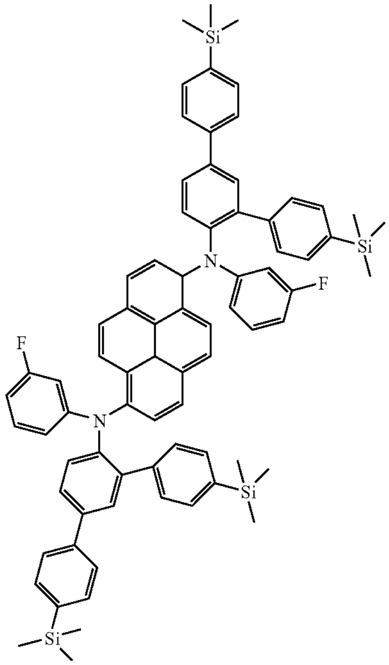
C-80
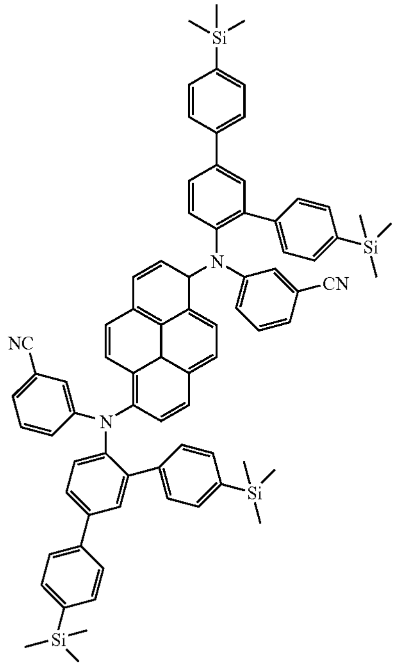
C-81
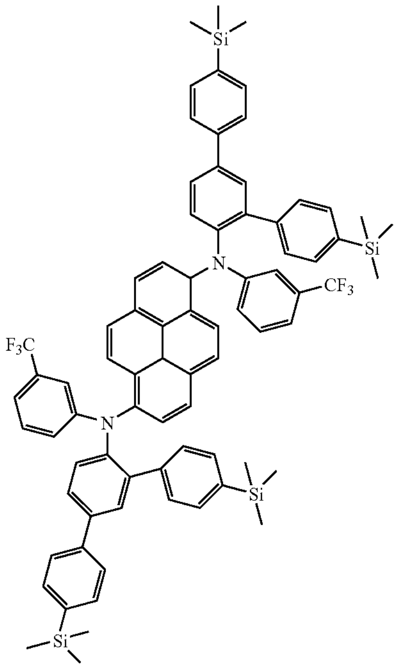

C-82
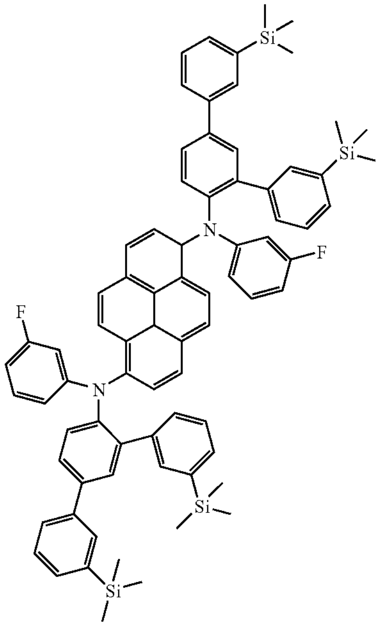
C-83
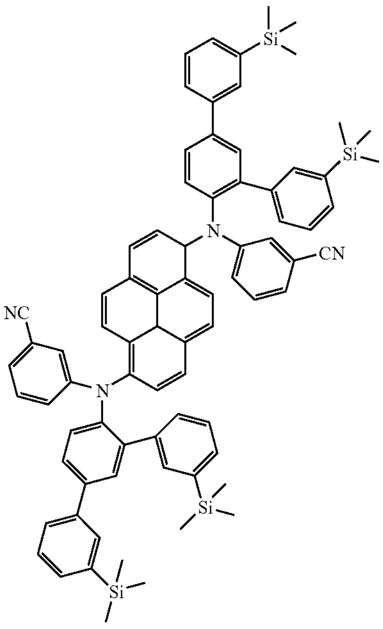
C-84
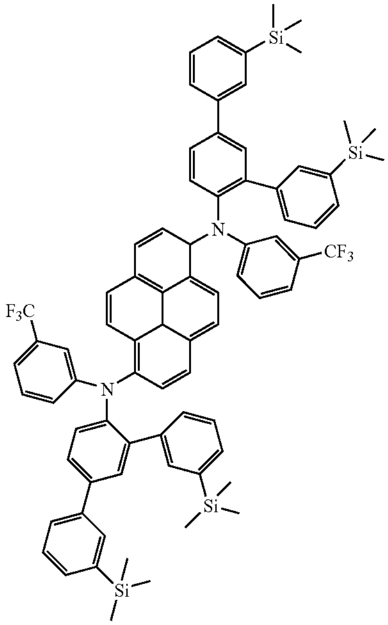
C-85
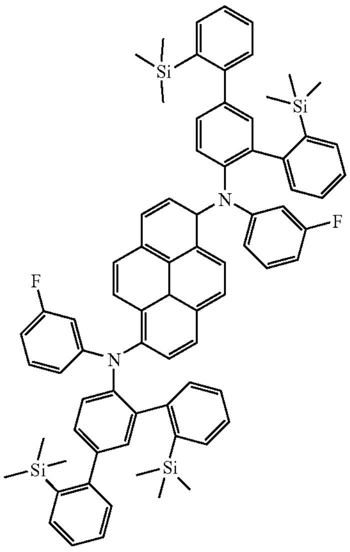

-continued
C-86
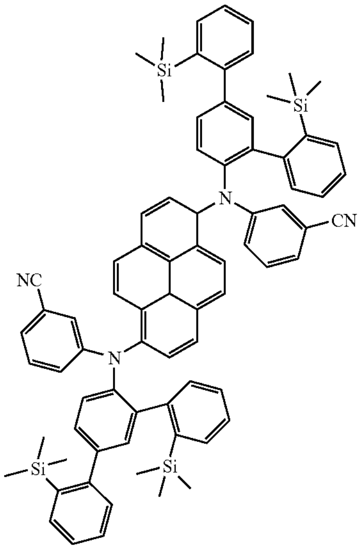
C-87
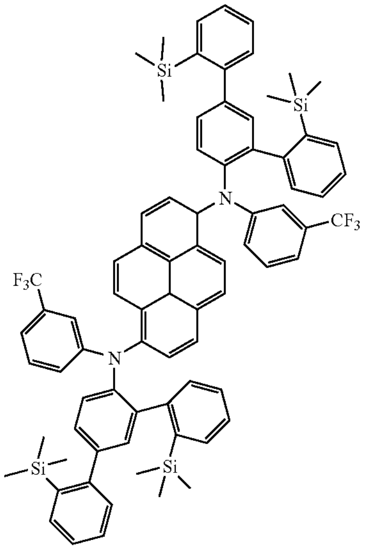
-continued
C-88
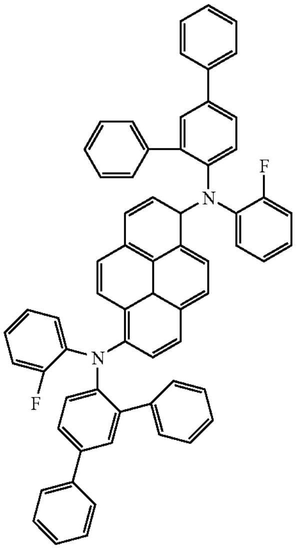
C-89
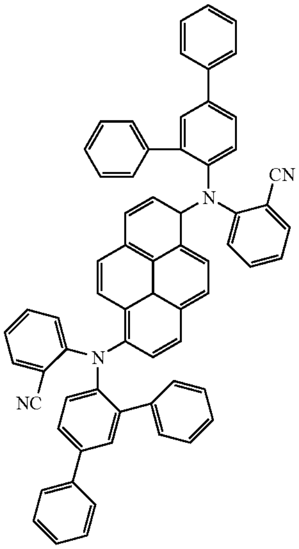

-continued
C-90
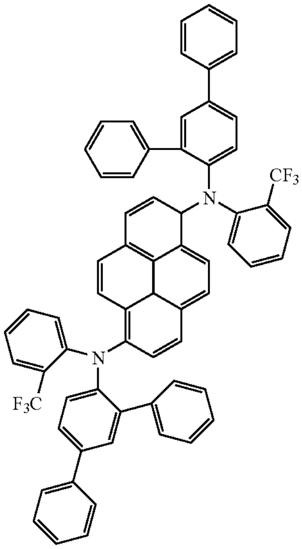
C-91
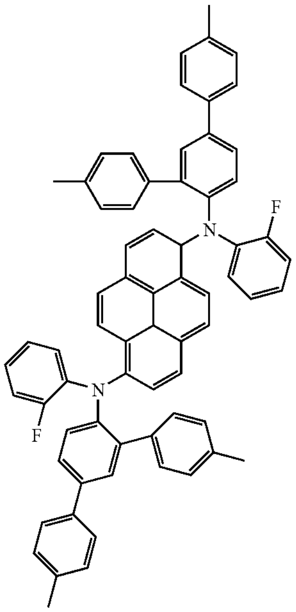
-continued
C-92
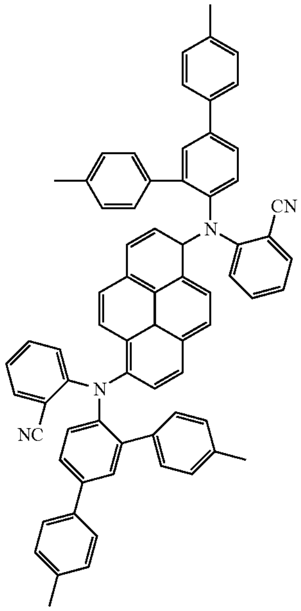
C-93
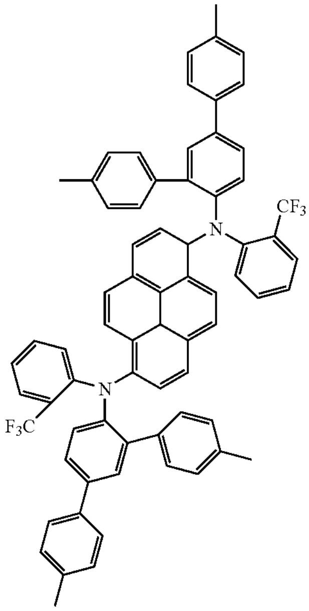

-continued
C-94
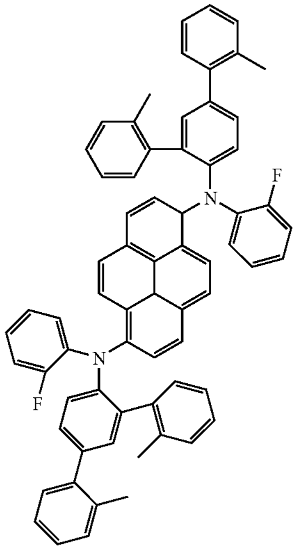
C-95
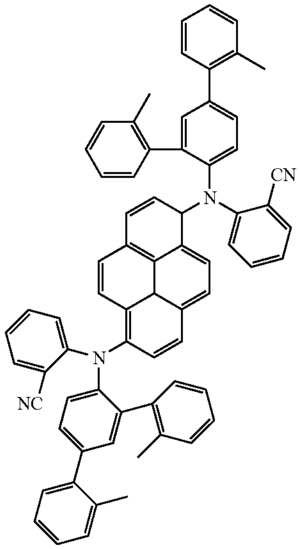
-continued
C-96
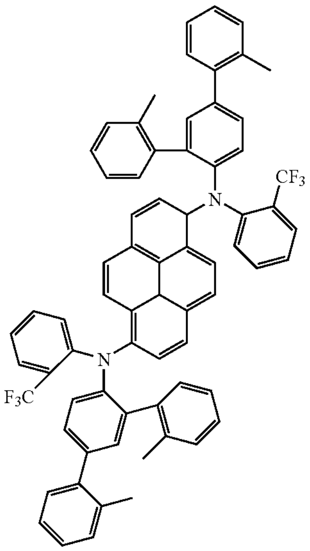
C-97
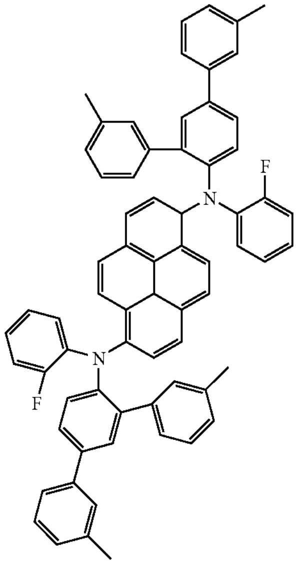

-continued
C-98
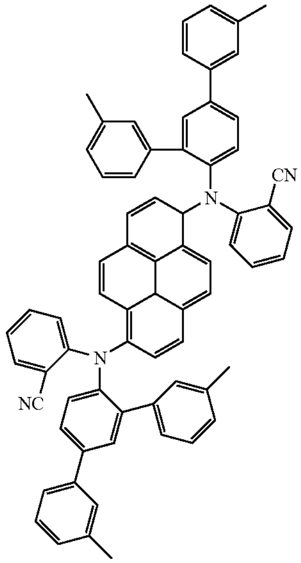
C-99
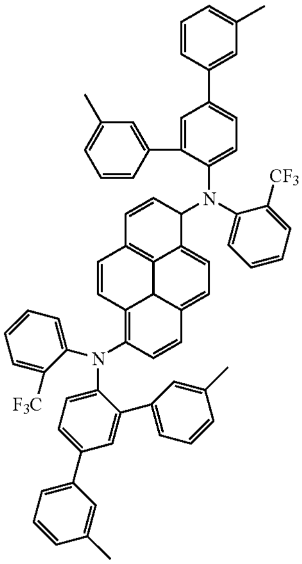
-continued
C-100
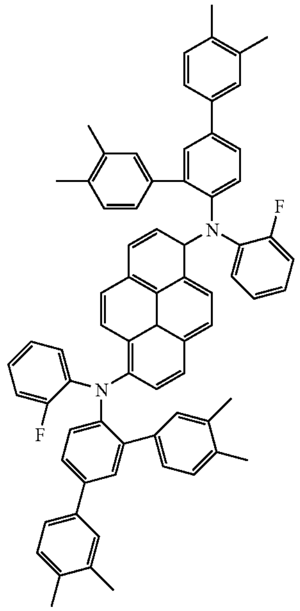
C-101
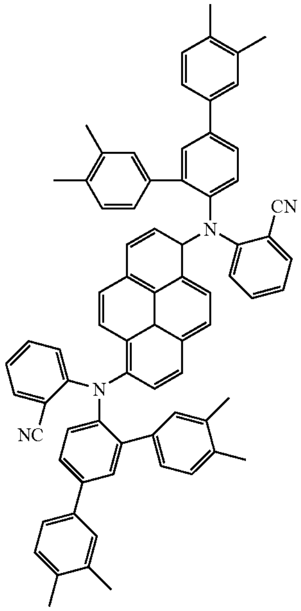

-continued
C-102
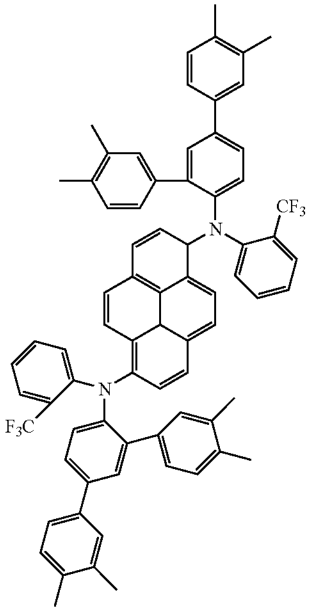
C-103
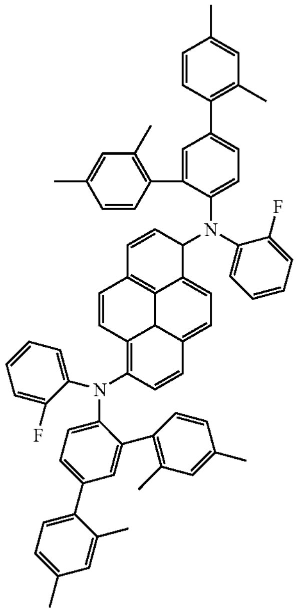
-continued
C-104
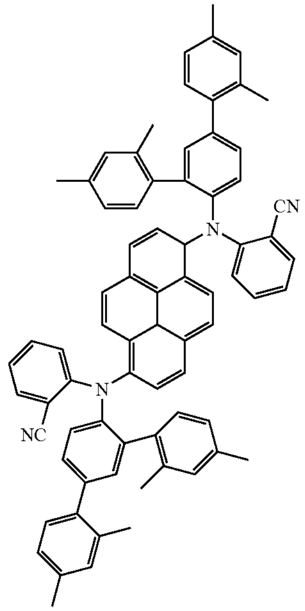
C-105
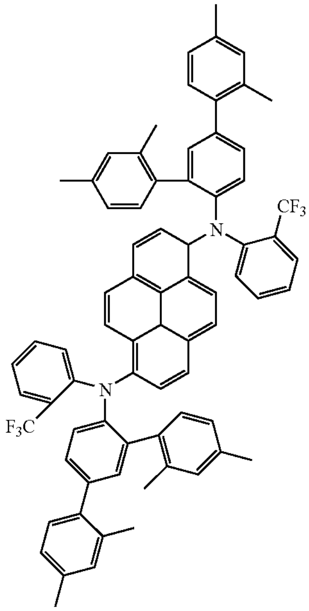

-continued
C-106
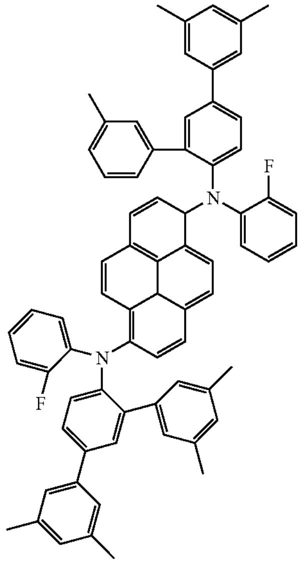
C-107
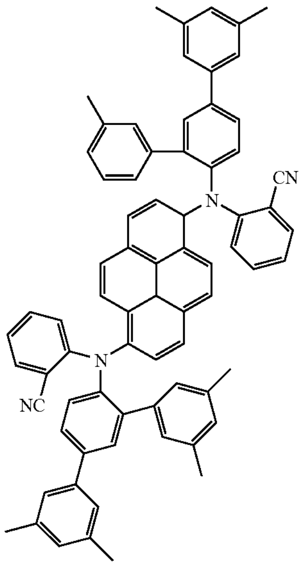
-continued
C-108
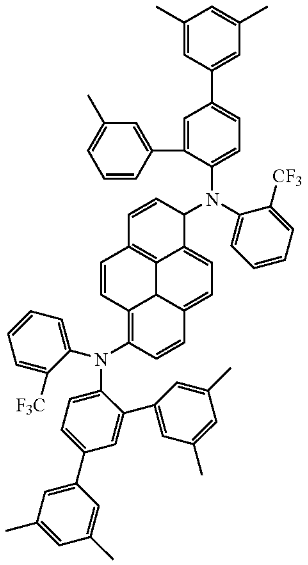
C-109
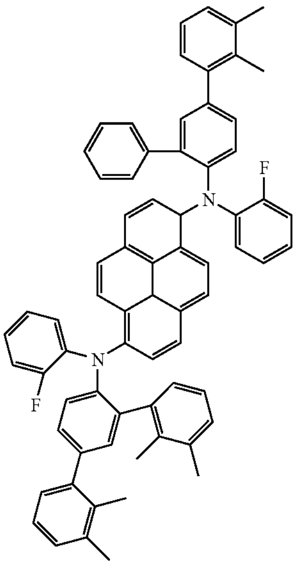

C-110
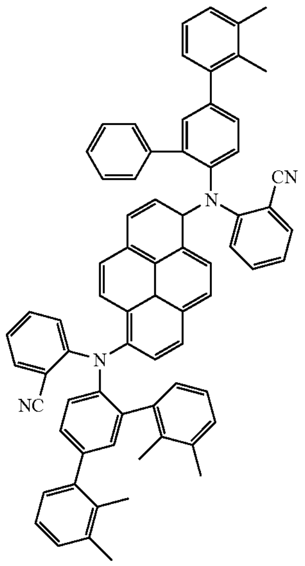
C-111
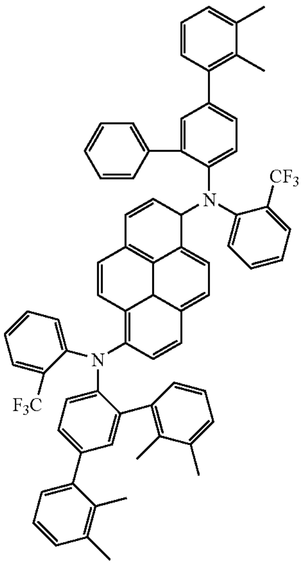
C-112
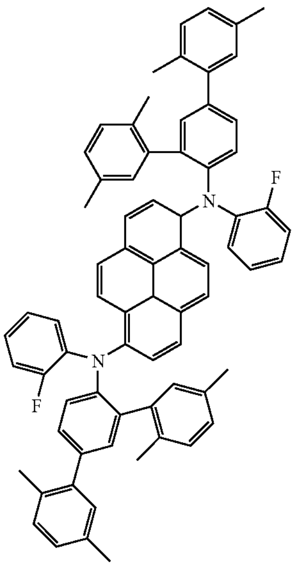
C-113
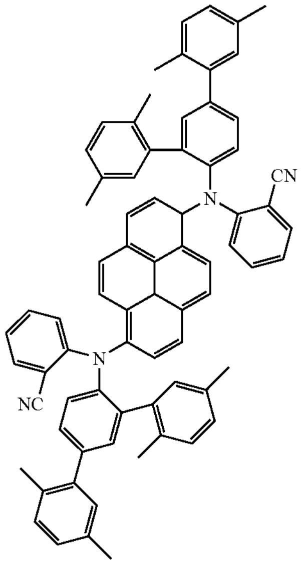

-continued
C-114
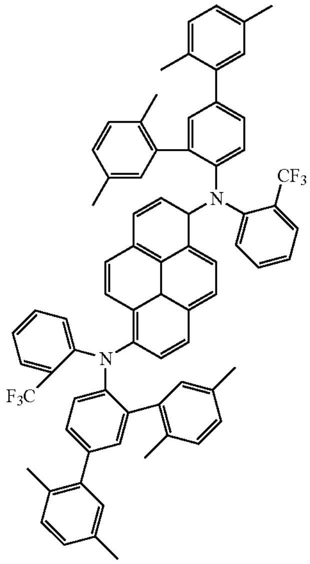
C-115
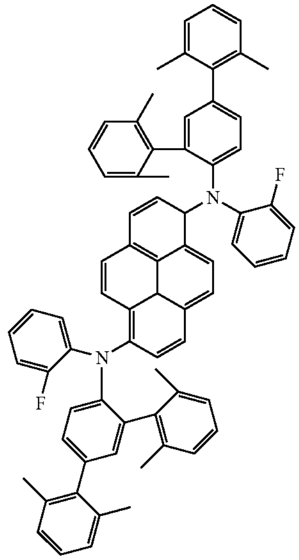
-continued
C-116
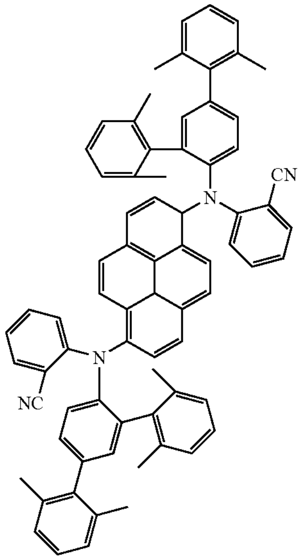
C-117
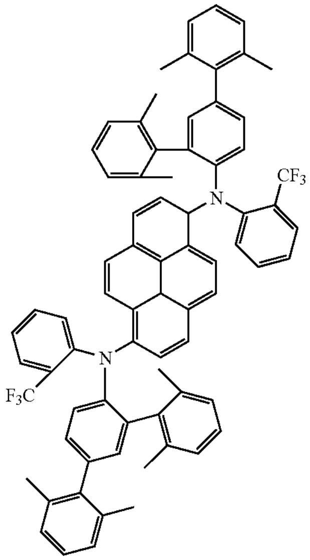

-continued
C-118
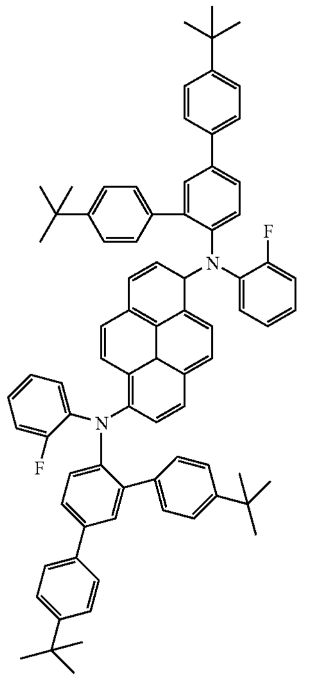
C-119
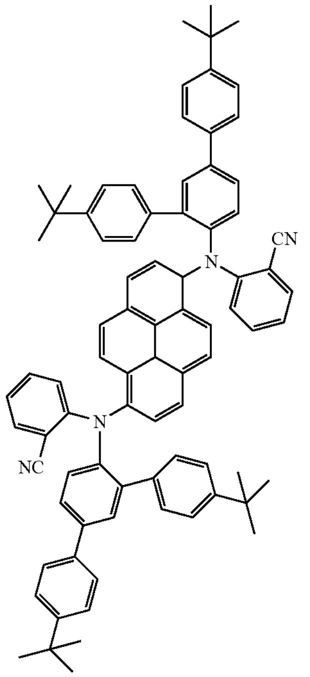
-continued
C-120
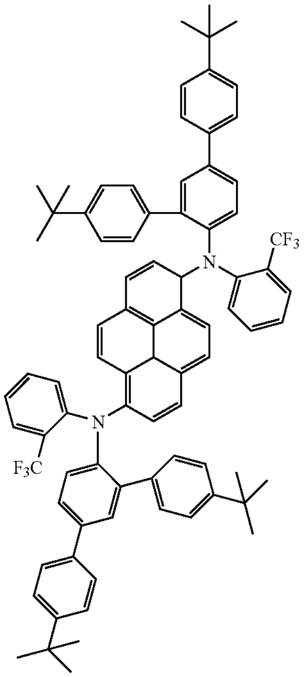
C-121
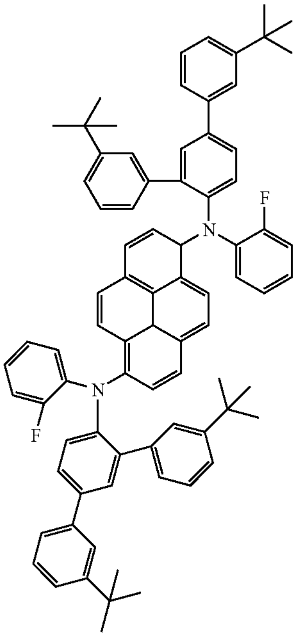

-continued
C-122
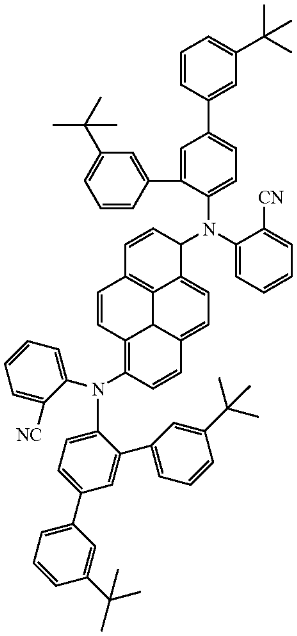
C-123
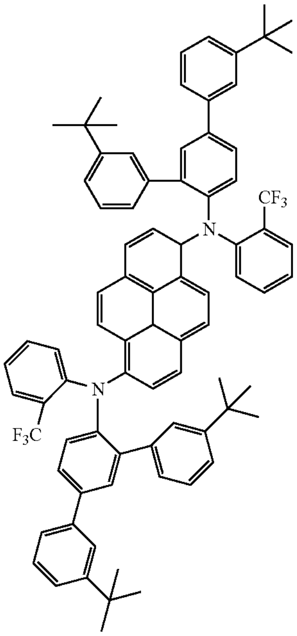
-continued
C-124
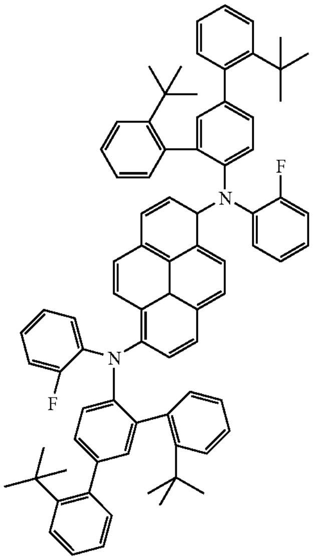
C-125
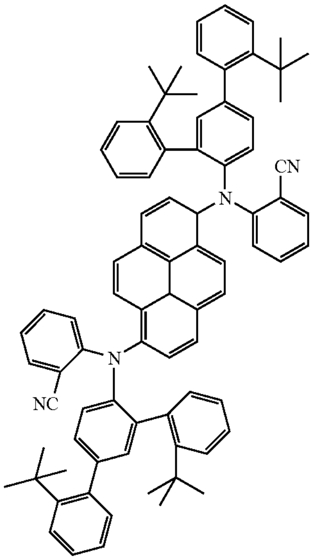

-continued
C-126
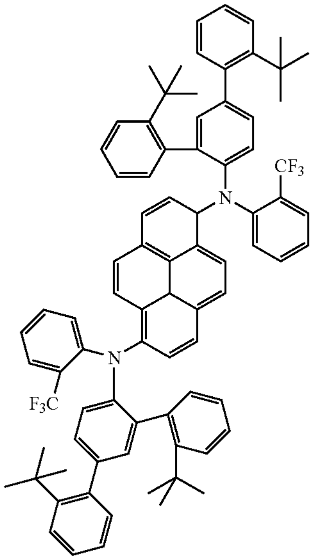
C-127
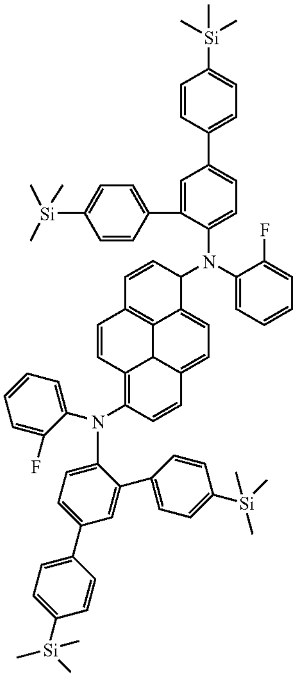
-continued
C-128
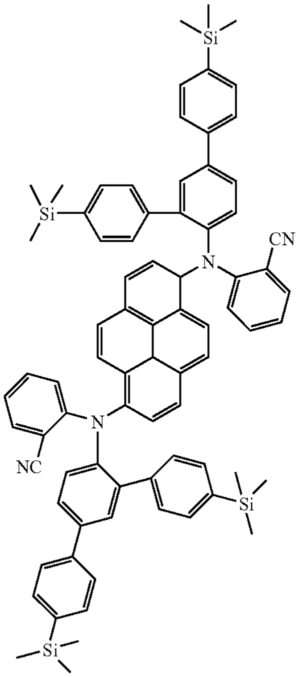
C-129
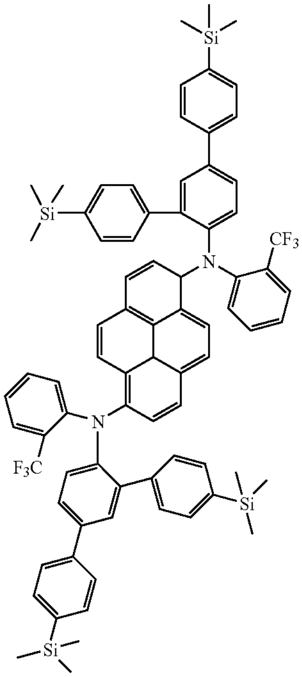

-continued
C-130
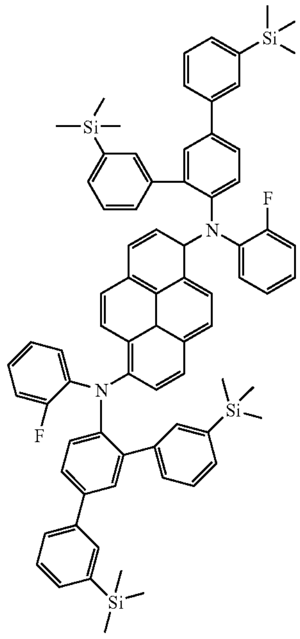
C-131
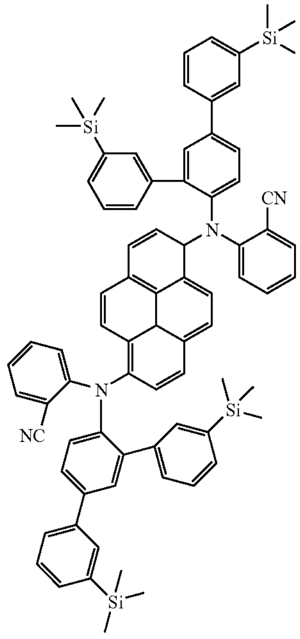
-continued
C-132
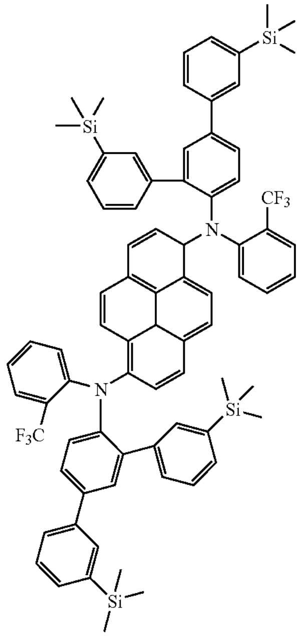
C-133
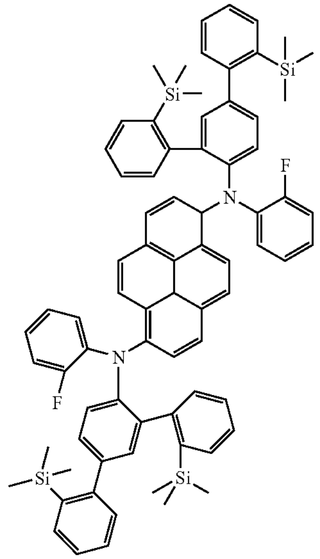

-continued
C-134
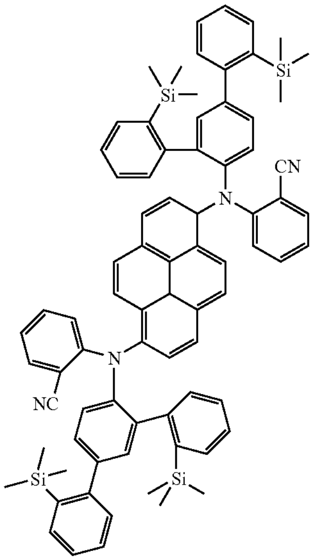
C-135
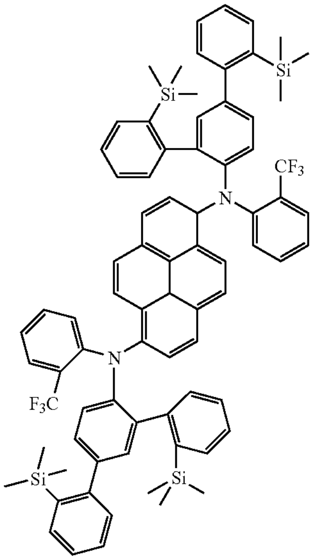
C-136
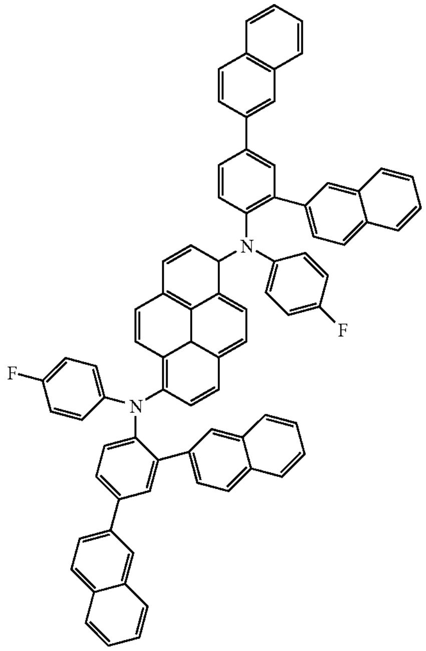
C-137
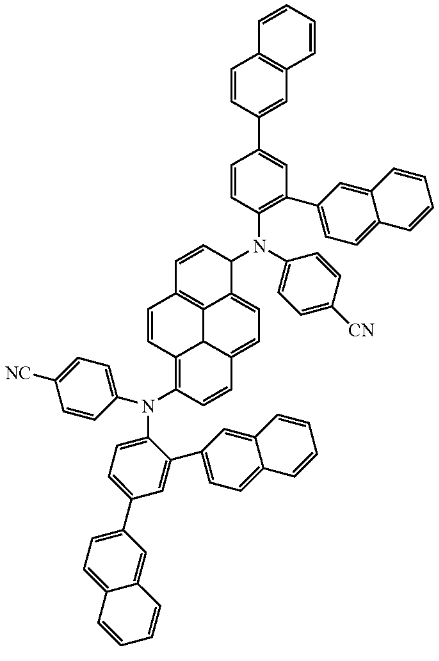

-continued
C-138
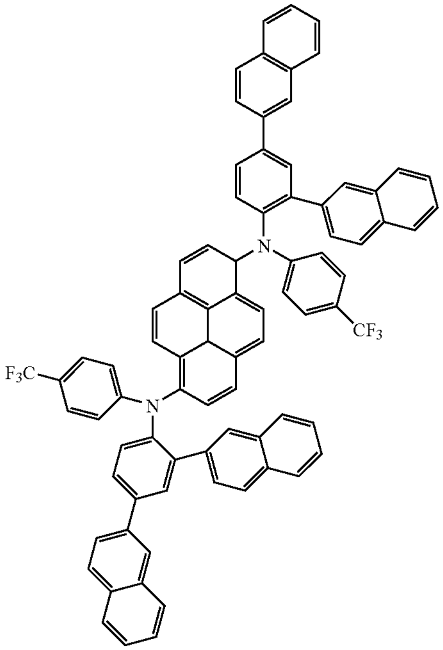
C-139
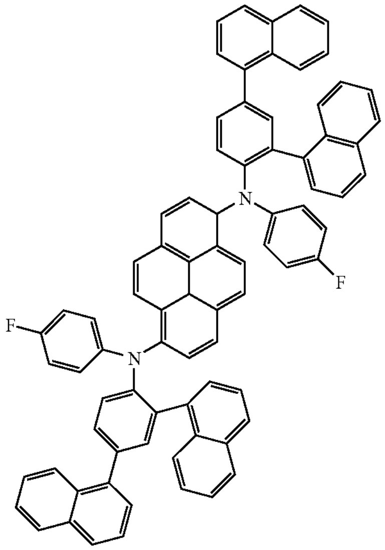
-continued
C-140
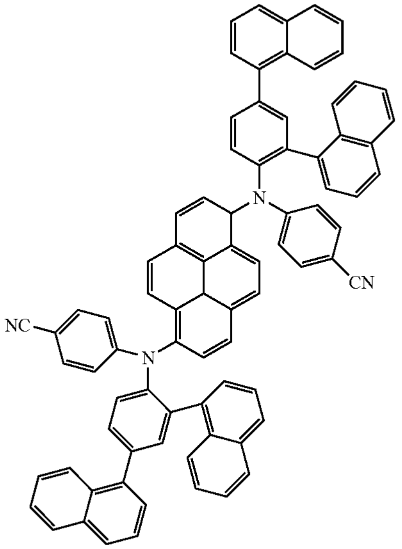
C-141
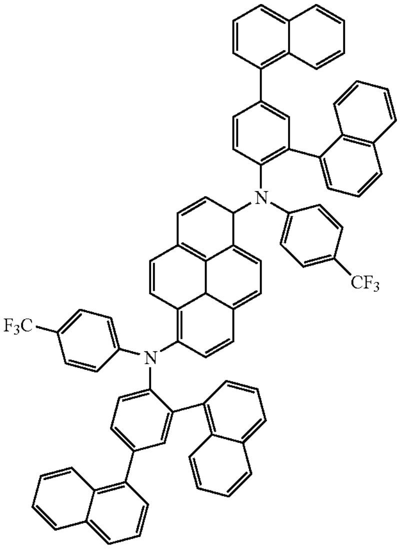

-continued
C-142
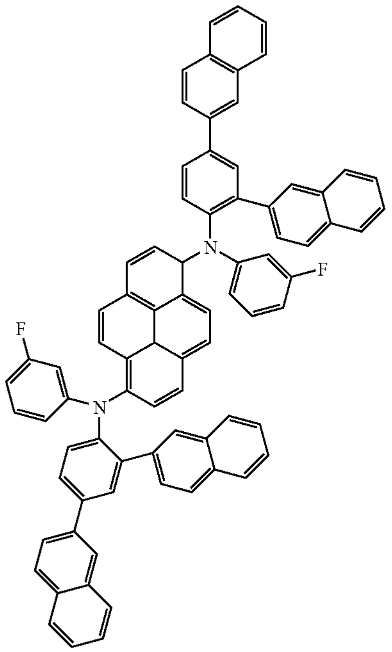
C-143
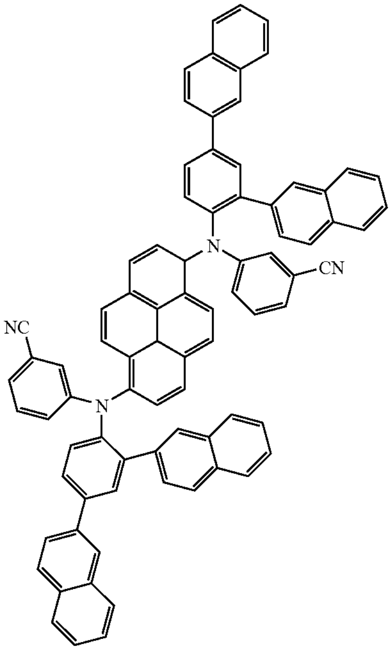
-continued
C-144
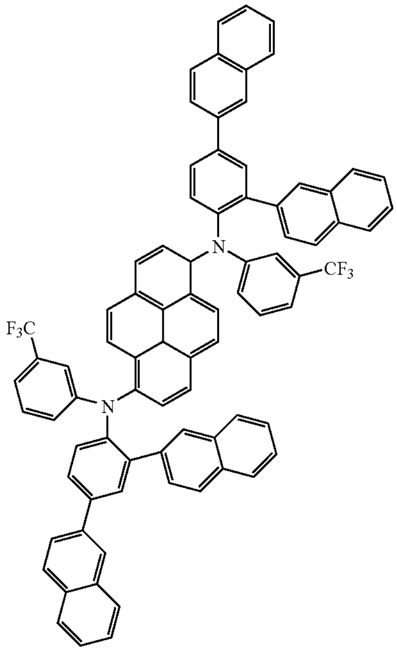
C-145
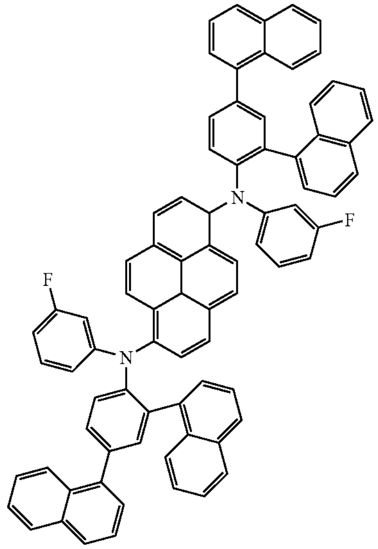

-continued
C-146
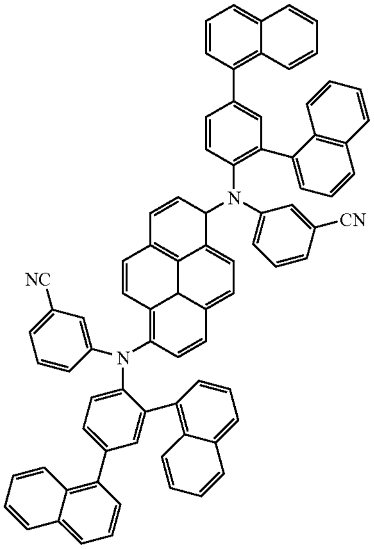
C-147
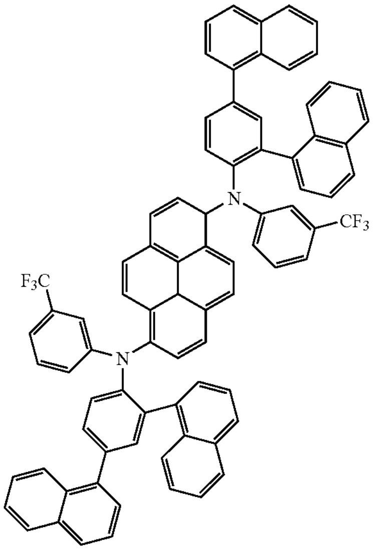
-continued
C-148
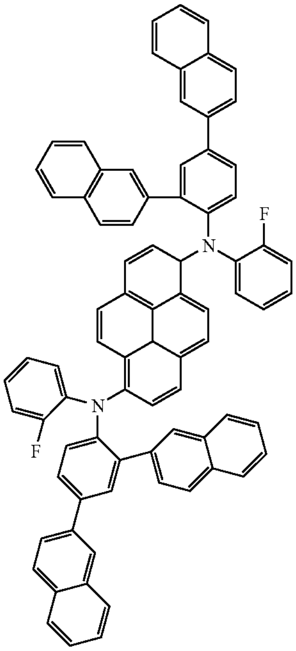
C-149
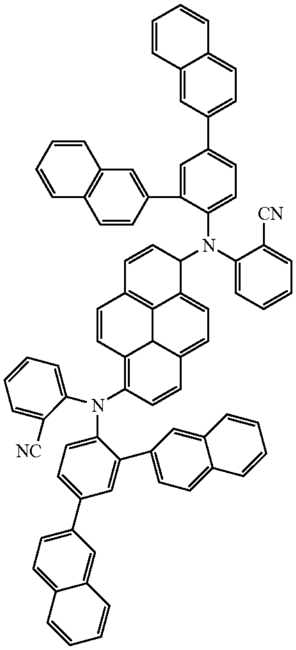

-continued
C-150
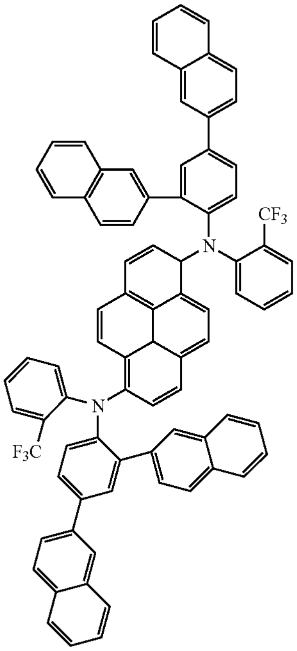
C-151
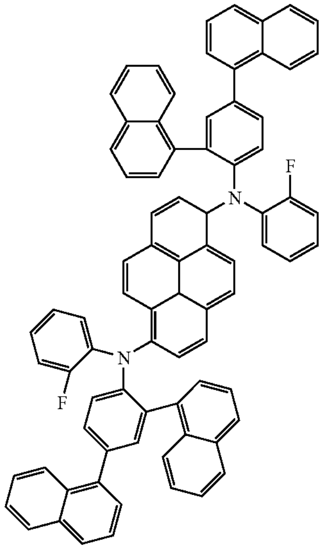
-continued
C-152
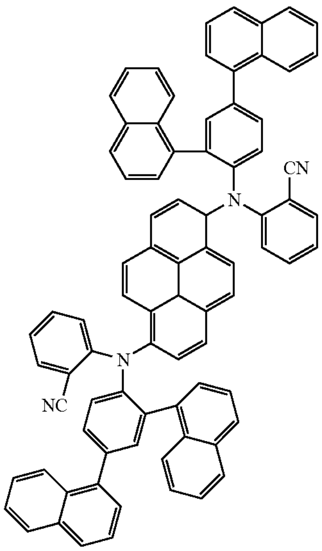
C-153
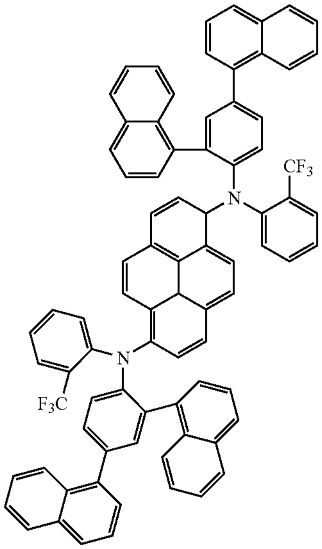
A synthesis example of the blue fluorescent compound marked by C-88 in the above Formula 8 is explained. The C-88 blue fluorescent compound is $N^1$,$N^6$-bis(2,4-diphenylphenyl-$N^1$,$N^6$-bis(2-fluorophenyl)pyrene-1,6-diamine.
1. Synthesis of 2,4-diphenylaniline
2,4-diphenylaniline is synthesized by following Reaction Formula 7.
[Reaction Formula 7]
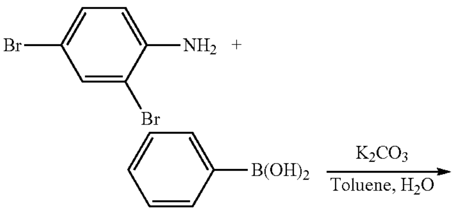

-continued

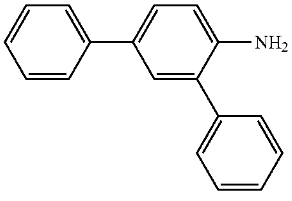

2,4-dibromoaniline (10 mmol), benzeneboronic acid (24 mmol), tetrakis(triphenylphosphine)palladium(0) (1 mmol) and potassium carbonate (12 g) are put in a two-neck round-bottom flask and dissolved in toluene (30 mL) and $H_2O$ (10 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-diphenylaniline (2.0 g) is yielded.

2. Synthesis of 2,4-diphenyl-N-2-fluorophenylbenzenamine 2,4-diphenyl-N-2-fluorophenylbenzenamine is synthesized by following Reaction Formula 8.

[Reaction Formula 8]

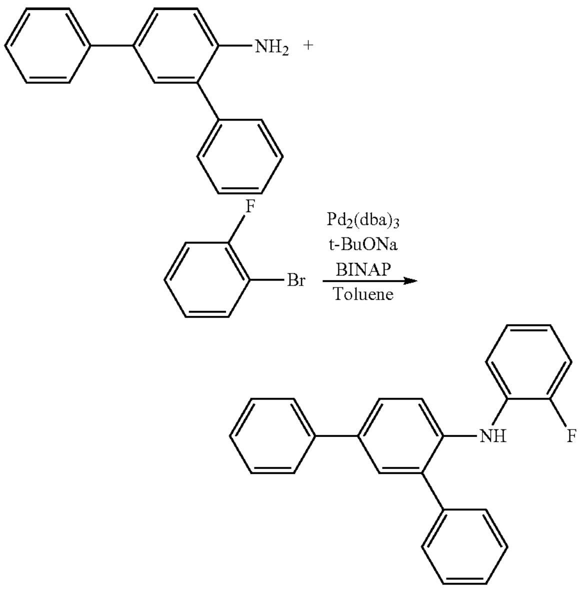

2,4-diphenylaniline (12 mmol), 1-bromo-2-fluorobenzene (10 mmol), tris(dibenzylideneacetone)dipalladium(0) (0.15 mmol), (±)-2,2'-bis(diphenylphosphine)-1,1'-binaphthalene (0.3 mmol) and sodium tert-butoxie (14 mmol) are put in a two-neck round-bottom flask and dissolved in toluene (30 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, by re-crystallizing and filtering with dichloromethane and petroleum ether, 2,4-diphenyl-N-2-fluorophenylbenzenamine (2.1 g) is yielded.

3. Synthesis of $N^1$,$N^6$-bis(2,4-diphenylphenyl-$N^1$,$N^6$-bis(2-fluorophenyl)pyrene-1,6-diamine $N^1$,$N^6$-bis(2,4-diphenylphenyl-$N^1$,$N^6$-bis(2-fluorophenyl)pyrene-1,6-diamine is synthesized by following Reaction Formula 9.

[Reaction Formula 9]

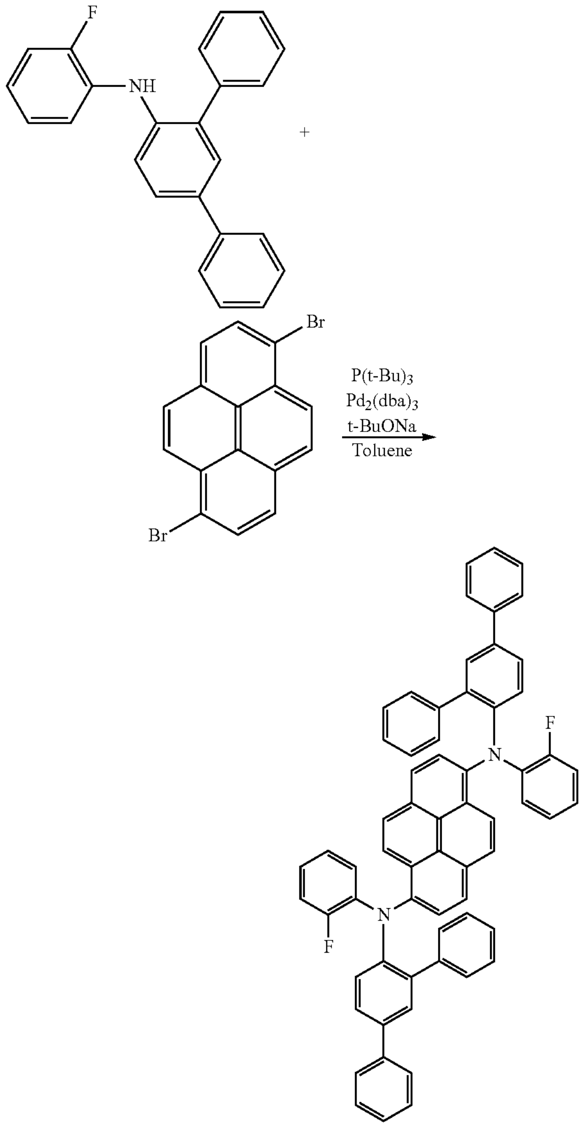

2,4-diphenyl-N-2-fluorophenylbenzenamine (6 mmol), 1,6-dibromopyrene (5 mmol), tris(dibenzylideneacetone)dipalladium(0) (0.075 mmol), tri-tert-butylphosphine (0.15 mmol) and sodium tert-butoxie (7 mmol) are put in a two-neck round-bottom flask and dissolved in toluene (15 mL). Subsequently, the resulting solution is stirred in a bath under a temperature of about 100° C. for 24 hours. After completion of the reaction, toluene is removed. The reaction mixture is extracted with dichloromethane and water, and then being distilled under reduced pressure. The resulting residence is filtered by silica gel column and distilled under reduced pressure again. Next, after re-crystallizing and filtering with dichloromethane and acetone, and then being thermally refined to yield $N^1$,$N^6$-bis(2,4-diphenylphenyl-$N^1$,$N^6$-bis(2-fluorophenyl)pyrene-1,6-diamine is yielded.

Hereinafter, a detailed description will be made of preferred examples associated with the OELD according to the present invention. More specifically, the examples relate to an OELD including an emission material layer which uses the blue fluorescent compound of Formula 7 as a dopant.

EXAMPLES

Example 10

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ ton. CuPC (about 200 angstroms), 4,4'-bis[N-(1-naphtyl)-N-phenylamino]-biphenyl (NPD) (about 400 angstroms), an emitting layer (about 200 angstroms) including DPVBi as a host and a compound represented by C-35 in the above Formula 8 as a dopant (about 3 weight %), Alq3 (about 350 angstroms), fluorolithium (LiF) (about 5 angstroms) and aluminum (Al) (about 1000 angstroms) are sequentially formed on the ITO layer such that an OELD is fabricated.

The OELD produces a brightness of 723 cd/$m^2$ at an electric current of 10 mA and a voltage of 4.30 V. At this time, the X index and Y index of CIE color coordinates are 0.132 and 0.152, respectively.

Example 11

An indium-tin-oxide (ITO) layer is patterned on a substrate and washed such that an emission area of the ITO layer is 3 mm*3 mm. The substrate is loaded in a vacuum chamber, and the process pressure is adjusted to $1*10^{-6}$ torr. CuPC (about 650 angstroms), NPD (about 400 angstroms), an emitting layer (about 200 angstroms) including DPVBi as a host and a compound represented by C-88 in the above Formula 8 as a dopant (about 3 weight %), Alq3 (about 350 angstroms), LiF (about 5 angstroms) and Al (about 1000 angstroms) are sequentially formed on the ITO layer such that an OELD is fabricated.

The OELD produces a brightness of 733 cd/$m^2$ at an electric current of 10 mA and a voltage of 4.26 V. At this time, the X index and Y index of CIE color coordinates are 0.135 and 0.157, respectively.

Comparative Example 3

An ITO layer is patterned on a substrate and washed such that an emission area of the ITO layer is 3 mm*3 mm. The substrate is loaded in a vacuum chamber, and the process pressure is adjusted to $1*10^{-6}$ ton. CuPC (about 200 angstroms), NPD (about 400 angstroms), an emitting layer (about 200 angstroms) including DPVBi as a host and BD-a represented by the above Formula 1-3 as a dopant (about 1 weight %), Alq3 (about 350 angstroms), LiF (about 5 angstroms) and Al (about 1000 angstroms) are sequentially formed on the ITO layer such that an OELD is fabricated.

The OELD produces a brightness of 526 cd/$m^2$ at an electric current of 10 mA and a voltage of 6.7 V. At this time, the X index and Y index of CIE color coordinates are 0.136 and 0.188, respectively.

The OELD fabricated in Examples 10 and 11 and Comparative Example 3 is evaluated for efficiency, brightness, and so on. A voltage has a dimension of [V], an electric current has a dimension of [mA], and a brightness has a dimension of [cd/m2. The evaluated results are shown in Table 3.

TABLE 3

| | voltage | Electric current | Brightness | CIE(X) | CIE(Y) |
|---|---|---|---|---|---|
| Ex. 1 | 4.30 | 10 | 723 | 0.132 | 0.152 |
| Ex. 2 | 4.26 | 10 | 733 | 0.135 | 0.157 |
| Com. Ex. 1 | 6.7 | 10 | 526 | 0.136 | 0.188 |

As shown in Table 3, the OELD in Examples 10 and 11 has high color purity and low driving voltage such that power consumption for the OELD is reduced. As a result, a lifetime of the OELD using the blue fluorescent compound according to the present invention is improved.

Figure 2:
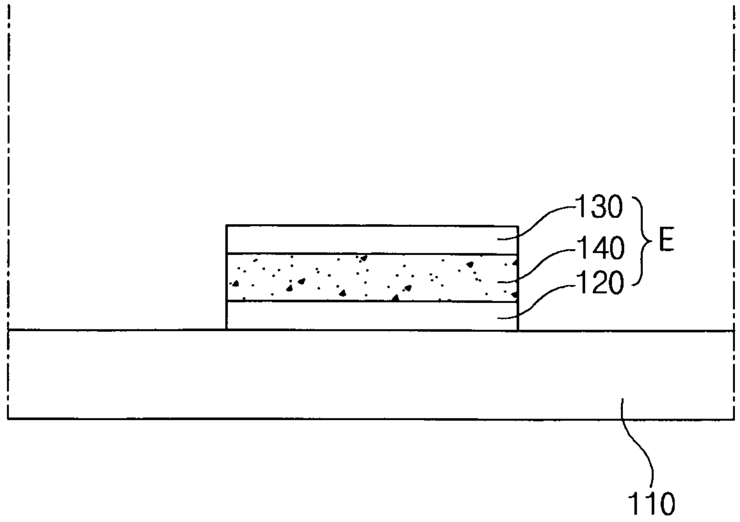
FIG. 2 is a schematic cross-sectional view of an OELD according to the present invention.

FIG. 2 is a schematic cross-sectional view of an OELD according to the present invention. In FIG. 2, an OELD includes a first substrate 101, a second substrate (not shown) facing the first substrate 101, and an organic electroluminescent diode E on the first substrate 101. Namely, the organic electroluminescent diode E is positioned between the first substrate 101 and the second substrate.

The organic electroluminescent diode E includes a first electrode 120 as an anode, a second electrode 130 as a cathode, and an organic emitting layer 140 between the first and second electrodes 120 and 130. The first electrode 120 being closer to the first substrate 110 than the second electrode 130 is shown. Alternatively, the second electrode 130 may be closer to the first substrate 110 than the first electrode 120.

The first electrode 120 is formed of a material having a large work function. For example, the first electrode 120 may be formed of ITO. The second electrode 130 is formed of a material having a small work function. For example, the second electrode 130 may be formed of one of Al and Al alloy (AlNd).

The organic emitting layer 140 includes red, green and blue organic emitting patterns. In this case, the blue emission pattern of the EML includes a host material, which is capable of transporting an electron and a hole, and the blue fluorescent compound according to the present invention as a dopant. The blue fluorescent compound according to the present invention is represented by the above Formulas 2, 5 and 7. The blue fluorescent compound as a dopant is added with a range of about 0.1 weight % to about 20 weight % with respect to a total weight of a material in the blue emission pattern. For example, the host for the blue emitting pattern may be DPVBi represented by the above Formula 1-2.

Although not shown, to maximize luminescence efficiency, the organic emission layer 140 has a multiple-layered structure. For example, a hole injection layer (HIL), a hole transporting layer (HTL), an emitting material layer (EML), an electron transporting layer (ETL) and an electron injection layer (EIL) are stacked on the first electrode 120.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A blue fluorescent composition, comprising:

a host material being capable of transporting an electron or a hole; and a dopant material represented by following Formula 1:

[Formula 1]

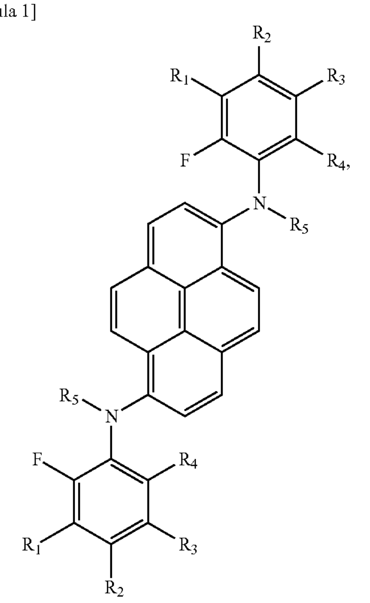

wherein each of the R1, the R2, the R3 and the R4 is selected from hydrogen (H), substituted or non-substituted aromatic group, or substituted or non-substituted heterocyclic group, wherein at least two of the R1, the R2, the R3, and the R4 are selected from substituted or non-substituted aromatic group or substituted or non-substituted heterocyclic group, and the R5 is selected from substituted or non-substituted aromatic group or substituted or non-substituted heterocyclic group, and wherein each of the R2 and R4 is selected from substituted or non-substituted aromatic group or substituted or non-substituted heterocyclic group, and the R2 is same as the R4, with the proviso that none of the substituted aromatic groups and substituted heterocyclic groups selected for any of the R1, the R2, the R3, the R4 and the R5 include deuterium (D) substituents.

2. The composition according to claim 1, wherein the non-substituted aromatic group includes phenyl, biphenyl, naphthyl, phenanthrene, terphenyl and fluorenyl, and the substituted aromatic group includes phenyl, biphenyl, naphthyl, phenanthrene, terphenyl and fluorenyl each of which is substituted by one of an alkyl group including methyl, ethyl, propyl, i-propyl, and t-butyl, a cyano group, a silyl group, and fluorine.

3. The composition according to claim 1, wherein the heterocyclic group includes furan, thiophene, pyrrole, pyridine and pyrimidine.

4. A blue fluorescent composition, comprising:

a host material being capable of transporting an electron or a hole; and a dopant material represented by following Formula 3:

[Formula 3]

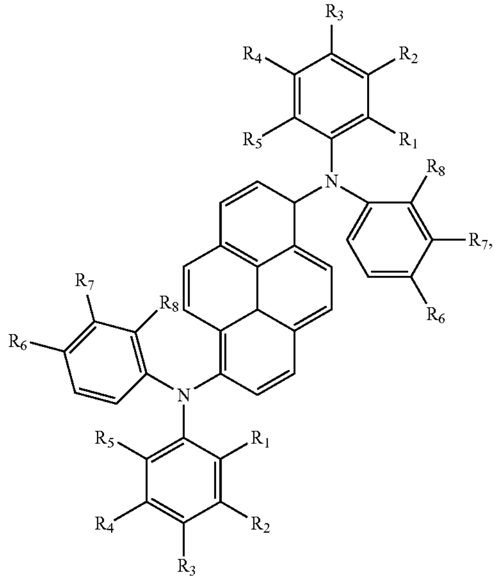

wherein each of the R1, the R2, the R3, the R4, and the R5 is hydrogen (H), C1 to C6 alkyl, or substituted or non-substituted aryl having at least six carbons (C) and two of the R1, the R2, the R3, the R4, and the R5 are selected from the substituted or non-substituted aryl having at least six carbons and same as each other, and wherein each of the R6, the R7, and the R8 is selected from hydrogen (H), C1 to C6 alkyl, substituted or non-substituted aryl having at least six carbons, fluorine, cyanide, or tri-fluoromethyl, and at least one of the R6, the R7, and the R8 is selected from fluorine, cyanide, or tri-fluoromethyl, with the proviso that any selected substituted aryl for the R6, the R7 and the R8 is not substituted with deuterium (D).

5. The composition according to claim 4, wherein the C1 to C6 alkyl is one of methyl, ethyl, n-propyl, i-propyl, n-butyl, i-butyl and t-butyl.

6. The composition according to claim 4, wherein the substituted or non-substituted aryl is one of phenyl, o-toluyl, m-toluyl, p-toluyl,o-xylyl, m-xylyl, p-xylyl, 1-naphthyl, 2-naphthyl, and 2, 3, 4, 5, 6-pentadeuteriumphenyl.

7. An organic electroluminescent device, comprising:

a first electrode;

a second electrode facing the first electrode: and an organic electroluminescent diode positioned between the first and second electrodes and includes an emitting material layer, the emitting material layer includes:

a host material being capable of transporting an electron or a hole; and a dopant material represented by following Formula 1:

[Formula 1]

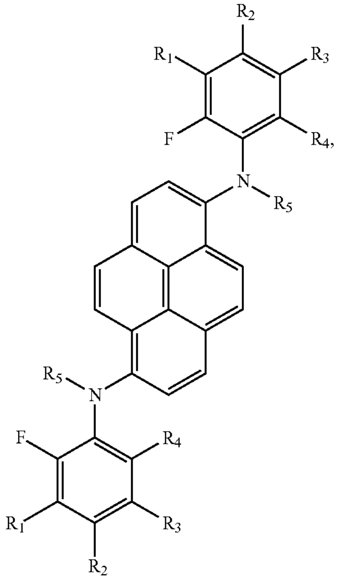

wherein each of the R1, the R2, the R3 and the R4 is selected from hydrogen (H), substituted or non-substituted aromatic group, or substituted or non-substituted heterocyclic group, wherein at least two of the R1, the R2, the R3, and the R4 are selected from substituted or non-substituted aromatic group or substituted or non-substituted heterocyclic group, and the R5 is selected from substituted or non-substituted aromatic group or substituted or non-substituted heterocyclic group, and wherein each of the R2 and R4 is selected from substituted or non-substituted aromatic group or substituted or non-substituted heterocyclic group, and the R2 is same as the R4, with the proviso that none of the substituted aromatic groups and substituted heterocyclic groups selected for any of the R1, the R2, the R3, the R4 and the R5 include deuterium (D) substituents.

8. The device according to claim 7, wherein the organic electroluminescent diode further includes:

a hole injection layer on the first electrode;

a hole transporting layer on the hole injection layer and under the emitting material layer;

an electron transporting layer on the emitting material layer; and an electron injection layer on the electron transporting layer and under the second electrode.

9. An organic electroluminescent device, comprising:

a first electrode;

a second electrode facing the first electrode: and an organic electroluminescent diode positioned between the first and second electrodes and includes an emitting material layer, the emitting material layer includes:

a host material being capable of transporting an electron or a hole; and a dopant material represented by following Formula 3:

[Formula 3]

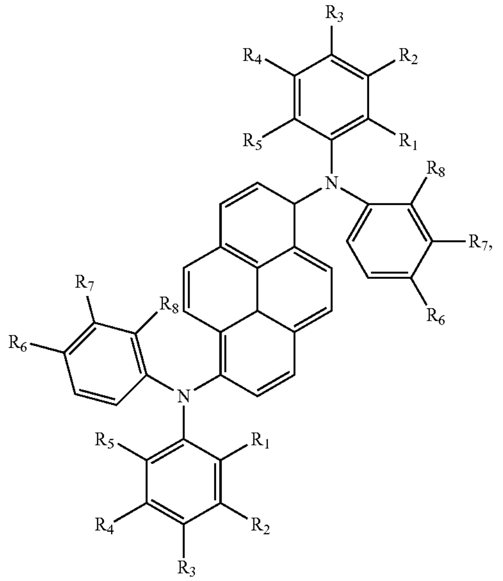

wherein each of the R1, the R2, the R3, the R4, and the R5 is hydrogen (H), C1 to C6 alkyl, or substituted or non-substituted aryl having at least six carbons (C), and two of the R1, the R2, the R3, the R4, and the R5 are selected from the substituted or non-substituted aryl having at least six carbons and same as each other, and wherein each of the R6, the R7, and the R8 is selected from hydrogen (H), C1 to C6 alkyl, substituted or non-substituted aryl having at least six carbons, fluorine, cyanide, or tri-fluoromethyl, and at least one of the R6, the R7, and the R8 is selected from fluorine, cyanide, or tri-fluoromethyl, with the proviso that any selected substituted aryl for the R6, the R7 and the R8 is not substituted with deuterium (D).

10. The device according to claim 9, wherein the organic electroluminescent diode further includes:

a hole injection layer on the first electrode;

a hole transporting layer on the hole injection layer and under the emitting material layer;

an electron transporting layer on the emitting material layer; and an electron injection layer on the electron transporting layer and under the second electrode.

11. A blue fluorescent composition, comprising:

a host material being capable of transporting an electron or a hole; and a dopant material represented by following Formula 1:

[Formula 1]

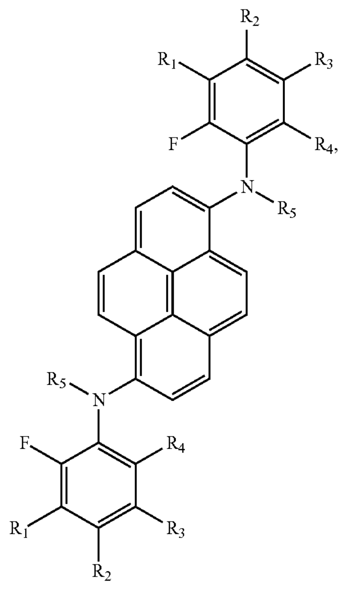

wherein each of the R1, the R2, the R3 and the R4 is selected from hydrogen (H), non-substituted aromatic group, or non-substituted heterocyclic group, wherein R5 and at least two of the R1, the R2, the R3, and the R4 are selected from non-substituted aromatic group or non-substituted heterocyclic group, and wherein each of the R2 and R4 is selected from non-substituted aromatic group or non-substituted heterocyclic group, and the R2 is same as the R4.

12. The composition according to claim 11, wherein the non-substituted aromatic group includes phenyl, biphenyl, naphthyl, phenanthrene, terphenyl and fluorenyl, and the substituted aromatic group includes phenyl, biphenyl, naphthyl, phenanthrene, terphenyl and fluorenyl each of which is substituted by one of an alkyl group including methyl, ethyl, propyl, i-propyl, and t-butyl, a cyano group, a silyl group, and fluorine.

13. The composition according to claim 11, wherein the heterocyclic group includes furan, thiophene, pyrrole, pyridine and pyrimidine.

14. An organic electroluminescent device, comprising:

a first electrode;

a second electrode facing the first electrode: and an organic electroluminescent diode positioned between the first and second electrodes and includes an emitting material layer, the emitting material layer includes:

a host material being capable of transporting an electron or a hole; and a dopant material represented by following Formula 1:

[Formula 1]

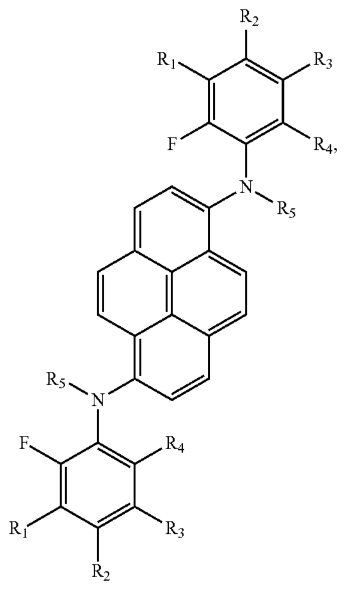

wherein each of the R1, the R2, the R3 and the R4 is selected from hydrogen (H), non-substituted aromatic group, or non-substituted heterocyclic group, wherein R5 and at least two of the R1, the R2, the R3, and the R4 are selected from non-substituted aromatic group or non-substituted heterocyclic group, and wherein each of the R2 and R4 is selected from non-substituted aromatic group or non-substituted heterocyclic group, and the R2 is same as the R4.

15. The device according to claim 14, wherein the organic electroluminescent diode further includes:

a hole injection layer on the first electrode;

a hole transporting layer on the hole injection layer and under the emitting material layer;

an electron transporting layer on the emitting material layer; and an electron injection layer on the electron transporting layer and under the second electrode.

16. A blue fluorescent composition, comprising: a host material being capable of transporting an electron or a hole; and a dopant material represented by following Formula 3:

[Formula 3]

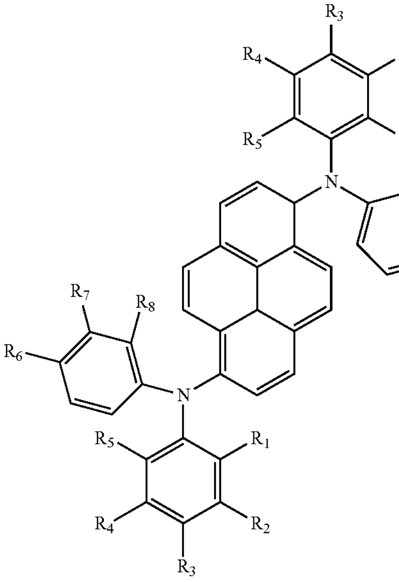

wherein each of the R1, the R2, the R3, the R4, and the R5 is hydrogen (H), C1 to C6 alkyl, or substituted or non-substituted aryl having at least six carbons (C) and two of the R1, the R2, the R3, the R4, and the R5 are selected from the substituted or non-substituted aryl having at least six carbons and same as each other, and wherein each of the R6, the R7, and the R8 is selected from hydrogen (H), C1 to C6 alkyl, substituted or non-substituted aryl having at least six carbons, cyanide, or tri-fluoromethyl, and at least one of the R6, the R7, and the R8 is selected from cyanide or tri-fluoromethyl.

17. The composition according to claim 16, wherein the C1 to C6 alkyl is one of methyl, ethyl, n-propyl, i-propyl, n-butyl, i-butyl and t-butyl.

18. The composition according to claim 16, wherein the substituted or non-substituted aryl is one of phenyl, o-toluyl, m-toluyl, p-toluyl,o-xylyl, m-xylyl, p-xylyl, 1-naphthyl, 2-naphthyl, and 2, 3, 4, 5, 6-pentadeuteriumphenyl.

19. An organic electroluminescent device, comprising:

a first electrode;

a second electrode facing the first electrode: and an organic electroluminescent diode positioned between the first and second electrodes and includes an emitting material layer, the emitting material layer includes:

a host material being capable of transporting an electron or a hole; and a dopant material represented by following Formula 3:

[Formula 3]

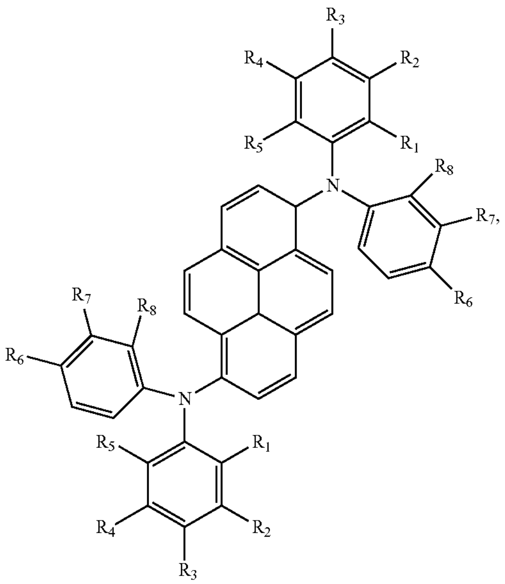

wherein each of the R1, the R2, the R3, the R4, and the R5 is hydrogen (H), C1 to C6 alkyl, or substituted or non-substituted aryl having at least six carbons (C) and two of the R1, the R2, the R3, the R4, and the R5 are selected from the substituted or non-substituted aryl having at least six carbons and same as each other, and wherein each of the R6, the R7, and the R8 is selected from hydrogen (H), C1 to C6 alkyl, substituted or non-substituted aryl having at least six carbons, cyanide, or tri-fluoromethyl, and at least one of the R6, the R7, and the R8 is selected from cyanide or tri-fluoromethyl.

20. The device according to claim 19, wherein the organic electroluminescent diode further includes:

a hole injection layer on the first electrode;

a hole transporting layer on the hole injection layer and under the emitting material layer;

an electron transporting layer on the emitting material layer; and an electron injection layer on the electron transporting layer and under the second electrode.

* * * * *